United States Patent
Vaske et al.

(10) Patent No.: US 11,043,282 B2
(45) Date of Patent: *Jun. 22, 2021

(54) PATHWAY ANALYSIS COMPUTING SYSTEM AND METHOD

(71) Applicant: The Regents of the University of California, Oakland, CA (US)

(72) Inventors: Charles J. Vaske, Santa Cruz, CA (US); Stephen C. Benz, Santa Cruz, CA (US); Joshua M. Stuart, Santa Cruz, CA (US); David Haussler, Santa Cruz, CA (US)

(73) Assignee: THE REGENTS OF THE UNVIERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,535

(22) Filed: Aug. 2, 2017

(65) Prior Publication Data

US 2018/0046751 A1 Feb. 15, 2018

Related U.S. Application Data

(62) Division of application No. 13/068,002, filed on Apr. 29, 2011, now Pat. No. 10,770,169.

(60) Provisional application No. 61/343,575, filed on Apr. 29, 2010.

(51) Int. Cl.
*G16B 5/00* (2019.01)
*G16B 25/00* (2019.01)
*G16B 40/00* (2019.01)

(52) U.S. Cl.
CPC ............ *G16B 5/00* (2019.02); *G16B 25/00* (2019.02); *G16B 40/00* (2019.02); *Y02A 90/10* (2018.01)

(58) Field of Classification Search
None
See application file for complete search history.

(56) References Cited

U.S. PATENT DOCUMENTS

| 7,848,890 | B2 | 12/2010 | Jung et al. |
| 8,515,680 | B2 | 8/2013 | Pipke et al. |
| 8,635,029 | B2 | 1/2014 | Gustafsson et al. |
| 10,192,641 | B2 | 1/2019 | Vaske et al. |
| 2002/0004792 | A1 | 1/2002 | Busa |
| 2003/0113761 | A1 | 6/2003 | Tan et al. |
| 2004/0167763 | A1 | 8/2004 | Liebman |
| 2006/0122792 | A1 | 6/2006 | Jung et al. |
| 2006/0241869 | A1* | 10/2006 | Schadt ............... C12Q 1/6883 702/19 |
| 2007/0009530 | A1 | 1/2007 | Altaba et al. |
| 2009/0112479 | A1 | 4/2009 | Kawai et al. |
| 2009/0186024 | A1 | 7/2009 | Nevins et al. |
| 2010/0100331 | A1 | 4/2010 | Gustafsson et al. |
| 2010/0130527 | A1 | 5/2010 | Lehrer et al. |
| 2011/0093244 | A1 | 4/2011 | Pipke et al. |

FOREIGN PATENT DOCUMENTS

| CN | 102985927 | 3/2019 |
| IL | 248378 | 3/2019 |
| IL | 11248380 | 11/2019 |
| JP | 11500309 | 1/1999 |
| JP | 2006122792 | 5/2006 |
| JP | 2006185412 | 7/2006 |
| JP | 2007011996 | 1/2007 |
| JP | 2013507949 | 3/2013 |
| KR | 102037019 | 10/2019 |
| WO | 2001050950 A2 | 7/2001 |
| WO | 2005096207 | 10/2005 |
| WO | 2007010677 A1 | 1/2007 |
| WO | 2011001844 | 1/2011 |
| WO | 2011055820 A1 | 5/2011 |
| WO | 2011139345 | 11/2011 |
| WO | 2013062505 | 5/2013 |
| WO | WO-2013062505 A1 * | 5/2013 |

OTHER PUBLICATIONS

Smyth et al. (Inference in Directed Acyclic Graphs with Applications to Hidden Markov Model Structures; Published 1995, pp. 1-8) (Year: 1995).*
U.S. Appl. No. 13/317,769, "Notice of Allowance", dated Sep. 17, 2018, 8 pages.
U.S. Appl. No. 14/577,522, "Final Office Action", dated Sep. 17, 2018, 23 pages.
KR10-2015-7010056, "Office Action", dated Aug. 23, 2018, 9 pages.
U.S. Appl. No. 13/068,002, "Non-Final Office Action", dated Sep. 21, 2018, 23 pages.
U.S. Appl. No. 13/317,769, "Notice of Allowability", dated Oct. 17, 2018, 2 pages.
CA3,007,713, "Office Action", dated Sep. 5, 2018, 6 pages.
EP11777686.4, "Office Action", dated Oct. 12, 2018, 5 pages.
KR10-2018-7027602, "Office Action", dated Nov. 2, 2018, 12 pages.
U.S. Appl. No. 13/068,002, "Final Office Action", dated Apr. 14, 2016, 13 pages.
U.S. Appl. No. 13/068,002, "Final Office Action", dated Jun. 25, 2014, 13 pages.
U.S. Appl. No. 13/068,002, "Non-Final Office Action", dated Aug. 27, 2013, 17 pages.
U.S. Appl. No. 13/068,002, "Non-Final Office Action", dated Jul. 2, 2015, 18 pages.
U.S. Appl. No. 13/068,002, "Restriction Requirement", dated Nov. 23, 2012, 8 pages.

(Continued)

*Primary Examiner* — Pablo S Whaley
(74) *Attorney, Agent, or Firm* — Kilpatrick Townsend & Stockton LLP

(57) ABSTRACT

The present invention relates to methods for evaluating the probability that a patient's diagnosis may be treated with a particular clinical regimen or therapy.

23 Claims, 59 Drawing Sheets

(56) References Cited

OTHER PUBLICATIONS

U.S. Appl. No. 13/317,769, "Final Office Action", dated Feb. 17, 2016, 16 pages.
U.S. Appl. No. 13/317,769, "Final Office Action", dated Mar. 20, 2014, 19 pages.
U.S. Appl. No. 13/317,769, "Non-Final Office Action", dated May 31, 2013, 13 pages.
U.S. Appl. No. 13/317,769, "Non-Final Office Action", dated Apr. 10, 2015, 14 pages.
U.S. Appl. No. 13/317,769, "Restriction Requirement", dated Dec. 14, 2012, 9 pages.
U.S. Appl. No. 14/577,522, "Non-Final Office Action", dated Jan. 26, 2018, 26 pages.
U.S. Appl. No. 14/577,522, "Restriction Requirement", dated Aug. 29, 2017, 6 pages.
U.S. Appl. No. 15/667,534, "Non-Final Office Action", dated May 17, 2018, 13 pages.
U.S. Appl. No. 15/667,534, "Restriction Requirement", dated Dec. 18, 2017, 7 pages.
U.S. Appl. No. 15/667,544, "Non-Final Office Action", dated May 23, 2018, 14 pages.
U.S. Appl. No. 15/667,544, "Restriction Requirement", dated Dec. 18, 2017, 8 pages.
AU2017201919, "First Examination Report", dated Jul. 4, 2018, 4 pages.
CA2,796,272, "Office Action", dated Jul. 27, 2018, 6 pages.
CA3,007,805, "Office Action", dated Jul. 30, 2018, 5 pages.
CN201180032521, "First Office Action", dated Jan. 30, 2015, 5 pages.
CN201180032521, "Second Office Action", dated Oct. 30, 2015.
CN201180075918.7, "First Office Action", dated Mar. 1, 2016.
Enerly et al., "miRNA-mRNA Integrated Analysis Reveals Roles for miRNAs in Primary Breast Tumors", 6: e16915, (2011).
EP11777686, "Extended European Search Report", dated Feb. 11, 2016, 10 pages.
IL248380, "Office Action", dated May 22, 2018.
JP2017-000264, "Notice of Decision to Grant", dated Aug. 6, 2018, 3 pages.
JP2017-78768, "Notice of Decision to Grant", dated Jul. 30, 2018, 3 pages.
KR10-2012-7031376, "Notice of Decision to Grant", dated Jun. 25, 2018, 3 pages.
Loo et al., "Allele-specific copy number analysis of tumors", Proceedings of the National Academy of Sciences USA, vol. 107, No. 39, 2010, pp. 16910-16915.
Muggerud et al., "Molecular diversity in Ductal carcinoma in situ (DCIS) and early invasive breast cancer", 4: 357-368 (2010).
PCT/US2011/000752, "International Preliminary Report on Patentability", dated Oct. 30, 2012, 4 pages.
PCT/US2011/000752, "International Search Report and Written Opinion", dated Feb. 8, 2012, 6 pages.
PCT/US2011/001844, "International Preliminary Report on Patentability", dated Apr. 29, 2014, 4 pages.
PCT/US2011/001844, "International Search Report and Written Opinion", dated Sep. 26, 2012, 6 pages.
Ronneberg et al., "Methylation profiling with a panel of cancer related genes: association with estrogen receptor, TP53 mutation status and expression subtypes in sporadic breast cancer", Molecular Oncology 5, 2011, 61-76.
Russnes et al., "Genomic architecture characterizes tumor progression paths and fate in breast cancer patients", Sci. Transl. Med. 38ra47, Jun. 2010.
Vaske et al., "Inference of Patient-Specific Pathway Activities from Multi-Dimensional Cancer Genomics Data using PARADIGM", Bioinformatics, vol. 26, No. 12, Jun. 15, 2010, pp. i237-i245.
U.S. Appl. No. 13/068,002, "Non-Final Office Action", dated Aug. 8, 2019, 12 pages.
CA3,007,805, "Notice of Allowance", dated Aug. 6, 2019, 1 pages.
KR10-2018-7027602, "Notice of Decision to Grant", dated Jul. 23, 2019, 4 pages.
U.S. Appl. No. 13/068,002, "Final Office Action", dated Apr. 26, 2019, 14 pages.
U.S. Appl. No. 15/667,534, "Advisory Action", dated May 1, 2019, 5 pages.
AU2017201919, "Second Examination Report", dated Mar. 18, 2019, 4 pages.
Blum et al., "Applied Mathematical Problem Solving, Modelling, Applications, and Links to Other Subjects—State, Trends and Issues in Mathematics Instruction", Educational Studies in Mathematics, vol. 22, Issue 1, 1991, pp. 37-68.
JP2018-160366, "Office Action", dated Nov. 27, 2019, 6 pages.
KR10-2019-7030625, "Office Action", dated Dec. 2, 2019, 14 pages.
Tanaka et al., "A Description Special Edition: Clinical Bioinformatics", Biomedical Engineering, Japan, and Japanese Society for Medical and Biological Engineering Ditch Shoji, vol. 44 No. 3, Sep. 10, 2006, pp. 377-385.
U.S. Appl. No. 14/577,522, "Final Office Action", dated Oct. 1, 2019, 14 pages.
U.S. Appl. No. 15/667,534, "Non-Final Office Action", dated Oct. 18, 2019, 15 pages.
U.S. Appl. No. 15/667,544, "Non-Final Office Action", dated Oct. 25, 2019, 28 pages.
AU2016219594, "Second Examination Report", dated Oct. 24, 2019, 3 pages.
CA3,007,713, "Office Action", dated Sep. 17, 2019, 4 pages.
EP11874850.8, "Summons to Attend Oral Proceedings", Sep. 16, 2019, 2 pages.
JP2018-165901, "Notice of Reasons for Rejection", dated Nov. 11, 2019.
Van De Vijver et al., "A Gene-Expression Signature as a Predictor of Survival in Breast Cancer," New England Journal Med., Dec. 2002; 347(25):1999-2009.
Weinstein et al., "Spotlight on molecular profiling: "Integromic" analysis of the NCI-60 cancer cell lines," Mol Cancer Ther 5, 2601-2605(2006).
Wirapati et al., "Meta-analysis of gene expression profiles in breast cancer: toward a unified understanding of breast cancer subtyping and prognosis signatures," Breast Cancer.
European Patent Office, Extended European Search Report, EP11874850, dated Feb. 24, 2015.
Schaefer et al., "PID: The Pathway Interaction Database," Nucleic Acieds Res., 2009 (37): D674-679.
Kwoh et al., "Network analysis approach for biology," Cell. Mol. Life Sci., 2007 (64): 1739-1751.
Cerami et al., "cPatch: open source software for collecting, storing, and querying biological pathways," bioinformatics, 2006, 7 (497): 1-9.
Naume et al. "Presence of bone marrow micrometastasis is associated with different recurrence risk within molecular subtypes of breast cancer," 1:160-17, (2007).
Neve et al., A collection of breast cancer cell lines for the study of functionally distinct cancer subtypes. Cancer Cell 10, 515-527 (2006).
Ogata et al., KEGG: Dyoto Encyclopedia of Genes and Genomes, Nucleic Acids Res. Jan. 1999; 27(1): 29-34.
Olshen et al., Circular binary segmentation for the analysis of array-based DNA copy number data, Biostatistics (Oxford, England) 5, 557-572 (2004).
Paez et al., EGFR Mutations in lung cancer: correlation with clinical response to gefitinib therapy. Science 304, 1497-1500 (2004).
Pagel et al., "The MIPS mammalian protein-protein interaction database," Bioinformatics Mar. 2005; 21(6): 832-834.
Parsons et al., "An Integrated Genomic Analysis of Human Glioblastoma Multiforme," Science Sep. 2008; 321(5897): 1807-1812.
Sachs et al., "Causal protein-signaling networks derived from multiparameter single-cell data," Science Apr. 2005; 308(5721):523-529.
Scappini et al., Changes associated with the development of resistance to imatinib (STI571) i two leukemia cell lines expressing p210 Bcr/Abl protein. Cancer 100, 1459-1471.
Segal et al., "From signatures to models: understanding cancer using microarrays," Nat Genet Jun. 2005; 37 Suppl: S38-45.

(56) References Cited

OTHER PUBLICATIONS

Stephens et al., "Complex landscapes of somatic rearrangement in human breast cancer genomes," 462: 1005-1010, (2009).
Storey et al., "Statistical significance for genomewide studies," Proc. Natl. Acad. Sci. U.S.A. Aug. 2003; 100(16): 9440-9445.
Subramanian et al., "Gene set enrichment analysis: a knowledge-based approach for interpreting genome-wide expression profiles," Proc. Natl. Acad. scl. U.S.A. Oct. 2005; 102(4).
Tamayo et al., "Interpreting patterns of gene expression with self-organizing maps: methods and application to hematopoietic differentiation," Proc. Natl. Acad. Sci. U.S.A. 19.
Tarca et al., "A ovel signaling pathway impact analysis," Bioinformatics Jan. 2009; 25(1):75-82.
Troyanskaya et al., "onparametric methods for identifying differentially expressed genes in microarray data," Bioinformatics Nov. 2002; 18(11):1454-1461.
Tusher et al., "Significance analysis of microarrays applied to the ionizing radiation response," Proc. Natl. Acad. Sci. U.S.A. Apr. 2001;98(9):5116-5121.
Tusher et al., "V.G., Tibshirani, R. & Chu, G. Significance analysis of microarrays applied to the ioizing radiation response," Proc Natl Acad Sci U.S.A 98, 5116-5121, dol:1.
Alizadeh et al., "Distinct types of diffuse large B-cell lymphoma identified by gene expression profiling," Nature Feb. 2000; 403(6769): 503-511.
Allison et al., "Microarray data analysis: from disarray to consolidation and consensus," Nat. Rev. Genet. Jan. 2006; 7(1):55-65.
Ashbumer et al., "Microarray data analysis: from disarray to consolidation and consensus," Nat. Rev. Genet. Jan. 2006;7(1):55-65.
Beer et al., "Predicting gene expression from sequence," Cell Apr. 2004;117(2): 185-198.
Bengtsson et al., "Estimation and assessment of raw copy numbers at the single locus level," Bioinformatics (Oxford, England) 24, 759-767, (2008).
Bussey et al., "Integrating data on DNA copy number with gene expression levels and drug sensitivities in the NCI-60 cell line panel," Mol Cancer Ther 5, 853-867 (2006).
Cancer Genome Atlas Research Network. Comprehensive genomic characterization defines human glioblastoma genes and core pathways. Nature Oct. 2008; 455(7216):1061-1068.
Chin et al., "Using array-comparative genomic hybridization to define molecular portraits of primary breast cancers," 26: 1959-1970 (2007).
De Visser et al., "Paradoxical roles of the immune system during cancer development," 6: 24-37 (2006).
Dudoit et al., "A prediction-based resampling method for estimating the number of clusters in a dataset," Genome Biol Jun. 2002;3(7):RESEARCH0036-RESEARCH0036.21.
Joshi-Tope et al., "reactome: a knowledgebase of biological pathways," Nucleic Acids Res. Jan. 2005;33(database issue):D428-32.
Kerr et al., "Analysis of variance for gene expression microarray data," J. Comput. Biol. 2000;7(6):819-837.
Konecny et al., Activity of the dual kinase inhibitor lapatinib (GW572016) against HER-2-overexpressing and trastuzumab-treated breast cancer cells. Cancer Res 66, 1630-1639 (2).
Kuo et al., "A systems analysis of the chemosensitivity of breast cancer cells to the polyamine analogue PG-11047," BMC Med 7, 77, doi:1741-1015-7-77[pil] 10.1186/1741-7015-7.
Lee et al., "Identifying regulatory mechanisms using individual variation reveals key role for chromatin modification," Proc. Natl. Acad. Sci. U.S.A. Sep. 2006; 103(38) 14062-14.
Monks et al., "Feasibility of a high-flux anticancer drug screen using a diverse panel of cultured human tumor cell lines," Journal Natl Cancer Inst 83, 757-766 (1991).
Monti et al., "Consensus VClustering: A Resampling-Based Method for Class Discovery and Visualization of Gene Expression Microarray Data," Machine Learning 52, 91-118 (2003).
Murphy et al., "Loopy belief propagatio for approximate inference: An empirical study," Proceedings of Uncertainty in AI. 1999.

Efroni et al., "Identification of key processes underlying cancer phenotypes using biologic pathway analysis," PLoS ONE 2007;2(5):e425.
Etemadmoghadam et al., "Integrated Genome-Wide DNA Copy Number and Expression Analysis Identifies Distinct Mechanisms of Primary Chemoresistance in Ovarian Carcinomas," Clinic.
Friedman et al., "Inferring cellular networks using probabilistic graphical models," Science Feb. 2004;303(5659):799-805.
Friedman e al., "Sequential Update of Bayesian Network Structure," Proceedings of the Thirteenth Conference on Uncertainty in Artificial Intelligence (UAI'97), Morgan Kaufman.
Gat-Viks et al., "A probabilistic methodology for integrating knowledge and experiments on biological networks," J. Comput. Biol. Mar. 2006; 13(2); 165-181.
Gat-Viks et al., "Refinement and expansion of signaling pathways: the osmotic response network in yeast," Genome Research Mar. 2007;17(3):358-367.
Gat-Viks et al., "The Factor Graph Network Model for Biological Systems," Recomb'05 Proceedings of the 9th Annual International Conference on Research in Computational Molecul.
Golub et al., "Molecular classification of cancer; class discovery and class prediction by gene expression monitoring," Science Oct. 1999; 286(5439): 531-537.
Gooch, J. L., Christy, B., and Yee, D., "STAT6 mediates interleukin-4 growth inhibition in human breast cancer cells," 4:324-331 (2002).
U.S. Appl. No. 13/317,769, "Notice of Allowance", dated Dec. 12, 2018, 3 pages.
U.S. Appl. No. 15/667,534, "Final Office Action", dated Jan. 7, 2019, 10 pages.
U.S. Appl. No. 15/667,544, "Final Office Action", dated Jan. 7, 2019, 17 pages.
AU2016219594, "First Examination Report", dated Jan. 9, 2019, 5 pages.
CA3,007,805, "Office Action", dated Jan. 14, 2019, 4 pages.
CN201180032521.X, "Notice of Decision to Grant", dated Dec. 5, 2018, 4 pages.
U.S. Appl. No. 15/667,537, "Notice of Allowance", dated Dec. 16, 2020, 9 pages.
U.S. Appl. No. 15/667,534, "Notice of Allowance", dated Sep. 10, 2020, 9 pages.
U.S. Appl. No. 15/667,537, "Final Office Action", dated Sep. 2, 2020, 15 pages.
AU2019204759, "First Examination Report", dated Aug. 25, 2020, 5 pages.
U.S. Appl. No. 14/577,522, "Non-Final Office Action", dated Mar. 14, 2019, 14 pages.
CA2,796,272, "Notice of Allowance", dated Mar. 5, 2019, 1 page.
CA3,007,713, "Office Action", dated Feb. 8, 2019, 4 pages.
U.S. Appl. No. 13/068,002, "Notice of Allowance", dated May 27, 2020, 8 pages.
U.S. Appl. No. 14/577,522, "Non-Final Office Action", dated Jun. 9, 2020, 11 pages.
U.S. Appl. No. 15/667,537, "Non-Final Office Action", dated May 22, 2020, 14 pages.
U.S. Appl. No. 15/667,544, "Final Office Action", dated Jun. 2, 2020, 23 pages.
CA3,021,833, "Office Action", dated Jun. 26, 2020, 6 pages.
JP2018-165901, "Notice of Decision to Grant", dated May 25, 2020, 3 pages.
KR10-2019-7030625, "Notice of Decision to Grant", dated Jun. 11, 2020, 4 pages.
U.S. Appl. No. 15/667,534, Advisory Action, dated Aug. 5, 2020, 3 pages.
EP20150552.6, Extended European Search Report, dated Jul. 24, 2020, 16 pages.
JP2018-160366, Office Action, dated Aug. 3, 2020, 8 pages.
U.S. Appl. No. 15/667,544, "Non-Final Office Action", dated Feb. 2, 2021, 15 pages.

* cited by examiner

Basal Super Pathway

ERBB2AMP Super Pathway

Luminal

Claudin-Low

PATHWAY ANALYSIS COMPUTING SYSTEM AND METHOD

RELATIONSHIP TO OTHER APPLICATIONS

This application is related to and claims priority to U.S. Non-Provisional patent application Ser. No. 13/068,002 entitled "PATHWAY RECOGNITION ALGORITHM USING DATA INTEGRATION ON GENOMIC MODELS (PARADIGM)" filed Apr. 29, 2011, which claims the benefit of U.S. Provisional Patent Application Ser. No. 61/343,575 entitled "PATHWAY RECOGNITION ALGORITHM USING DATA INTEGRATION ON GENOMIC MODELS (PARADIGM)" filed 29 Apr. 2010, which is herein incorporated by reference in its entirety.

This invention was made partly using funds from the following United Stated Federal agencies: NSF CAREER award 0845783, National Cancer Institute Contract/Grant numbers 5R21CA135937-02 and 1U24CA143858-01, and National Institute of Health Training Grant number T32 GM070386-01. The US Federal Government has certain rights to this invention.

FIELD OF THE INVENTION

The present invention relates to a method for identifying components of biological pathways in an individual or subject and determining if the individual or subject is a candidate for a clinical regimen or treatment. The invention also relates to using the methods to diagnose whether a subject is susceptible to cancer, autoimmune diseases, cell cycle disorders, or other disorders.

BACKGROUND

A central premise in modern cancer treatment is that patient diagnosis, prognosis, risk assessment, and treatment response prediction can be improved by stratification of cancers based on genomic, transcriptional and epigenomic characteristics of the tumor alongside relevant clinical information gathered at the time of diagnosis (for example, patient history, tumor histology and stage) as well as subsequent clinical follow-up data (for example, treatment regimens and disease recurrence events).

While several high-throughput technologies have been available for probing the molecular details of cancer, only a handful of successes have been achieved based on this paradigm. For example, 25% of breast cancer patients presenting with a particular amplification or overexpression of the ERBB2 growth factor receptor tyrosine kinase can now be treated with trastuzumab, a monoclonal antibody targeting the receptor (Vogel C, Cobleigh M A, Tripathy D, Gutheil J C, Harris L N, Fehrenbacher L, Slamon D J, Murphy M, Novotny W F, Burchmore M, Shak S, Stewart S J. First-line, single-agent Herceptin® (trastuzumab) in metastatic breast cancer. A preliminary report. Eur. J. Cancer 2001 January; 37 Suppl 1:2529).

However, even this success story is clouded by the fact that fewer than 50% of patients with ERBB2-positive breast cancers actually achieve any therapeutic benefit from trastuzumab, emphasizing our incomplete understanding of this well-studied oncogenic pathway and the many therapeutic-resistant mechanisms intrinsic to ERBB2-positive breast cancers (Park J W, Neve R M, Szollosi J, Benz C C. Unraveling the biologic and clinical complexities of HER2. Clin. Breast Cancer 2008 October; 8(5):392-401.)

This overall failure to translate modern advances in basic cancer biology is in part due to our inability to comprehensively organize and integrate all of the omic features now technically acquirable on virtually any type of cancer. Despite overwhelming evidence that histologically similar cancers are in reality a composite of many molecular subtypes, each with significantly different clinical behavior, this knowledge is rarely applied in practice due to the lack of robust signatures that correlate well with prognosis and treatment options.

Cancer is a disease of the genome that is associated with aberrant alterations that lead to disregulation of the cellular system. What is not clear is how genomic changes feed into genetic pathways that underlie cancer phenotypes. High-throughput functional genomics investigations have made tremendous progress in the past decade (Alizadeh A A, Eisen M B, Davis R E, Ma C, Lossos I S, Rosenwald A, Boldrick J C, Sabet H, Tran T, Yu X, Powell J I, Yang L, Marti G E, Moore T, Hudson J, Lu L, Lewis D B, Tibshirani K SHERLOCK G, Chan W C, Greiner T C, Weisenburger D D, Armitage J O, Wamke R, Levy R, Wilson W, Greyer M R, Byrd J C, Botstcin D, Brown P O, Staudt L M. Distinct types of diffuse large B-cell lymphoma identified by gene expression profiling. Nature 2000 February; 403(6769):503-511.; Golub T R, Slonim D K, Tamayo P, Huard C, Gaasenbeek M, Mesirov J P, Coller H, Loh M L, Downing J R, Caligiuri M A, Bloomfield C D, Lander E S. Molecular classification of cancer: class discovery and class prediction by gene expression monitoring. Science 1999 October; 286(5439): 531-537.; van dc Vijver M J, He Y D, van t Veer L I, Dai H. Hart A A M, Voskuil D W, Schreiber G J, Peterse J L, Roberts C, Marton M J, Parrish M, Atsma D, Witteveen A, Glas A, Delahaye L, van der Velde T, Bartelink H, Rodenhuis S, Rutgers E T, Friend S H, Bernards R. A Gene-Expression Signature as a Predictor of Survival in Breast Cancer. N Engl J Med 2002 December:347(25):1999-2009.)

However, the challenges of integrating multiple data sources to identify reproducible and interpretable molecular signatures of tumorigenesis and progression remain elusive. Recent pilot studies by TCGA and others make it clear that a pathway-level understanding of genomic perturbations is needed to understand the changes observed in cancer cells. These findings demonstrate that even when patients harbor genomic alterations or aberrant expression in different genes, these genes often participate in a common pathway. In addition, and even more striking, is that the alterations observed (for example, deletions versus amplifications) often alter the pathway output in the same direction, either all increasing or all decreasing the pathway activation. (See Parsons D W, Jones S, Zhang X, Lin J C H, Leary R J, Angenendt P, Mankoo P, Carter H, Siu I, Gallia G L, Olivi A, McLendon R, Rasheed B A, Keir S, Nikolskaya T, Nikolsky Y, Busam D A, Tekleab H, Diaz L A, Hartigan J, Smith D R, Strausberg R L, Marie S K N, Shinjo S M O, Yan H, Riggins G J, Bigner D D, Karchin R, Papadopoulos N, Parmigiani G, Vogelstein B, Velculescu V E, Kinzler K W. An Integrated Genomic Analysis of Human Glioblastoma Multiforme. Science 2008 September; 321(5897):1807-1812.; Cancer Genome Atlas Research Network. Comprehensive genomic characterization defines human glioblastoma genes and core pathways. Nature 2008 October; 455 (7216):1061-1068.)

Approaches for interpreting genome-wide cancer data have focused on identifying gene expression profiles that are highly correlated with a particular phenotype or disease state, and have led to promising results. Methods using analysis of variance, false-discovery, and non-parametric methods have been proposed. (See Troyanskaya et al., 2002) have been proposed. Allison D B, Cui X, Page G P, Sabripour M. Microarray data analysis: from disarray to consolidation and consensus. Nat. Rev. Genet. 2006 January; 7(1):55-65.; Dudoit S, Fridlyand J. A prediction-based resampling method for estimating the number of clusters in a dataset. Genome Biol 2002 June; 3(7):RESEARCH0036-RESEARCH0036.21.; Tusher V G, Tibshirani R, Chu G. Significance analysis of microarrays applied to the ionizing radiation response. Proc. Natl. Acad. Sci. U.S.A. 2001 April; 98(9):5116-5121; Kerr M K, Martin M, Churchill G A. Analysis of variance for gene expression microarray data. J. Comput. Biol. 2000; 7(6):819-837; Storey J D, Tibshirani R. Statistical significance for genomewide studies. Proc. Natl. Acad. Sci. U.S.A. 2003 August; 100(16):9440-9445; and Troyanskaya O G, Garber M E, Brown P O, Botstein D, Altman R B. Nonparametric methods for identifying differentially expressed genes in microarray data. Bioinformatics 2002 November; 18(11):1454-1461.)

Several pathway-level approaches use statistical tests based on overrepresentation of genesets to detect whether a pathway is perturbed in a disease condition. In these approaches, genes are ranked based on their degree of differential activity, for example as detected by either differential expression or copy number alteration. A probability score is then assigned reflecting the degree to which a pathway's genes rank near the extreme ends of the sorted list, such as is used in gene set enrichment analysis (GSEA) (Subramanian A, Tamayo P, Mootha V K, Mukherjee S, Ebert B L, Gillette M A, Paulovich A, Pomeroy S L, Golub T R, Lander E S, Mesirov J P. Gene set enrichment analysis: a knowledge-based approach for interpreting genome-wide expression profiles. Proc. Natl. Acad. Sci. U.S.A. 2005 October; 102(43):15545-15550.). Other approaches include using a hypergeometric test-based method to identify Gene Ontology (Ashburner M, Ball C A, Blake J A, Botstein D, Butler H, Cherry J M, Davis A P, Dolinski K, Dwight S S, Eppig J T, Harris M A, Hill D P, Issel-Tarver L, Kasarskis A, Lewis S, Matese J C, Richardson J E, Ringwald M, Rubin G M, SHERLOCK G. Gene ontology: tool for the unification of biology. The Gene Ontology Consortium. Nat Genet 2000 May; 25(1):25-29.) or MIPS mammalian protein-protein interaction (Pagel P, Kovac S, Oesterheld M, Brauner B, Dunger-Kaltenbach I, Frishman G, Montrone C, Mark P, Sttimpflen V, Mewes H, Ruepp A, Frishman D. The MIPS mammalian protein-protein interaction database. Bioinformatics 2005 March; 21(6):832-834.) categories enriched in differentially expressed genes (Tamayo P, Slonim D, Mesirov J, Zhu Q, Kitareewan S, Dmitrovsky E, Lander E S, Golub T R. Interpreting patterns of gene expression with self-organizing maps: methods and application to hematopoietic differentiation. Proc. Natl. Acad. Sci. U.S.A. 1999 March; 96(6):2907-2912.).

Overrepresentation analyses are limited in their efficacy because they do not incorporate known interdependencies among genes in a pathway that can increase the detection signal for pathway relevance. In addition, they treat all gene alterations as equal, which is not expected to be valid for many biological systems.

Further complicating the issue is the fact that many genes (for example, microRNAs) are pleiotropic, acting in several pathways with different roles (Maddika S, Ande S R, Panigrahi S, Paranjothy T, Weglarczvk K, Zuse A, Eshraghi M, Manda K D, Wiechec E, Los M. Cell survival, cell death and cell cycle pathways are interconnected: implications for cancer therapy. Drug Resist. Updat. 2007 January; 10(1-2):13-29). Because of these factors, overrepresentation analyses often miss functionally-relevant pathways whose genes have borderline differential activity. They can also produce many false positives when only a single gene is highly altered in a small pathway. Our collective knowledge about the detailed interactions between genes and their phenotypic consequences is growing rapidly.

While the knowledge was traditionally scattered throughout the literature and hard to access systematically, new efforts are cataloging pathway knowledge into publicly available databases. Some of the databases that include pathway topology are Reactome (Joshi-Tope G, Gillespie M, Vastrik 1, D'Eustachio P, Schmidt E, de Bono B, Jassal B, Gopinath G R, Wu G R. Matthews L, Lewis S, Birney E, Stein L. Reactome: a knowledgebase of biological pathways. Nucleic Acids Res. 2005 January; 33(Database issue): D428-32; Ogata H, Goto S, Sato K, Fujibuchi W, Bono H, Kanehisa M. KEGG: Kyoto Encyclopedia of Genes and Genomes. Nucleic Acids Res. 1999 January; 27(1):29-34.)) and the NCI Pathway Interaction Database. Updates to these databases are expected to improve our understanding of biological systems by explicitly encoding how genes regulate and communicate with one another. A key hypothesis is that the interaction topology of these pathways can be exploited for the purpose of interpreting high-throughput datasets.

Until recently, few computational approaches were available for incorporating pathway knowledge to interpret high-throughput datasets. However, several newer approaches have been proposed that incorporate pathway topology (Efroni S, Schaefer C F, Buetow K H. Identification of key processes underlying cancer phenotypes using biologic pathway analysis. PLoS ONE 2007; 2(5):e425.). One approach, called Signaling Pathway Impact Analysis (SPIA), uses a method analogous to Google's PageRank to determine the influence of a gene in a pathway (Tarca A L, Draghici S, Khatri P, Hassan S S, Mittal P, Kim J, Kim C J, Kusanovic J P, Romero R. A novel signaling pathway impact analysis. Bioinformatics 2009 January; 25(1):75-82.) In SPIA, more influence is placed on genes that link out to many other genes. SPIA was successfully applied to different cancer datasets (lung adenocarcinoma and breast cancer) and shown to outperform overrepresentation analysis and Gene Set Enrichment Analysis for identifying pathways known to be involved in these cancers. While SPIA represents a major step forward in interpreting cancer datasets using pathway topology, it is limited to using only a single type of genome-wide data.

New computational approaches are needed to connect multiple genomic alterations such as copy number, DNA methylation, somatic mutations, mRNA expression and microRNA expression. Integrated pathway analysis is expected to increase the precision and sensitivity of causal interpretations for large sets of observations since no single data source is likely to provide a complete picture on its own.

In the past several years, approaches in probabilistic graphical models (PGMs) have been developed for learning causal networks compatible with multiple levels of observations. Efficient algorithms are available to learn pathways automatically from data (Friedman N, Goldszmidt M. (1997) Sequential Update of Bayesian Network Structure. In: Proceedings of the Thirteenth Conference on Uncertainty in Artificial Intelligence (UAI'97), Morgan Kaufinann Publishers, pp. 165-174; Murphy K, Weiss Y. Loopy belief propagation for approximate inference: An empirical study. In: Proceedings of Uncertainty in AI. 1999) and are well adapted to problems in genetic network inference (Friedman N. Inferring cellular networks using probabilistic graphical models. Science 2004 February; 303(5659):799-805.). As an example, graphical models have been used to identify sets of genes that form 'modules' in cancer biology (Segal E, Friedman N, Kaminski N, Regev A, Koller D. From signatures to models: understanding cancer using microarrays. Nat Genet 2005 June; 37 Suppl:S38-45.). They have also been applied to elucidate the relationship between tumor genotype and expression phenotypes (Lee S, Pe'er D, Dudley A M, Church G M, Koller D. Identifying regulatory mechanisms using individual variation reveals key role for chromatin modification. Proc. Natl. Acad. Sci. U.S.A. 2006 September; 103(38):14062-14067.), and infer protein signal networks (Sachs K, Perez O, Pe'er D, Lauffenburger D A, Nolan G P. Causal protein-signaling networks derived from multiparameter single-cell data. Science 2005 April; 308 (5721):523-529.) and recombinatorial gene regulatory code (Beer M A, Tavazoie S. Predicting gene expression from sequence. Cell 2004 April; 117(2):185-198.). In particular, factor graphs have been used to model expression data (Gat-Viks I, Shamir R. Refinement and expansion of signaling pathways: the osmotic response network in yeast. Genome Research 2007 March; 17(3):358-367.; Gat-Viks I, Tanay A, Raijman D, Shamir R. The Factor Graph Network Model for Biological Systems. In: Hutchison D, Kanade T, Kittler J, Kleinberg J M, Mattem F, Mitchell J C, Naor M, Nierstrasz O, Pandu Rangan C, Steffen B, Sudan M, Terzopoulos D, Tygar D, Vardi M Y, Weikum G, Mivano S. Mesirov J, Kasif S, Istrail S, Pevzner P A, Waterman M, editors. Berlin, Heidelberg: Springer Berlin Heidelberg; 2005 p. 31-47.; Gat-Viks I, Tanay A, Raijman D, Shamir R. A probabilistic methodology for integrating knowledge and experiments on biological networks. J. Comput. Biol. 2006 March; 13(2):165-181.).

Breast cancer is clinically and genomically heterogeneous and is composed of several pathologically and molecularly distinct subtypes. Patient responses to conventional and targeted therapeutics differ among subtypes motivating the development of marker guided therapeutic strategies. Collections of breast cancer cell lines mirror many of the molecular subtypes and pathways found in tumors, suggesting that treatment of cell lines with candidate therapeutic compounds can guide identification of associations between molecular subtypes, pathways and drug response. In a test of 77 therapeutic compounds, nearly all drugs show differential responses across these cell lines and approximately half show subtype-, pathway and/or genomic aberration-specific responses. These observations suggest mechanisms of response and resistance that may inform clinical drug deployment as well as efforts to combine drugs effectively.

The accumulation of high throughput molecular profiles of tumors at various levels has been a long and costly process worldwide. Combined analysis of gene regulation at various levels may point to specific biological functions and molecular pathways that are deregulated in multiple epithelial cancers and reveal novel subgroups of patients for tailored therapy and monitoring. We have collected high throughput data at several molecular levels derived from fresh frozen samples from primary tumors, matched blood, and with known micrometastases status, from approximately 110 breast cancer patients (further referred to as the MicMa dataset). These patients are part of a cohort of over 900 breast cancer cases with information about presence of disseminated tumor cells (DTC), long-term follow-up for recurrence and overall survival. The MicMa set has been used in parallel pilot studies of whole genome mRNA expression (I Naume, B. et al., (2007), Presence of bone marrow micrometastasis is associated with different recurrence risk within molecular subtypes of breast cancer, 1: 160-171), arrayCGH (Russnes H G, Vollan H K M, Lingjaerde O C, Krasnitz A, Lundin P, Naume B, lie T, Borgen E, Rye I H, LangerOcl A, Chin S, Teschendorff A E, Stephens P J, MAner S, Schlichting E, Baumbusch L O, KAresen R, Stratton M P, Wigler M, Caldas C, Zetterberg A, Hicks J, Borresen-Dale A. Genomic architecture characterizes tumor progression paths and fate in breast cancer patients. Sci Transl Med 2010 June; 2(38):38ra47), DNA methylation (Ronneberg J A. Fleischer T, Solvang H K, Nordgard S H, Edvardsen H, Potapenko I, Nebdal D, Daviaud C, Gut I, Bukholm I, Naume B, Borresen-Dale A, Tost J, Kristensen V. Methylation profiling with a panel of cancer related genes: association with estrogen receptor, TP53 mutation status and expression subtypes in sporadic breast cancer. Mol Oncol 2011 February; 5(1):61-76), whole genome SNP and SNP-CGH (Van, Loo P. et al., (2010), Allele-specific copy number analysis of tumors, 107: 16910-169154), whole genome miRNA expression analyses (5 Enerly, E. et al., (2011), miRNA-mRNA Integrated Analysis Reveals Roles for miRNAs in Primary Breast Tumors, 6: e 16915-), TP53 mutation status dependent pathways and high throughput paired end sequencing (7 Stephens, P. J. et al., (2009), Complex landscapes of somatic rearrangement in human breast cancer genomes, 462: 1005-1010). This is a comprehensive collection of high throughput molecular data performed by a single lab on the same set of primary tumors of the breast.

A topic of great importance in cancer research is the identification of genomic aberrations that drive the development of cancer. Utilizing whole-genome copy number and expression profiles from the MicMa cohort, we defined several filtering steps, each designed to identify the most promising candidates among the genes selected in the previous step. The first two steps involve identification of commonly aberrant and in-cis correlated to expression genes, i.e. genes for which copy number changes have substantial effect on expression. Subsequently, the method considers in-trans effects of the selected genes to further narrow down the potential novel candidate driver genes (Miriam Ragle Aure, Israel Steinfeld Lars Oliver Baumbusch Knut Liestol Doron Lipson Bjorn Naume Vessela N. Kristensen Anne-Lise Borresen-Dale Ole-Christian Lingjwrde and Zohar Yakhini, (2011), A robust novel method for the integrated analysis of copy number and expression reveals new candidate driver genes in breast cancer). Recently we developed an allele-specific copy number analysis enabling us to accurately dissect the allele-specific copy number of solid tumors (ASCAT), and simultaneously estimating and adjusting for both tumor ploidy and nonaberrant cell admixture (Van, Loo P. et al., (2010), Allele-specific copy number analysis of tumors, 107: 16910-169154). This allows calculation of genome-wide allele-specific copy-number profiles from which gains, losses, copy number-neutral events, and loss of heterozygosity (LOH) can accurately be determined. Observing DNA aberrations in allele specific manner allowed us to construct a genome-wide map of allelic skewness in breast cancer, indicating loci where one allele is preferentially lost, whereas the other allele is preferentially gained. We hypothesize that these alternative alleles have a different influence on breast carcinoma development. We could also see that Basal-like breast carcinomas have a significantly higher frequency of LOH compared with other subtypes, and their ASCAT profiles show large-scale loss of genomic material during tumor development, followed by a whole-genome duplication, resulting in near-triploid genomes (Van et al. (2010) supra). Distinct global DNA methylation profiles have been reported in normal breast epithelial cells as well as in breast tumors.

There is currently a need to provide methods that can be used in characterization, diagnosis, prevention, treatment, and determining outcome of diseases and disorders.

BRIEF DESCRIPTION OF THE INVENTION

In one embodiment, the invention provides a method of generating a dynamic pathway map (DPM), the method comprising: providing access to a pathway element database storing a plurality of pathway elements, each pathway element being characterized by its involvement in at least one pathway; providing access to a modification engine coupled to the pathway element database; using the modification engine to associate a first pathway element with at least one a priori known attribute; using the modification engine to associate a second pathway element with at least one assumed attribute; using the modification engine to cross-correlate and assign an influence level of the first and second pathway elements for at least one pathway using the known and assumed attributes, respectively, to form a probabilistic pathway model; and using the probabilistic pathway model, via an analysis engine, to derive from a plurality of measured attributes for a plurality of elements of a patient sample the DPM having reference pathway activity information for a particular pathway. In one preferred embodiment, the pathway element is a protein. In a more preferred embodiment, the protein is selected from the group consisting of a receptor, a hormone binding protein, a kinase, a transcription factor, a methylase, a histone acetylase, and a histone deacetylase. In an alternative preferred embodiment, the pathway element is a nucleic acid. In a more preferred embodiment, the nucleic acid is selected from the group consisting of a protein coding sequence, a genomic regulatory sequence, a regulatory RNA, and a trans-activating sequence. In another more preferred embodiment, the reference pathway activity information is specific with respect to a normal tissue, a diseased tissue, an ageing tissue, or a recovering tissue. In a preferred embodiment, the known attribute is selected from the group consisting of a compound attribute, a class attribute, a gene copy number, a transcription level, a translation level, and a protein activity. In another preferred embodiment, the assumed attribute is selected from the group consisting of a compound attribute, a class attribute, a gene copy number, a transcription level, a translation level, and a protein activity. In another alternative embodiment, the measured attributes are selected from the group consisting of a mutation, a differential genetic sequence object, a gene copy number, a transcription level, a translation level, a protein activity, and a protein interaction. In a preferred embodiment, the pathway is within a regulatory pathway network. In a more preferred embodiment, the regulatory pathway network is selected from the group consisting of an ageing pathway network, an apoptosis pathway network, a homeostasis pathway network, a metabolic pathway network, a replication pathway network, and an immune response pathway network. In a yet more preferred embodiment, the pathway is within a signaling pathway network. In an alternative yet more preferred embodiment, the pathway is within a network of distinct pathway networks. In a most preferred embodiment, the signaling pathway network is selected from the group consisting of a calcium/calmodulin dependent signaling pathway network, a cytokine mediated signaling pathway network, a chemokine mediated signaling pathway network, a growth factor signaling pathway network, a hormone signaling pathway network, a MAP kinase signaling pathway network, a phosphatase mediated signaling pathway network, a Ras superfamily mediated signaling pathway network, and a transcription factor mediated signaling pathway network.

The invention also provides a method of generating a dynamic pathway map (DPM), the method comprising: providing access to a model database that stores a probabilistic pathway model that comprises a plurality of pathway elements; wherein a first number of the plurality of pathway elements are cross-correlated and assigned an influence level for at least one pathway on the basis of known attributes; wherein a second number of the plurality of pathway elements are cross-correlated and assigned an influence level for at least one pathway on the basis of assumed attributes; and using a plurality of measured attributes for a plurality of elements of a patient sample, via an analysis engine, to modify the probabilistic pathway model to obtain the DPM, wherein the DPM has reference pathway activity information for a particular pathway.

In one preferred embodiment, the pathway is within a regulatory pathway network, a signaling pathway network, or a network of distinct pathway networks. In another preferred embodiment, the pathway element is a protein selected from the group consisting of a receptor, a hormone binding protein, a kinase, a transcription factor, a methylase, a histone acetylase, and a histone deacetylase or a nucleic acid is selected from the group consisting of a genomic regulatory sequence, a regulatory RNA, and a trans-activating sequence. In a still further preferred embodiment, the reference pathway activity information is specific with respect to a normal tissue, a diseased tissue, an ageing tissue, or a recovering tissue. In another preferred embodiment, the known attribute is selected from the group consisting of a compound attribute, a class attribute, a gene copy number, a transcription level, a translation level, and a protein activity. In another preferred embodiment, the assumed attribute is selected from the group consisting of a compound attribute, a class attribute, a gene copy number, a transcription level, a translation level, and a protein activity. In a still further preferred embodiment, the measured attributes are selected from the group consisting of a mutation, a differential genetic sequence object, a gene copy number, a transcription level, a translation level, a protein activity, and a protein interaction.

The invention further provides a method of analyzing biologically relevant information, comprising: providing access to a model database that stores a dynamic pathway map (DPM), wherein the DPM is generated by modification of a probabilistic pathway model with a plurality of measured attributes for a plurality of elements of a first cell or patient sample; obtaining a plurality of measured attributes for a plurality of elements of a second cell or patient sample; and using the DPM and the plurality of measured attributes for the plurality of elements of the second cell or patient sample, via an analysis engine, to determine a predicted pathway activity information for the second cell or patient sample. In one preferred embodiment, the measured attributes for the plurality of elements of the first cell or patient sample are characteristic for a healthy cell or tissue, a specific age of a cell or tissue, a specific disease of a cell or tissue, a specific disease stage of a diseased cell or tissue, a specific gender, a specific ethnic group, a specific occupational group, and a specific species. In another preferred embodiment, the measured attributes for the plurality of elements of the second cell or patient sample are selected from the group consisting of a mutation, a differential genetic sequence object, a gene copy number, a transcription level, a translation level, a protein activity, and a protein interaction. In an alternative preferred embodiment, the first and second samples are obtained from the same cell or patient, and further comprising providing a treatment to the cell or patient before obtaining the plurality of measured attributes for the plurality of elements of the second cell or patient sample. In a more preferred embodiment, the treatment is selected from the group consisting of radiation, administration of a pharmaceutical to the patient, and administration of a candidate molecule to the cell. In another more preferred embodiment, the candidate molecule is a member of a library of candidate molecules. In another preferred embodiment, the predicted pathway activity information identifies an element as a hierarchical-dominant element in at least one pathway. In a more preferred embodiment, the predicted pathway activity information identifies an element as a disease-determinant element in at least one pathway with respect to a disease. In an alternative embodiment, the method further comprises a step of generating a graphical representation of predicted pathway activity information. In an alternative embodiment, the method further comprises a step of generating a treatment recommendation that is at least in part based on the predicted pathway activity information. In an alternative embodiment, the method further comprises a step of using the predicted pathway activity information to formulate a diagnosis, a prognosis for a disease, or a recommendation selected from the group consisting of a selection of a treatment option, and a dietary guidance. In an alternative embodiment, the method further comprises a step of using the predicted pathway activity information to identify an epigenetic factor, a stress adaptation, a state of an organism, and a state of repair or healing.

In another embodiment, The invention provides a transformation method for creating a matrix of integrated pathway activities (IPAs) for predicting a clinical outcome for an individual in need, the method comprising the steps of (i) providing a set of curated pathways, wherein the pathways comprise a plurality of entities; (ii) converting each curated pathway into a distinct probabilistic graphical model (PGM), wherein the PGM is derived from factor graphs of each curated pathway, (iii) providing a biological sample from the individual wherein the biological sample comprises at least one endogenous entity comprised in one of the curated pathways; (iv) determining the levels of endogenous entity in the biological sample; (v) comparing the levels of the endogenous entity with those levels of the entity in a previously determined control sample from another individual; (vi) determining whether the levels of the endogenous entity relative to the control entity levels are activated, nominal, or inactivated; (vii) assigning the endogenous entity a numeric state, wherein the state representing activated is +1, the state representing nominal activity is 0, and wherein the state representing inactivated is −1; (viii) repeating steps ii through (vi) for another endogenous entity; (x) compiling the numeric states of each endogenous entity into a matrix of integrated pathway activities (IPAs), (x) wherein the matrix of integrated pathway activities is A wherein A, represents the inferred activity of entity i in biological sample j; the method resulting in a matrix of integrated pathway activities for predicting a clinical outcome for the individual.

In one embodiment the method for creating a matrix of IPAs comprises predicting a clinical outcome, providing a diagnosis, providing a treatment, delivering a treatment, administering a treatment, conducting a treatment, managing a treatment, or dispensing a treatment to an individual in need. In another embodiment, the set of curated pathways is from an analysis of human biology. In yet another alternative embodiment, the set of curated pathways is from an analysis of non-human biology. In another embodiment, the determining of the levels of the endogenous entity relative to the control entity levels is performed using Student's t-test. In an alternative embodiment, the determining of the levels of the endogenous entity relative to the control entity levels is performed using ANOVA. In another embodiment, the transforming method comprise the steps of wherein a plurality of matrices of integrated pathway activities from more than one individual are combined, the combined plurality of matrices resulting in a cluster, and where the distances between the individuals' matrices of the resulting cluster are determined. In one embodiment, the determined distances are analysed using K-means cluster analysis. In another alternative embodiment, the determined distances are analysed using $K^2$-means cluster analysis. In a yet other embodiment, the transforming method comprises the step of determining the levels of endogenous entity in the biological sample comprises detecting the endogenous entity with an antibody and thereby determining the levels of endogenous entity. In an alternative embodiment the step of determining the levels of endogenous entity in the biological sample comprises detecting the endogenous entity with a nucleic acid probe and thereby determining the levels of endogenous entity. In another alternative embodiment, the step of determining the levels of endogenous entity in the biological sample comprises detecting the endogenous entity with an organic reagent, wherein the organic reagent binds to the endogenous entity thereby resulting in a detectable signal and thereby determining the levels of endogenous entity.

In a still further alternative embodiment, the step of determining the levels of endogenous entity in the biological sample comprises detecting the endogenous entity with an inorganic reagent, wherein the inorganic reagent binds to the endogenous entity thereby resulting in a detectable signal and thereby determining the levels of endogenous entity. In another alternative embodiment, the step of determining the levels of endogenous entity in the biological sample comprises detecting the endogenous entity with an organic reagent, wherein the organic reagent reacts with the endogenous entity thereby resulting in a detectable signal and thereby determining the levels of endogenous entity. In another alternative embodiment, the step of determining the levels of endogenous entity in the biological sample comprises detecting the endogenous entity with an inorganic reagent, wherein the inorganic reagent reacts with the endogenous entity thereby resulting in a detectable signal and thereby determining the levels of endogenous entity. In a preferred embodiment, the step of determining the levels of endogenous entity in the biological sample comprises measuring the absorbance of the endogenous entity at the optimal wavelength for the endogenous entity and thereby determining the levels of endogenous entity. In an alternative preferred embodiment, the step of determining the levels of endogenous entity in the biological sample comprises measuring the fluorescence of the endogenous entity at the optimal wavelength for the endogenous entity and thereby determining the levels of endogenous entity. In a still further alternative preferred embodiment, the step of determining the levels of endogenous entity in the biological sample comprises reacting the endogenous entity with an enzyme, wherein the enzyme selectively digests the endogenous entity to create at least one product, detecting the at least one product, and thereby determining the levels of endogenous entity. In a more preferred embodiment, the step of reacting the endogenous entity with an enzyme results in creating at least two products. In a yet more preferred embodiment, the step of reacting the endogenous entity with an enzyme resulting at least two products is followed by a step of treating the products with another enzyme, wherein the enzyme selectively digests at least one of the products to create at least a third product, detecting the at least a third product, and thereby determining the levels of endogenous entity.

In another preferred embodiment the individual is selected from the group of a healthy individual, an asymptomatic individual, and a symptomatic individual. In a more preferred embodiment, the individual is selected from the group consisting of an individual diagnosed with a condition, the condition selected from the group consisting of a disease and a disorder. In a preferred embodiment, the condition is selected from the group consisting of acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and utenis, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. In an alternative preferred embodiment, the condition is selected from the group consisting of cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system. In another preferred embodiment, the condition is selected from the group consisting of endocrinological disorders such as disorders associated with hypopituitarism including hypogonadism, Sheehan syndrome, diabetes insipidus, Kaftan's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalcmia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

The Invention also provides the transforming method as disclosed herein wherein matrix A can then be used in place of the original constituent datasets to identify associations with clinical outcomes. In a more preferred embodiment the curated pathways are selected from the group consisting of biochemical pathways, genetic pathways, metabolic pathways, gene regulatory pathways, gene transcription pathways, gene translation pathways. In another more preferred embodiment, the entities are selected from the group consisting of nucleic acids, peptides, proteins, peptide nucleic acids, carbohydrates, lipids, proteoglycans, factors, co-factors, biochemical metabolites, organic compositions, inorganic compositions, and salts. In a yet other preferred embodiment, the biological sample is selected from the group consisting of patient samples, control samples, experimentally-treated animal samples, experimentally-treated tissue culture samples, experimentally-treated cell culture samples, and experimentally-treated in vitro biochemical composition samples. In a more preferred embodiment, the biological sample is a patient sample.

The invention also provides a probabilistic graphical model (PGM) framework having an output that infers the molecular pathways altered in a patient sample, the PGM comprising a plurality of factor graphs, wherein the factor graphs represent integrated biological datasets, and wherein the inferred molecular pathways that are altered in a patient sample comprise molecular pathways known from data and wherein said molecular pathways effect a clinical or nonclinical condition, wherein the inferred molecular pathways are known to be modulated by a clinical regimen or treatment, and wherein the output indicates a clinical regimen. In a preferred embodiment, the data is selected from experimental data, clinical data, epidemiological data, and phenomenological data. In another preferred embodiment, the condition is selected from the group consisting of a disease and a disorder. In a more preferred embodiment, the condition is selected from the group consisting of acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia. Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. In an alternative more preferred embodiment, the condition is selected from the group consisting of cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system. In a yet other more preferred embodiment, the condition is selected from the group consisting of endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

BRIEF DESCRIPTION OF THE DRAWINGS

FIG. 2A Data on a single patient is integrated for a single gene using a set of four different biological entities for the gene describing the DNA copies, mRNA and protein levels, and activity of the protein. FIG. 2B PARADIGM models various types of interactions across genes including transcription factors to targets' (upper-left), subunits aggregating in a complex (upper-right), post-translational modification (lower-left), and sets of genes in a family performing redundant functions (lower-right). FIG. 2C Toy example of a small sub-pathway involving P53, an inhibitor MDM2, and the high level process, apoptosis as represented in the model.

Biological entities were sorted by mean IPA in the patient samples (red) and compared with the mean IPA for the peruted samples. The colored areas around each mean denote the standard deviation (SD) of each set. The IPAs of the right include AKT1, CHUK, and MDM2.

Figure 7:
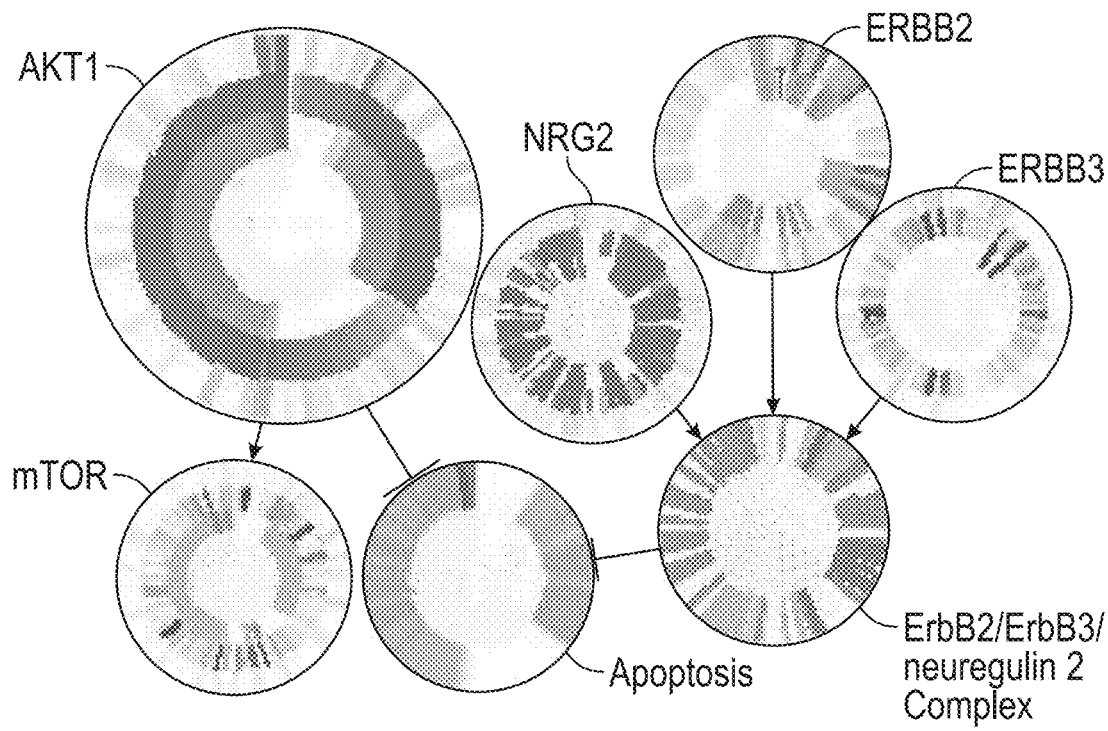

FIG. 7 illustrates an exemplary CIRCLEMAP display of the ErbB2 pathway. For each node, estrogen receptor (ER) status, IPAs, expression data, and copy-number data are displayed as concentric circles, from innermost to outermost respectively. The apoptosis node and the ErbB2/ErbB3/neuregulin 2 complex node have circles only for ER status and for IPAs, as there are no direct observations of these entities. Each patient's data is displayed along one angle from the circle center to edge.

Figure 8:
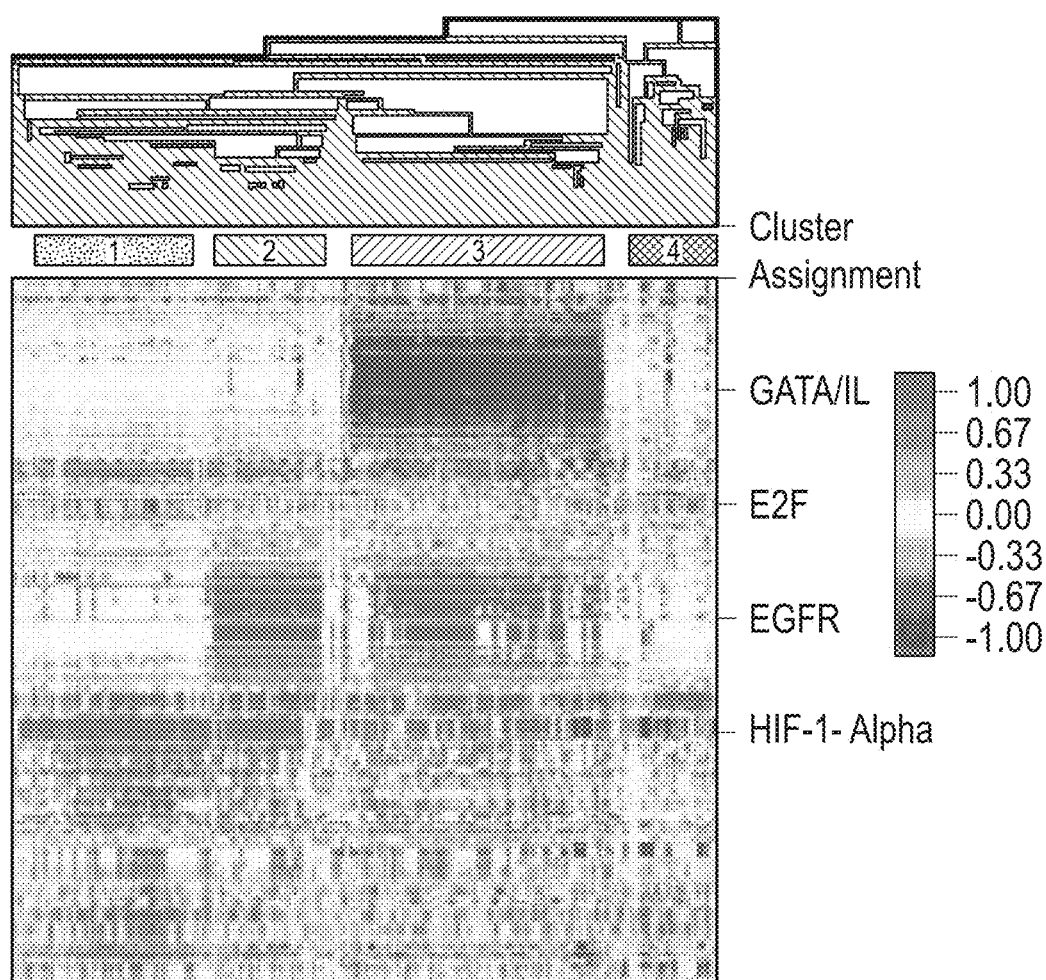

FIG. 8 illustrates exemplary clustering of IPAs for TCGA GBM. Each column corresponds to a single sample, and each row to a biomolecular entity. Color bars beneath the hierarchical clustering tree denote clusters used for FIG. 9.

Figure 9:
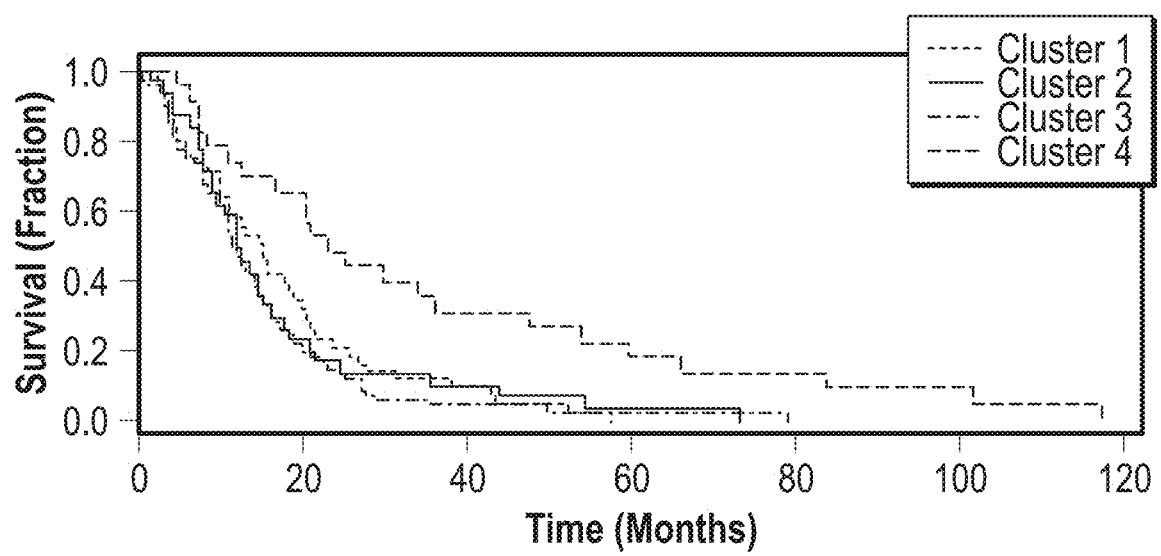

FIG. 9 illustrates Kaplan-Meier survival plots for the clusters from FIG. 8.

Figure 10A:
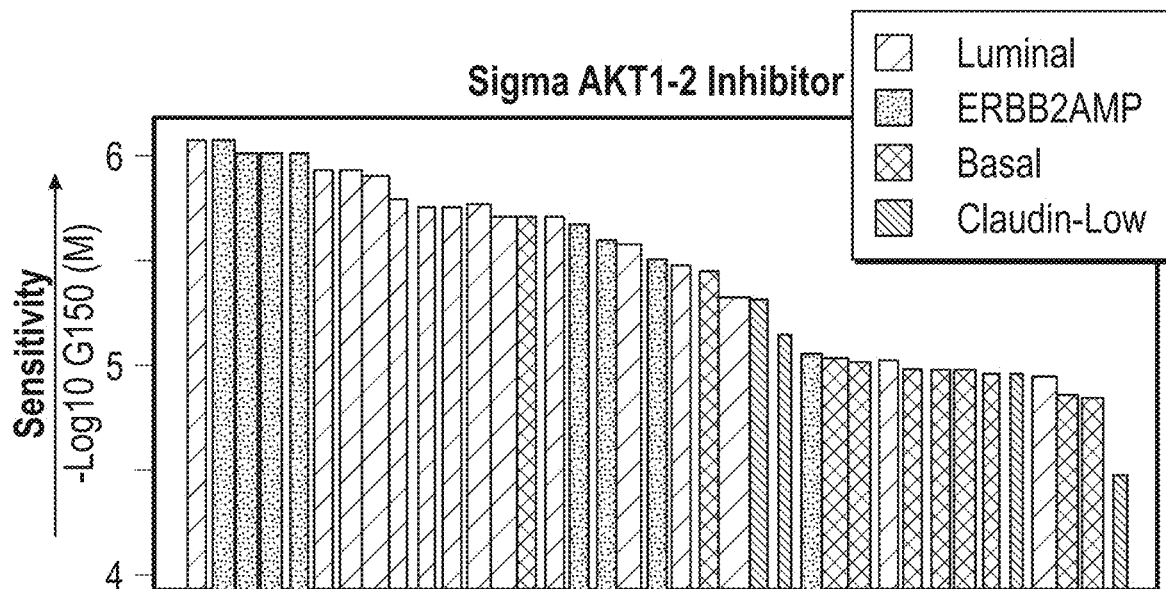
Figure 10B:
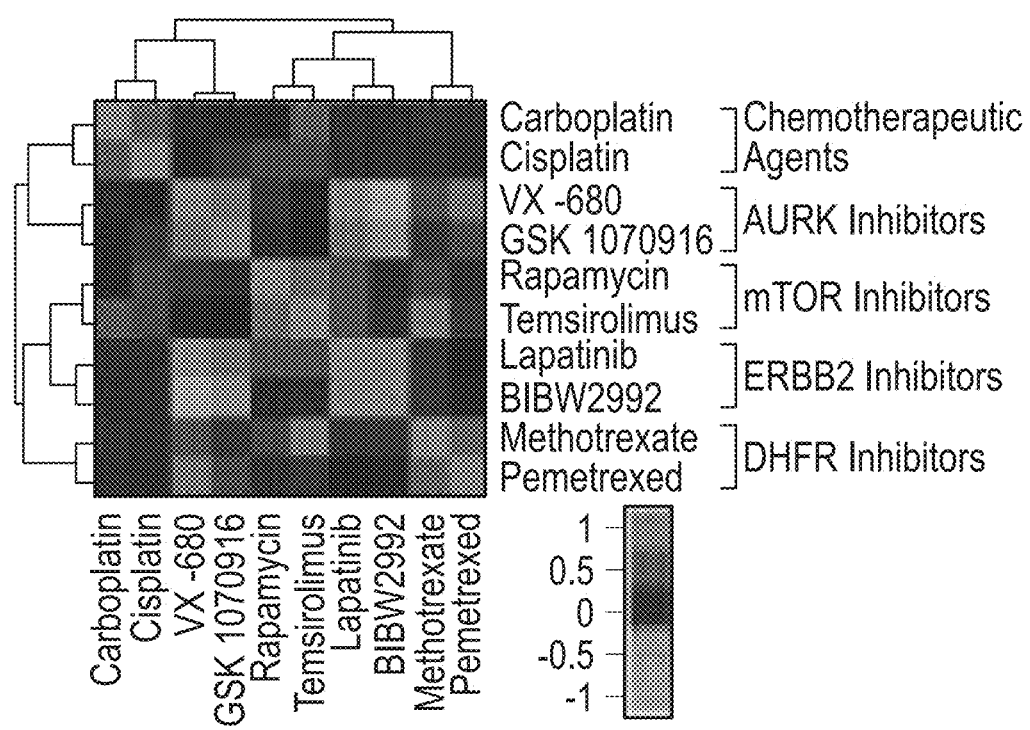
Figure 10C:
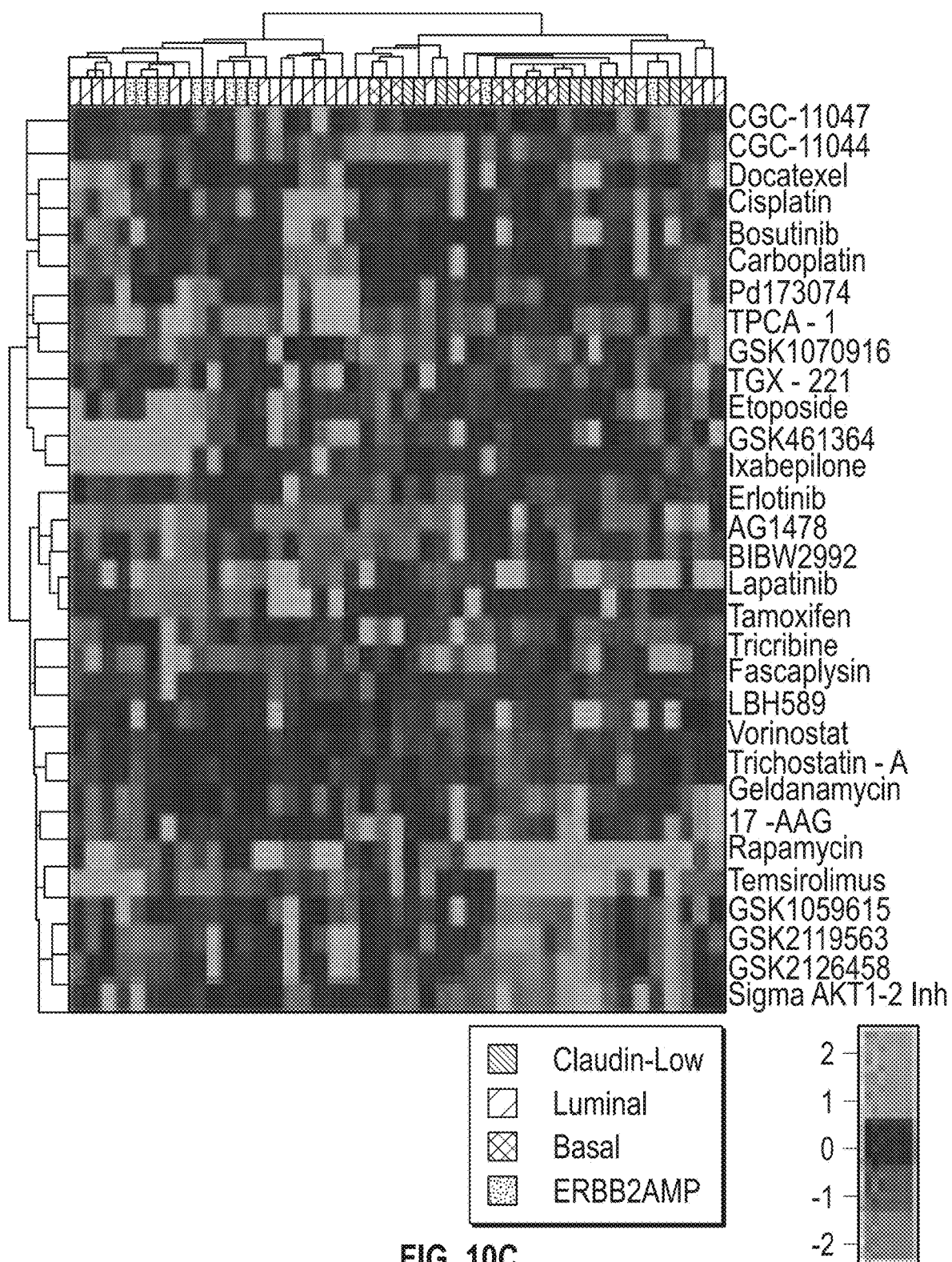
Figure 10D:
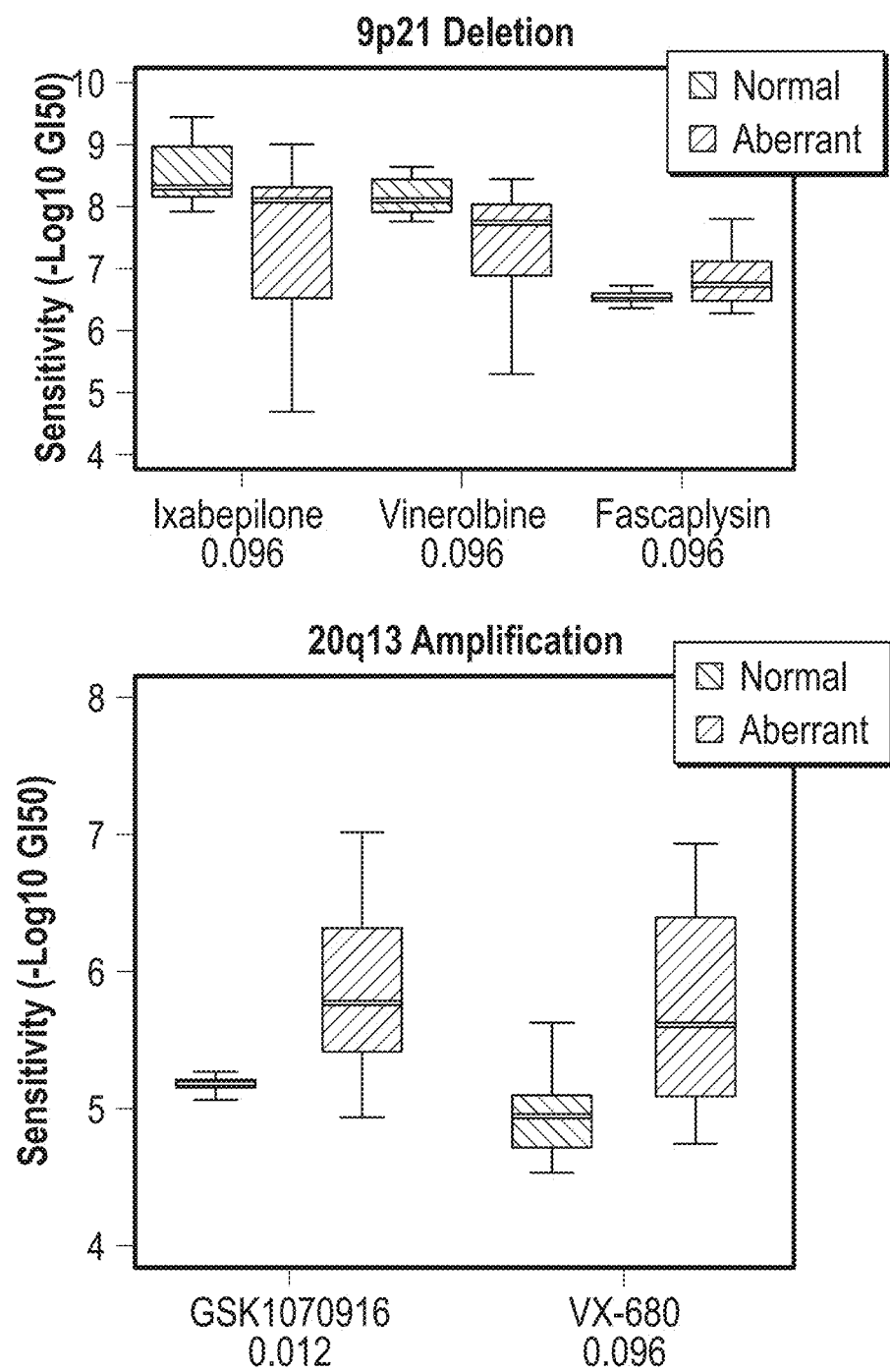
Figure 10D:
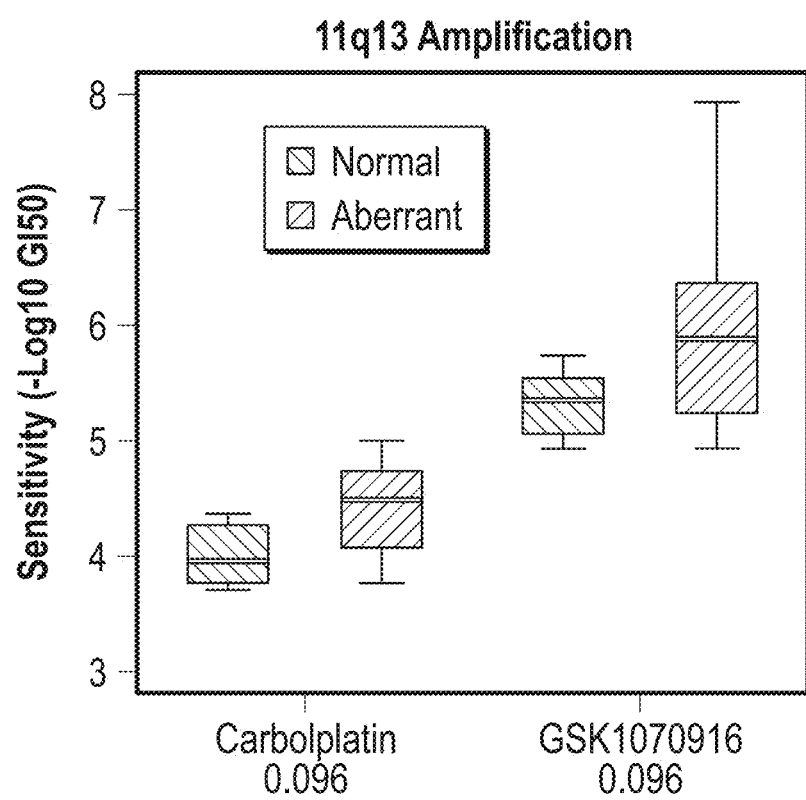

FIGS. 10A-10D illustrate that cell lines show a broad range of responses to therapeutic compounds. FIG. 10A Luminal and ERBB2AMP cell lines preferentially respond to AKT inhibition. Each bar represents the response of a single breast cancer cell line to the Sigma AKT1-2 inhibitor. Cell lines are ordered by increasing sensitivity ($-\log_{10}$ ($GI_{50}$)) and colored according to subtype. FIG. 10B $GI_{50}$ values for compounds with similar mechanisms are highly correlated. Heatmap shows hierarchical clustering of correlations between responses breast cancer cell lines treated with various compounds. FIG. 10C Compounds with similar modes of action show similar patterns of response across the panel of cell lines. Each column represents one cell line, each row represents a compound tested. 0150 values are hierarchically clustered. Only compounds with a significant subtype effect are included. Cell lines of similar subtype tend to cluster together, indicating that they are responsive to the same compounds. Gray represents missing values. FIG. 10D CNAs are associated sensitivity. Boxplots show distribution of response sensitivity for cell lines with aberrant (A) and normal (N) copy number at the noted genomic locus. FDR p values for the association between drug response and CNA are noted. a. 9p21 (CDKN2A) deletion is associated with response to ixabepilone, vinerolbine and fascaplysin. b. 20q13 (STK15/AURKA) amplification is associated with VX-680 and GSK1070916. c. Amplification at 11q13 (CCND1) is associated with response to carboplatin and GSK1070916.

Figure 11:
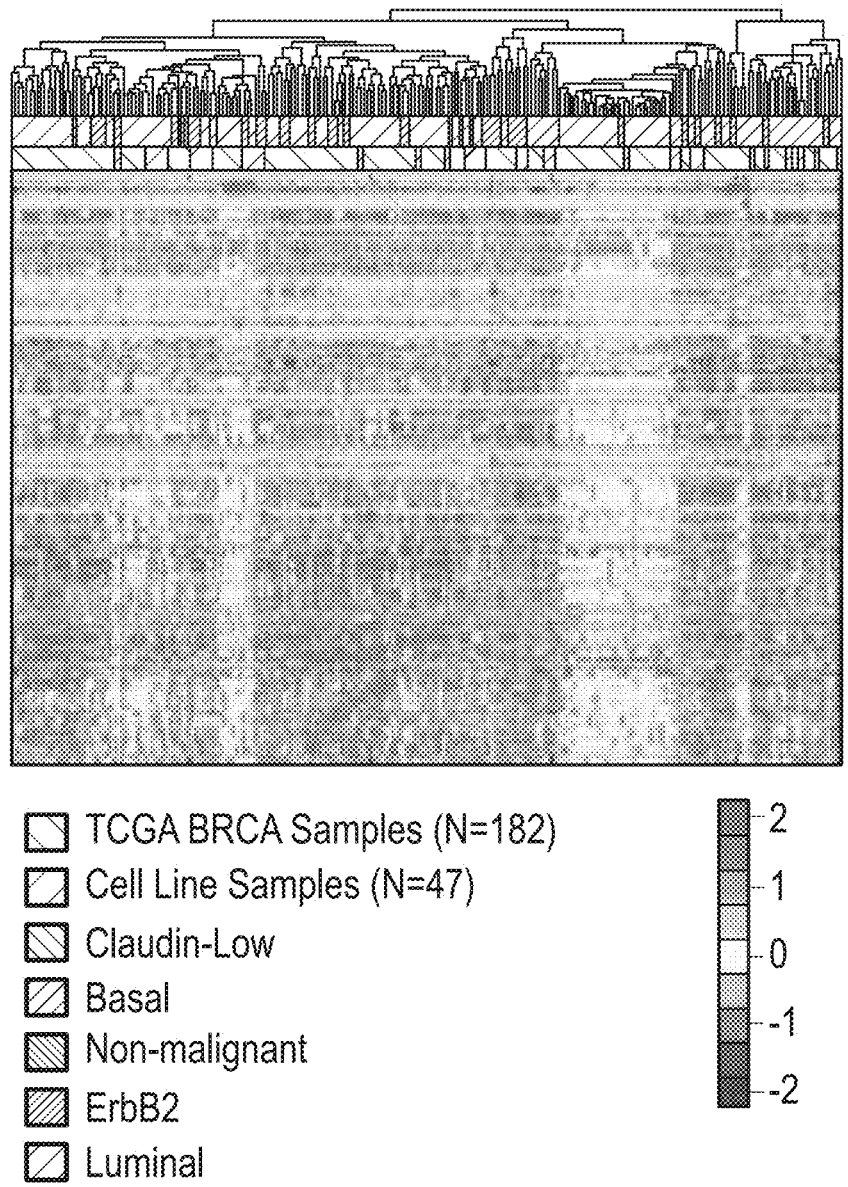

FIG. 11 shows a heatmap of non-redundant PARADIGM activities both cell line and TCGA samples. Cluster dendrogram represents Euclidian distance between samples and was created using Eisen Cluster and drawn using Java Treeview. Colored bars below dendrogram represent sample subtype (top) and sample cohort (bottom).

Figure 12A:
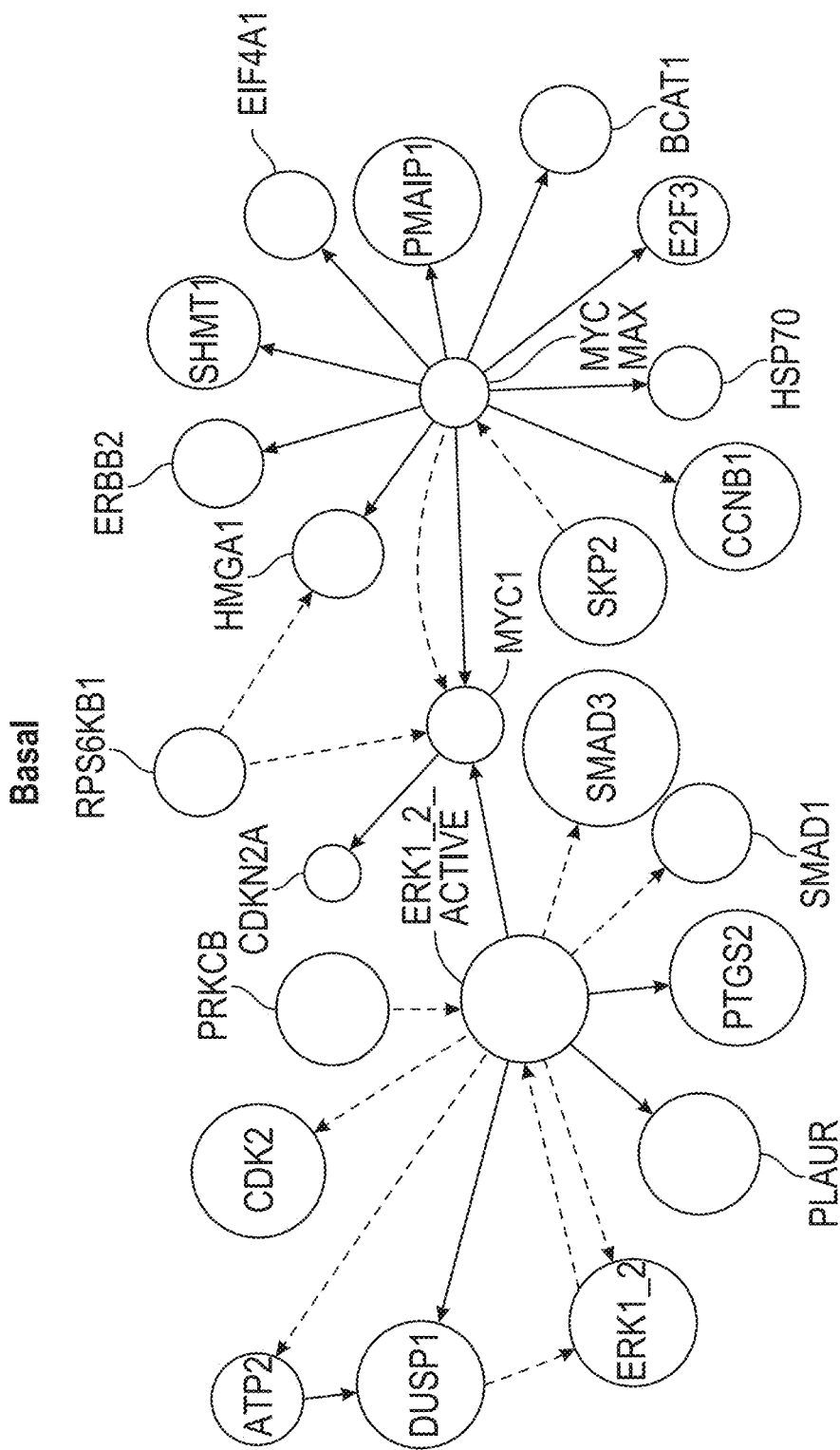
Figure 12B:
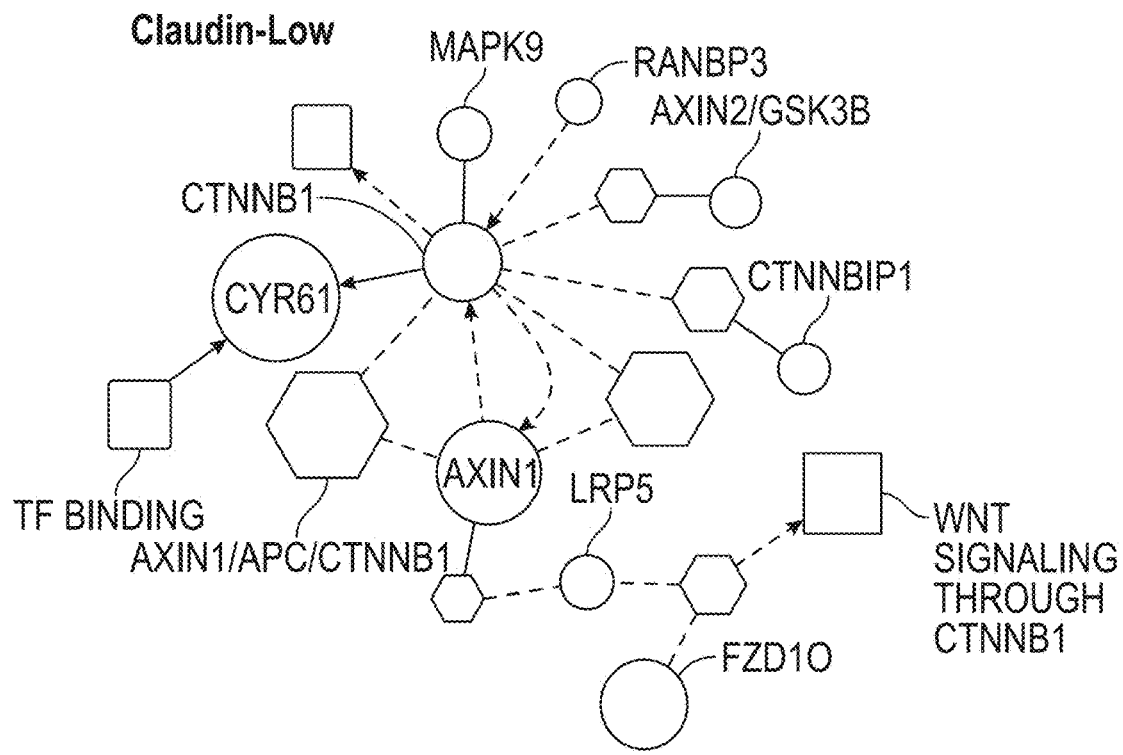
Figure 12C:
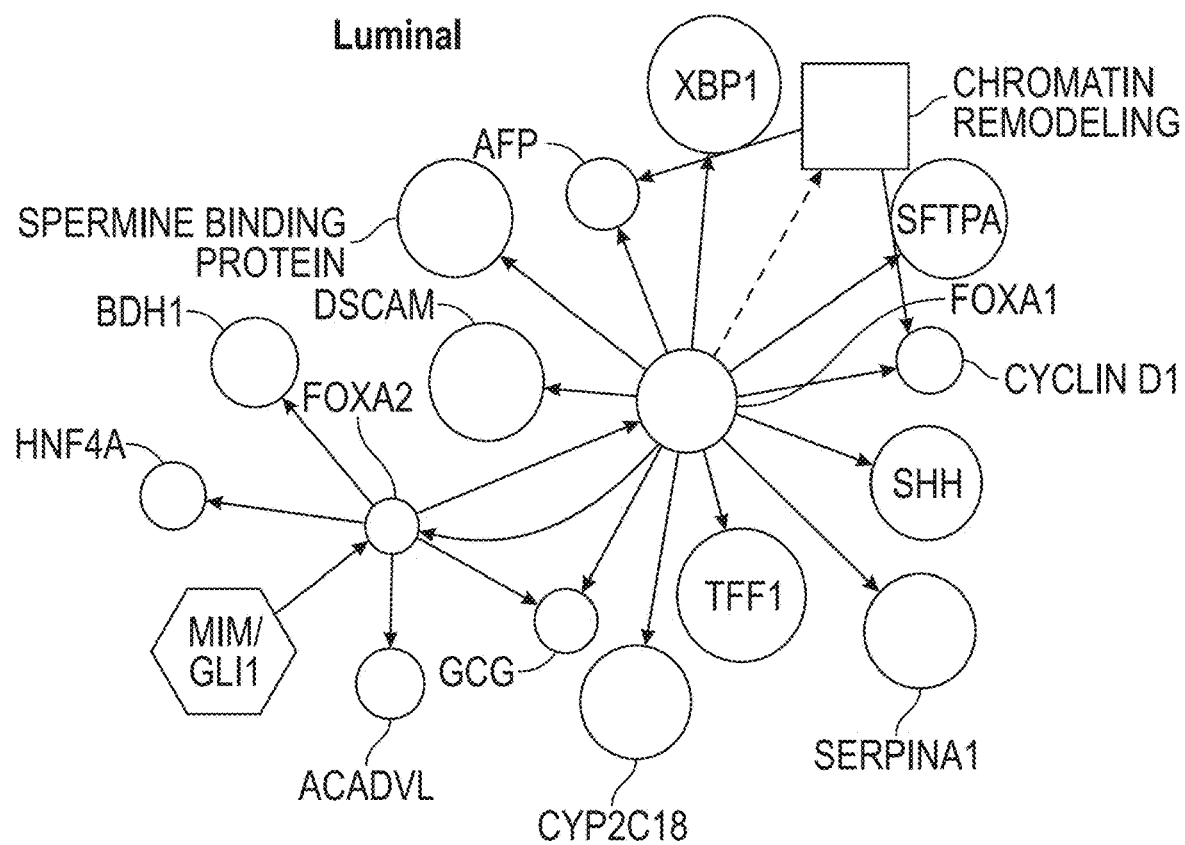
Figure 12D:
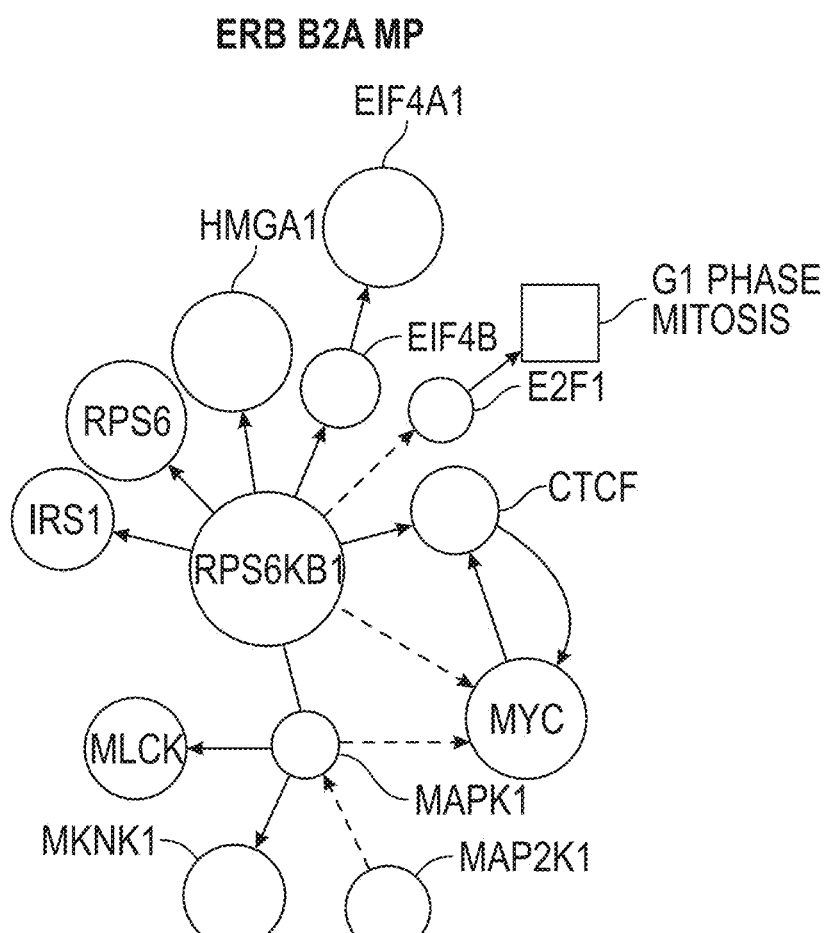

FIGS. 12A-12D illustrate that cell line subtypes have unique network features. In all panels, each node in the graph represents a different pathway "concept" corresponding to either a protein (circles), a multimeric complex (hexagons), or a an abstract cellular process (squares). The size of the nodes were drawn in proportion to the differential activity score such that larger nodes correspond to pathway concepts with activities more correlated with basal versus non-basal cell lines. Color indicates whether the concept is positively correlated (red) or negatively correlated (blue) with the basal subtype. Links represent different interactions including protein-protein level interactions (dashed lines) and transcriptional (solid lines). Interactions were included in the map only if they interconnect concepts whose absolute level of differential activity is higher than the mean absolute level. FIG. 12A The MYC/MAX and ERK1/2 subnet is preferentially activated in basal breast cancer cell lines. FIG. 12B The CTTNB I network is activated in claudin-low cell lines. FIG. 12C A FOXA1/FOXA2 network is upregulated in the luminal subtype. FIG. 12D The ERBB2AMP subtype shows down-regulation of the RPS6KB1 pathway.

Figure 13A:
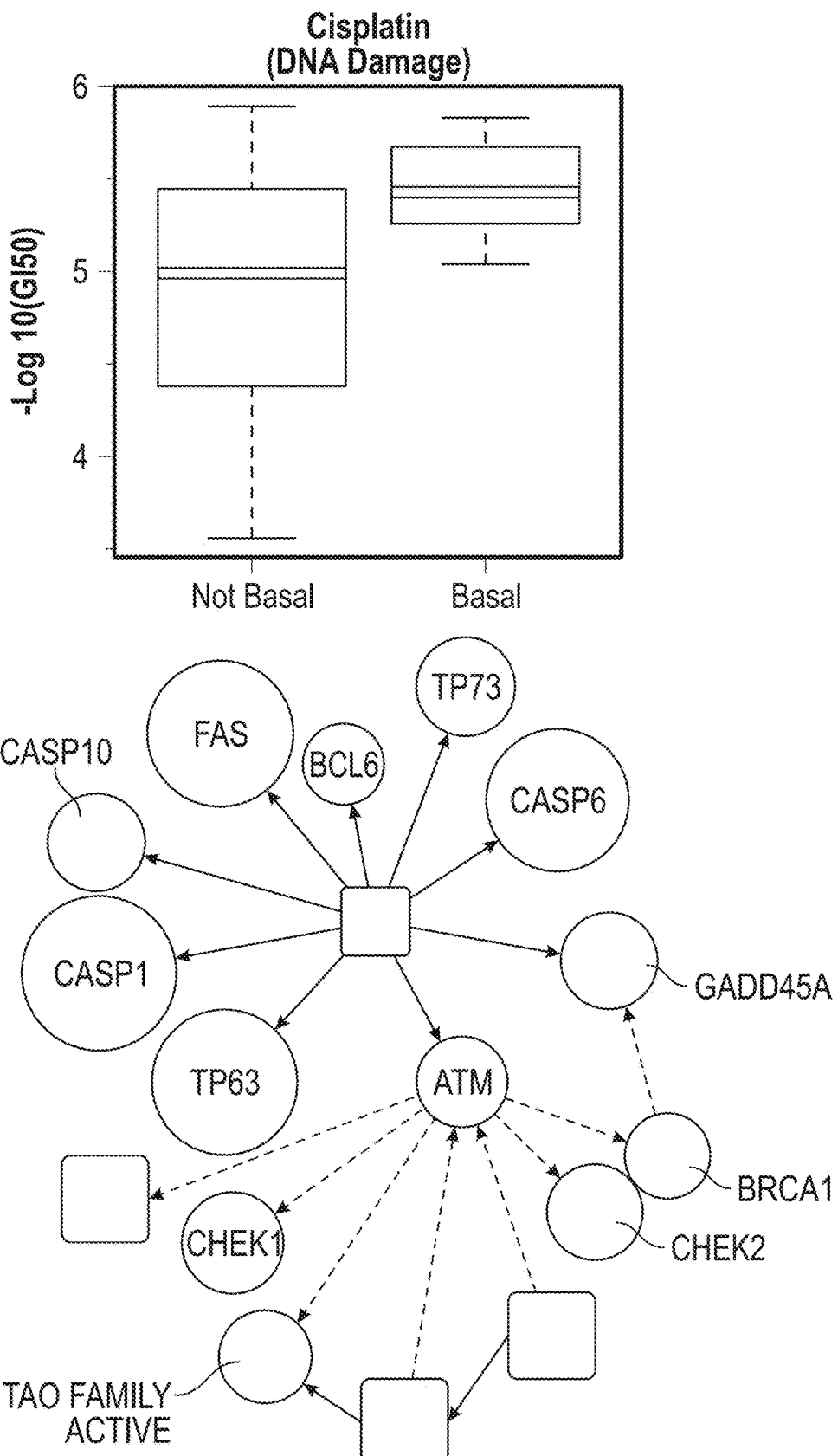
Figure 13B:
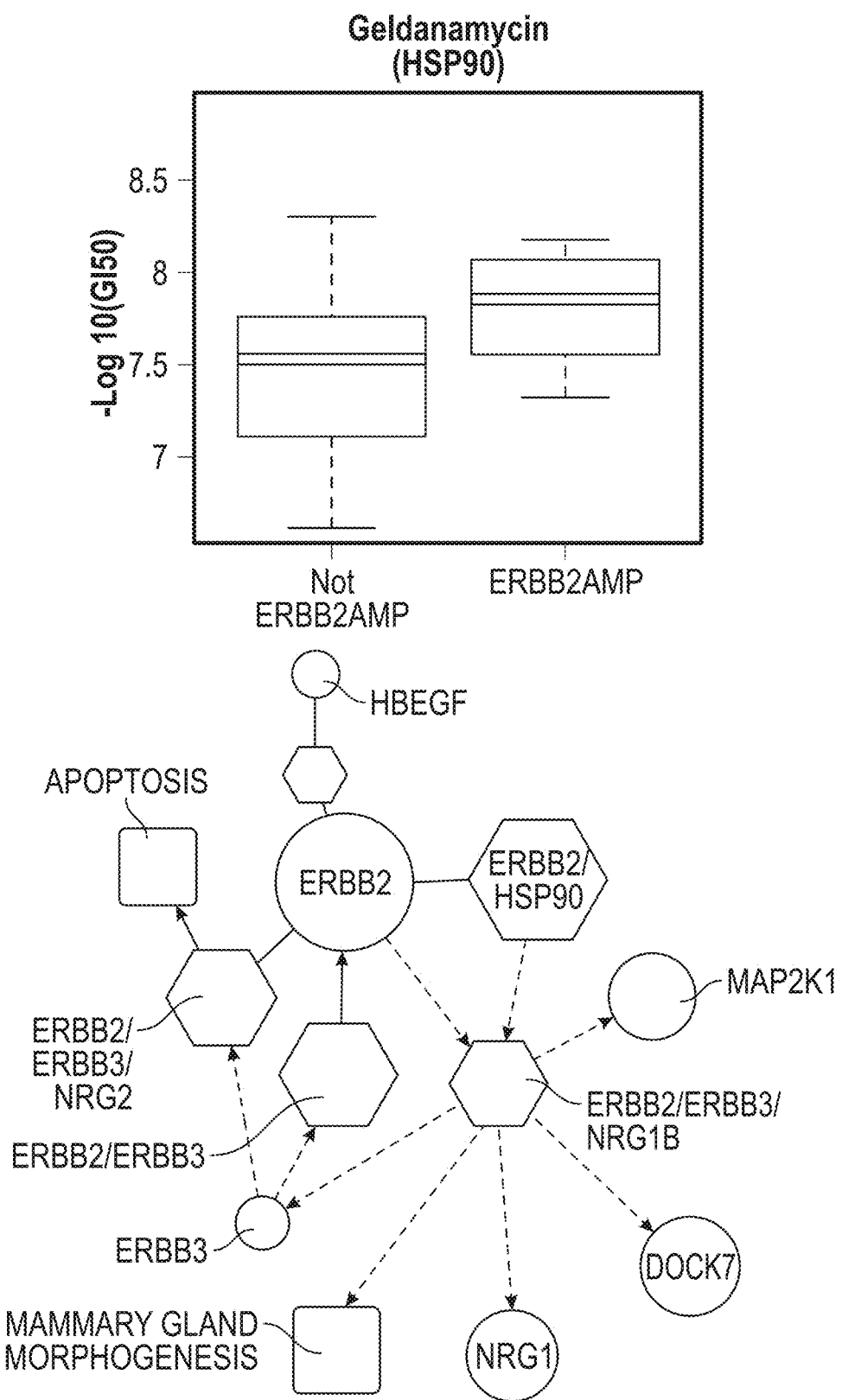

FIGS. 13A-13B illustrate how pathway diagrams can be used to predict response to therapies. FIG. 13A Upper panel. Basal breast cancer cell lines preferentially respond to the DNA damaging agent cisplatin. Lower panel. Basal cell lines show enhanced activity in pathways associated with the DNA damage response, providing a possible mechanism by which cisplatin acts in these cell lines. FIG. 13B Upper panel. ERBB2AMP cell lines are sensitive to the HSP90 inhibitor geldanamycin. Lower panel. The ERBB2-HSP90 network is upregulated in ERBBP2AMP cell lines. Convention as in FIG. 3 12.

Figure 14A:
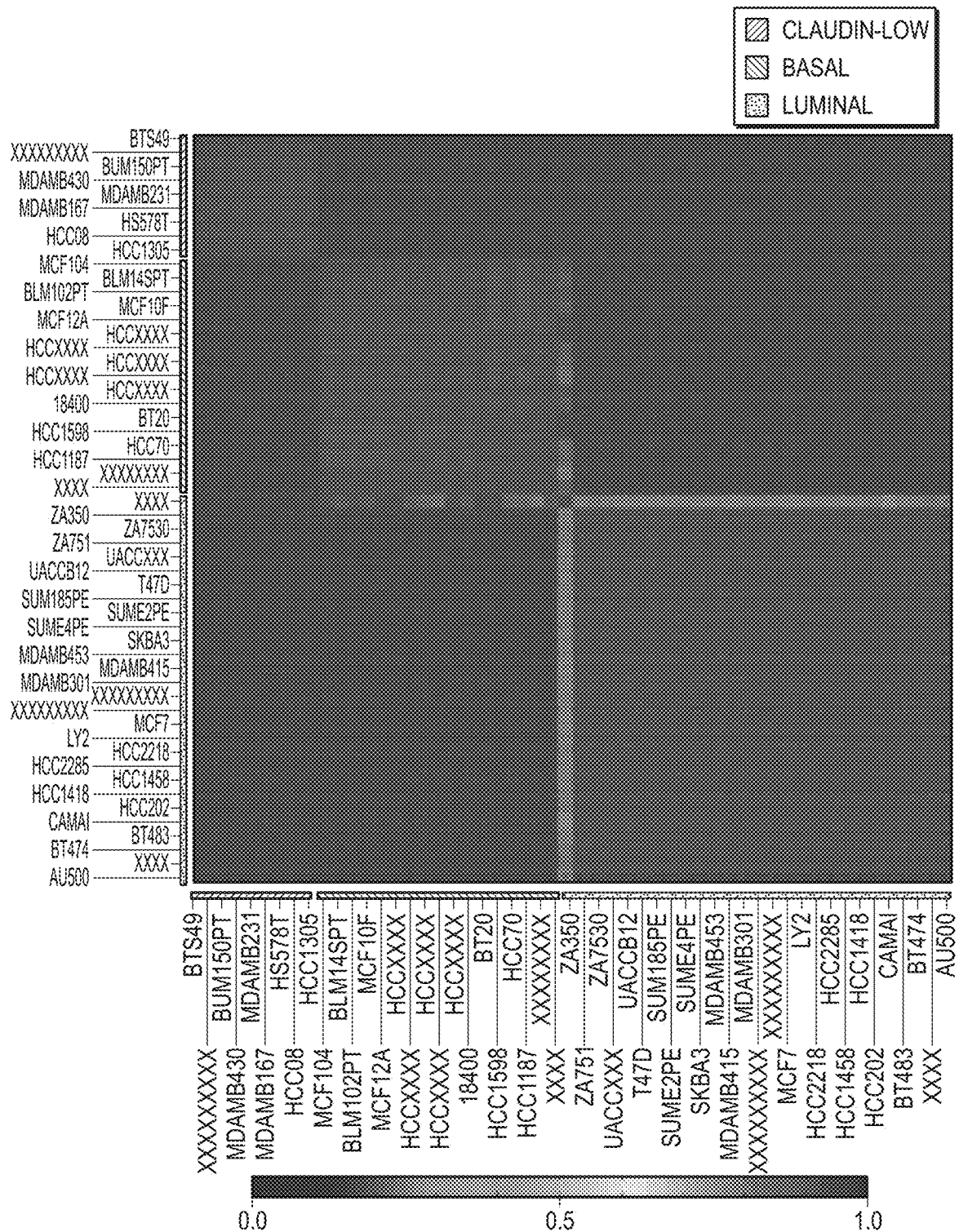
Figure 14B:
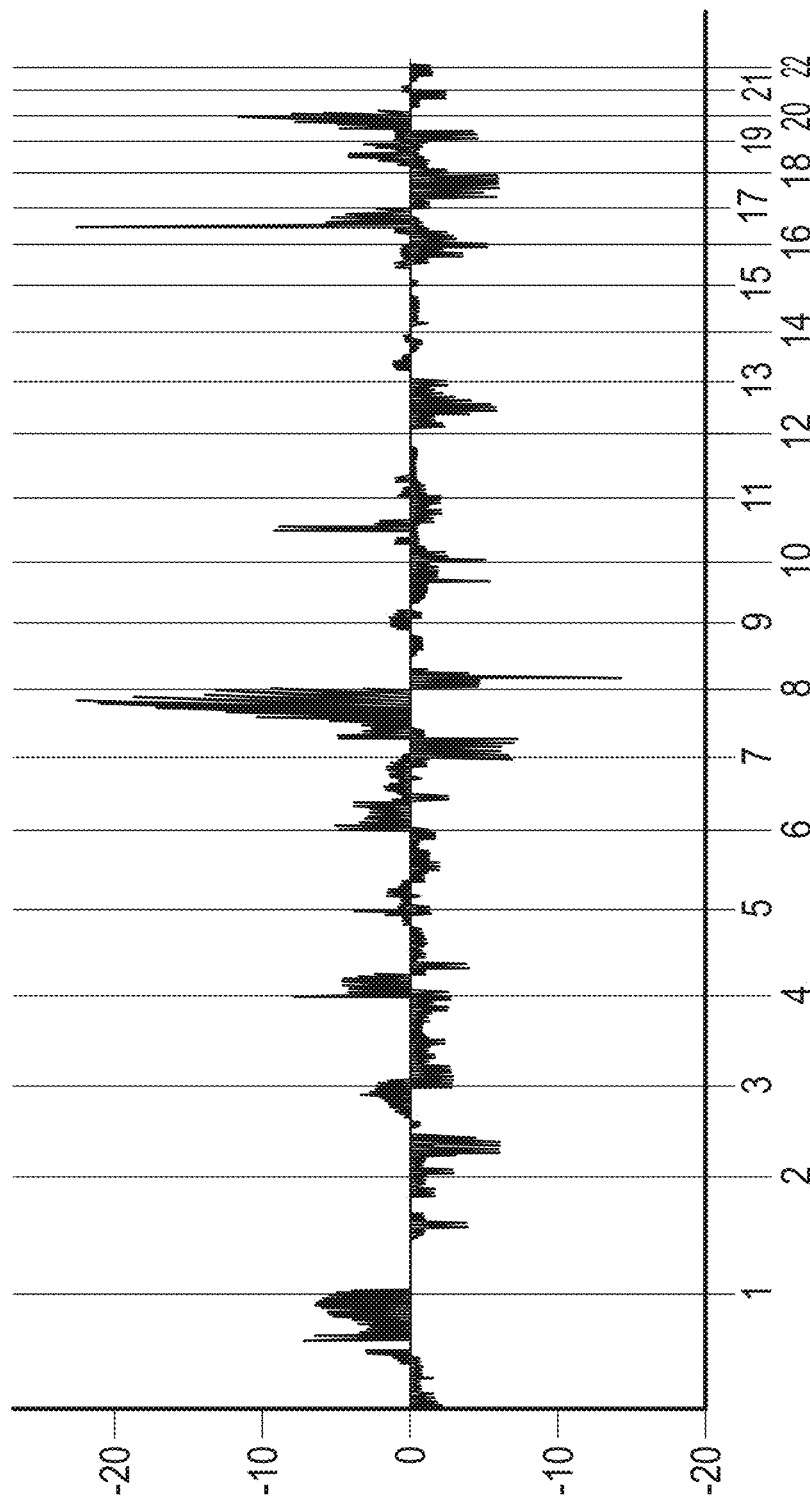

FIGS. 14A-14B illustrates exemplary genomic and transcriptional profiles of the breast cancer cell lines. FIG. 14A DNA copy number aberrations for 43 breast cancer cell lines are plotted with $\log_{10}(FDR)$ of GISTIC analysis on the y-axis and chromosome position on the x-axis. Copy number gains are shown in red with positive $\log_{10}(FDR)$ and losses are shown in green with negative $\log_{10}(FDR)$. FIG. 14B Hierarchical concensus clustering matrix for 55 breast cancer cell lines showing 3 clusters (claudin-low, luminal, basal) based on gene expression signatures. For each cell line combination, color intensity is proportional to consensus.

Figure 15A:
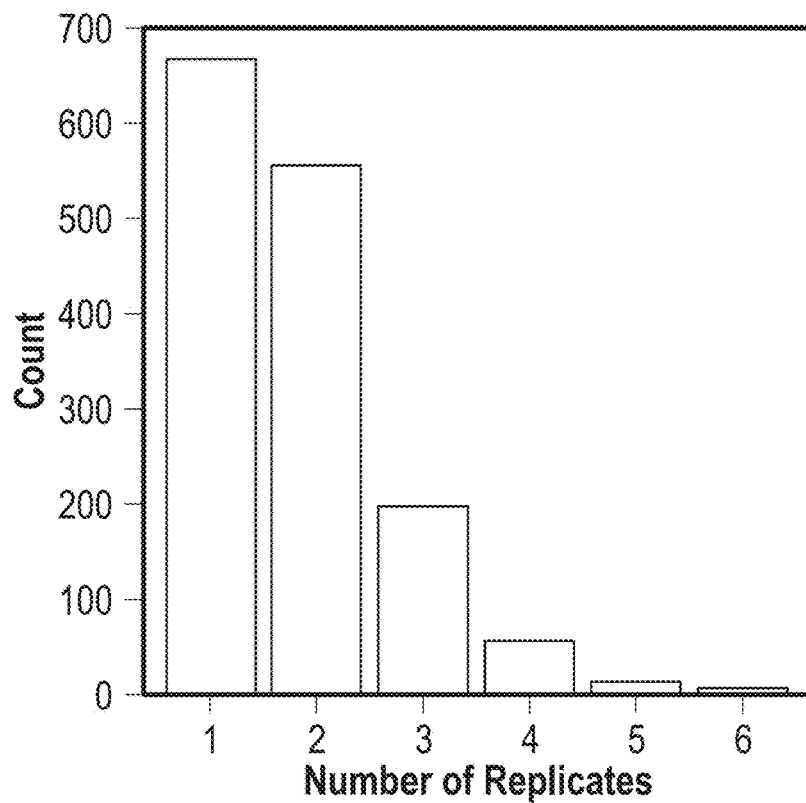
Figure 15B:
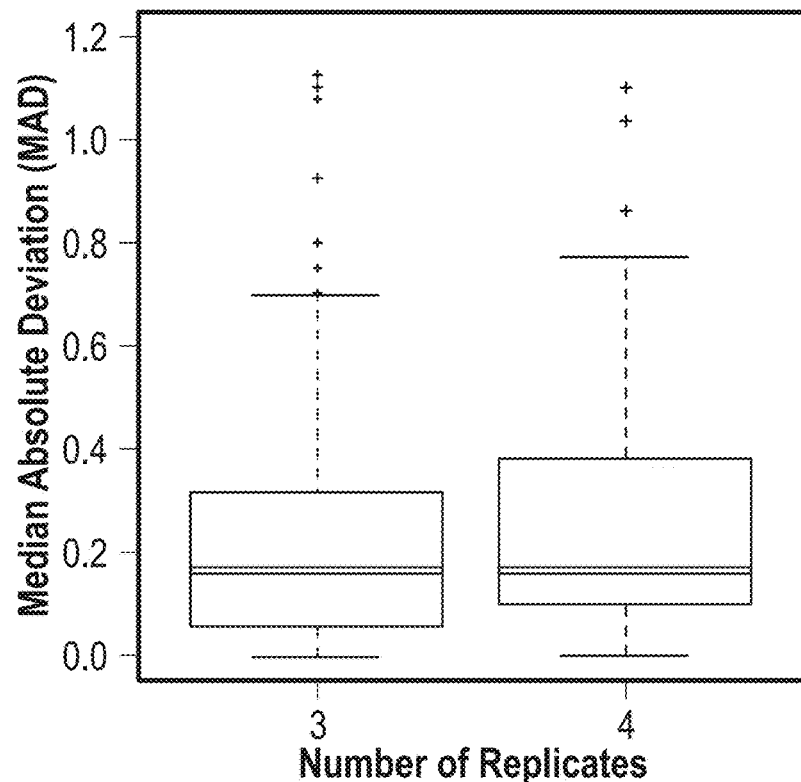

FIGS. 15A-15B illustrate that $GI_{50}$ calculations are highly reproducible. FIG. 15A Each bar a count of the frequency of replicated drug/cell line combinations. Most cell lines were tested only one time against a particular compound, but some drug/cell line combinations were tested multiple times. FIG. 15B Each boxplot represents the distribution of median average deviations for drug/cell line pairs with 3 or 4 replicates.

Figure 16A:
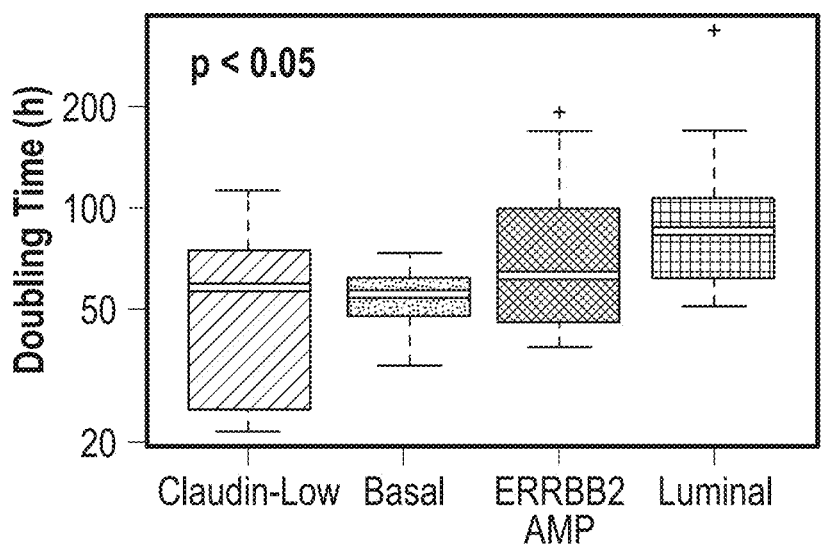
Figure 16B:
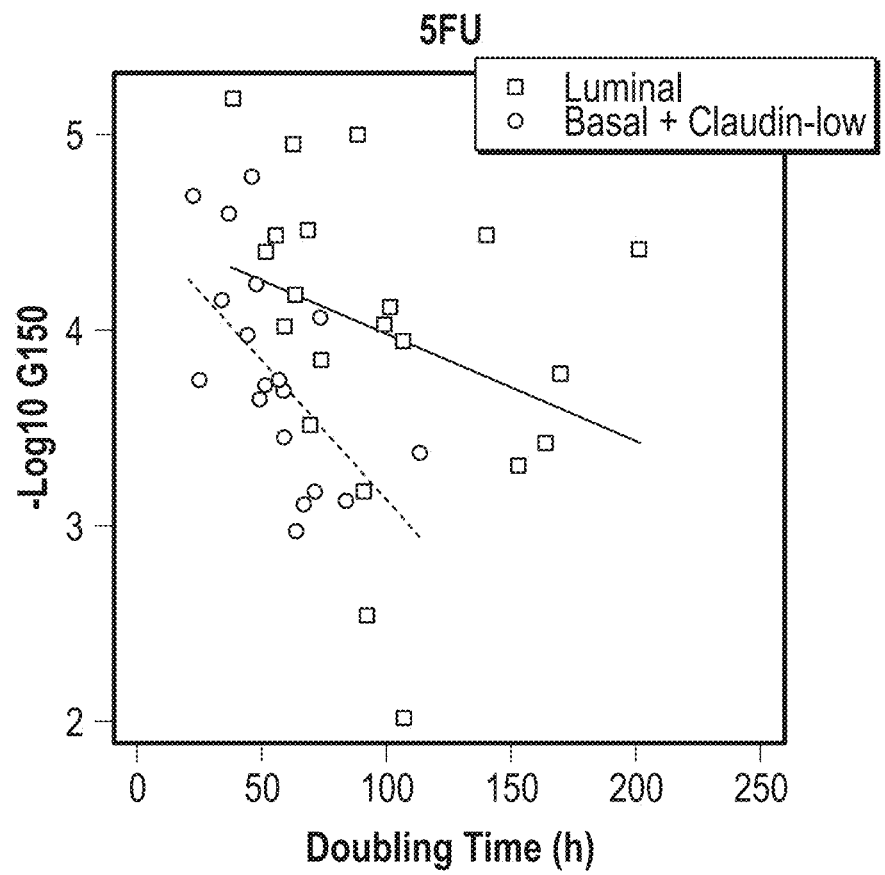

FIGS. 16A-16B show that doubling time varies across cell line subtype. FIG. 16A Growth rate, computed as the median doubling time in hours, of the breast cancer cell lines subtypes are shown as boxplots. The basal and claudin-low subtypes have shorter median doubling time as compared to lumina (and ERBB2$^{AmP}$ subtypes, Kruskal-Wallis p value (p=0.006). FIG. 16B The ANCOVA model shows strong effects of both subtype and growth rate on response to 5'FU. Luminal (black) and basal/claudin-low (red) breast cancer lines each show significant associations to growth rate but have distinct slopes.

Figure 17:
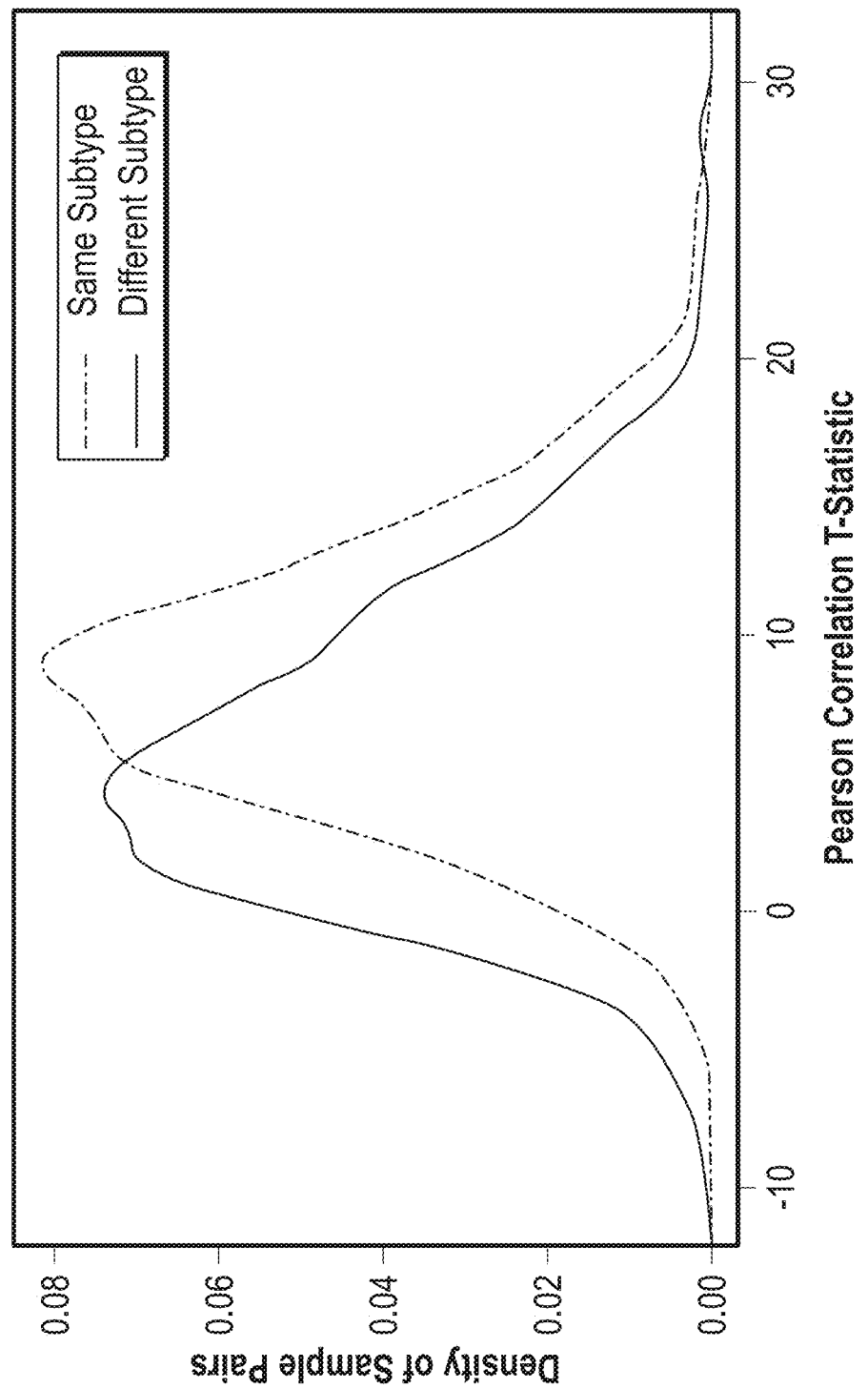

FIG. 17 shows that inferred pathway activities are more strongly correlated within subtypes than within cohorts. Shown is a histogram of t-statistics derived from Pearson correlations computed between cell lines and TCGA samples of the same subtype (red) compared to t-statistics of Pearson correlations between cell lines of different subtypes (black). X-axis corresponds to the Pearson correlation t-statistic; y-axis shows the density of (cell-line, cell-line) or (cell-line, TCGA sample) pairs. K-S test ($P<1\times10^{-22}$) indicates cell lines and TCGA samples of the same subtype are more alike than cell lines of other subtypes.

Supplementary FIGS. 18-21 illustrate an exemplary network architecture for each of the four subnetworks identified from the SuperPathway.

Figure 18:
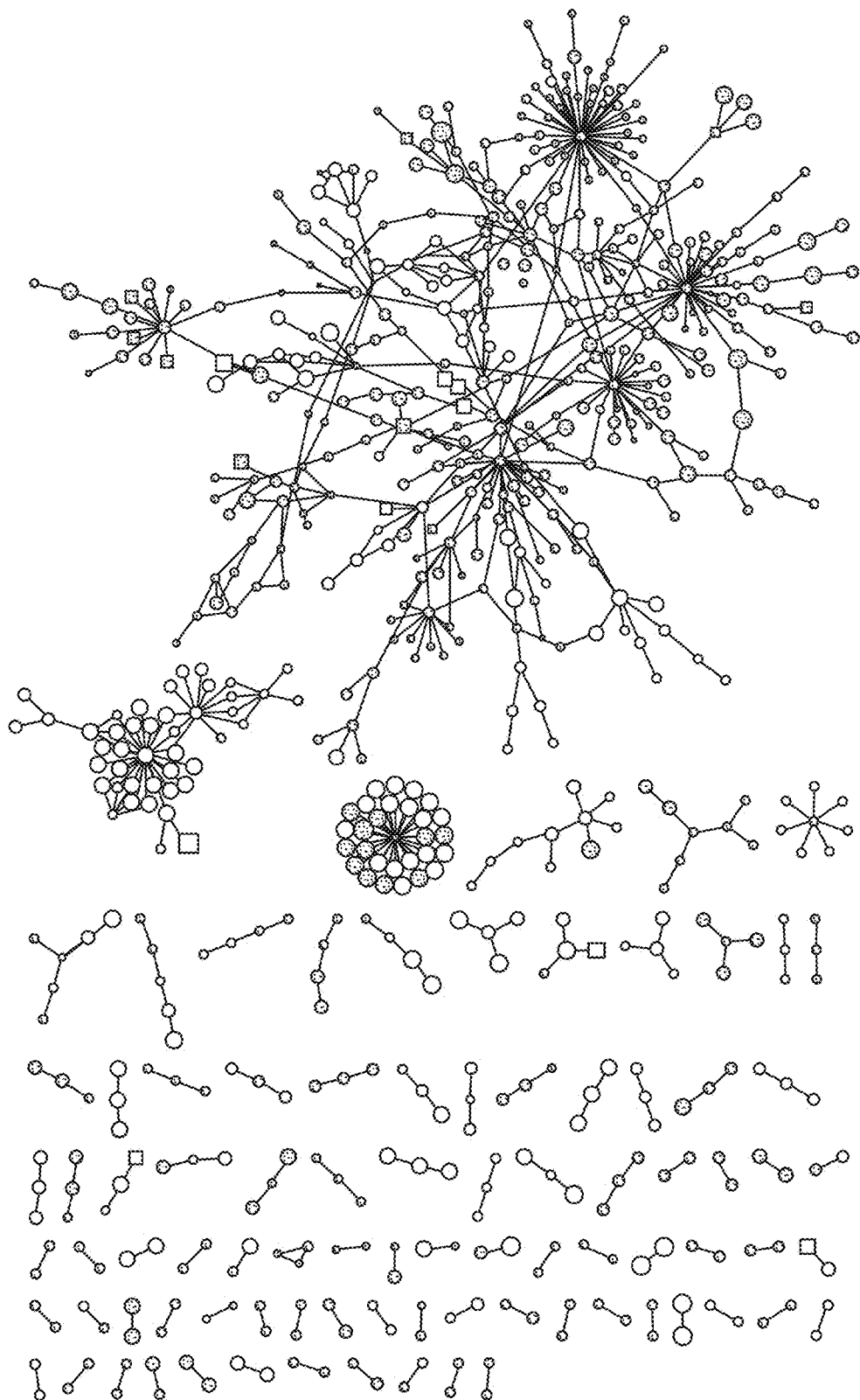

FIG. 18 illustrates a network diagram of basal pathway markers. Each node in the graph represents a different pathway "concept" corresponding to either a protein (circles), a multimeric complex (hexagons), or a an abstract cellular process (squares). The size of the nodes are drawn in proportion to the differential activity score such that larger nodes correspond to pathway concepts with activities more correlated with basal versus non-basal cell lines. Color indicates whether the concept is positively correlated (red) or negatively correlated (blue) with the basal subtype. Links represent different interactions including protein-protein level interactions (dashed lines) and transcriptional (solid lines). Interactions were included in the map only if they interconnect concepts whose absolute level of differential activity is higher than the mean absolute level.

Figure 19:
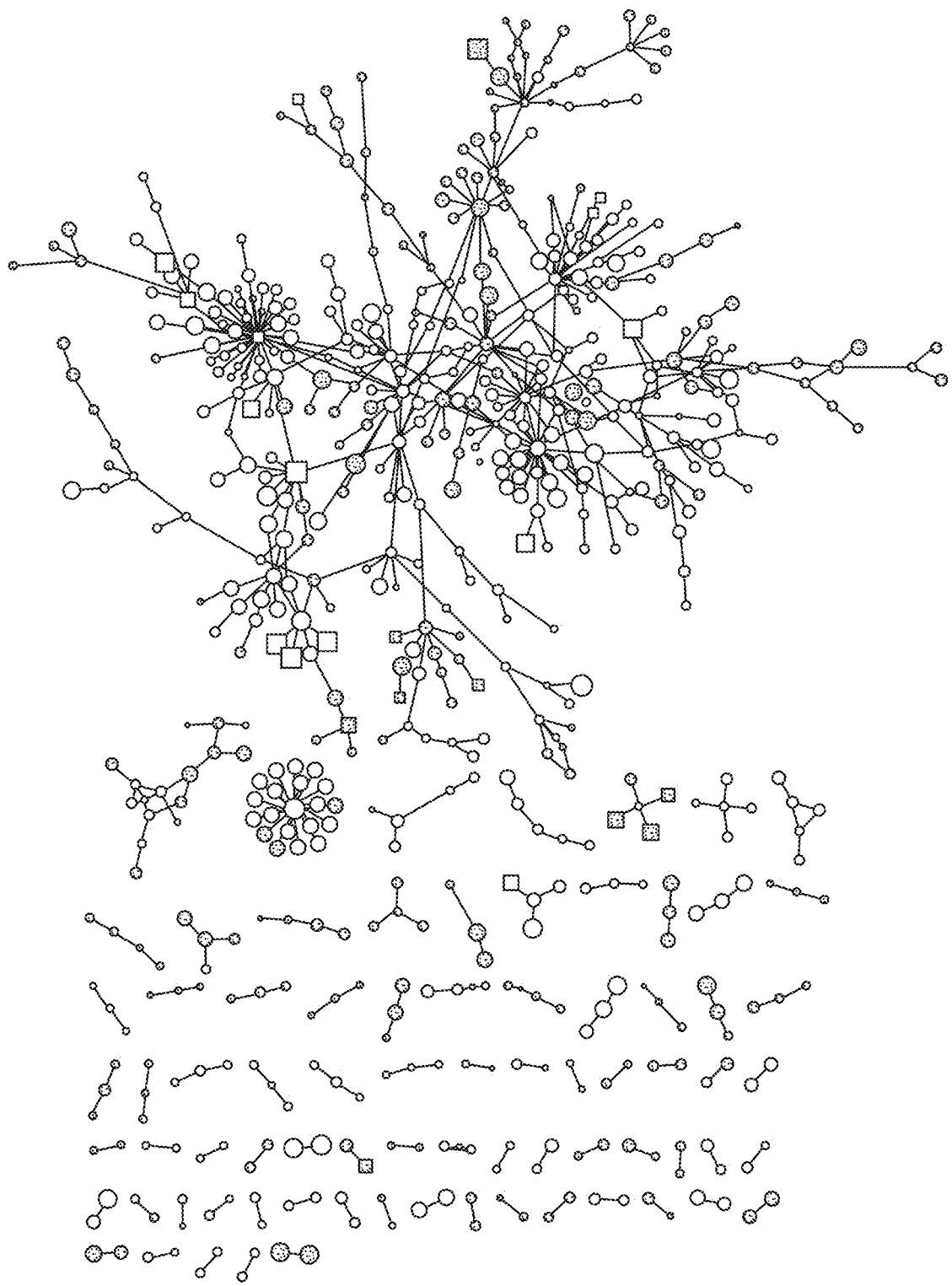

FIG. 19 illustrates an exemplary network diagram of claudin-low pathway markers. Convention as in FIG. 18.

Figure 20:
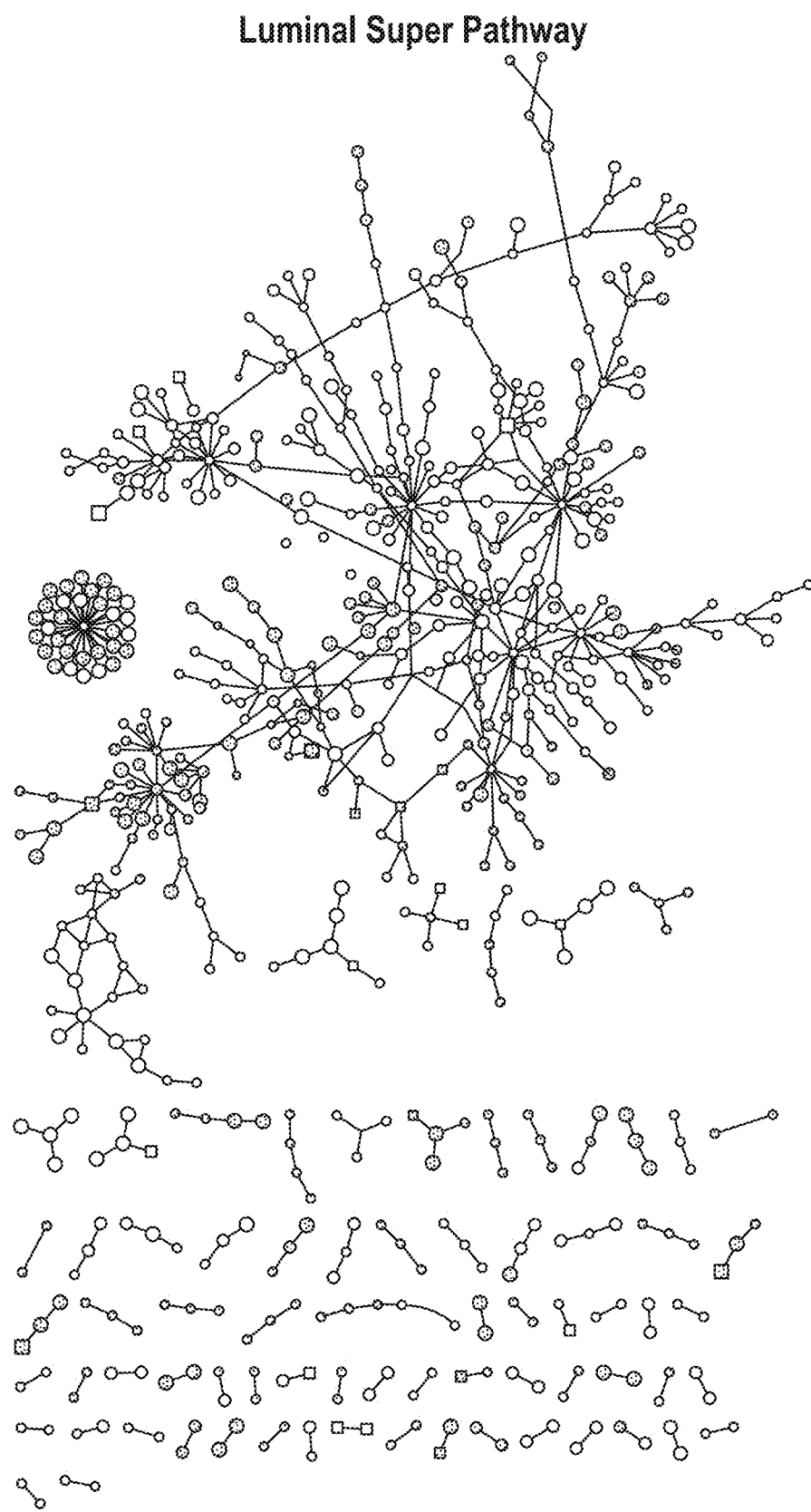

FIG. 20 illustrates an exemplary network diagram of luminal pathway markers. Convention as in FIG. 18.

Figure 21:
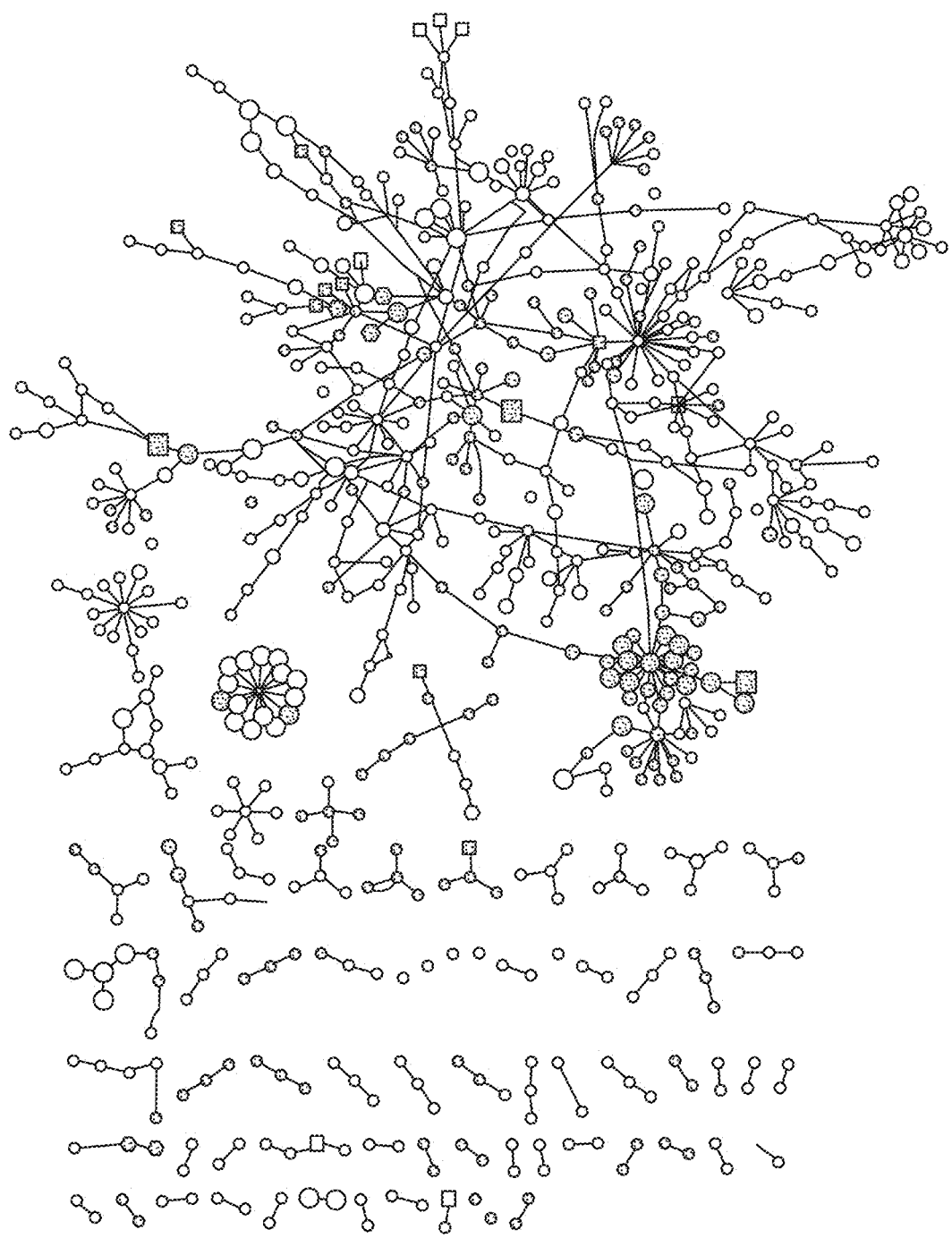

FIG. 21 illustrates an exemplary network diagram of ERBB2AMP pathway markers. Convention as in FIG. 18.

Figure 22A:
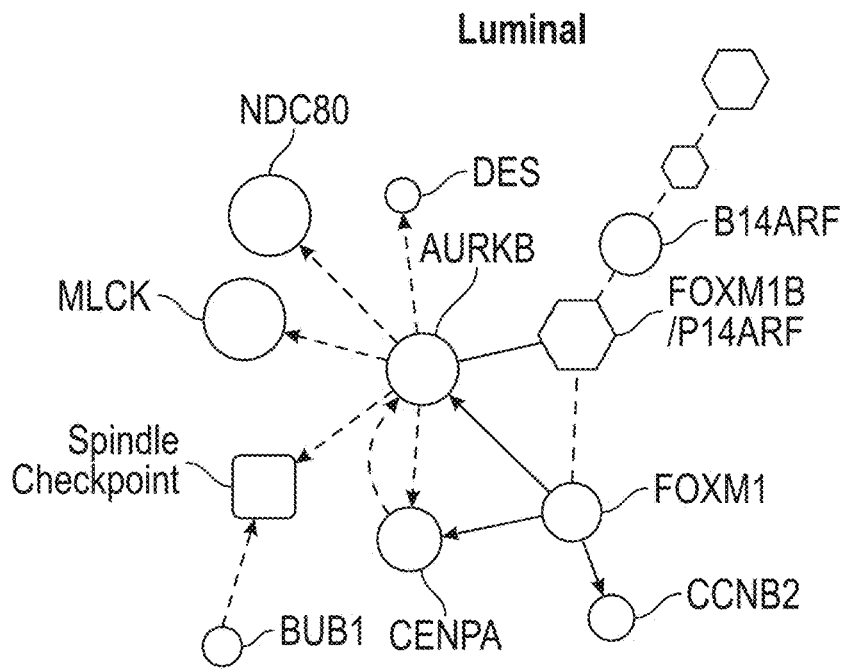
Figure 22B:
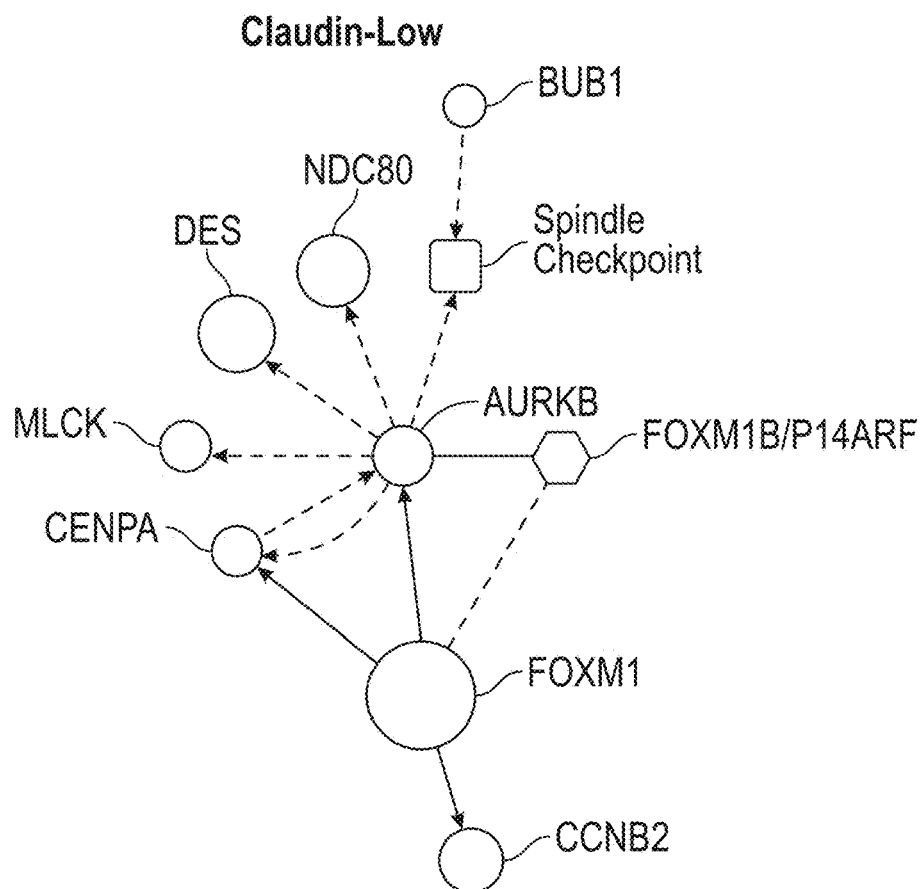
Figure 22C:
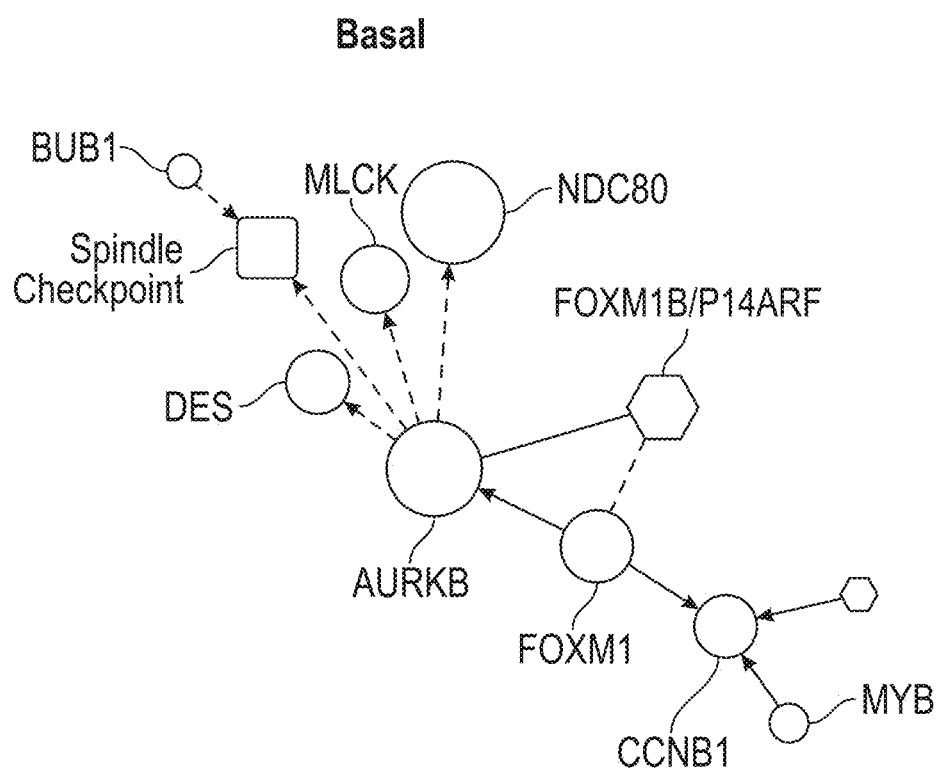

FIGS. 22A-22C illustrates an exemplary URICB-FOXM1-CCNB1 networks in luminal, claudin-low and basal cell lines. FIG. 22A Network surrounding AURKB and FOXM1 in luminal cell lines. CCNB1 was not significantly downregulated and therefore does not appear on the pathway map. FIG. 22B In claudin-low cell lines, AURKB and FOXM1 both up-regulated; activity for CCNB1 was not significant. FIG. 22C AURKB, FOXM1 and CCNB1 are all up-regulated in basal cell lines. Convention as in FIG. 18.

Figure 23:
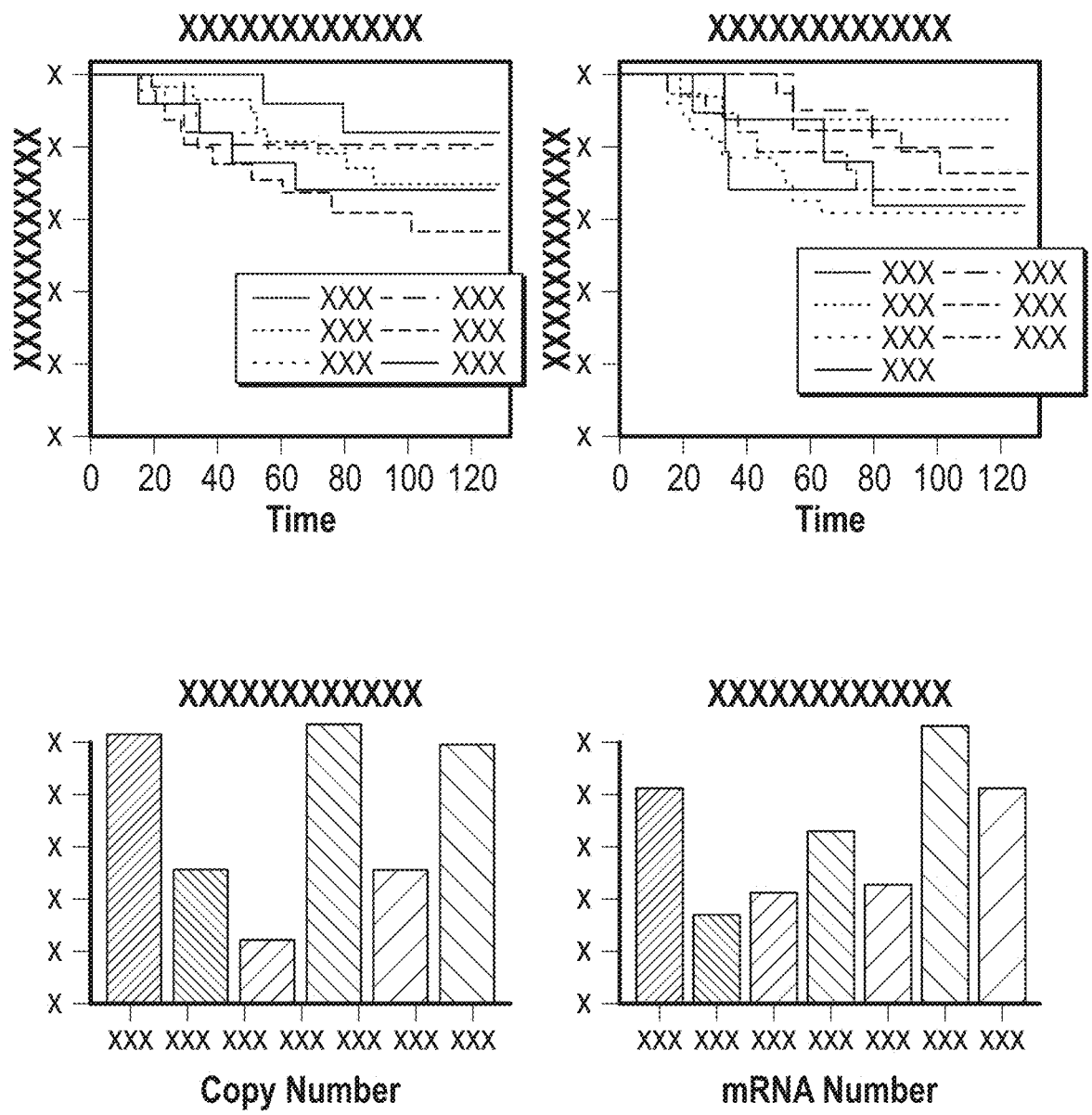
Figure 23:
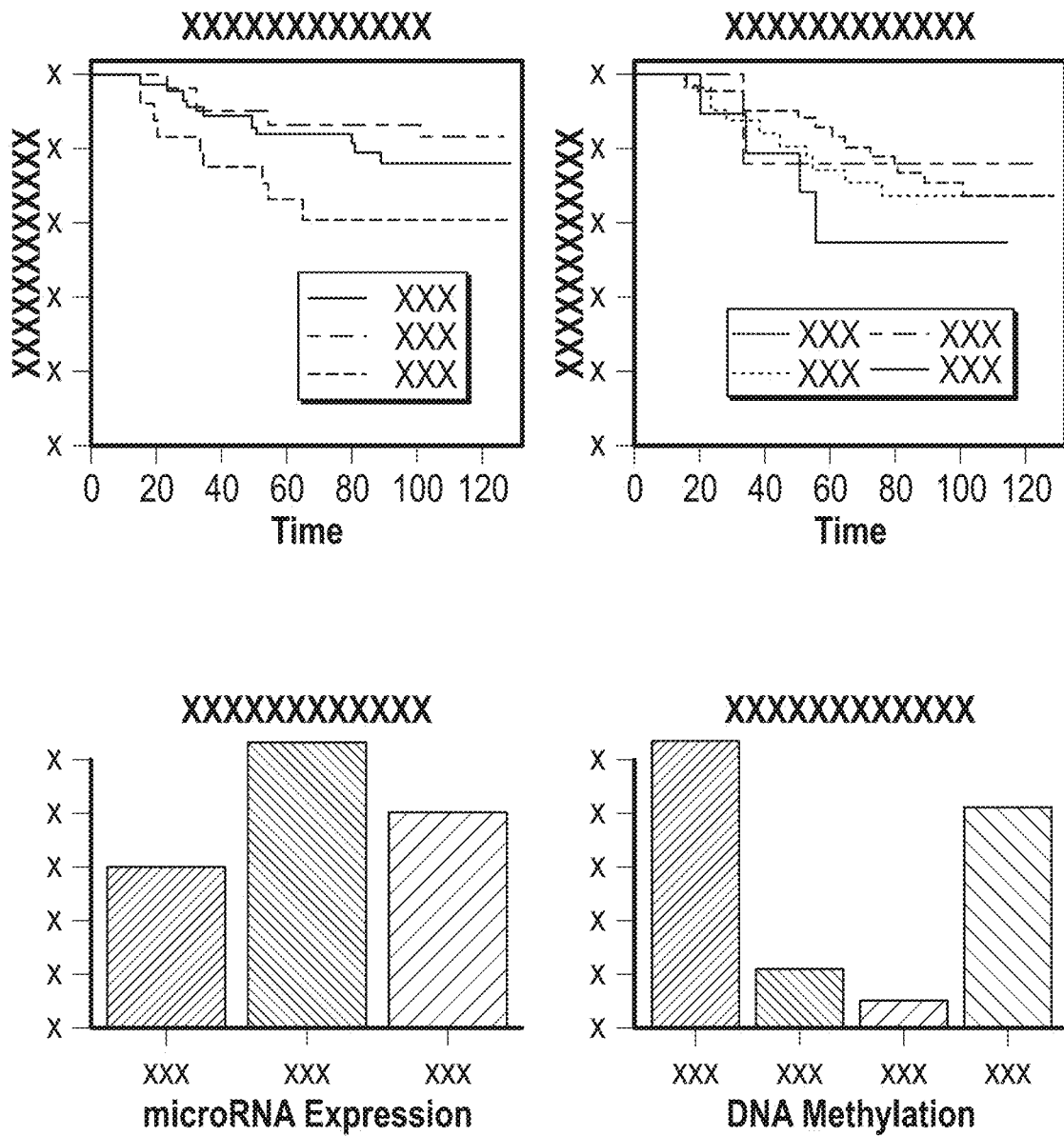

FIG. 23 illustrates an exemplary distribution of unsupervised clusters and survival curves of the patients of the MicMa cohort according to CNA, mRNA expression, DNA methylation and miRNA expression. For each type of genomic level the size of each cluster are plotted on the left, and to the right, survival curves are shown. Significance of differential survival are assessed by two methods (see Examples).

Figure 24:
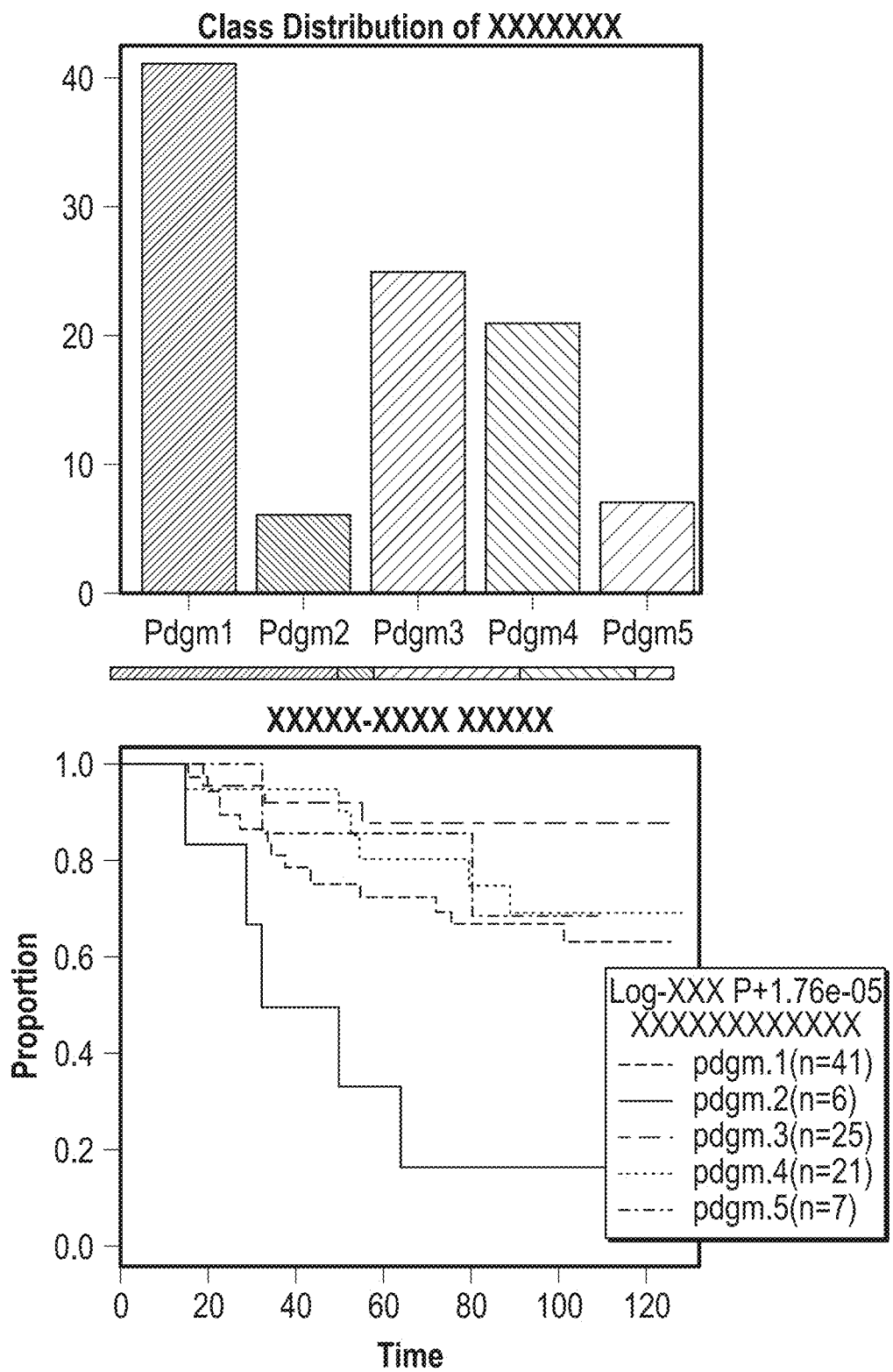

FIG. 24 illustrates an exemplary distribution of indentified PARADIGM clusters and survival. Each bar represents the size of each cluster. Heatmap of Paradigm IPLs for the MicMa dataset. Survival curves of the MicMa Paradigm clusters after mapping to the Chin-Naderi-Caldas datasets.

Figure 25:
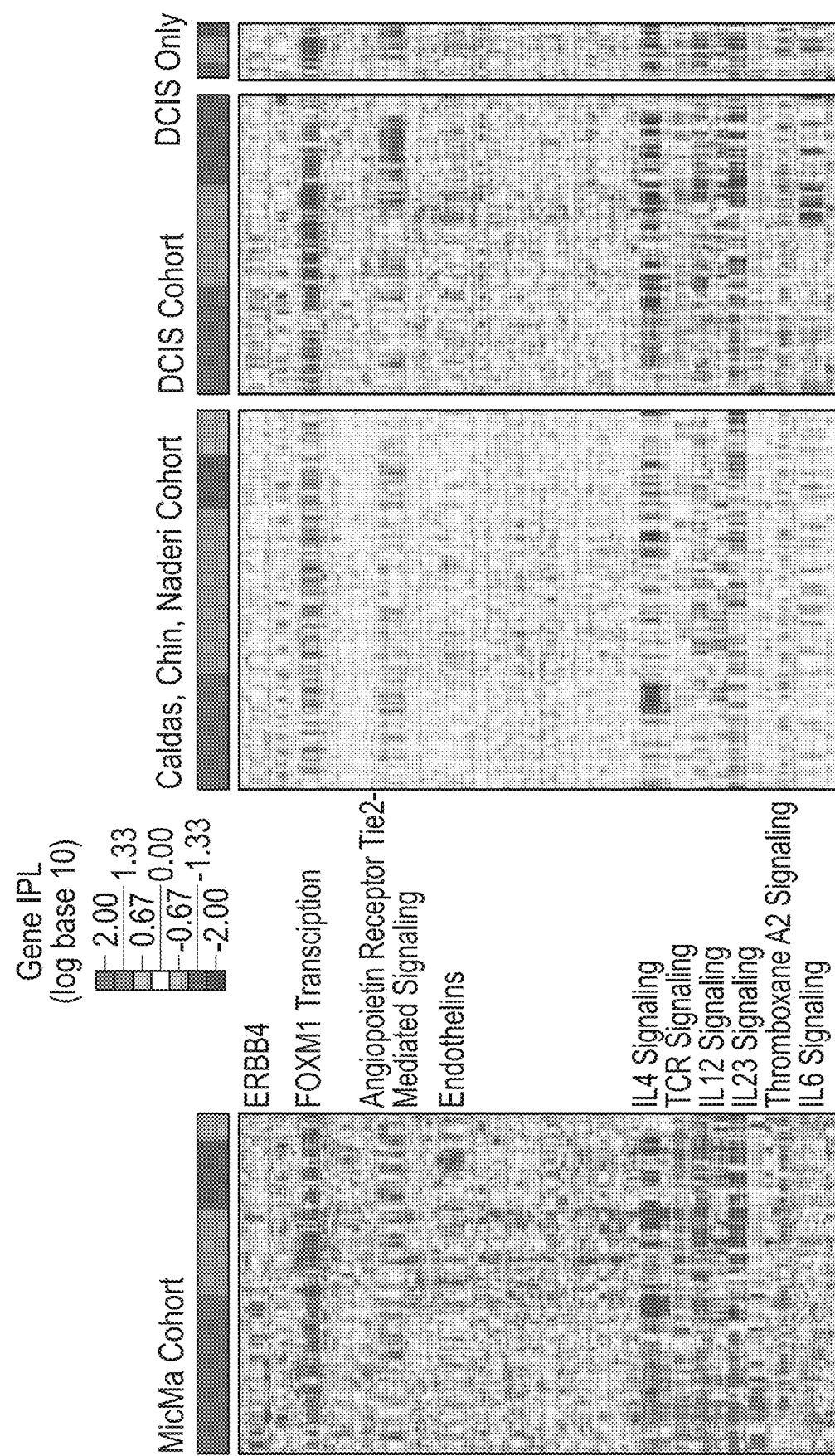

FIG. 25 illustrates an exemplary heatmaps of Paradigm IPLs for each dataset. Each row shows the IPL of a gene or complex across all three cohorts. The colored bar across the top shows the MicMa-derived Paradigm clusters, as in FIG. 2. Members of pathways of interest are labeled by their pathway. Red represents an activated IPL, blue a deactivated IPL.

Figure 26:
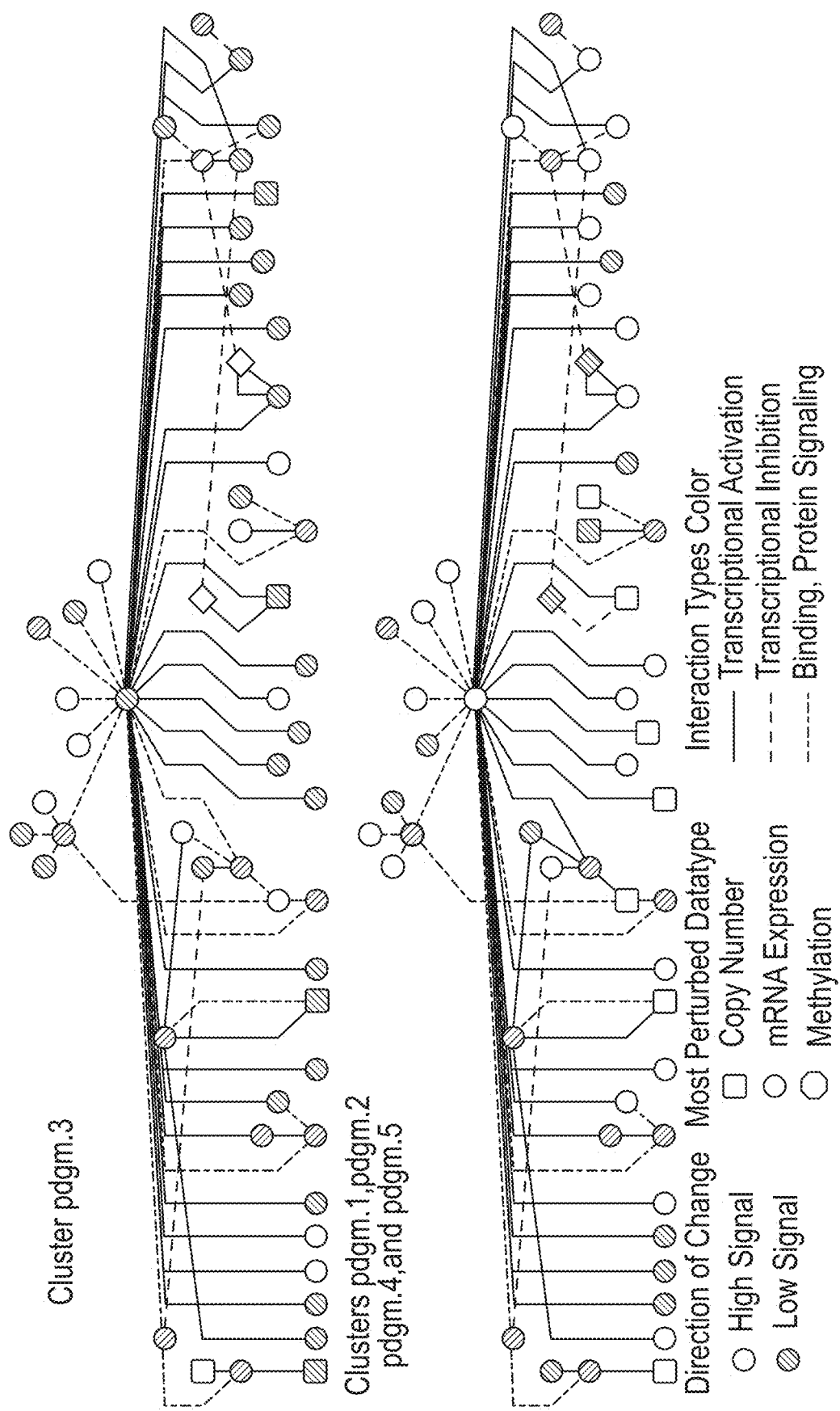

FIG. 26 illustrates the FOXM1 Transcription Factor Network. The upper network diagram summarizes data from cluster pdgm 0.3, whereas the lower cluster summarizes the data from other clusters. Nodes shapes denote the data type which was most frequently perturbed within each cluster, and node color denote the direction of perturbation. Edge arrows denote the sign of interactions, and color denotes the type of interaction.

Figure 27:
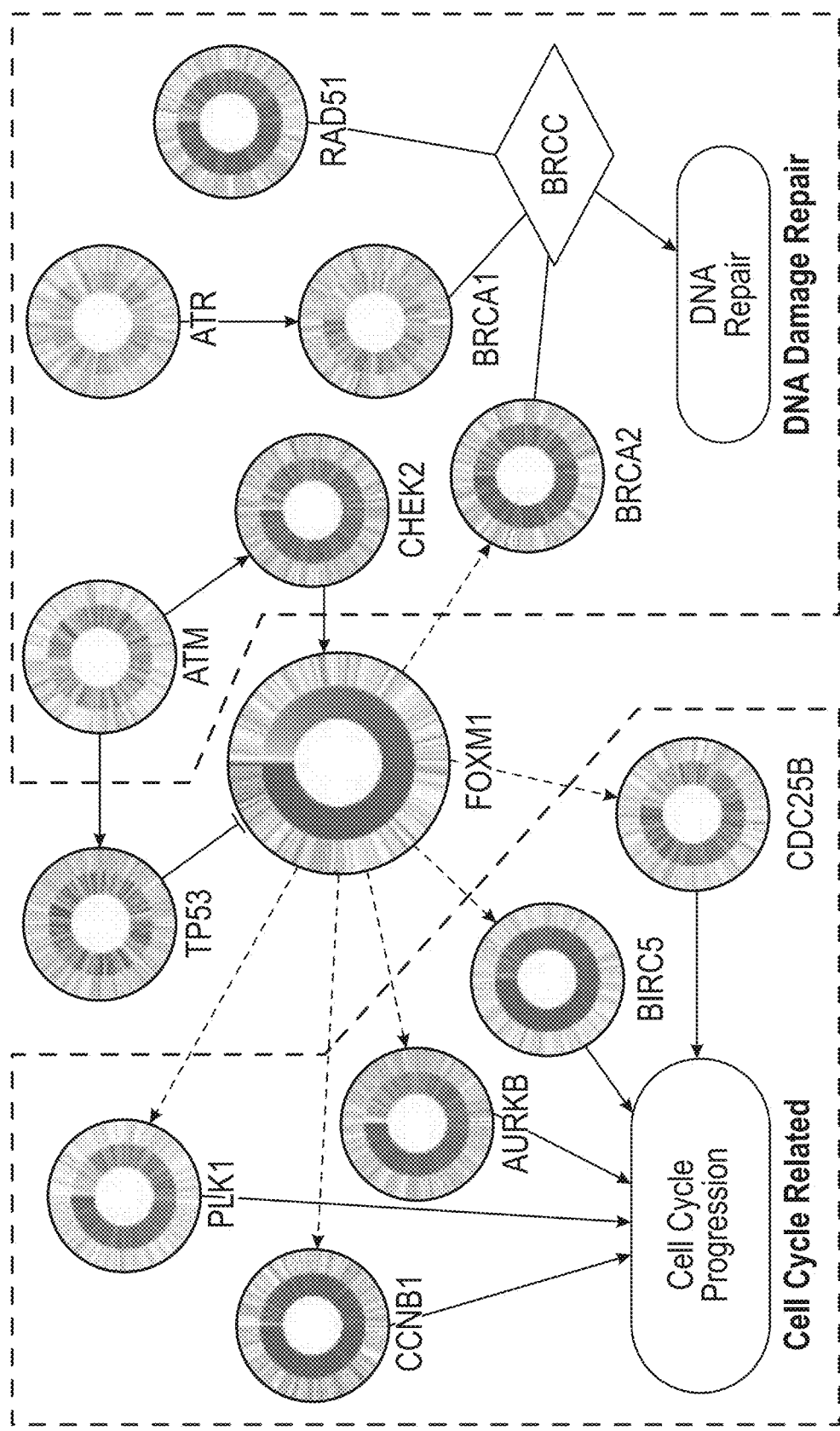

FIG. 27 illustrates a toy example of a small fragment of the p53 apoptosis pathway. A pathway diagram from NCI was converted into a factor graph that includes both hidden and observed states.

Figure 28:
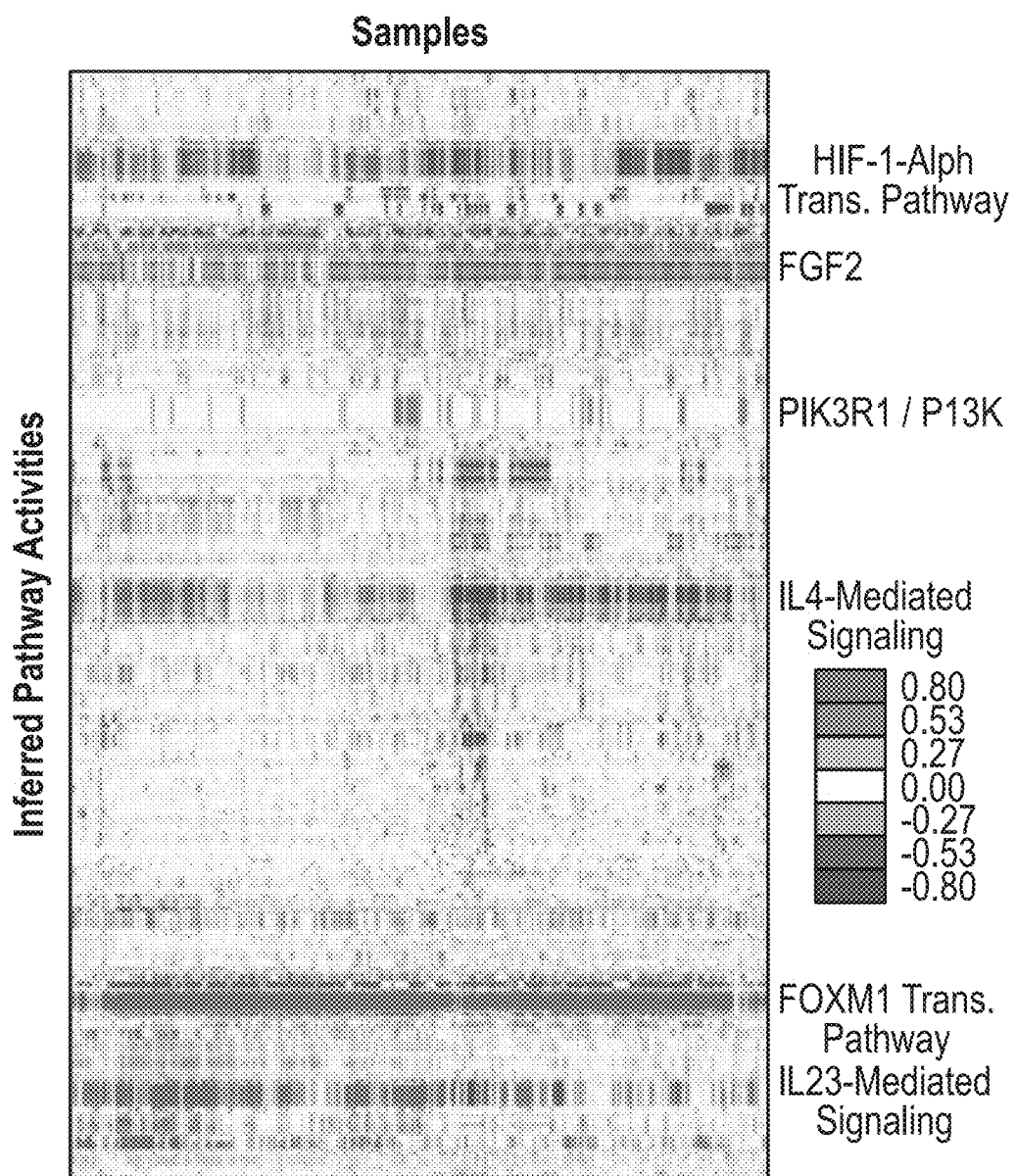

FIG. 28 illustrates an exemplary heatmap of Inferred Pathway Activities (IPAs). IPAs representing 1598 inferences of molecular entities (rows) inferred to be activated (red) or inactivated (blue) are plotted for each of 316 patient tumor samples (columns). IPAs were hierarchically clustered by pathway entity and tumor sample, and labels on the right show sections of the heatmap enriched with entities of individual pathways. The colorbar legend is in log base 10.

Figure 29:
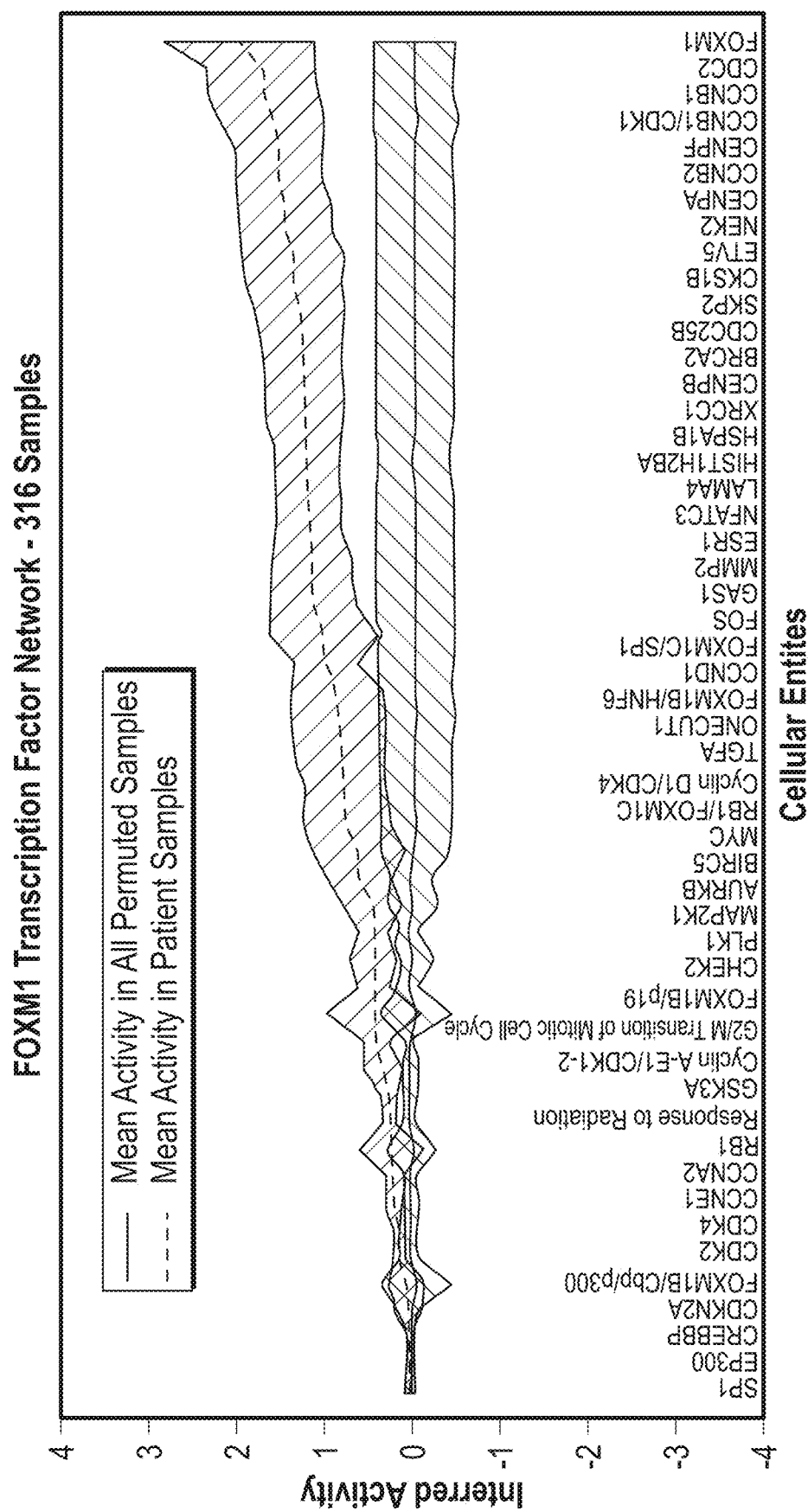

FIG. 29 summarises FOXM1 integrated pathway activities (IPAs) across all samples. The arithmetic mean of IPAs across tumor samples for each entity in the FOXM1 transcription factor network is shown in red, with heavier red shading indicating two standard deviations. Gray line and shading indicates the mean and two standard deviations for IPAs derived from the 1000 "null" samples.

Figure 30A:
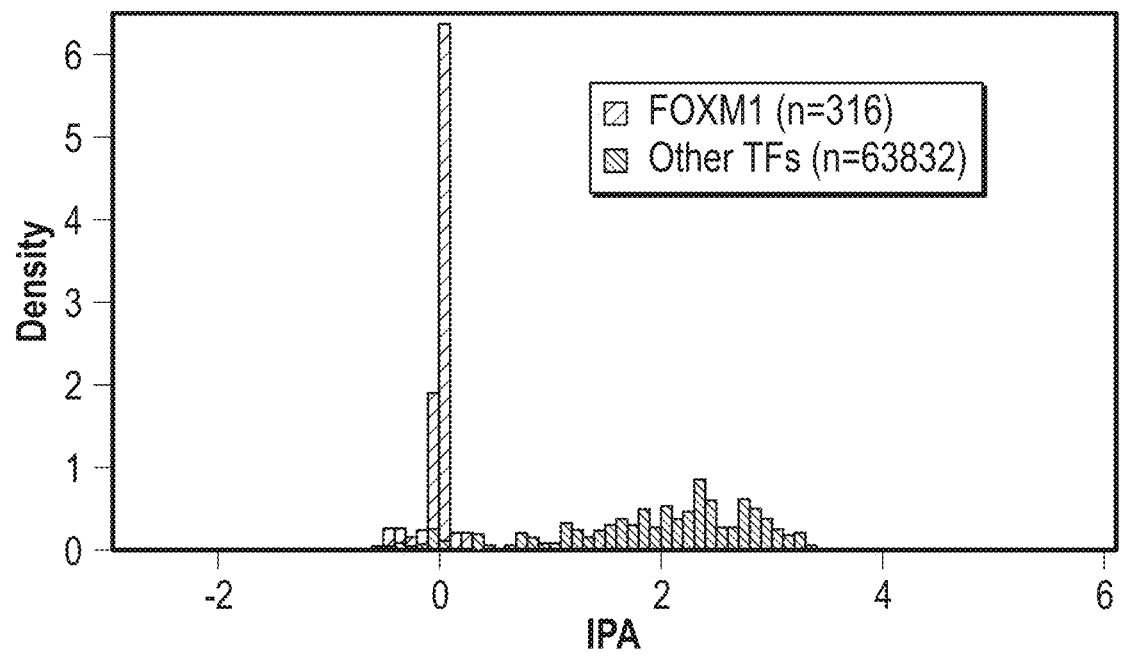
Figure 30B:
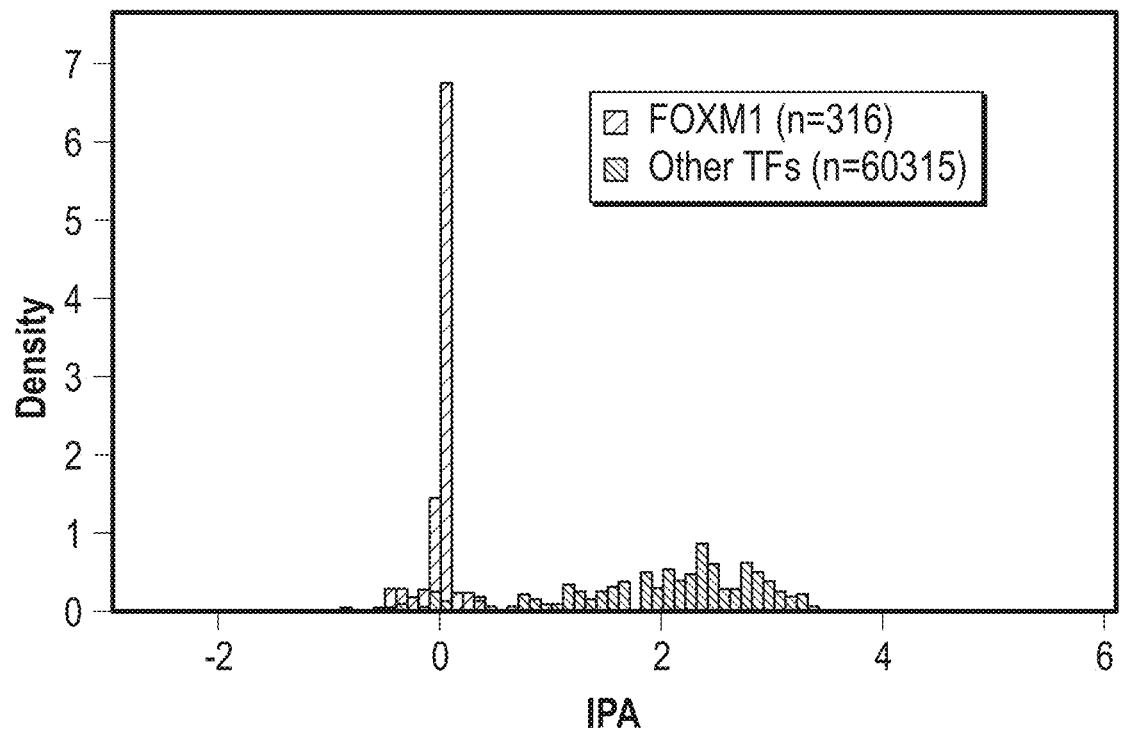

FIGS. 30A-30B show a comparison of IPAs of FOXM1 to those of other tested transcription factors (TFs) in NCI Pathway Interaction Database. FIG. 30A Histogram of IPAs with non-active (zero-valued) IPAs removed. FOXM1 targets are significantly more activated than other NCI TFs ($P<_{10}{}^{267}$, Kolmogorov-Smirnov (KS) test). FIG. 30B Histogram of all IPAs including non-active IPAs. Using all IPAs, FOXM1's activity relative to other TFs is interpreted with somewhat higher significance ($P<10^{-31}$; KS test).

Figure 31:
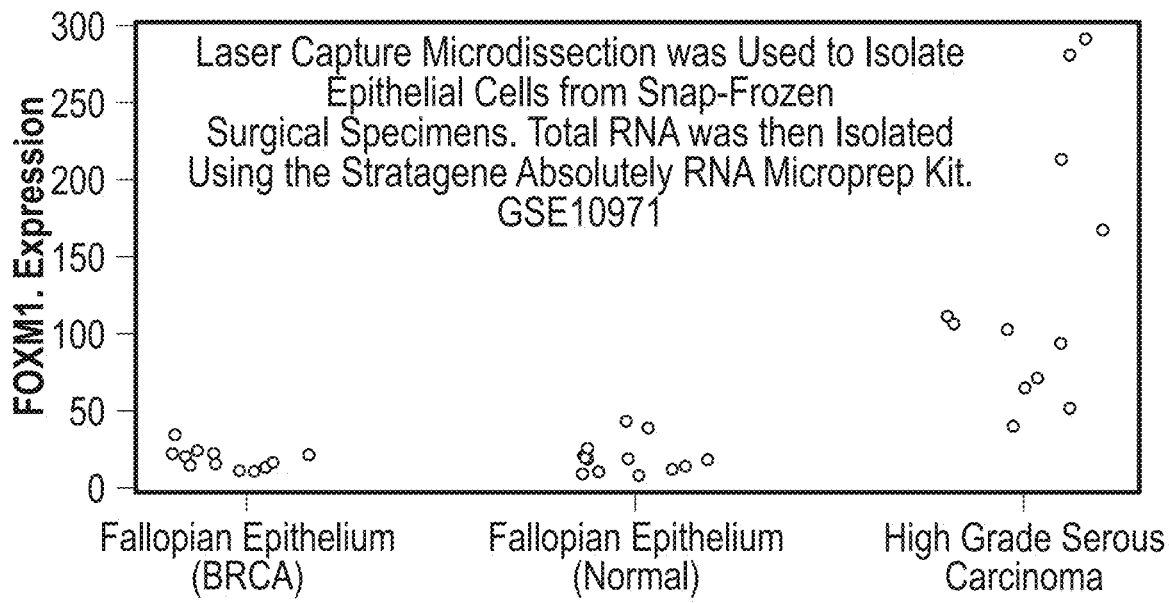

FIG. 31 illustrates that FOXM1 is not expressed in fallopian epithelium compared to serous ovarian carcinoma. FOXM1's expression levels in fallopian tube was compared to its levels in serous ovarian carcinoma using the data from Tone et al (PMID: 18593983). FOXM1's expression is much lower in fallopian tube, including in samples carrying BRCA1/2 mutations, indicating that FOXM1's elevated expression observed in the TCGA serous ovarian cancers is not simply due to an epithelial signature.

Figure 32:
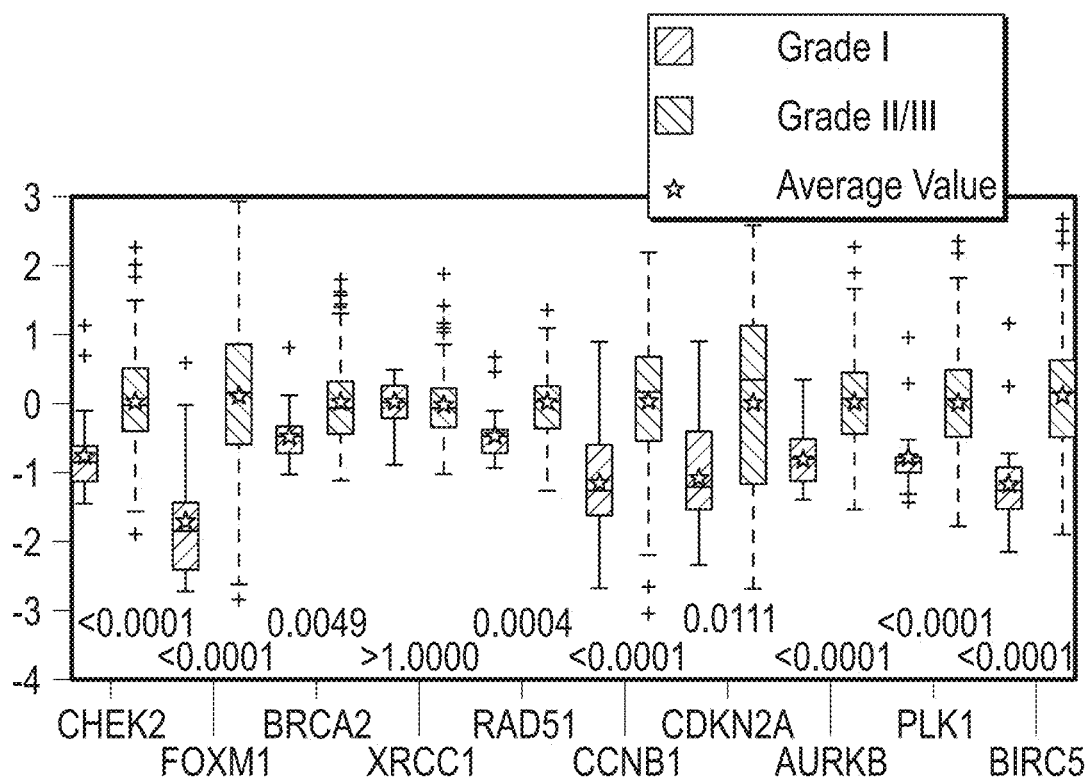

FIG. 32 shows expression of FOXM1 transcription factor network genes in high grade versus low grade carcinoma. Expression levels for FOXM1 and nine selected FOXM1 targets (based on NCI-PID) were plotted for both low-grade (I; tan boxes; 26 samples) and high-grade (II/III; blue boxes; 296 samples) ovarian carcinomas. Seven out of the nine targets were showed to have significantly high expression of FOXM1 in the high-grade carcinomas (Student's t-test; p-values noted under boxplots). CDKN2A may also be differentially expressed but had a borderline t-statistic (P=0.01). XRCC I was detected as differentially expressed.

Figure 33A:
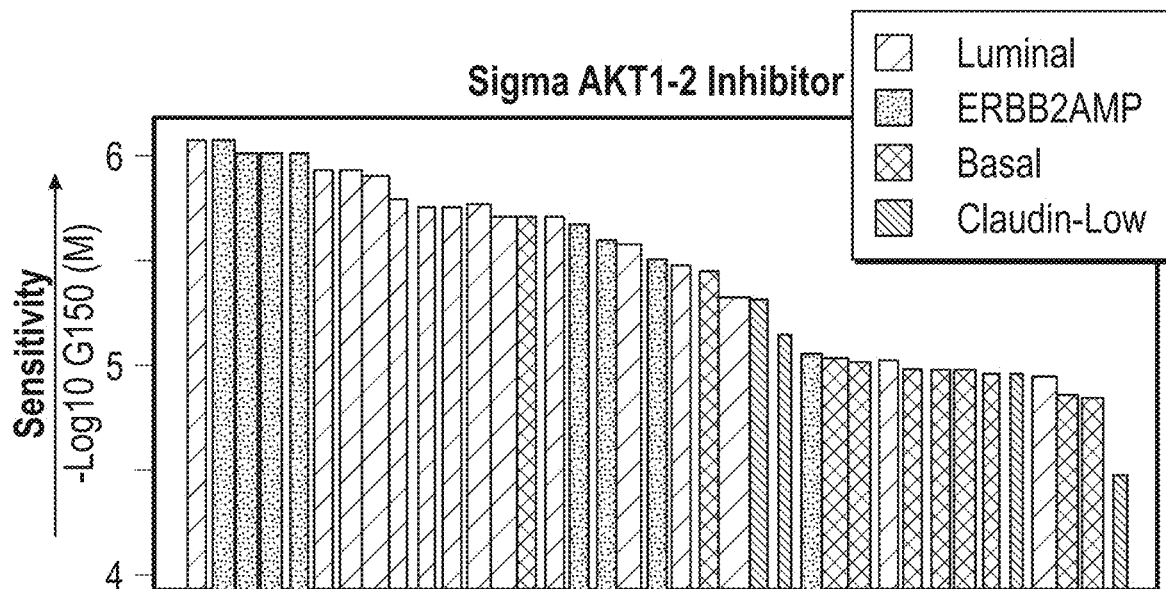
Figure 33B:
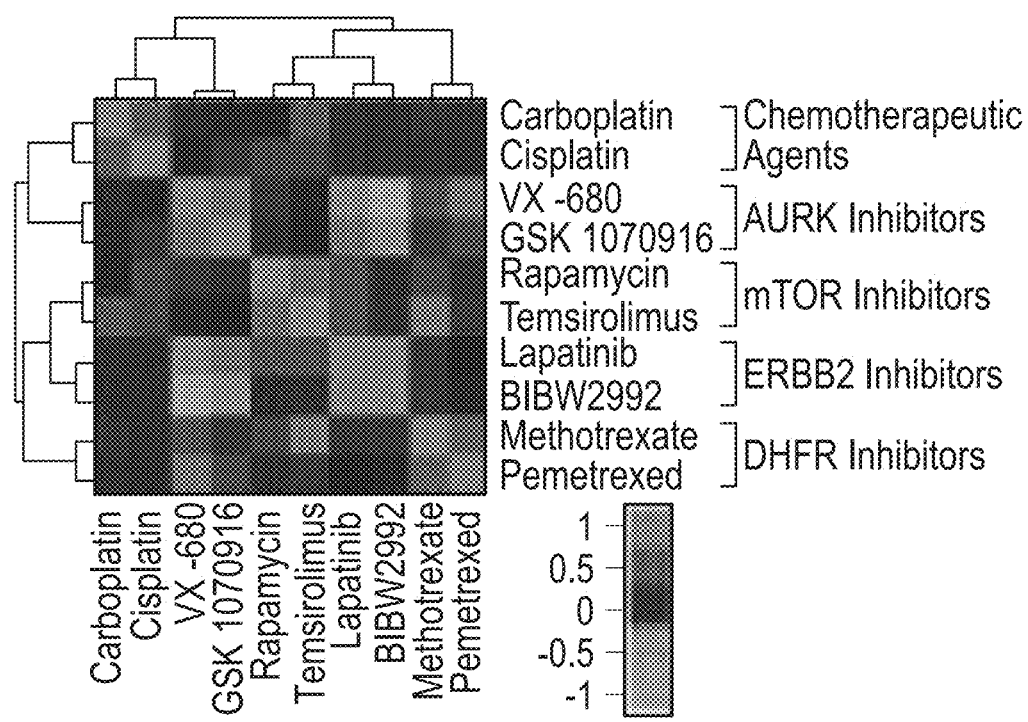
Figure 33C:
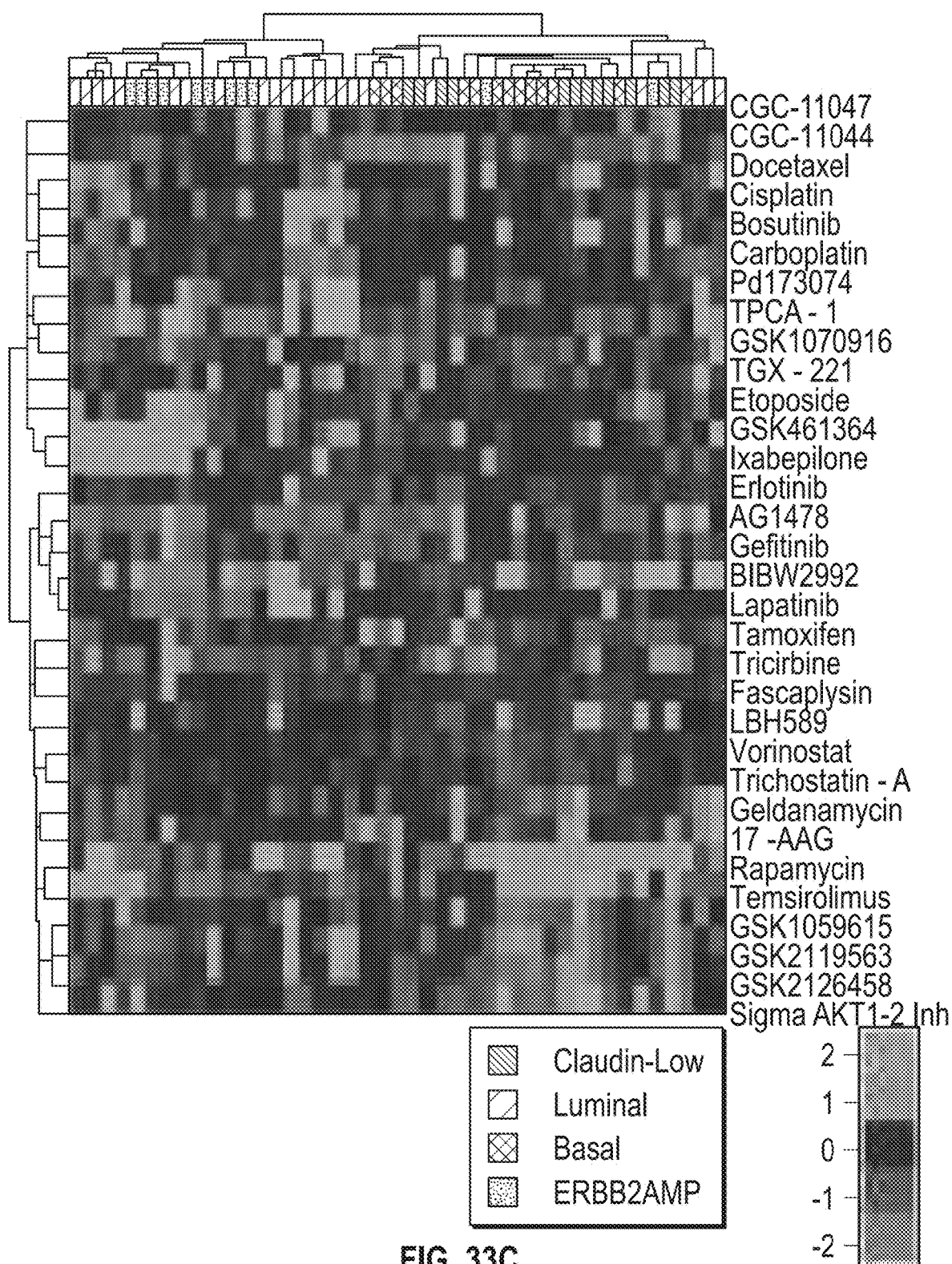
Figure 33D:
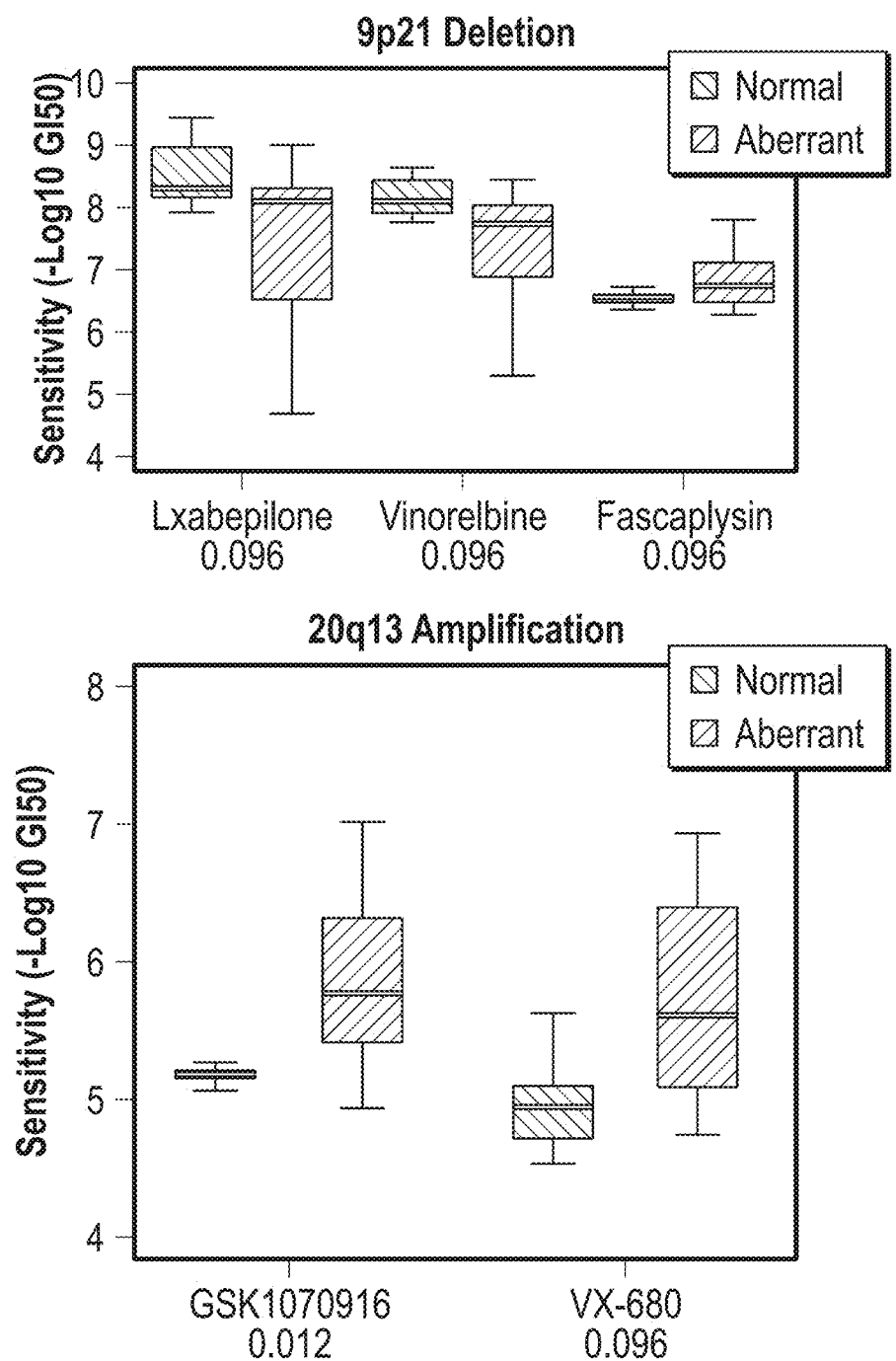
Figure 33D:
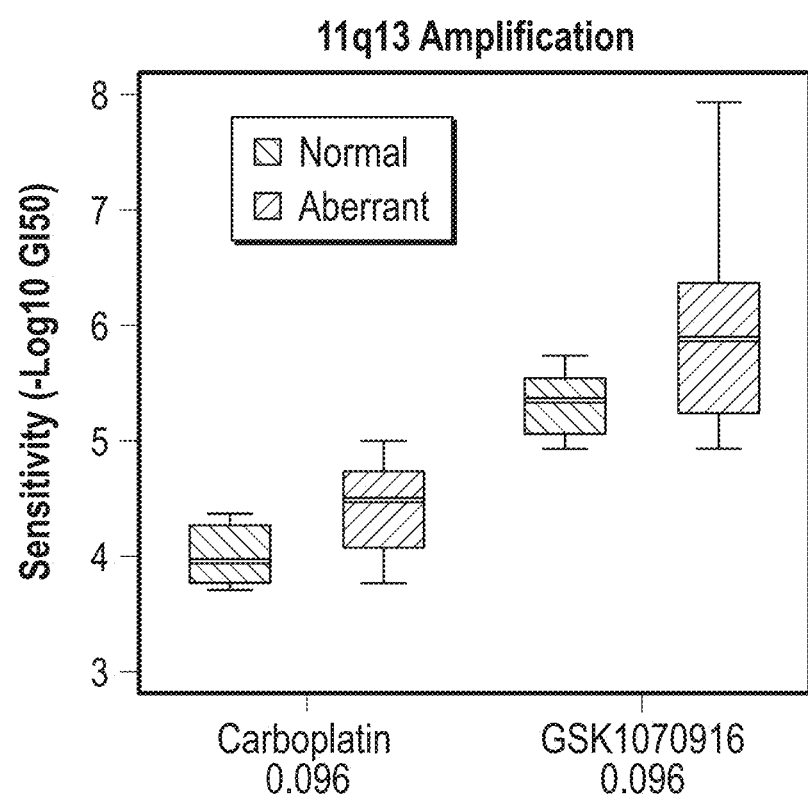

FIGS. 33A-33D show that the cell lines show a broad range of responses to therapeutic compounds. FIG. 33A Luminal and ERBB2AMP cell lines preferentially respond to AKT inhibition. Each bar represents the response of a single breast cancer cell line to the Sigma AKT1-2 inhibitor. Cell lines are ordered by increasing sensitivity ($-\log_{10}$ ($GI_{50}$)) and colored according to subtype. FIG. 33B $GI_{50}$ values for compounds with similar mechanisms are highly correlated. Heatmap shows hierarchical clustering of correlations between responses breast cancer cell lines treated with various compounds. FIG. 33C Compounds with similar modes of action show similar patterns of response across the panel of cell lines. Each column represents one cell line, each row represents a compound tested. $GI_{50}$ values are hierarchically clustered. Only compounds with a significant subtype effect are included. Cell lines of similar subtype tend to cluster together, indicating that they are responsive to the same compounds. Gray represents missing values. FIG. 33D CNAs are associated sensitivity. Boxplots show distribution of response sensitivity for cell lines with aberrant (A) and normal (N) copy number at the noted genomic locus. FDR p values for the association between drug response and CNA are noted. a. 9p2I (CDKN2A) deletion is associated with response to ixabepilone, vinerolbine and fascaplysin. b. 20q13 (STK15/AURKA) amplification is associated with VX-680 and GSK1070916. c. Amplification at 11q13 (CCND I) is associated with response to carboplatin and GSK1070916.

Figure 34:
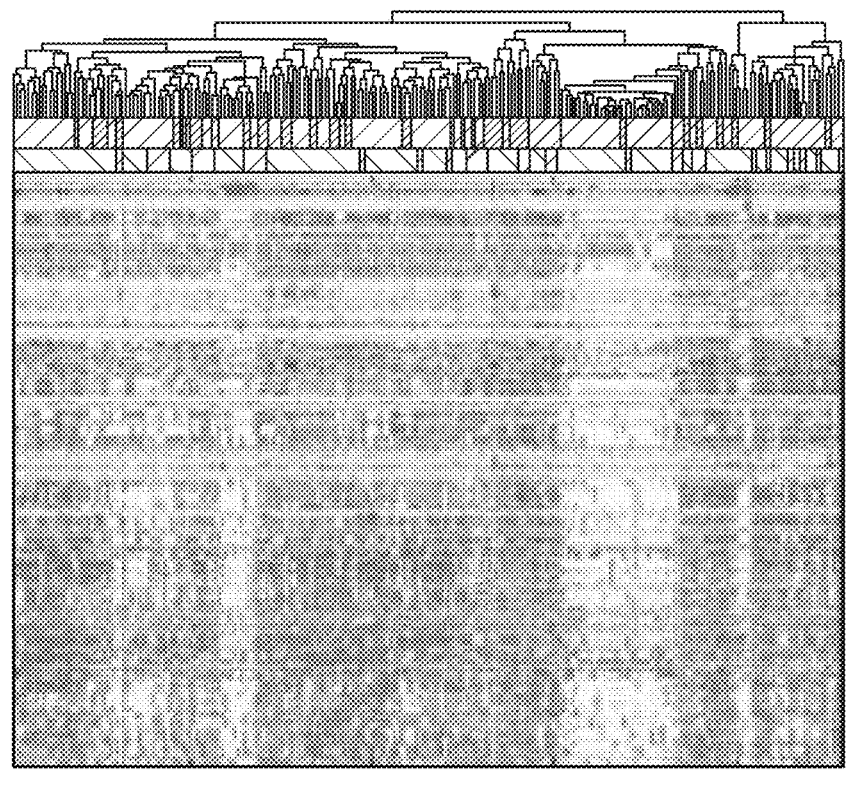
Figure 34:
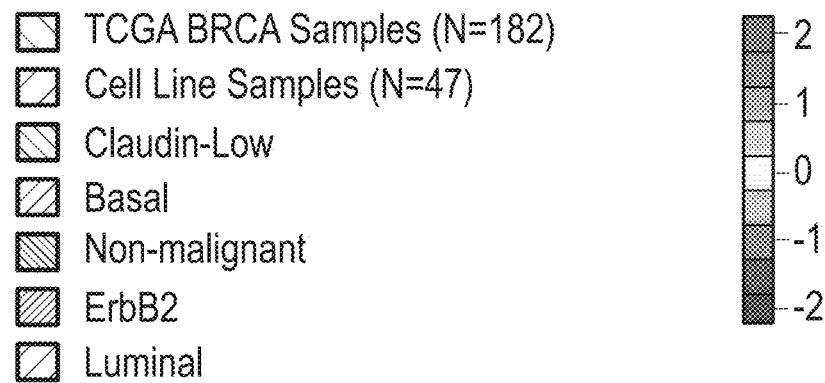

FIG. 34 Heatmap of non-redundant PARADIGM activities both cell line and TCGA samples. Cluster dendrogram represents Euclidian distance between samples and was created using Eisen Cluster and drawn using Java Treeview. Colored bars below dendrogram represent sample subtype (top) and sample cohort (bottom).

Figure 35A:
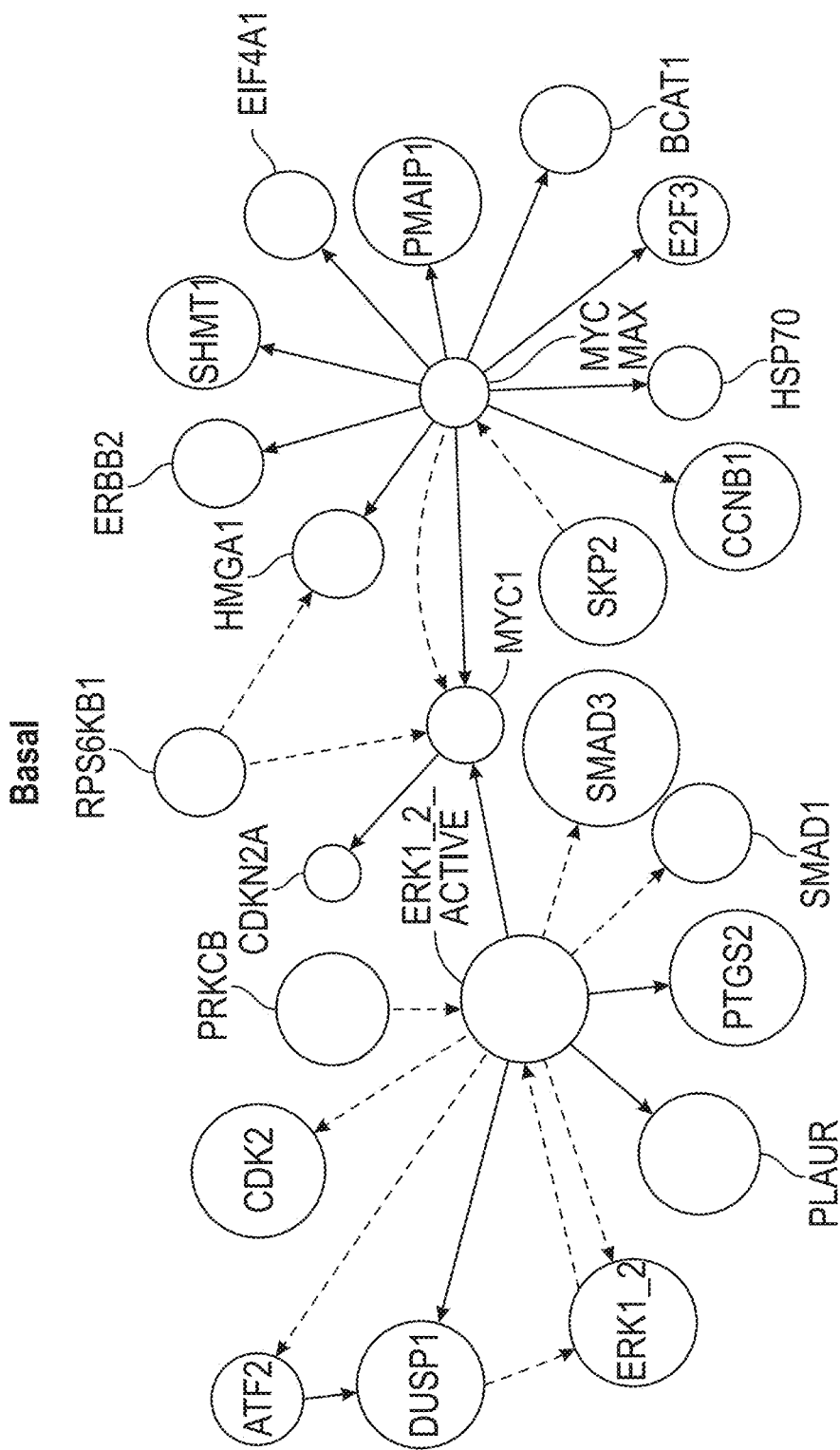
Figure 35B:
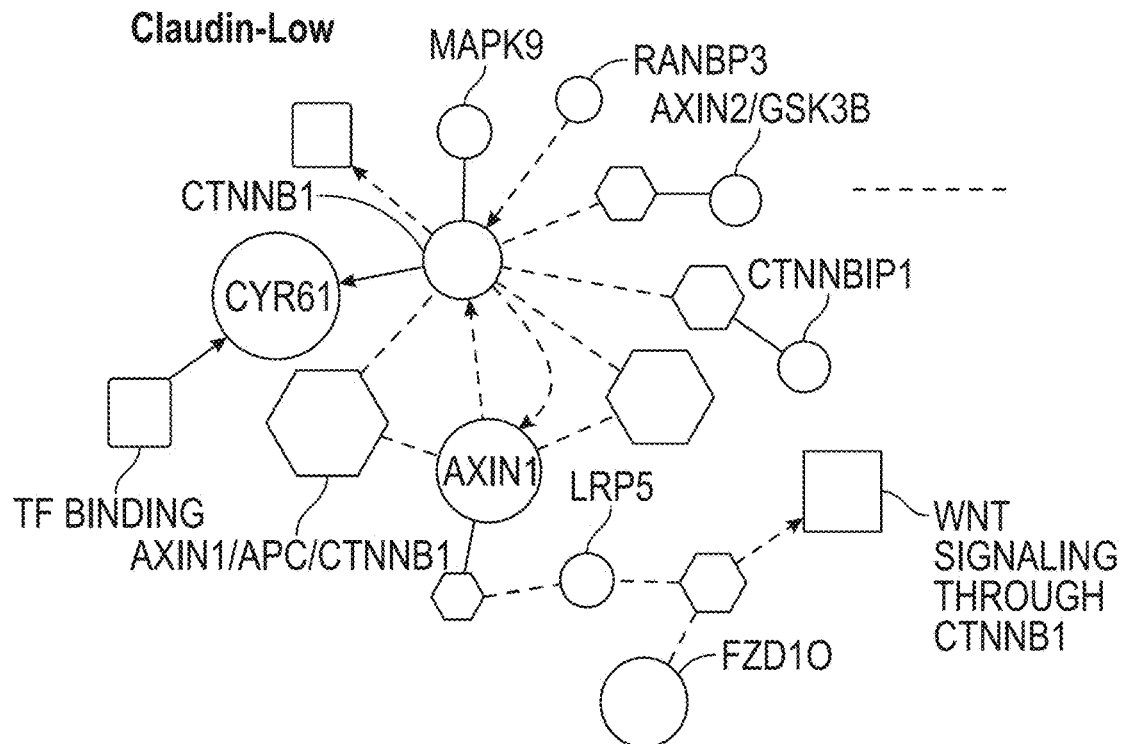
Figure 35C:
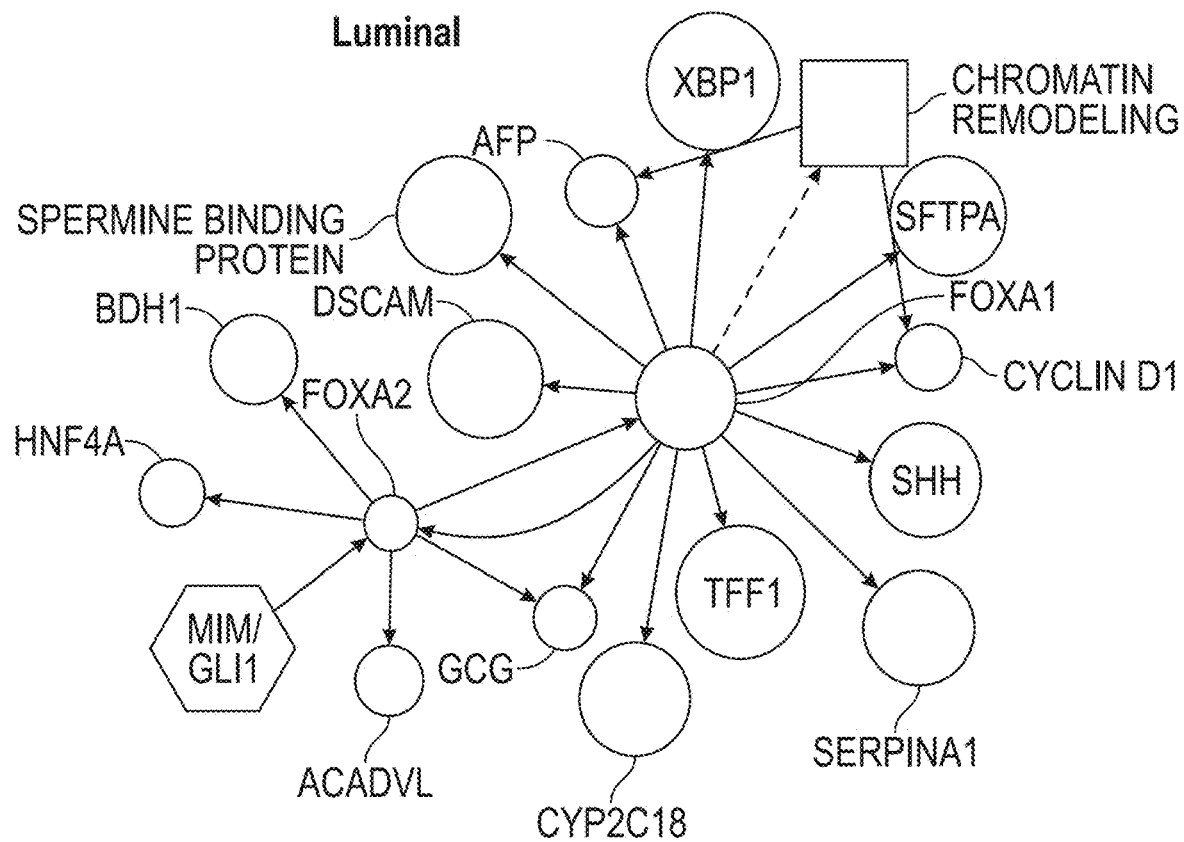
Figure 35D:
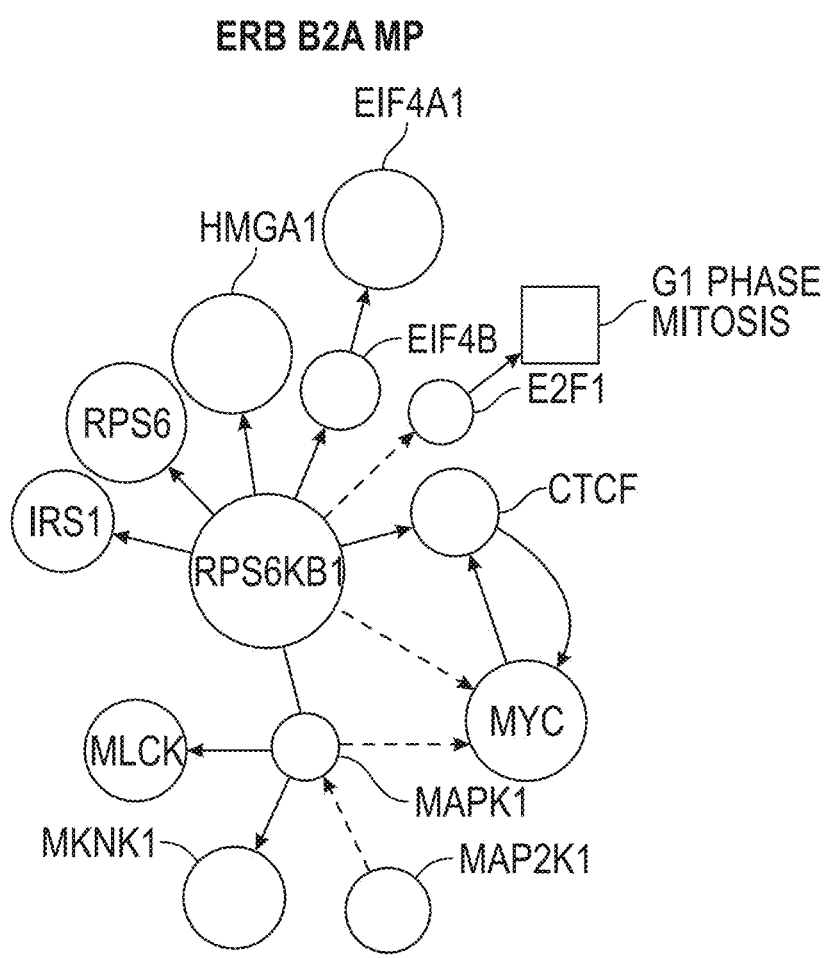

FIGS. 35A-35D show that the cell line subtypes have unique network features. In all panels, each node in the graph represents a different pathway "concept" corresponding to either a protein (circles), a multimeric complex (hexagons), or a an abstract cellular process (squares). The size of the nodes were drawn in proportion to the differential activity score such that larger nodes correspond to pathway concepts with activities more correlated with basal versus non-basal cell lines. Color indicates whether the concept is positively correlated (red) or negatively correlated (blue) with the basal subtype. Links represent different interactions including protein-protein level interactions (dashed lines) and transcriptional (solid lines). Interactions were included in the map only if they interconnect concepts whose absolute level of differential activity is higher than the mean absolute level. FIG. 35A The MYC/MAX and ERK1/2 subnet is preferentially activated in basal breast cancer cell lines. FIG. 35B The C'FTNB1 network is activated in claudin-low cell lines. FIG. 35C A FOXA1/FOXA2 network is upregulated in the luminal subtype. FIG. 35D The ERBB2AMP subtype shows down-regulation of the RPS6KB1 pathway.

Figure 36A:
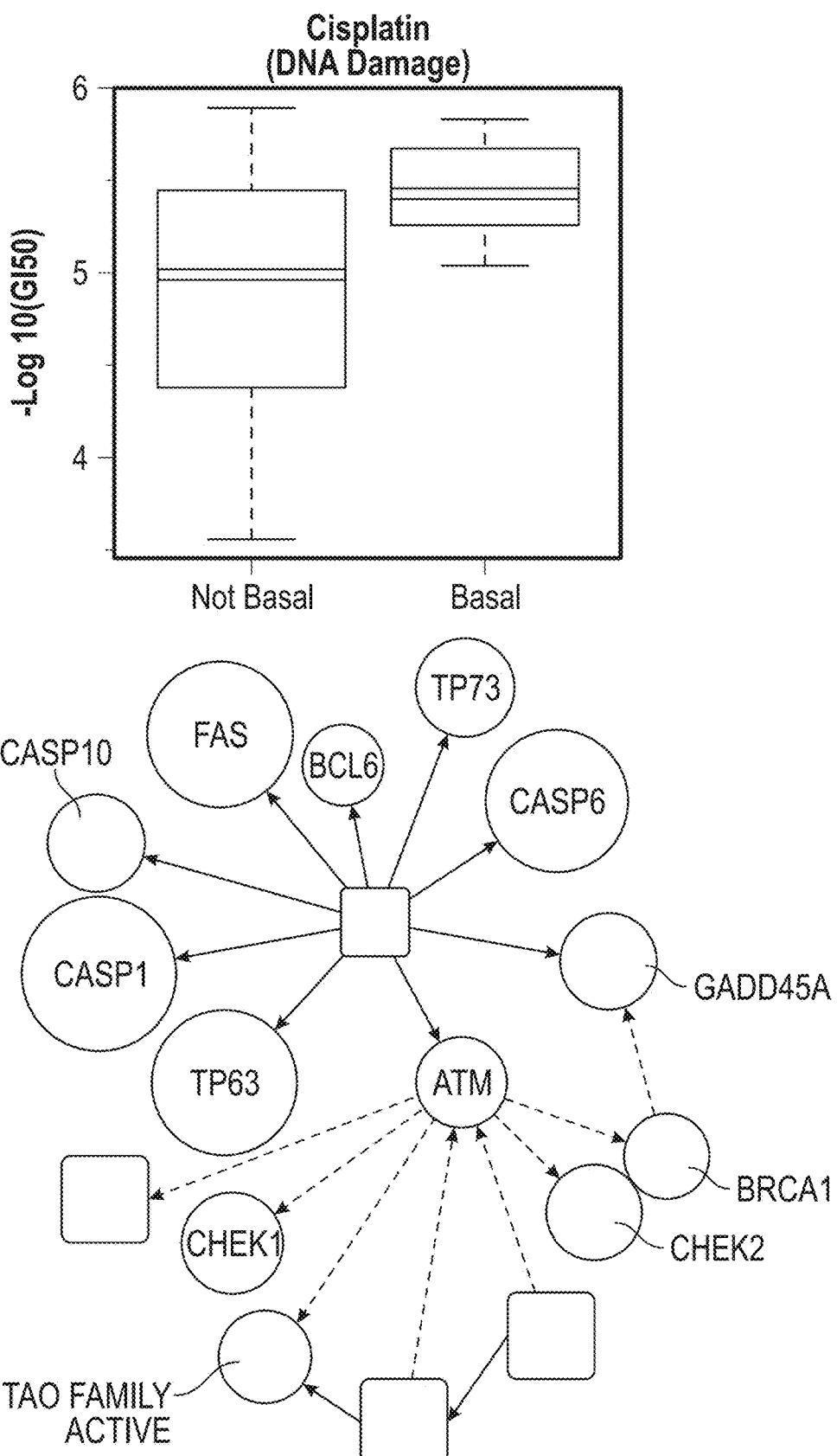
Figure 36B:
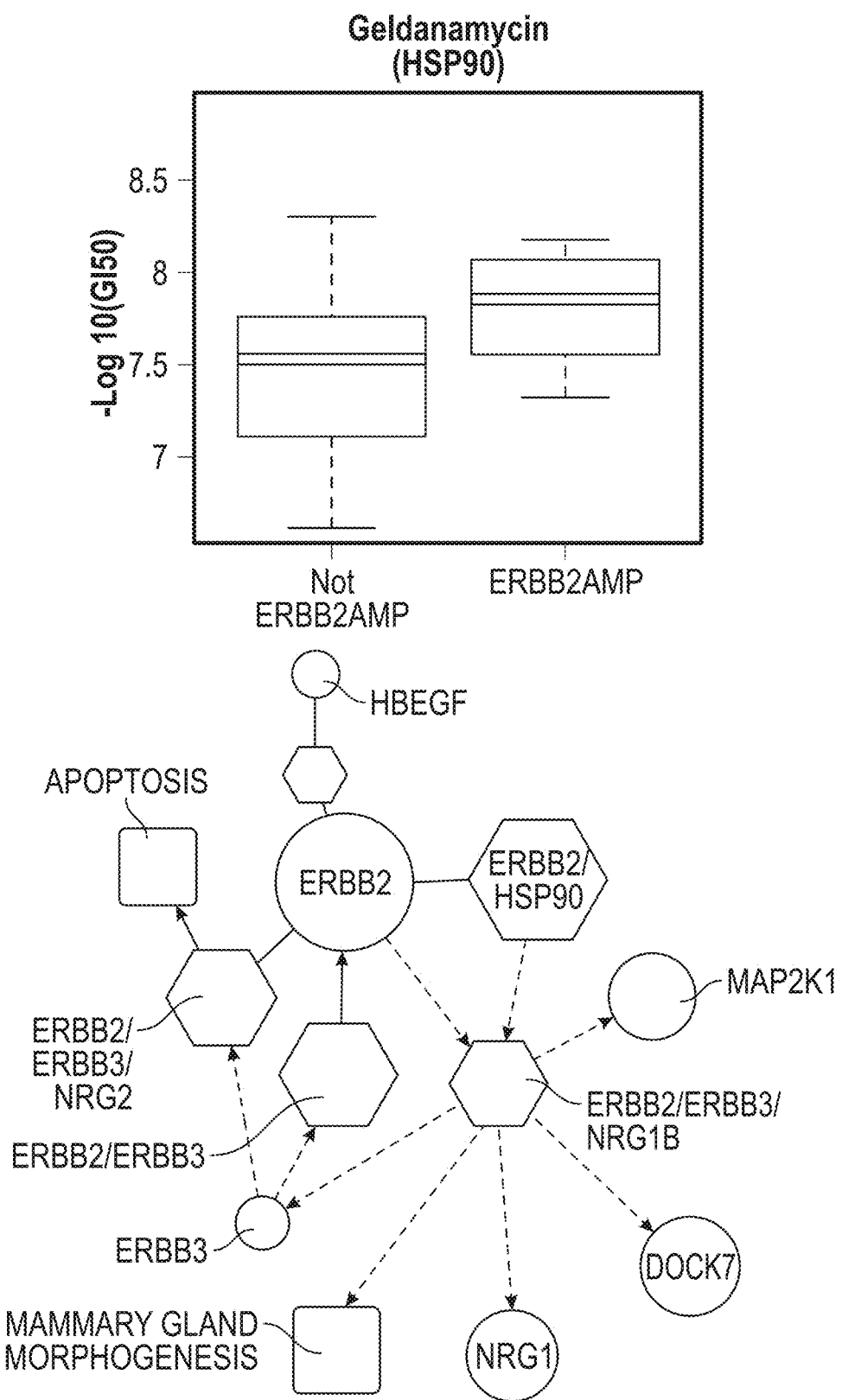

FIGS. 36A-36B show that the pathway diagrams can be used to predict response to therapies. FIG. 36A Upper panel. Basal breast cancer cell lines preferentially respond to the DNA damaging agent cisplatin. Lower panel. Basal cell lines show enhanced activity in pathways associated with the DNA damage response, providing a possible mechanism by which cisplatin acts in these cell lines. FIG. 36B Upper panel. ERBB2AMP cell lines are sensitive to the HSP90 inhibitor geldanamycin. Lower panel. The ERBB2-HSP90 network is upregulated in ERBBP2AMP cell lines. Convention as in FIG. 3 36.

Figure 37A:
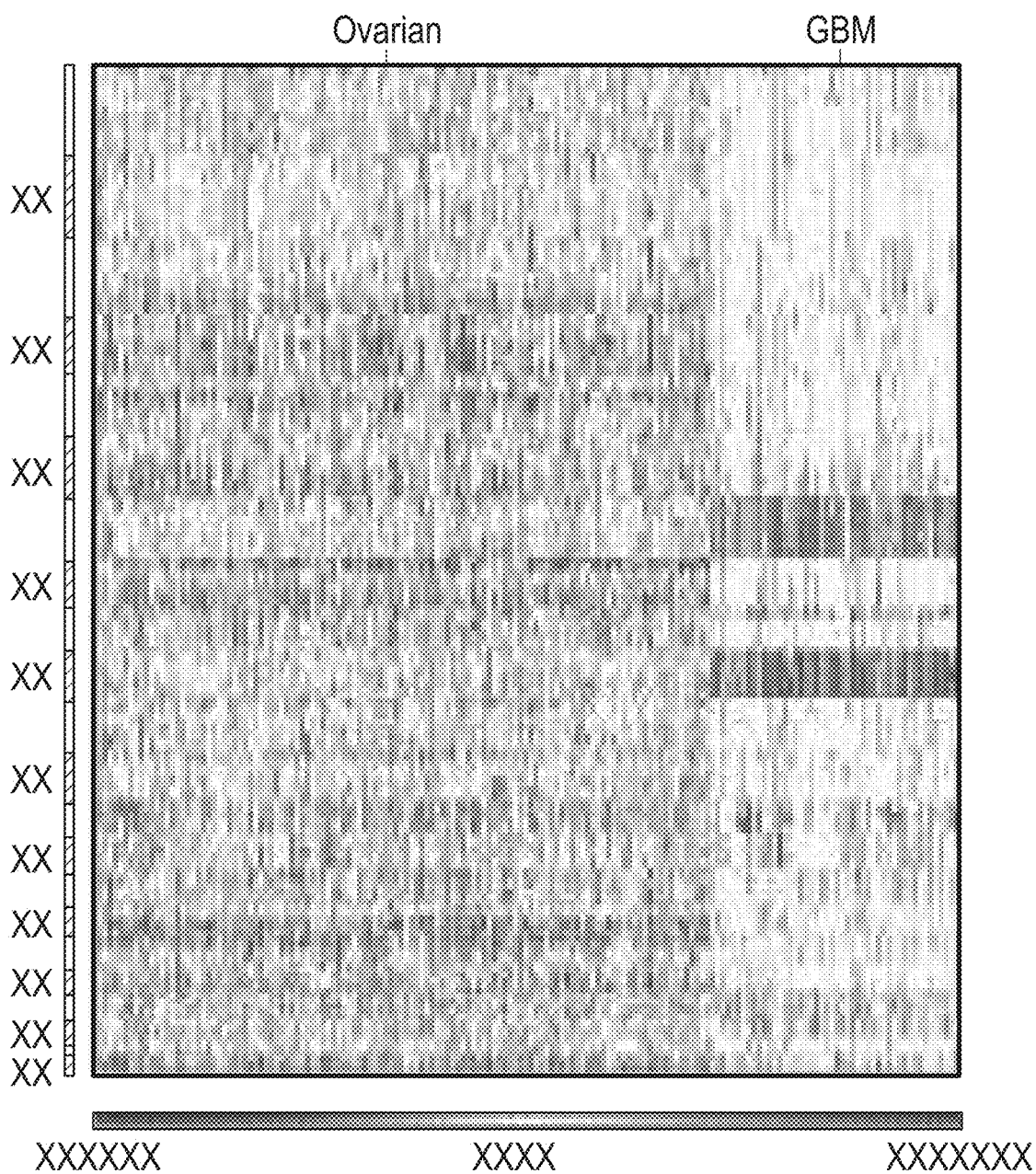
Figure 37B:
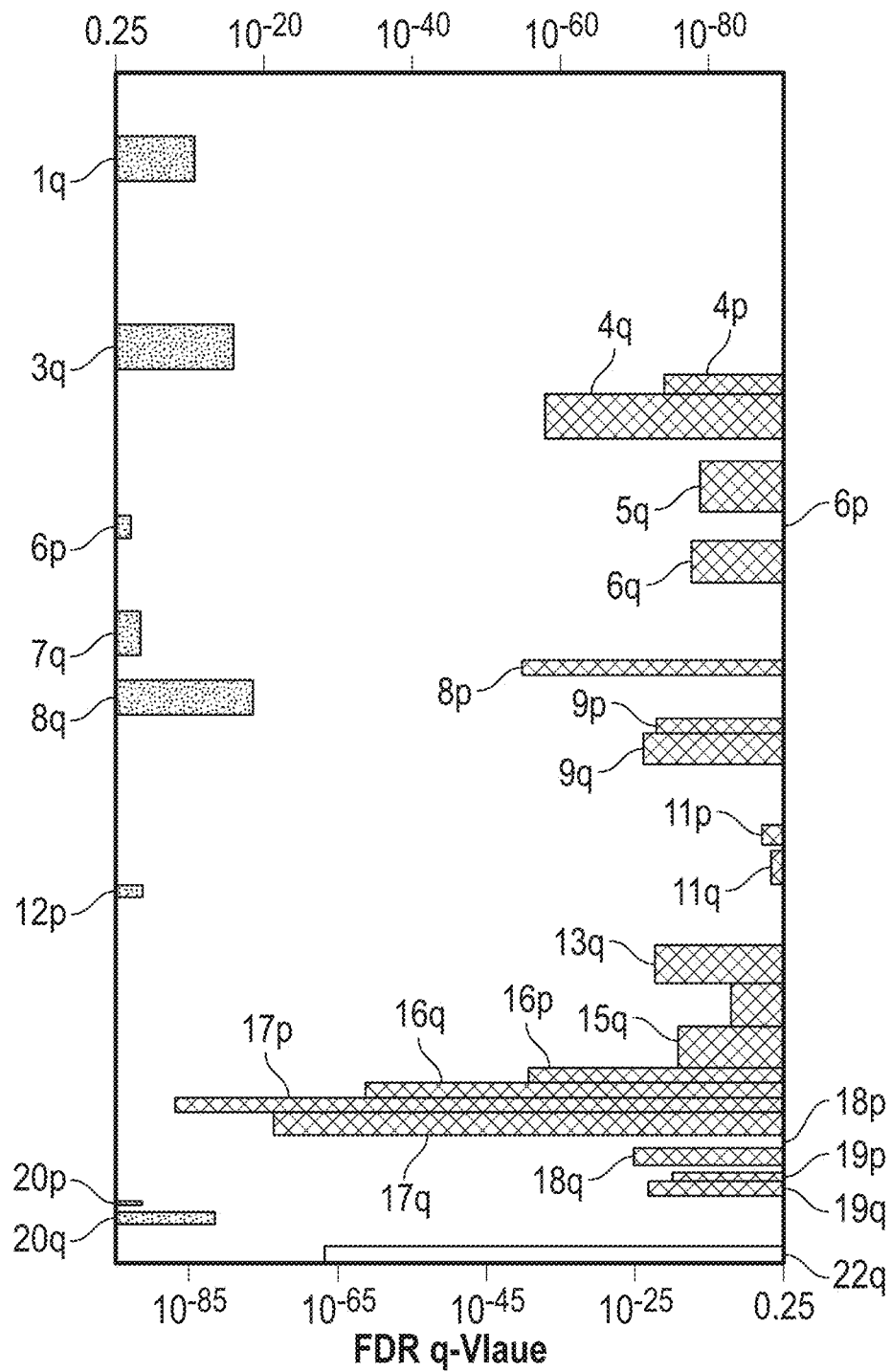
Figure 37C:
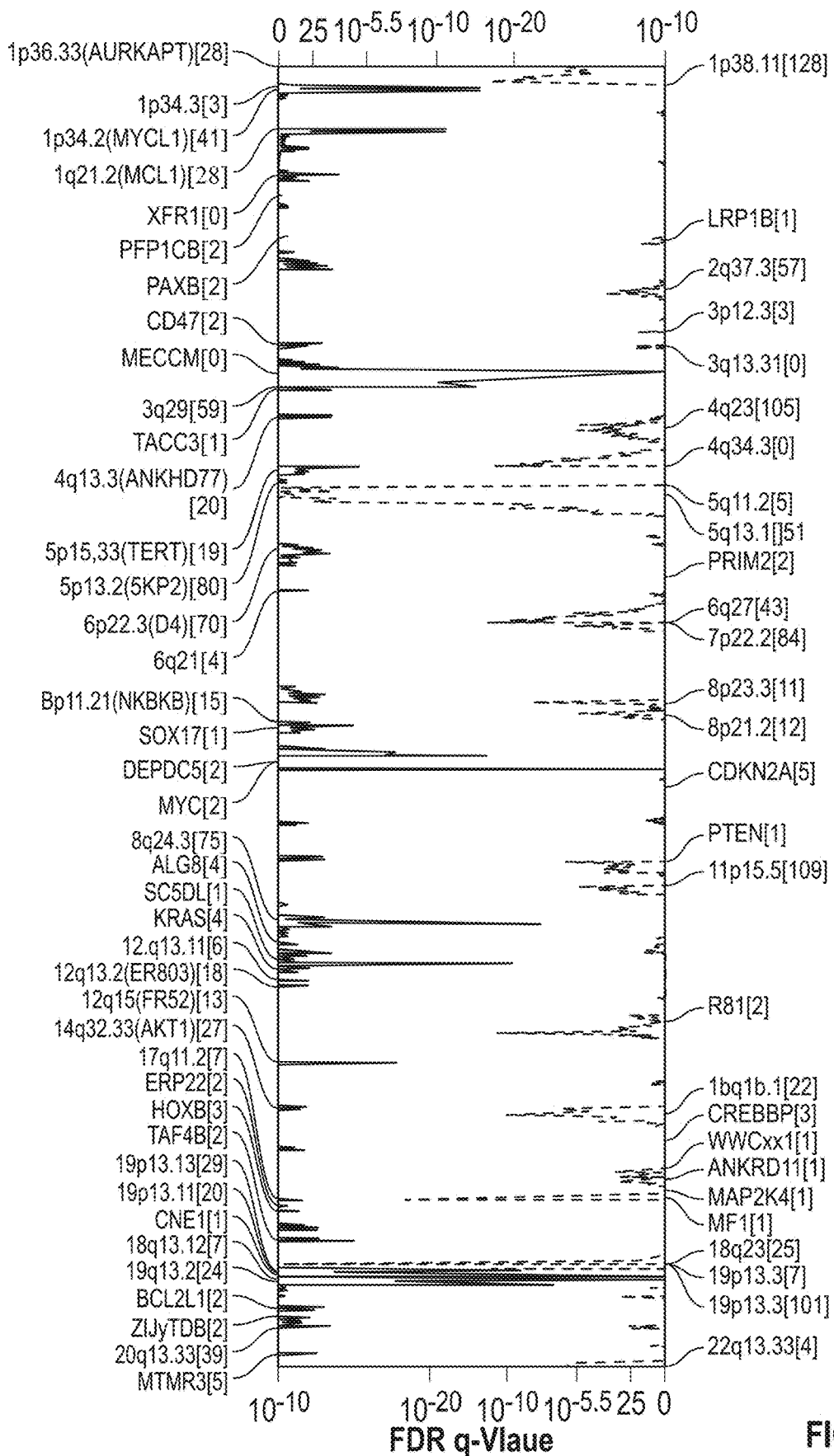

FIGS. 37A-37C illustrate genome copy number abnormalities. FIG. 37A Copy-number profiles of 489 HGS-OvCa, compared to profiles of 197 glioblastoma multiforme (GBM) tumors46. Copy number increases (red) and decreases (blue) are plotted as a function of distance along the normal genome. FIG. 37B Significant, focally amplified (red) and deleted (blue) regions are plotted along the gnome. Annotations include the 20 most significant amplified and deleted regions, well-localized regions with 8 or fewer genes, and regions with known cancer genes or genes identified by genome-wide loss-of-function screens. The number of genes included in each region is given in brackets. FIG. 37C Significantly amplified (red) and deleted (blue) chromosome arms.

Figure 38A:
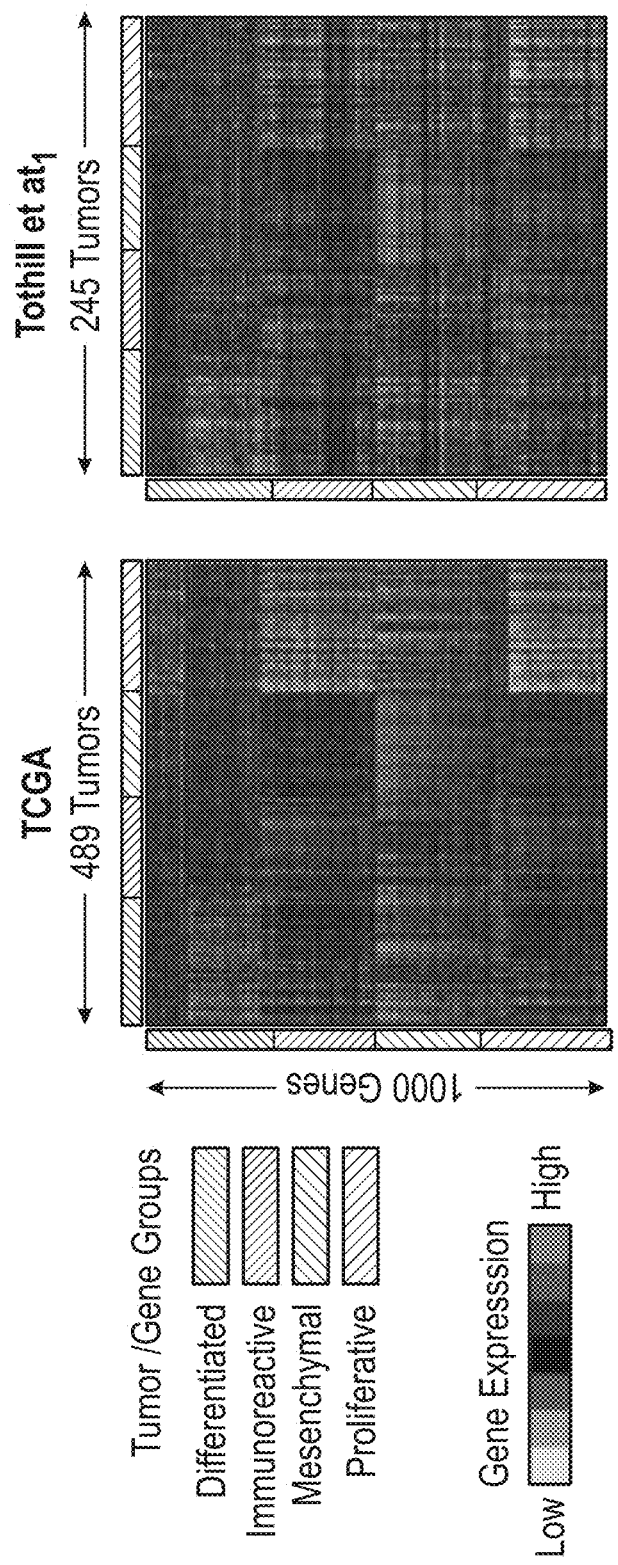
Figure 38B:
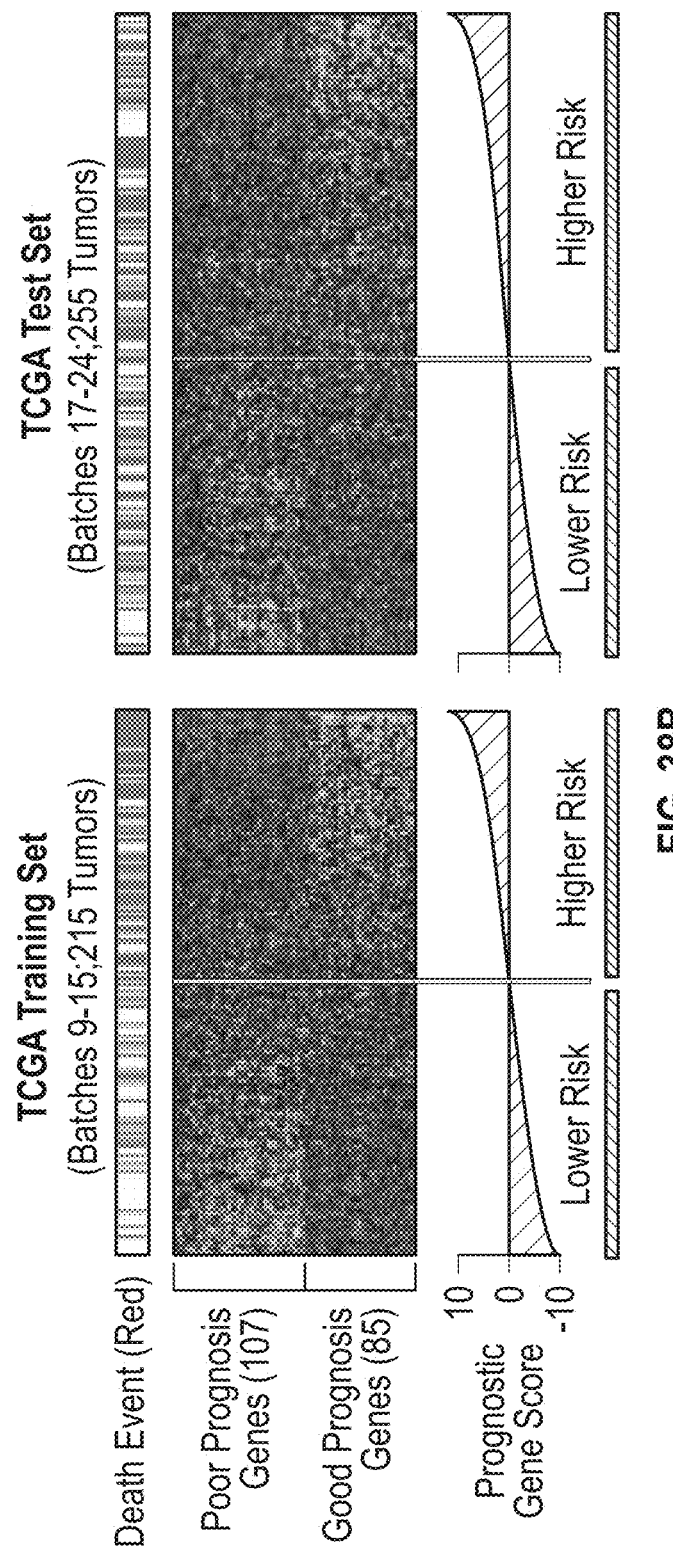
Figure 38C:
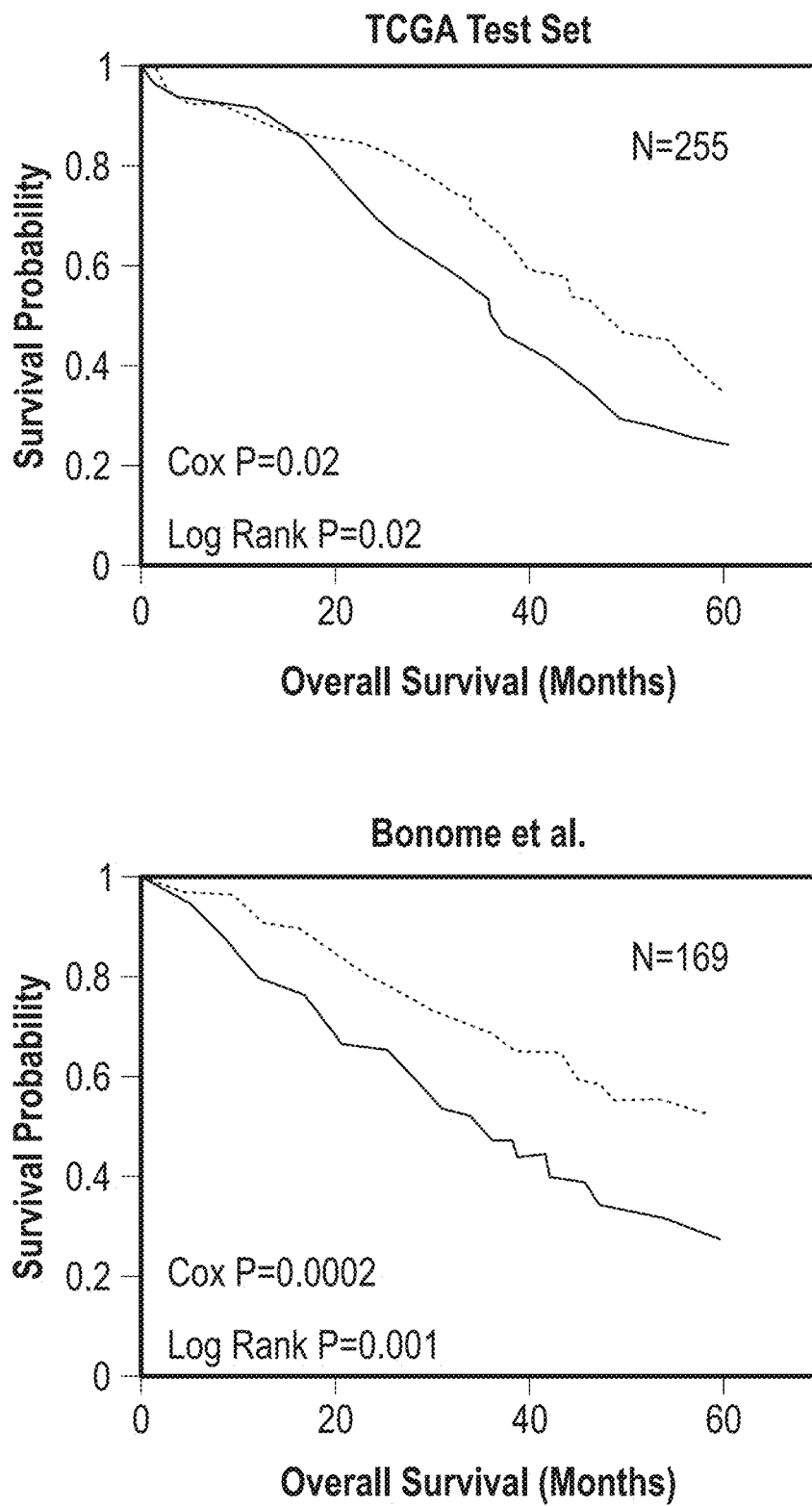
Figure 38C:
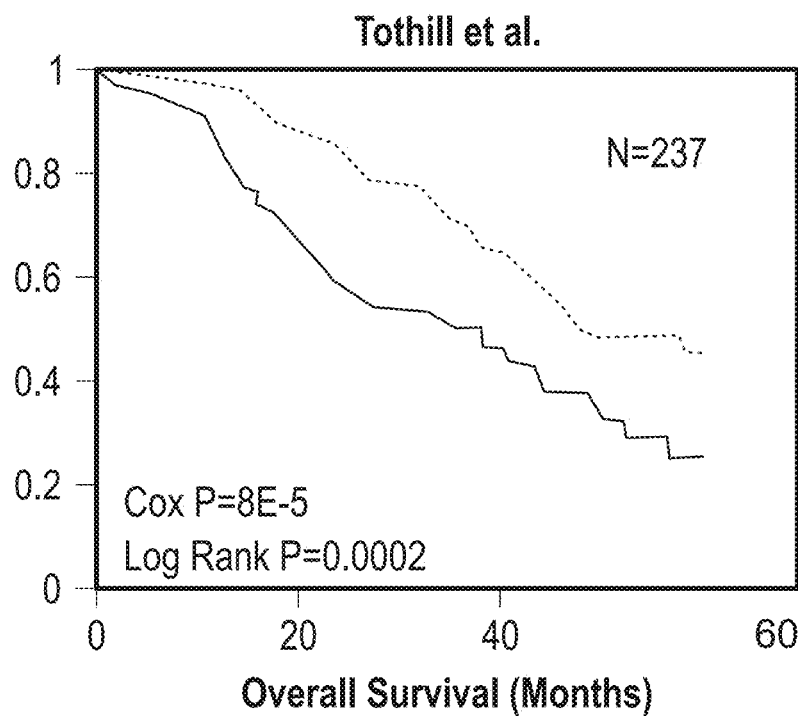
Figure 38C:
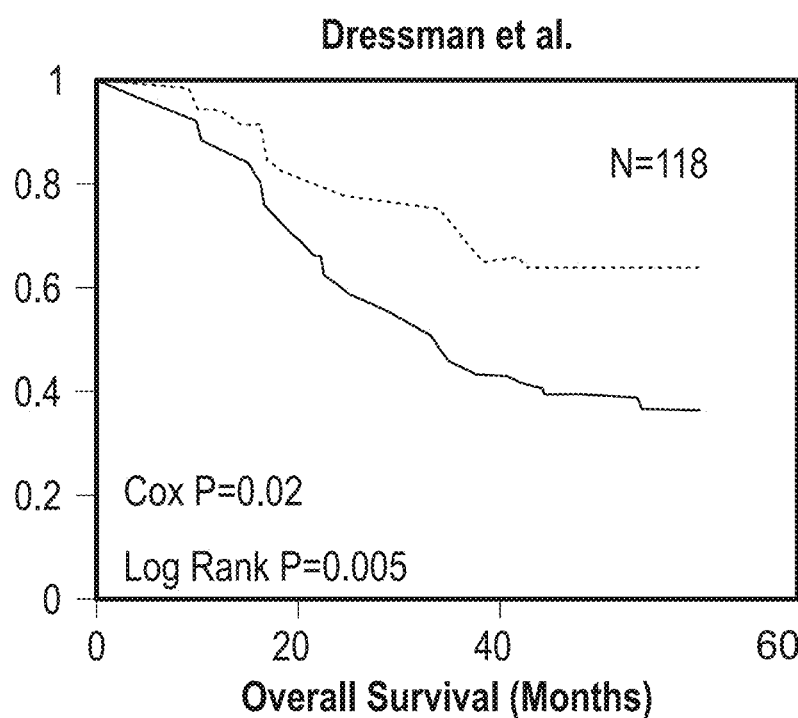

FIGS. 38A-38E illustrate gene and miRNA expression patterns of molecular subtype and outcome prediction in HGS-OvCa. FIG. 38A Tumors from TCGA and Tothill et al. separated into four clusters, based on gene expression. FIG. 38B Using a training dataset, a prognostic gene signature was defined and applied to a test dataset. FIG. 38C Kaplan-Meier analysis of four independent expression profile datasets, comparing survival for predicted higher risk versus lower risk patients. Univariate Cox p-value for risk index included.

Figures 38D, 38E:
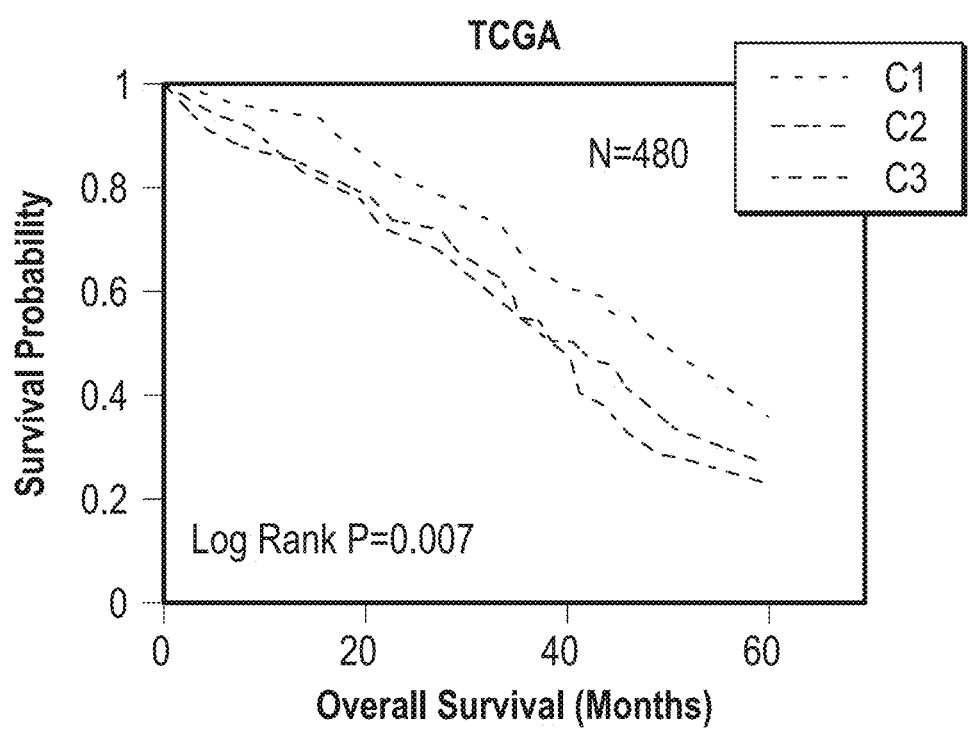

FIG. 38D Tumors separated into three clusters, based on miRNA expression, overlapping with gene-based clusters as indicated. FIG. 38E Differences in patient survival among the three miRNA-based clusters.

Figure 39A:
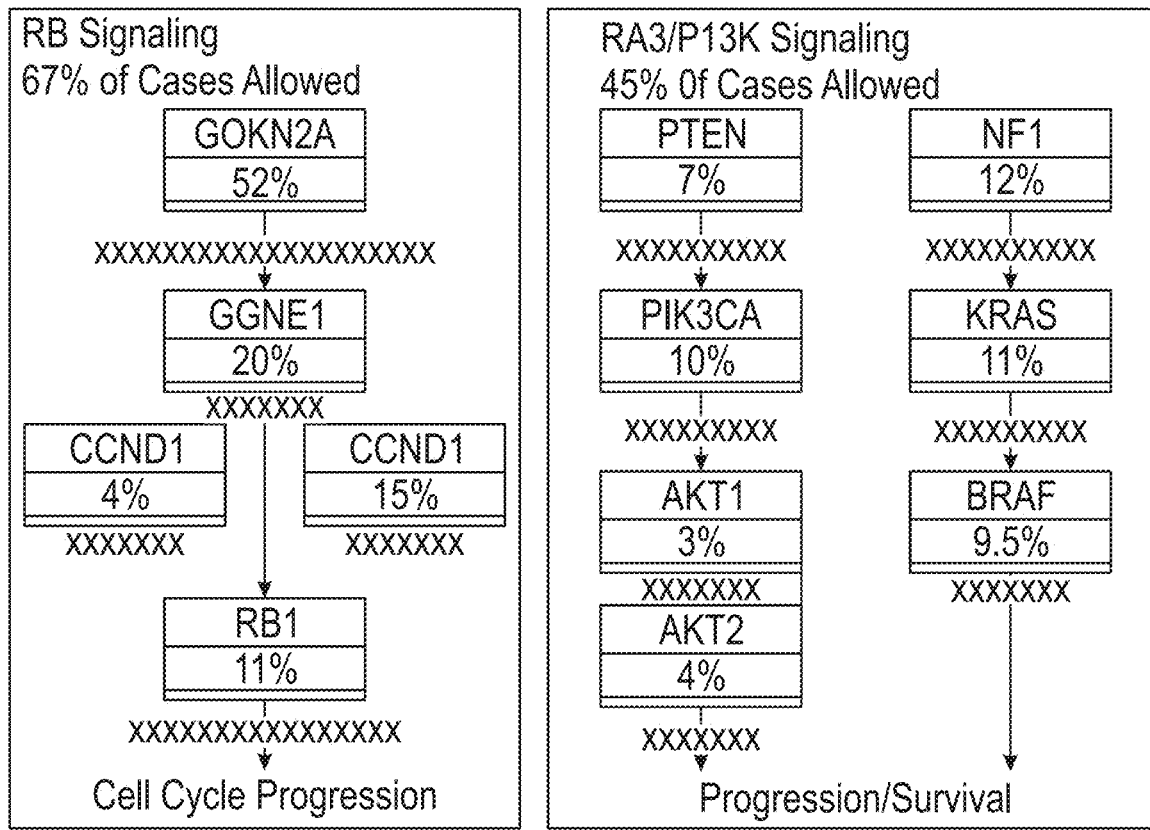
Figure 39B:
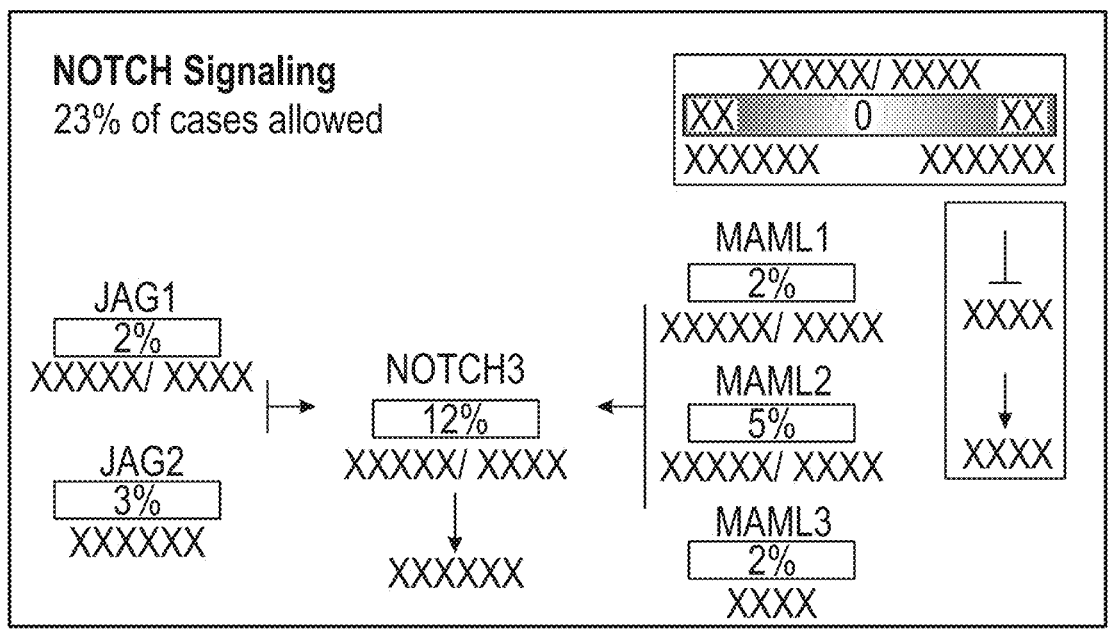
Figure 39C:
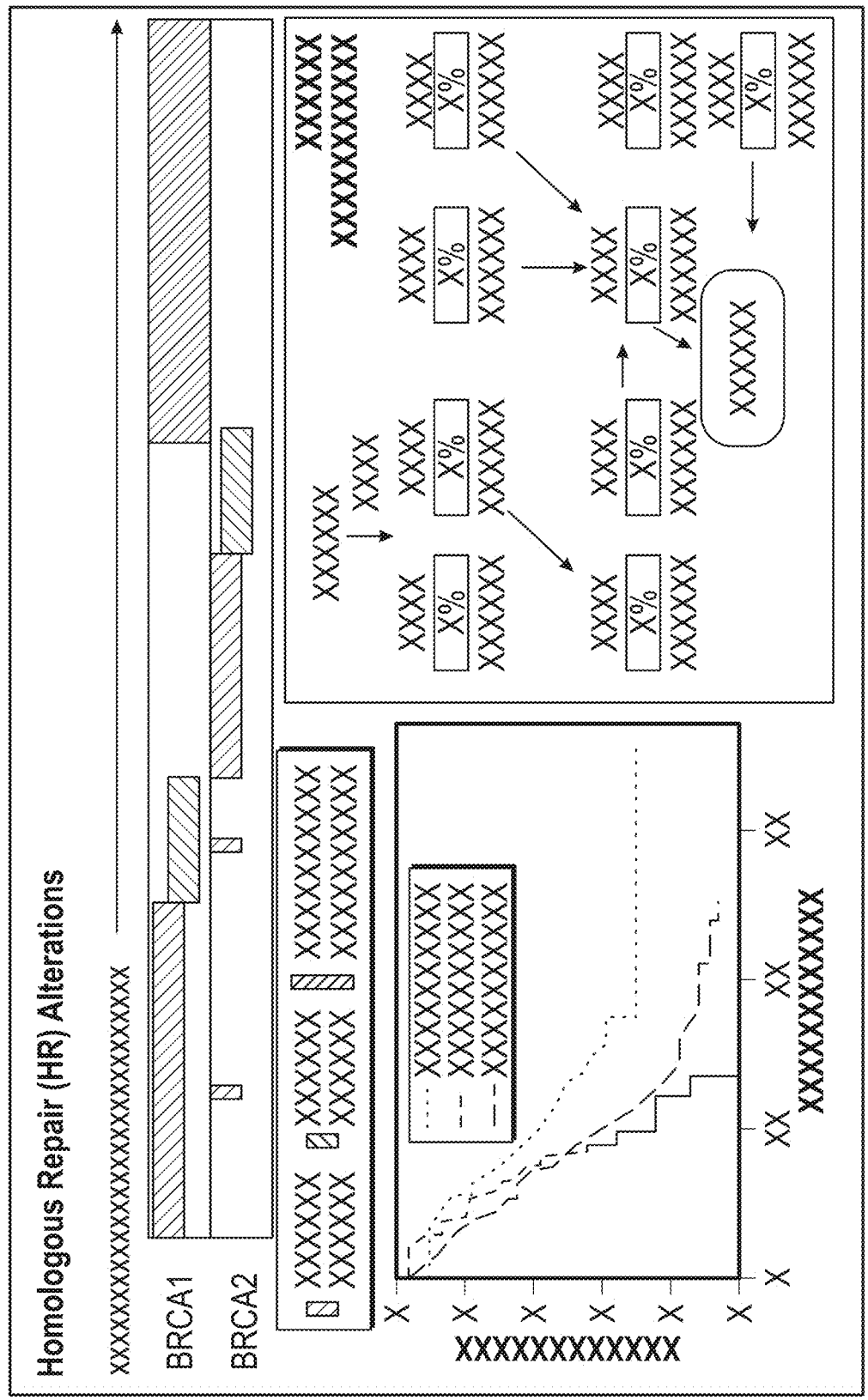
Figure 39D:
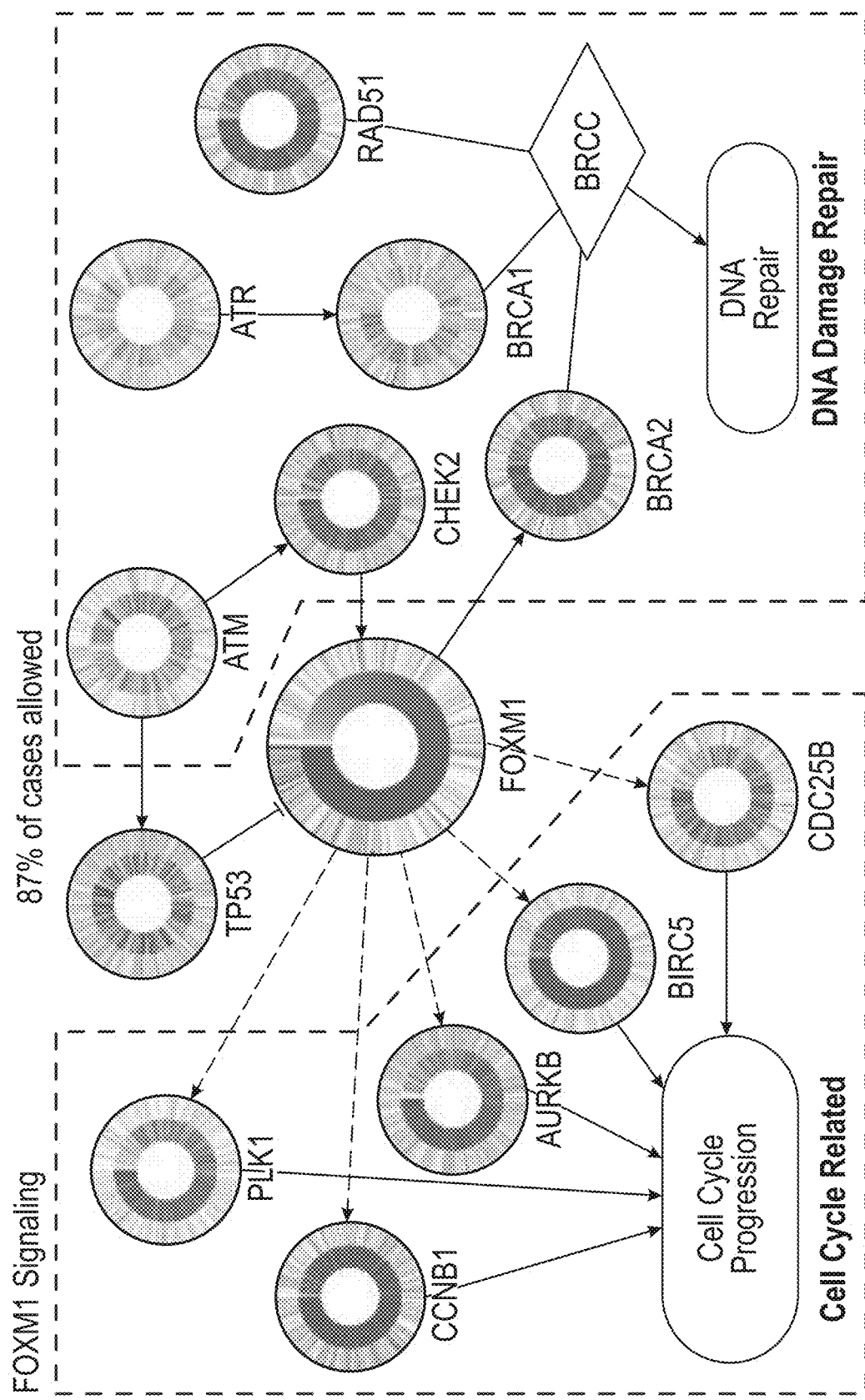

FIGS. 39A-39D illustrate altered Pathways in HGS-OvCa. FIG. 39A The RB and PI3K/RAS pathways, identified by curated analysis and FIG. 39B NOTCH pathway, identified by HotNet analysis, are commonly altered. Alterations are defined by somatic mutations, DNA copy-number changes, or in some cases by significant up- or down-regulation compared to expression in diploid tumors. Alteration frequencies are in percentage of all cases; activated genes are red, inactivated genes are blue. FIG. 39C Genes in the HR pathway are altered in up to 49% of cases. Survival analysis of BRCA status shows divergent outcome for BRCA mutated cases (exhibiting better overall survival) than BRCA wild-type, and BRCA/epigenetically silenced cases exhibiting worse survival. FIG. 39D The FOXM1 transcription factor network is activated in 87% of cases. Each gene is depicted as a multi-ring circle in which its copy number (outer ring) and gene expression (inner ring) are plotted such that each "spoke" in the ring represents a single patient sample, with samples sorted in increasing order of FOXAV expression. Excitatory (red arrows) and inhibitory interactions (blue lines) were taken from the NCI Pathway Interaction Database. Dashed lines indicate transcriptional regulation.

DETAILED DESCRIPTION OF THE INVENTION

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "an miRNA" includes a plurality of such miRNAs, and a reference to "a phannaceutical carrier" is a reference to one or more phannaceutical carriers and equivalents thereof; and so forth.

As used herein, the term "curated" means the relationships between a set of biological molecules and/or non-biological molecules that has been tested, analyzed, and identified according to scientific and/or clinical principles using methods well known in the art, such as molecular biological, biochemical, physiological, anatomical, genomic, transcriptomic, proteomic, metabolomic, ADME, and bioinformatic techniques, and the like. The relationships may be biochemical such as biochemical pathways, genetic pathways, metabolic pathways, gene regulatory pathways, gene transcription pathways, gene translation pathways, miRNA-regulated pathways, pseudogene-regulated pathways, and the like.

High-throughput data is providing a comprehensive view of the molecular changes in cancer tissues. New technologies allow for the simultaneous genome-wide assay of the state of genome copy number variation, gene expression, DNA methylation, and epigenetics of tumor samples and cancer cell lines.

Studies such as The Cancer Genome Atlas (TCGA), Stand Up To Cancer (SU2C), and many more are planned in the near future for a wide variety of tumors. Analyses of current data sets find that genetic alterations between patients can differ but often involve common pathways. It is therefore critical to identify relevant pathways involved in cancer progression and detect how they are altered in different patients.

We disclose a novel method for inferring patient-specific genetic activities incorporating curated pathway interactions among genes. A gene is modeled by a factor graph as a set of interconnected variables encoding the expression and known activity of a gene and its products, allowing the incorporation of many types of -omic data as evidence.

The method predicts the degree to which a pathway's activities (for example, internal gene states, interactions, or high-level "outputs") are altered in the patient using probabilistic inference. Compared to a competing pathway activity inference approach, called SPIA, our method identifies altered activities in cancer-related pathways with fewer false-positives in, but not limited to, both a glioblastoma multiform (GBM) and a breast cancer dataset.

Pathway Recognition Algorithm using Data integration on Genomic Models (PARADIGM) identified consistent pathway-level activities for subsets of the GBM patients that are overlooked when genes are considered in isolation. Further, grouping GBM patients based on their significant pathway perturbations using the algorithm divides them into clinically-relevant subgroups having significantly different survival outcomes.

These findings suggest that therapeutics might be chosen that can target genes at critical points in the commonly perturbed pathway(s) of a group of patients or of an individual.

We describe a probabilistic graphical model (PGM) framework based on factor graphs (Kschischang:2001 supra) that can integrate any number of genomic and functional genomic datasets to infer the molecular pathways altered in a patient sample. We tested the model using copy number variation and gene expression data for both a glioblastoma and breast cancer dataset. The activities inferred using a structured pathway model successfully stratify the glioblastoma patients into clinically-relevant subtypes. The results suggest that the pathway-informed inferences are more informative than using gene-level data in isolation.

In addition to providing better prognostics and diagnostics, integrated pathway activations offer important clues about potential therapeutics that could be used to abrogate disease progression.

Figure 1:
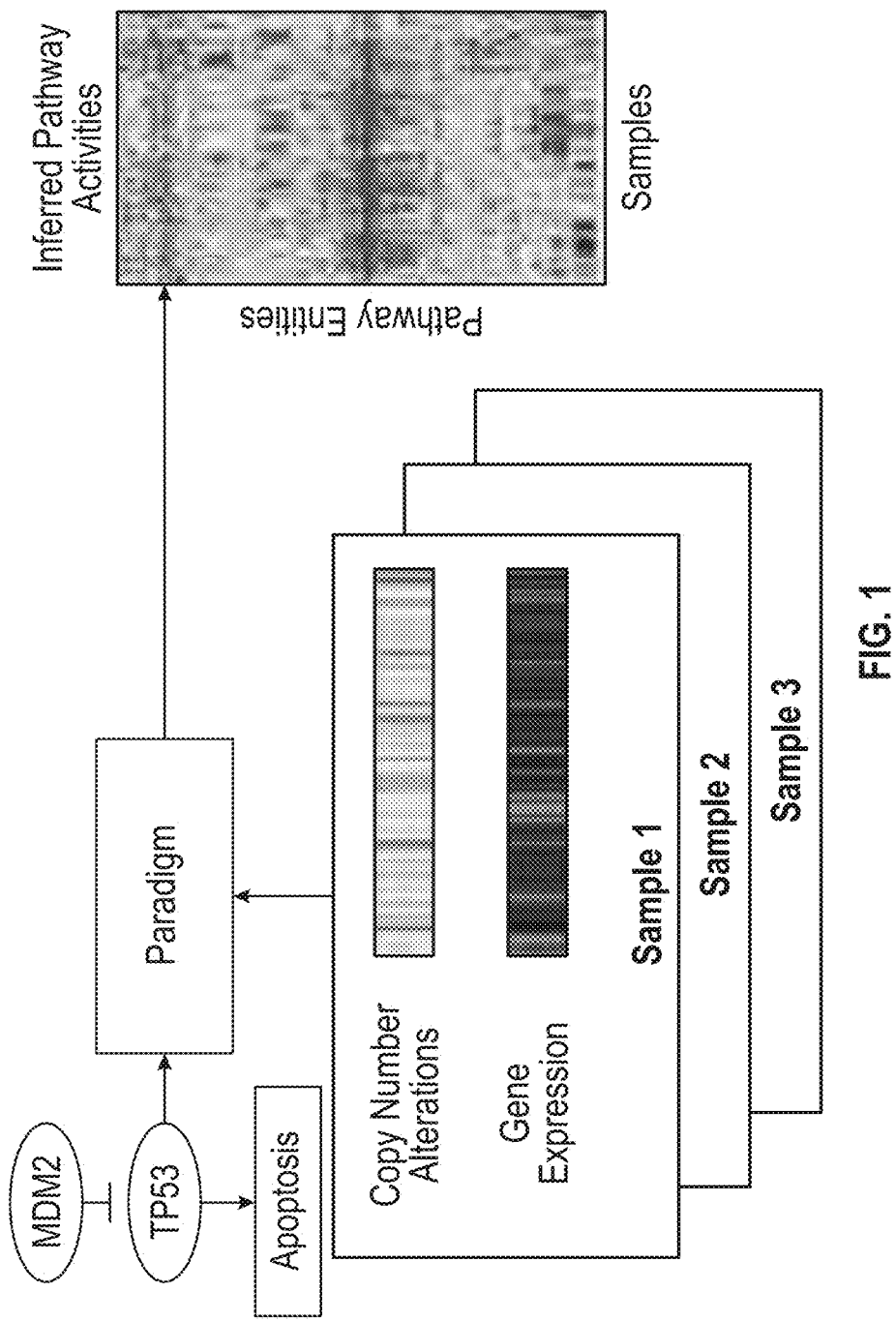
FIG. 1 illustrates an overview of the PARADIGM method. PARADIGM uses a pathway schematic with functional genomic data to infer genetic activities that can be used for further downstream analysis. NCI Pathway interactions in TCGA GBM data. For all (n=462) pairs where A was found to be an upstream activator of gene B in NCI-Nature Pathway Database, the Pearson correlation (x-axis) computed from the TCGA GBM data was calculated in two different ways. The histogram plots the correlations between the A's copy number and B's expression (C2E, solid red) and between A's expression and B's expression (E2E, solid blue). A histogram of correlations between randomly paired genes is shown for C2E (dashed red) and E2E (dashed blue). Arrows point to the enrichment of positive correlations found for the C2E (red) and E2E (blue) correlation

We developed an approach called PARADIGM (PAthway Recognition Algorithm using Data Integration on Genomic Models) to infer the activities of genetic pathways from integrated patient data. FIG. 1 illustrates the overview of the approach. Multiple genome-scale measurements on a single patient sample are combined to infer the activities of genes, products, and abstract process inputs and outputs for a single National Cancer Institute (NCI) pathway. PARADIGM produces a matrix of integrated pathway activities (IPAs) A where Au represents the inferred activity of entity i in patient sample j. The matrix A can then be used in place of the original constituent datasets to identify associations with clinical outcomes.

Figure 2A:
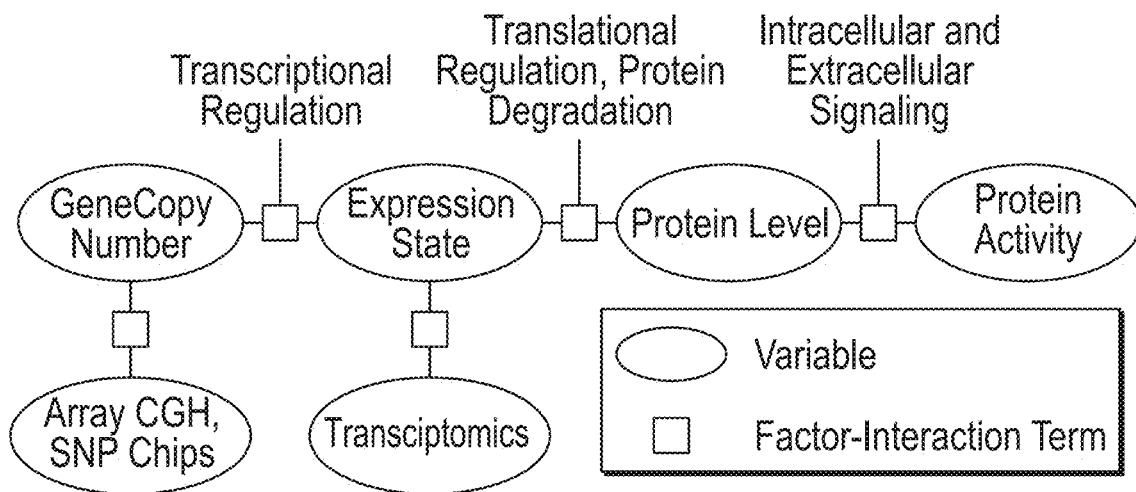
FIGS. 2A-2C illustrate the conversion of a genetic pathway diagram into a PARADIGM model. Overview of the PARADIGM method. PARADIGM uses a pathway schematic with functional genomic data to infer genetic activities that can be used for further downstream analysis.
Figure 2B:
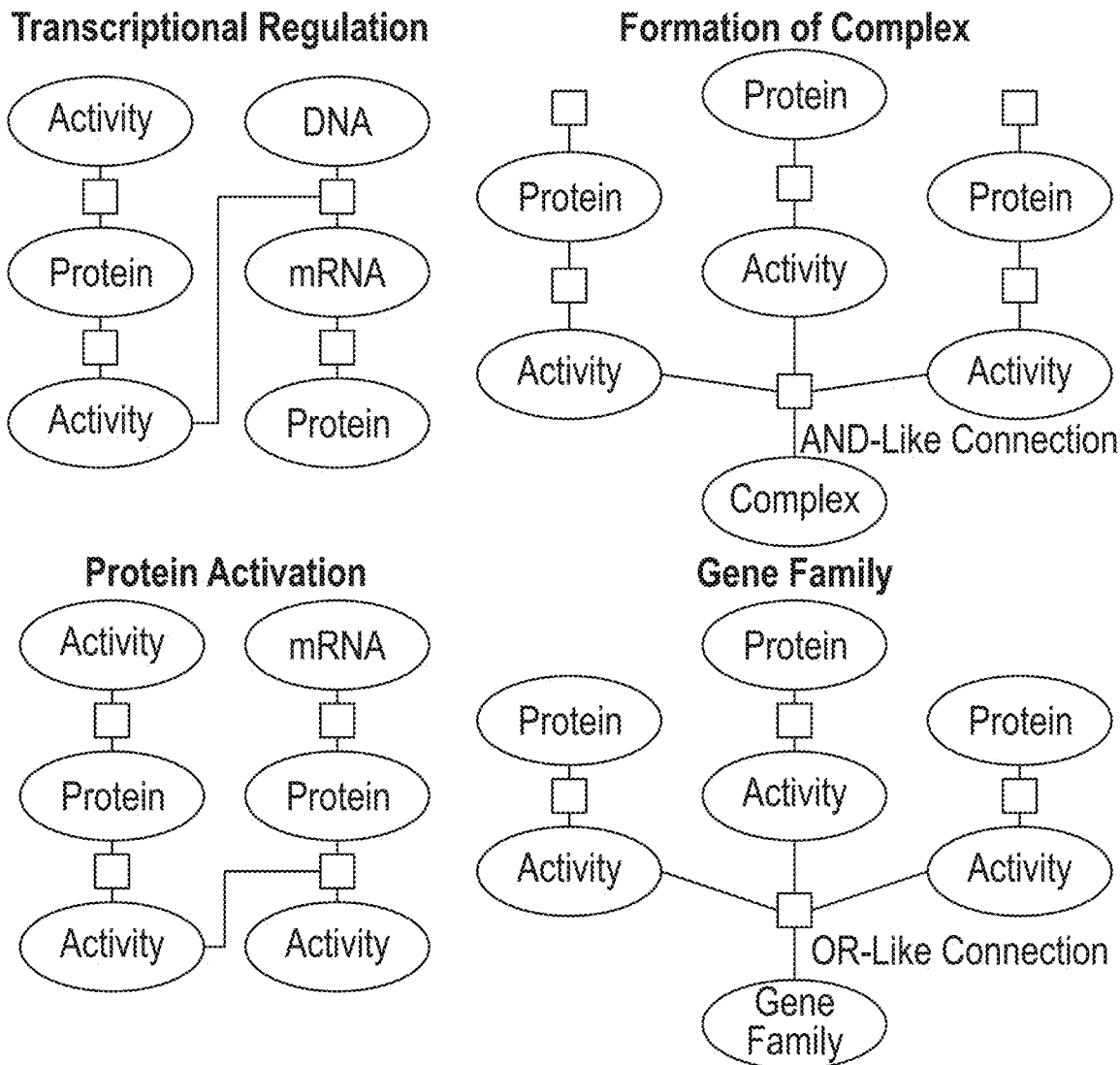
Figure 2C:
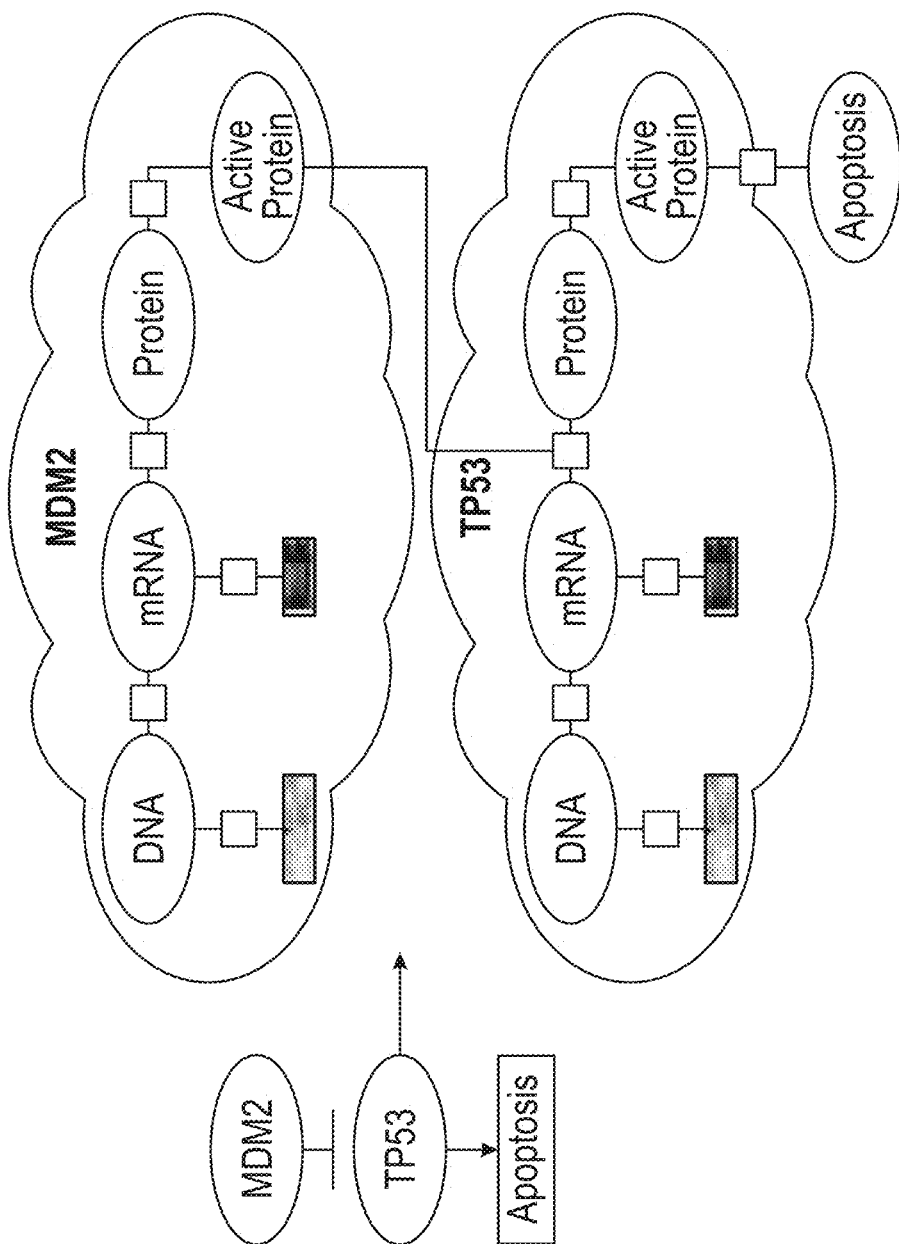

We first converted each NCI pathway into a distinct probabilistic model. A toy example of a small fragment of the p53 apoptosis pathway is shown in FIG. 2C. A pathway diagram from NCI was converted into a factor graph that includes both hidden and observed states (FIGS. 2A-2C). The factor graph integrates observations on gene- and biological process-related state information with a structure describing known interactions among the entities.

To represent a biological pathway with a factor graph, we use variables to describe the states of entities in a cell, such as a particular mRNA or complex, and use factors to represent the interactions and information flow between these entities. These variables represent the differential state of each entity in comparison to a "control" or normal level rather than the direct concentrations of the molecular entities. This representation allows us to model many high-throughput datasets, such as gene expression detected with DNA microarrays that often either directly measure the differential state of a gene or convert direct measurements to measurements relative to matched controls. It also allows for many types of regulatory relationships among genes. For example, the interaction describing MDM2 mediating ubiquitin-dependent degradation of p53 can be modeled as activated MDM2 inhibiting levels of p53 protein.

In one embodiment, the method may be used to provide clinical information that can be used in a variety of diagnostic and therapeutic applications, such as detection of cancer tissue, staging of cancer tissue, detection of metastatic tissue, and the like; detection of neurological disorders, such as, but not limited to, Alzheimer's disease, amyotrophic lateral sclerosis (ALS), Parkinson's disease, schizophrenia, epilepsy, and their complications; developmental disorders such as DiGeorge Syndrome, autism, autoimmune disorders such as multiple sclerosis, diabetes, and the like; treatment of an infection, such as, but not limited to, viral infection, bacterial infection, fungal infection, *leishmania*, schistosomiasis, malaria, tape-worm, elephantiasis, infections by nematodes, nematines, and the like.

In one embodiment, the method may be used to provide clinical information to detect and quantify altered gene expression, absence/presence versus excess, expression of mRNAs or to monitor mRNA levels during therapeutic intervention. Conditions, diseases or disorders associated with altered expression include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dennnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

In one embodiment, the method may be used to provide clinical information to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In one embodiment, the method may be used to provide clinical information for a condition associated with altered expression or activity of the mammalian protein. Examples of such conditions include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In one embodiment the methods disclosed herein may be used to detect, stage, diagnose, and/or treat a disorder associated with decreased expression or activity of the nucleic acid sequences. Examples of such disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

In one embodiment the methods disclosed herein may be used to detect, stage, diagnose, and/or treat a disorder associated with expression of the nucleic acid sequences. Examples of such a disorder include, but are not limited to, endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalcemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences may be used in Southern or Northern analysis, dot blot, or other membrane-based technologies; in PCR technologies; in dipstick, pin, and ELISA assays; and in microarrays utilizing fluids or tissues from patients to detect altered nucleic acid sequence expression. Such qualitative or quantitative methods are well known in the art.

CHARACTERIZATION AND BEST MODE OF THE INVENTION

PARADIGM: Inference of Patient-Specific Pathway Activities from Multi-Dimensional Cancer Genomics Data Using PARADIGM.

One hypothesis of pathway-based approaches is that the genetic interactions found in pathway databases carry information for interpreting correlations between gene expression changes detected in cancer. For example, if a cancer-related pathway includes a link from a transcriptional activator A to a target gene T, we expect the expression of A to be positively correlated with the expression of T (E2E correlation). Likewise, we also expect a positive correlation between A's copy number and T's expression (C2E correlation). Further, we expect C2E correlation to be weaker than E2E correlation because amplification in A docs not necessarily imply A is expressed at higher levels, which in turn is necessary to upregulate B. In this way, each link in a pathway provides an expectation about the data; pathways with many consistent links may be relevant for further consideration. We tested these assumptions and found that the NCI pathways contain many interactions predictive of the recent TCGA GBM data (The TCGA research network 2008).

We have developed an approach called PARADIGM (PAthway Recognition Algorithm using Data Integration on Genomic Models) to infer the activities of genetic pathways from integrated patient data.

The PARADIGM method integrates diverse high-throughput genomics information with known signaling pathways to provide patient-specific genomic inferences on the state of gene activities, complexes, and cellular processes. The core of the method uses a factor graph to leverage inference for combining the various data sources. The use of such inferences in place of, or in conjunction with, the original high-throughput datasets improves our ability to classify samples into clinically relevant subtypes. Clustering the GBM patients based on the PARADIGM-integrated activities revealed patient subtypes correlated with different survival profiles. In contrast, clustering the samples either using the expression data or the copy-number data did not reveal any significant clusters in the dataset.

PARADIGM produces pathway inferences of significantly altered gene activities in tumor samples from both GBM and breast cancer. Compared to a competing pathway activity inference approach called SPIA, our method identifies altered activities in cancer-related pathways with fewer false-positives. For computational efficiency, PARADIGM currently uses the NCI pathways as is.

While it infers hidden quantities using EM, it makes no attempt to infer new interactions not already present in an NCI pathway. One can imagine expanding the approach to introduce new interactions that increase the likelihood function. While this problem is intractable in general, heuristics such as structural EM (Friedman (1997) supra) can be used to identify interactions using computational search strategies.

Rather than searching for novel connections de novo one could speed up the search significantly by proposing interactions derived from protein-protein interaction maps or gene pairs correlated in a significant number of expression datasets. The power of the pathway-based approach is it may provide clues about the possible mechanisms underlying the differences in observed survival. Informative IPAs may be useful for suggesting therapeutic targets or to select the most appropriate patients for clinical trials. For example, the ErbB2 amplification is a well-known marker of particular forms of breast cancer that are treatable by the drug trastuzumab.

However, some patients with the ErbB2 amplification have tumors that are refractory to treatment. Inspection of a CircleMap display could identify patients with ErbB2 amplifications but have either inactive or unchanged IPAs as inferred by PARADIGM. Patients harboring the ErbB2 amplification but without predicted activity could be considered for alternative treatment.

As more multidimensional datasets become available in the future, it will be interesting to test whether such pathway inferences provide robust biomarkers that generalize across cohorts.

Subtype and Pathway Specific Responses to Anti-Cancer Compounds in Breast Cancer More than 800 small molecule inhibitors and biologics are now under development for treatment of human malignancies (New Medicines Database I PHRMA. newmeds.phrma.org (2010). Many of these agents target molecular features thought to distinguish tumor from normal cells, and range from broad-specificity conventional therapeutics, including anti-metabolites and DNA cross-linking agents, such as trastuzumab and lapatinib, that selectively target molecular events and pathways deregulated in cancer subsets (see for example, Slamon, D. J. et al. Use of chemotherapy plus a monoclonal antibody against HER2 for metastatic breast cancer that overexpresses HER2. *N Engl J Med* 344, 783-792 (2001),Vogel, C. L. et al. Efficacy and safety of trastuzumab as a single agent in first-line treatment of HER2-overexpressing metastatic breast cancer. *J Clin Oncol* 20, 719-726 (2002); Rusnak, D. W. et al. The effects of the novel, reversible epidermal growth factor receptor/ErbB-2 tyrosine kinase inhibitor, GW2016, on the growth of human normal and tumor-derived cell lines in vitro and in vivo. *Mol Cancer Ther* 1, 85-94 (2001)). Effects of chemotherapy and hormonal therapy for early breast cancer on recurrence and 15-year survival: an overview of the randomised trials. *Lancet* 365, 1687-1717 (2005).

The general trend in drug development today is moving toward targeted agents that show increased efficacy and lower toxicity than conventional agents (Sawyers, C. Targeted cancer therapy. *Nature* 432, 294-297 (2004)). Some drugs, such as the ERBB2/EGFR inhibitor lapatinib, show high target specificity while others, such as the SRC inhibitor dasatinib, inhibit a broad range of kinases (Karaman, M. W. et al. A quantitative analysis of kinase inhibitor selectivity. *Nat Biotechnol* 26, 127-132 (2008)).

There is growing recognition that clinical trials must include predictors of response and stratify patients entering the trial. While many molecularly targeted therapeutic agents offer obvious molecular features on which to stratify patients, most do not. Moreover, molecular and biological differences between tumors, complex cross-coupling and feedback regulation of targeted pathways and imprecise targeting specificity frequently complicate basic mechanistic predictions. While responsive subsets can be identified during the course of molecular marker based clinical trials, this approach is logistically difficult, expensive, and does not allow experimental compounds to be initially tested in selected subpopulations most likely to respond. Indeed, the majority of drugs now under development will never be tested in breast cancer, so the probability is high that compounds that are very effective only in subpopulations of patients with breast cancer will be missed. A promising approach is to employ predictors of response derived from preclinical models to stratify patients entering clinical trials, which would reduce development costs and identify those drugs that may be particularly effective in subsets of patients.

Preclinical testing in panels of cell lines promises to allow early and efficient identification of responsive molecular subtypes as a guide to early clinical trials. Evidence for the utility of this approach comes from studies showing that cell line panels predict (a) lung cancers with EGFR mutations as responsive to gefitinib (Paez, J. G. et al. EGFR mutations in lung cancer: correlation with clinical response to gefitinib therapy. *Science* 304, 1497-1500 (2004)), (b) breast cancers with HER2/ERBB2 amplification as responsive to trastuzumab and/or lapatinib (Neve, R. M. et al. A collection of breast cancer cell lines for the study of functionally distinct cancer subtypes. *Cancer Cell* 10, 515-527 (2006); Konecny, G. E. et al. Activity of the dual kinase inhibitor lapatinib (GW572016) against HER-2-overexpressing and trastuzumab-treated breast cancer cells. *Cancer Res* 66, 1630-1639 (2006)), and (c) tumors with mutated or amplified BCR-ABL as resistant to imatinib mesylate (Scappini, B. et al. Changes associated with the development of resistance to imatinib (STI571) in two leukemia cell lines expressing p210 Bcr/Abl protein. *Cancer* 100, 1459-1471 (2004)). The NCI's Discovery Therapeutic Program has pursued this approach on large scale, identifying associations between molecular features and responses to >100,000 compounds in a collection of ~60 cancer cell lines (Weinstein, J. N. Spotlight on molecular profiling: "Integromic" analysis of the NCI-60 cancer cell lines. *Mol Cancer Ther* 5, 2601-2605 (2006); Bussey, K. J. et al. Integrating data on DNA copy number with gene expression levels and drug sensitivities in the NCI-60 cell line panel. *Mol Cancer Ther* 5, 853-867 (2006)). Although useful for detecting compounds with diverse responses, the NCI60 panel is arguably of limited power in detecting subtype specific responses because of the relatively sparse representation of specific cancer subtypes in the collection. For example, the collection carries only 6 breast cancer cell lines, which is not enough to adequately represent the known heterogeneity. We have therefore promoted the use of a collection of ~50 breast cancer cell lines for more statistically robust identification of associations between in vitro therapeutic compound response and molecular subtypes and activated signaling pathways in breast cancer. Here we report the assessment of associations between quantitative growth inhibition responses and molecular features defining subtypes and activated pathways for 77 compounds, including both FDA approved drugs and investigational compounds. Approximately half show aberration or subtype specificity. We also show via integrative analysis of gene expression and copy number data that some of the observed subtype-associated responses can be explained by specific pathway activities.

Integrated Molecular Profiles Reveal Distorted Interleukin Signalling in Dcis and Improved Prognostic Power in Invasive Breast Cancer The accumulation of high throughput molecular profiles of tumors at various levels has been a long and costly process worldwide. Combined analysis of gene regulation at various levels may point to specific biological functions and molecular pathways that are deregulated in multiple epithelial cancers and reveal novel subgroups of patients for tailored therapy and monitoring. We have collected high throughput data at several molecular levels derived from fresh frozen samples from primary tumors, matched blood, and with known micrometastases status, from approximately 110 breast cancer patients (further referred to as the MicMa dataset). These patients are part of a cohort of over 900 breast cancer cases with information about presence of disseminated tumor cells (DTC), long-term follow-up for recurrence and overall survival. The MicMa set has been used in parallel pilot studies of whole genome mRNA expression (Naume, B. et al., (2007), Presence of bone marrow micrometastasis is associated with different recurrence risk within molecular subtypes of breast cancer, 1: 160-17), arrayCGH (Russnes, H. G. et al., (2010), Genomic architecture characterizes tumor progression paths and fate in breast cancer patients, 2: 38ra472), DNA methylation (Ronneberg, J. A. et al., (2011), Methylation profiling with a panel of cancer related genes: association with estrogen receptor, TP53 mutation status and expression subtypes in sporadic breast cancer, 5: 61-76), whole genome SNP and SNP-CGH (Van, Loo P. et al., (2010), Allele-specific copy number analysis of tumors, 107: 16910-169154), whole genome miRNA expression analyses (Enerly E, Steinfeld I, Kleivi K, Leivonen S, Aure M R, Russnes H G, Ronneberg J A, Johnsen H, Navon R, Rodland E, Makela R, Naume B, Perath. M, Kallioniemi O, Kristensen V N, Yakhini Z, BOrresen-Dale A. miRNA-mRNA integrated analysis reveals roles for miRNAs in primary breast tumors. PLoS ONE 2011; 6(2):e16915). TP53 mutation status dependent pathways and high throughput paired end sequencing (Stephens, P. J. et al., (2009), Complex landscapes of somatic rearrangement in human breast cancer genomes, 462: 10051010). This is a comprehensive collection of high throughput molecular data performed by a single lab on the same set of primary tumors of the breast.

Below we summarize the findings of these studies, each of which has attempted to integrate mRNA expression with either DNA copy numbers, deregulation in DNA methylation or miRNA expression. While in the past we and others have looked at breast cancer mechanisms on multiple molecular levels, there has been very sparse attempt to integrate these views by modeling mRNA, CNAs, miRNAs, and methylation in a pathway context. In this paper we have analyzed such data from breast cancers in concert to both detect pathways perturbed and molecular subtypes with distinct phenotypic characteristics.

In the MicMa dataset discussed here we have identified three major clusters (and one minor) based on the methylation profiles; one of the major clusters consisted mainly of tumors of myoepithelial origin and two others with tumors of predominantly luminal epithelial origin. The clusters were different with respect to TP53 mutation and ER, and ErbB2 expression status, as well as grade. Pathway analyses identified a significant association with canonical (curated) pathways including genes like EGF, NGFR and TNF, dendritic cell maturation and the NF-KB signaling pathway. Pyrosequencing of candidate genes on samples from DCIS's and invasive cancers identified ABCB1, FOXC1, PPP2R2B and PTEN as novel genes methylated in DCIS. Understanding how these epigenetic changes are involved in triggering tumor progression is important for a better understanding of which lesions are "at risk" of becoming invasive.

We have also investigated the relationship between miRNA and mRNA expression in the MicMa dataset, in terms of their correlation with each other and with clinical characteristics. We were able to show that several cellular processes, such as proliferation, cell adhesion and immune response, are strongly associated with certain miRNAs. Statistically significant differential expression of miRNAs was observed between molecular intrinsic subtypes, and between samples with different levels of proliferation. We validated the role of miRNAs in regulating proliferation using high-throughput lysate-microarrays on cell lines and point to potential drivers of this process (Enerly et al. (2001) supra).

Over 40 KEGG pathways were identified showing differential enrichment according to TP53 mutation status at the p-value cut-off level of 10e-6 in this cohort of breast cancer patients. The differential enrichment of pathways was also observed on the cross-platform dataset consisting of 187 breast cancer samples, based on two different microarray platforms. Differentially enriched pathways included several known cancer pathways such as TP53 signaling and cell cycle, signaling pathways including immune response and cytokine activation and metabolic pathways including fatty acid metabolism (Joshi et al, 2011 supra).

Each of the studies described earlier has attempted to derive biological interactions from high throughput molecular data in a pair-wise fashion (CNA/mRNA, miRNA/mRNA, DNAmeth/mRNA, TP53/inRNA). In the present study we have attempted to focus on the deregulated pathways and develop an integrated prognostic index taking into account all molecular levels simultaneously. We applied the Pathway Recognition Algorithm using Data integration on Genomic Models (PARADIGM) to elucidate the relative activities of various genetic pathways and to evaluate their joint prognostic potential. The clusters and deregulated pathways identified by PARADIGM were then validated in another dataset (Chin, S. F. et al., (2007), Using array-comparative genomic hybridization to define molecular portraits of primary breast cancers, 26: 1959-1970), and also studied in a dataset of premalignant neoplasia such as DCIS, (ductal carcinoma in situ) (Muggerud, A. A. et al., (2010), Molecular diversity in ductal carcinoma in situ (DCIS) and early invasive breast cancer, 4: 357-368).

Frequently Altered Pathways in Ovarian Serous Carcinomas

To identify significantly altered pathways through an integrated analysis of both copy number and gene expression, we applied the recently developed pathway activity inference method PARADIGM (PM1D: 20529912). The computational model incorporates copy number changes, gene expression data, and pathway structures to produce an integrated pathway activity (IPA) for every gene, complex, and genetic process present in the pathway database. We use the term "entity" to refer to any molecule in a pathway be it a gene, complex, or small molecule. The IPA of an entity refers only to the final activity. For a gene, the IPA only refers to the inferred activity of the active state of the protein, which is inferred from copy number, gene expression, and the signaling of other genes in the pathway. We applied PARADIGM to the ovarian samples and found alterations in many different genes and processes present in pathways contained in the National Cancer Institutes' Pathway Interaction Database (NCI-PID). We assessed the significance of the inferred alterations using 1000 random simulations in which pathways with the same structure were used but arbitrary genes were assigned at different points in the pathway. In other words, one random simulation for a given pathway kept the set of interactions fixed so that an arbitrary set of genes were connected together with the pathway's interactions. The significance of all samples' IPAs was assessed against the same null distribution to obtain a significance level for each entity in each sample. IPAs with a standard deviation of at least 0.1 are displayed as a heatmap in FIG. 28.

Table 3 shows the pathways altered by at least three standard deviations with respect to pennuted samples found by PARADIGM. The FOXM1 transcription factor network was altered in the largest number of samples among all pathways tested—67% of entities with altered activities when averaged across samples. In comparison, pathways with the next highest level of altered activities in the ovarian cohort included PLK1 signaling events (27%), Aurora B signaling (24%), and Thromboxane A2 receptor signaling (20%). Thus, among the pathways in NCI-PID, the FOXM1 network harbors significantly more altered activities than other pathways with respect to the ovarian samples.

The FOXM1 transcription factor network was found to be differentially altered in the tumor samples compared to the normal controls in the highest proportion of the patient samples (FIG. 29). FOXM1 is a multifunctional transcription factor with three known dominant splice forms, each regulating distinct subsets of genes with a variety of roles in cell proliferation and DNA repair. The FOXM1c isofonn directly regulates several targets with known roles in cell proliferation including AUKB, PLK1, CDC25, and BIRC5 (PM D:15671063). On the other hand, the FOXM1b isofonn regulates a completely different subset of genes that include the DNA repair genes BRCA2 and XRCC1 (PMID: 17101782). CHEK2, which is under indirect control of ATM, directly regulates FOXMIs expression level.

We asked whether the IPAs of the FOXM1 transcription factor itself were more highly altered than the IPAs of other transcription factors. We compared the FOXM1 level of activity to all of the other 203 transcription factors in the NCI-PID. Even compared to other transcription factors in the NCI set, the FOXM1 transcription factor had significantly higher levels of activity (p<0.0001; K-S test) suggesting further that it may be an important signature (FIGS. 30A-30B).

Because FOXM1 is also expressed in many different normal tissues of epithelial origin, we asked whether the signature identified by PARADIGM was due to an epithelial signature that would be considered normal in other tissues. To answer this, we downloaded an independent dataset from GEO (GSE10971) (PMID:18593983) in which fallopian tube epithelium and ovarian tumor tissue were microdissected and gene expression was assayed. We found that the levels of FOXM1 were significantly higher in the tumor samples compared to the normals, suggesting FOXM1 regulation is indeed elevated in cancerous tissue beyond what is seen in normal epithelial tissue (FIG. 31).

Because the entire cohort for the TCGA ovarian contained samples derived from high-grade serous tumors, we asked whether the FOXM1 signature was specific to high-grade serous. We obtained the log expression of FOXM1 and several of its targets from the dataset of Etemadmoghadam et al. (2009) (Etemadmoghadam D, deFazio A, Beroukhim R, Mermel C, George J, Getz G, Tothill R, Okamoto A, Raeder M B, AOCS Study Group, Harnett P, Lade S, Akslen L A, Tinker A V, Locandro B, Alsop K, Chiew Y E, Traficante N, Fereday S, Johnson D, Fox S, Sellers W, Urashima M, Salvesen H B, Meyerson M, Bowtell D. Integrated Genome-Wide DNA Copy Number and Expression Analysis Identifies Distinct Mechanisms of Primary Chemoresistance in Ovarian Carcinomas. Clinical Cancer Research 2009 February; 15(4):1417-1427) in which both low- and high-grade serous tumors had been transcriptionally profiled. This independent data confirmed that FOXM1 and several of its targets are significantly up-regulated in serous ovarian relative to low-grade ovarian cancers (FIG. 32). To determine if the 25 genes in the FOXM1 transcription factor network contained a significant proportion of genes with higher expression in high-grade disease, we performed a Student's t-test using the data from Etemadmoghadam. 723 genes in the genome (5.4%) were found to be significantly up-regulated in high- versus low-grade cancer at the 0.05 significance level (corrected for multiple testing using the Benjamini-Hochberg method). The FOXM1 network was found to have 13 of its genes (52%) differentially regulated, which is a significant proportion based on the hypergeometric test (P<3.8*10$^{12}$). Thus, high expression of the FOXM1 network genes does appear to be specifically associated with high-grade disease when compared to the expression of typical genes in the genome.

The role of FOXM1 in many different cancers including breast and lung has been well documented but its role in ovarian cancer has not been investigated. FOXM1 is a multifunctional transcription factor with three known splice forms, each regulating distinct subsets of genes with a variety of roles in cell proliferation and DNA repair. An excerpt of FOXM1's interaction network relevant to this analysis is shown in FIG. 27. The FOXM1a isoform directly regulates several targets with known roles in cell proliferation including AUKB, PLK1, CDC25, and BIRC5. In contrast, the FOXM1b isoform regulates a completely different subset of genes that include the DNA repair genes BRCA2 and XRCC1. CHEK2, which is under indirect control of ATM, directly regulates FOXM1's expression level. In addition to increased expression of FOXM1 in most of the ovarian patients, a small subset also have increased copy number amplifications detected by CBS (19% with copy number increases in the top 5% quantile of all genes in the genome measured). Thus the alternative splicing regulation of FOXM1 may be involved in the control switch between DNA repair and cell proliferation. However, there is insufficient data at this point to support this claim since the exon structure distinguishing the isoforms and positions of the Exon array probes make it difficult to distinguish individual isoform activities. Future high-throughput sequencing of the mRNA of these samples may help determine the differential levels of the FOXM1 isoforms. The observation that PARADIGM detected the highest level of altered activity centered on this transcription factor suggests that FOXM1 resides at a critical regulatory point in the cell.

Diagnostics

The methods herein described may be used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, non-proliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In another aspect, the nucleic acid of the invention.

The methods described herein may be used to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level that is observed in a normal subject. The results obtained from successive assays may be used to show the efficacy of treatment over a period ranging from several days to months.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations. Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle that produces the number of organisms needed to satisfy statistical requirements.

Acute toxicity tests are based on a single administration of the agent to the subject to determine the symptomology or lethality of the agent. Three experiments are conducted: (a) an initial dose-range-finding experiment, (b) an experiment to narrow the range of effective doses, and (c) a final experiment for establishing the dose-response curve.

Prolonged toxicity tests are based on the repeated administration of the agent. Rats and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. Nos. 4,736,866; 5,175,383; and 5,767,337; incorporated herein by reference.) In some cases, the introduced gene may be activated at a specific time in a specific tissue type during fetal development or postnatally. Expression of the transgene is monitored by analysis of phenotype or tissue-specific mRNA expression in transgenic animals before, during, and after challenge with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene that disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Transformed ES cells are identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168: 342-357; Wiles and Keller (1991) Development 111: 259-267; and Klug et al. (1996) J. Clin. Invest. 98: 216-224). Recent developments demonstrate that ES cells derived from human blastocysts may also be manipulated in vitro to differentiate into eight separate cell lineages, including endoderm, mesoderm, and ectodermnal cell types (Thomson (1998) Science 282: 1145-1147).

Knockout Analysis

In gene knockout analysis, a region of a human disease gene candidate is enzymatically modified to include a non-mammalian gene such as the neomycin phosphotransferase gene (neo; see, for example, Capecchi (1989) Science 244: 1288-1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells that contain the integrated human gene are handled as described above. Inbred animals are studied and treated to obtain information on the analogous human condition. These methods have been used to model several human diseases. (See, for example, Lee et al. (1998) Proc. Natl. Acad. Sci. 95: 11371-11376; Baudoin et al. (1998) Genes Dev. 12: 1202-1216; and Zhuang et al. (1998) Mol. Cell Biol. 18: 3340-3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulata*) and common marmosets (Callithrix jacchus) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as "extensive metabolizers" and "poor metabolizers" of these agents.

Exemplary Uses of the Invention

Personalized medicine promises to deliver specific treatment(s) to those patients mostly likely to benefit. We have shown that approximately half of therapeutic compounds are preferentially effective in one or more of the clinically-relevant transcriptional or genomic breast cancer subtypes. These findings support the importance of defining response-related molecular subtypes in breast cancer treatment. We also show that pathway integration of the transcriptional and genomic data on the cell lines reveals subnetworks that provide mechanistic explanations for the observed subtype specific responses. Comparative analysis of subnet activities between cell lines and tumors shows that the majority of subtype-specific subnetworks are conserved between cell lines and tumors. These analyses support the idea that preclinical screening of experimental compounds in a well-characterized cell line panel can identify candidate response-associated molecular signatures that can be used for sensitivity enrichment in early-phase clinical trials. We suggest that this in vitro assessment approach will increase the likelihood that responsive tumor subtypes will be identified before a compound's clinical development begins, thereby reducing cost, increasing the probability of eventual FDA approval and possibly avoiding toxicity associated with treating patients unlikely to respond. In this study we have assessed only molecular signatures that define transcriptional subtypes and selected recurrent genome CNAs. We anticipate that the power and precision of this approach will increase as additional molecular features such as genetic mutation, methylation and alternative splicing, are included in the analysis. Likewise, increasing the size of the cell line panel will increase the power to assess less common molecular patterns within the panel and increase the probability of representing a more complete range of the diversity that exists in human breast cancers.

Breast cancer development is characterized by significant increases in the presence of both innate and adaptive immune cells, with B cells, T cells, and macrophages representing the most abundant leukocytes present in neoplastic stroma (DeNardo D G, Coussens L M. Inflammation and breast cancer. Balancing immune response: crosstalk between adaptive and innate immune cells during breast cancer progression. Breast Cancer Res. 2007; 9(4):212). High immunoglobulin (Ig) levels in tumor stoma (andserum), and increased presence of extra follicular B cells, T regulatory cells, and high ratios of CD4/CD8 or TH2/TH1 T lymphocytes in primary tumors or in lymph nodes have been shown to correlate with tumor grade, stage, and overall patient survival (Bates, G. J. et al., (2006), Quantification of regulatory T cells enables the identification of high-risk breast cancer patients and those at risk of late relapse, 24: 5373-5380); Some leukocytes exhibit antitumor activity, including cytotoxic T lymphocytes (CTLs) and natural killer (NK) cells (34 Dunn, G. P., Koebel, C. M., and Schreiber, R. D., (2006), Interferons, immunity and cancer immunoediting, 6: 836-848), other leukocytes, such as mast cells, Bcells, dendritic cells, granulocytes, and macrophages, exhibit more bipolar roles, through their capacity to either hamper or potentiate tumor progression (35 de Visser, K. E. and Coussens, L. M., (2006), The inflammatory tumor microenvironment and its impact on cancer development, 13: 118-137). The most prominent finding in these studies was the identification of the perturbation in the immune response (TCR) and interleukin signaling, IL4, IL6, IL12 and IL23 signaling leading to classification of subclasses with prognostic value. We provide here evidence that these events are mirrored in high throughput molecular data and interfere strongly with molecular sub-classification of breast tumors.

This disclosure also provides the first large scale integrative view of the aberrations in HGS-OvCa. Overall, the mutational spectrum was surprisingly simple. Mutations in TP53 predominated, occurring in at least 96% of HGS-OvCa while BRCA1/2 were mutated in 22% of tumors due to a combination of germline and somatic mutations. Seven other significantly mutated genes were identified, but only in 2-6% of HGS-OvCa. In contrast, HGS-OvCa demonstrates a remarkable degree of genomic disarray. The frequent SCNAs are in striking contrast to previous TCGA findings with glioblastoma46 where there were more recurrently mutated genes with far fewer chromosome arm-level or focal SCNAs (FIG. 37A). A high prevalence of mutations and promoter methylation in putative DNA repair genes including HR components may explain the high prevalence of SCNAs. The mutation spectrum marks HGS-OvCa as completely distinct from other OvCa histological subtypes. For example, clear-cell OvCa have few TP53 mutations but have recurrent ARID1A and PIK3CA47-49 mutations: endometrioid OvCa have frequent CTINBI, ARID1A, and PIK3CA mutations and a lower rate of TP5348,49 while mucinous OvCa have prevalent KRAS mutations50. These differences between ovarian cancer subtypes likely reflect a combination of etiologic and lineage effects, and represent an opportunity to improve ovarian cancer outcomes through subtype-stratified care.

Identification of new therapeutic approaches is a central goal of the TCGA. The ~50% of HGS-OvCa with HR defects may benefit from PARP inhibitors. Beyond this, the commonly deregulated pathways, RB, RAS/PI3K, FOXM1, and NOTCH, provide opportunities for therapeutic attack. Finally, inhibitors already exist for 22 genes in regions of recurrent amplification (see Examples XIII et seq.), warranting assessment in HGS-OvCa where the target genes are amplified. Overall, these discoveries set the stage for approaches to treatment of HGS-OvCa in which aberrant genes or networks are detected and targeted with therapies selected to be effective against these specific aberrations.

In additional embodiments, the polynucleotide nucleic acids may be used in any molecular biology techniques that have yet to be developed, provided the new techniques rely on properties of nucleic acid molecules that are currently known, including, but not limited to, such properties as the triplet genetic code and specific base pair interactions.

The invention will be more readily understood by reference to the following examples, which are included merely for purposes of illustration of certain aspects and embodiments of the present invention and not as limitations.

EXAMPLES

Example I: Data Sources

Breast cancer copy number data from Chin (2007 supra) was obtained from NCBI Gene Expression Omnibus (GEO) under accessions GPL5737 with associated array platform annotation from GSE8757.

Probe annotations were converted to BED15 format for display in the UCSC Cancer Genomics Browser (Zhu:2009, supra) and subsequent analysis. Array data were mapped to probe annotations via probe ID. Matched expression data from Naderi (2007, supra) was obtained from MIAM1Express at EBI using accession number E-UCon-1. Platform annotation information for Human 1A (V2) was obtained from the Agilent website. Expression data was probe-level median-normalized and mapped via probe ID to HUGO gene names.

All data was non-parametrically normalized using a ranking procedure including all sample-probe values and each gene-sample pair was given a signed p-value based on the rank. A maximal p-value of 0.05 was used to determine gene-samples pairs that were significantly altered.

The glioblastoma data from TCGA was obtained from the TCGA Data Portal providing gene expression for 230 patient samples and 10 adjacent normal tissues on the Affymetrix U133A platform. The probes for the patient samples were normalized to the normal tissue by subtracting the median normal value of each probe. In addition, CBS segmented (Olshen:2004 supra p1618) copy number data for the same set of patients were obtained. Both datasets were non-parametrically normalized using the same procedure as the breast cancer data.

Example II: Pathway Compendium

We collected the set of curated pathways available from the National Cancer Institute Pathway Interaction Database (NCI PID) (Schaefer:2009 supra). Each pathway represents a set of interactions logically grouped together around high-level biomolecular processes describing intrinsic and extrinsic sub-cellular-, cellular-, tissue-, or organism-level events and phenotypes. BioPAX level 2 formatted pathways were downloaded. All entities and interactions were extracted with SPARQL queries using the Rasqal RDF engine.

We extracted five different types of biological entities (entities) including three physical entities (protein-coding genes, small molecules, and complexes), gene families, and abstract processes. A gene family was created whenever the cross-reference for a BioPAX protein listed proteins from distinct genes. Gene families represent collections of genes in which any single gene is sufficient to perform a specific function. For example, homologs with redundant roles and genes found to functionally compensate for one another are combined into families.

The extraction produced a list of every entity and interaction used in the pathway with annotations describing their different types. We also extracted abstract processes, such as "apoptosis," that refer to general processes that can be found in the NCI collection. For example, pathways detailing the interactions involving the p53 tumor suppressor gene include links into apoptosis and senescence that can be leveraged as features for machine-learning classification.

Figure 3:
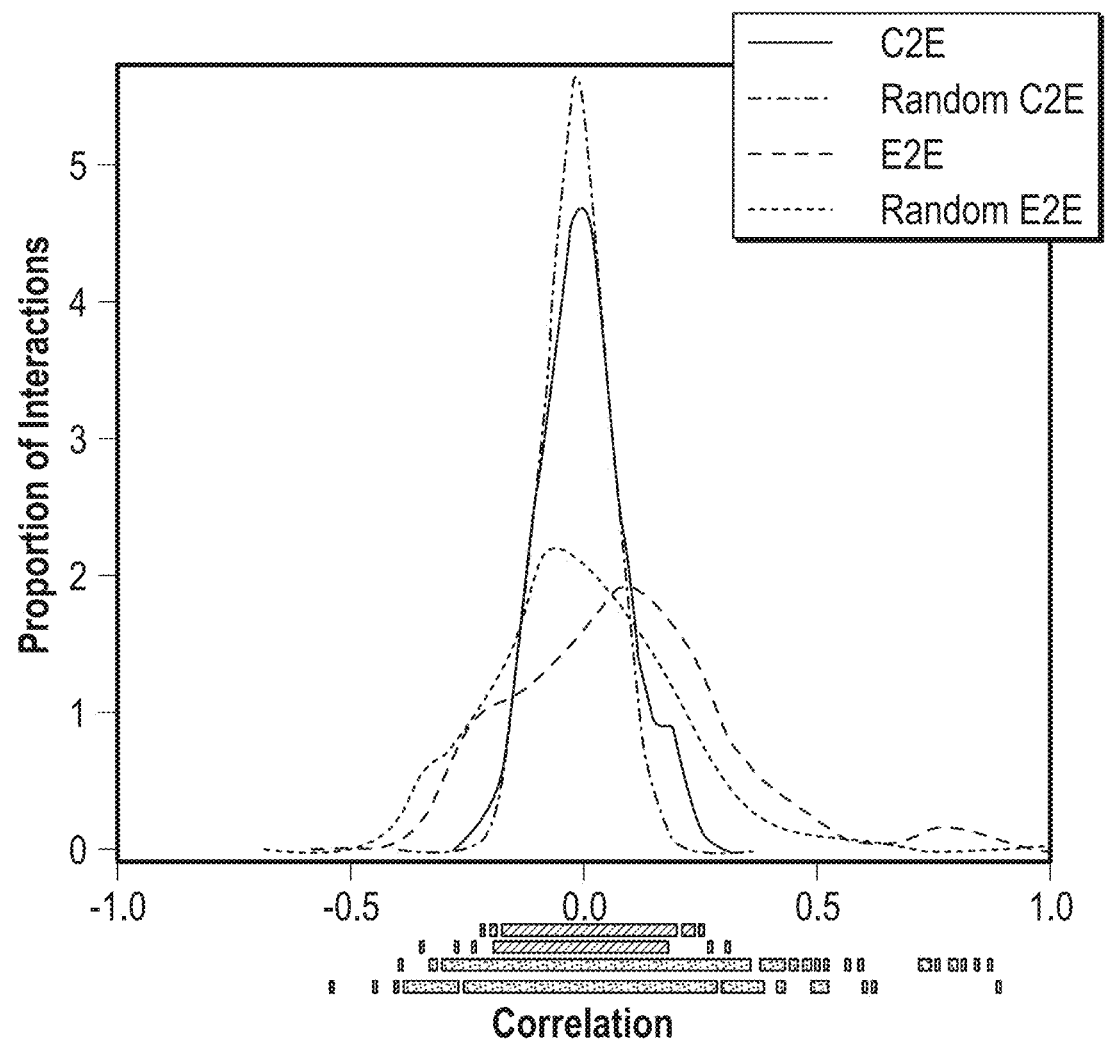
FIG. 3 illustrates exemplary NCI pathway interactions in The Cancer Genome Atlas (TCGA) project (cancergerionic.nih.gov) glioblastoma multiform (GMB) data. For all (n=462) pairs where A was found to be an upsterama ctivator of gene B in NCI-Nature Pathway Database, the Pearson correlation (x-axis) computed from the TCGA GMB data was calculated in two different ways. The histogram plots the correlations between the A's copy number and B's expression (C2E, solid red) and between A's expression and B's expression (E2E, solid blue). A histogram of correlations between randomly paired genes is shown for C2E (dashed red) and E2E (dashed blue). Arrows point to the enrichment of positive correlations found for the C2E (red) and E2E (blue) correlation.

As expected, C2E correlations were moderate, but had a striking enrichment for positive correlations among activating interactions than expected by chance (FIG. 3). E2E correlations were even stronger and similarly enriched. Thus, even in this example of a cancer that has eluded characterization, a significant subset of pathway interactions connect genomic alterations to modulations in gene expression, supporting the idea that a pathway-level approach is worth pursuing.

Example III: Modeling and Predicting Biological Pathways

We first converted each NCI pathway into a distinct probabilistic model. A toy example of a small fragment of the p53 apoptosis pathway is shown in FIGS. 2A-2C. A pathway diagram from NCI was converted into a factor graph that includes both hidden and observed states. The factor graph integrates observations on gene- and biological process-related state information with a structure describing known interactions among the entities.

To represent a biological pathway with a factor graph, we use variables to describe the states of entities in a cell, such as a particular mRNA or complex, and use factors to represent the interactions and information flow between these entities. These variables represent the \textit{differential state of each entity in comparison to a "control" or normal level rather than the direct concentrations of the molecular entities. This representation allows us to model many high-throughput datasets, such as gene expression detected with DNA microarrays, that often either directly measure the differential state of a gene or convert direct measurements to measurements relative to matched controls. It also allows for many types of regulatory relationships among genes. For example, the interaction describing MDM2 mediating ubiquitin-dependent degradation of p53 can be modeled as activated MDM2 inhibiting p53's protein level.

The factor graph encodes the state of a cell using a random variable for each entity $X = x_1, x_1 \ldots, x_n,$} and a set of m non-negative functions, or factors, that constrain the entities to take on biologically meaningful values as functions of one another. The j-th factor I defines a probability distribution over a subset of entities $X_j \subset X$.

The entire graph of entities and factors encodes the joint probability distribution over all of the entities as:

$$P(X) = \frac{1}{Z} \prod_{j=1}^{m} \Phi_j(X_j) \tag{1}$$

where $Z = \Pi \Sigma_{s\ xj} \Phi_j(S)$ is a normalization constant and S Xdenotes that S is a 'setting' of the variables in X.

Each entity can take on one of three states corresponding to activated, nominal, or deactivated relative to a control level (for example, as measured in normal tissue) and encoded as 1, 0, or −1 respectively. The states may be interpreted differently depending on the type of entity (for example, gene, protein, etc). For example, an activated mRNA entity represents overexpression, while an activated genomic copy entity represents more than two copies are present in the genome.

FIGS. 2A-2C show the conceptual model of the factor graph for a single protein-coding gene. For each protein-coding gene G in the pathway, entities are introduced to represent the copy number of the genome ($G_{DNA}$), mRNA expression ($G_{mRNA}$), protein level ($G_{protein}$), and protein activity ($G_{protein}$) (ovals labeled "DNA", "mRNA", "protein", and "active" in FIGS. 2A-2C). For every compound, protein complex, gene family, and abstract process in the pathway, we include a single variable with molecular type "active."

While the example in FIGS. 2A-2C show only one process ("Apoptosis"), in reality many pathways have multiple such processes that represent everything from outputs (for example, "Apoptosis" and "Senescence") to inputs (for example, "DNA damage") of gene activity.

In order to simplify the construction of factors, we first convert the pathway into a directed graph, with each edge in the graph labeled with either positive or negative influence. First, for every protein coding gene G, we add edges with a label "positive" from $G_{DNA}$ to $G_{mRNA}$ from $G_{mRNA}$ to $G_{mRNA}$ to $G_{protein}$ and from $G_{protein}$ to $G_{protein}$ to reflect the expression of the gene from its number of copies to the presence of an activated form of its protein product. Every interaction in the pathway is converted to a single edge in the directed graph.

Using this directed graph, we then construct a list of factors to specify the factor graph. For every variable $x_i$, we add a single factor $\Phi(X_i)$, where $X_i = \{x_i\} \cup \{\text{Parents}\}(x_i)\}$ and Parents ($x_i$) refers to all the parents of $x_i$ in the directed graph. The value of the factor for a setting of all values is dependent on whether $x_i$ is in agreement with its expected value due to the settings of Parents ($x_i$).

For this study, the expected value was set to the majority vote of the parent variables. If a parent is connected by a positive edge it contributes a vote of +1 times its own state to the value of the factor. Conversely, if the parent is connected by a negative edge, then the variable votes −1 times its own state. The variables connected to $x_i$ by an edge labeled "minimum" get a single vote, and that vote's value is the minimum value of these variables, creating an AND-like connection. Similarly the variables connected to $x_i$ by an edge labeled "maximum" get a single vote, and that vote's value is the maximum value of these variables, creating an OR-like connection. Votes of zero are treated as abstained votes. If there are no votes the expected state is zero. Otherwise, the majority vote is the expected state, and a tie between 1 and −1 results in an expected state of −1 to give more importance to repressors and deletions. Given this definition of expected state, $\Phi_i(x_i, \text{Parents}(x_i))$ is specified as:

$$\Phi_i(x_i, \text{Parents}(x_i)) = \begin{cases} 1 - \varepsilon & x_i \text{ is the expected state from Parents}(x_i) \\ \frac{\varepsilon}{2} & \text{otherwise} \end{cases}$$

For the results shown here, E was set to 0.001, but orders of magnitude differences in the choice of epsilon did not significantly affect results. Finally, we add observation variables and factors to the factor graph to complete the integration of pathway and multi-dimensional functional genomics data (FIGS. 2A-2C). Each discretized functional genomics dataset is associated with one of the molecular types of a protein-coding gene.

Array CGH/SNP estimates of copy number alteration are associated with the 'genome' type. Gene expression data is associated with the 'mRNA' type. Though not presented in the results here, future expansion will include DNA methylation data with the 'mRNA' type, and proteomics and gene-resequencing data with the 'protein' and 'active' types. Each observation variable is also ternary valued. The factors associated with each observed type of data are shared across all entities and learned from the data, as described next.

Example IV: Inference and Parameter Estimation

Let the set of assignments $D = \{x_1 = s_1, x_2 = s_2, x_2, \ldots, X_k = S_k,\}$ represent a complete set of data for a patient on the observed variables indexed 1 through k. Let $\{S_D X\}$ represent the set of all possible assignments of a set of variables X that are consistent with the assignments in D; i.e. any observed variables $x_1$ are fixed to their assignments in D while hidden variables can vary.

Given patient data, we would like to estimate whether a particular hidden entity x, is likely to be in state a, for example, how likely TP53's protein activity is −1 (inactivated) or 'Apoptosis' is +1 (activated). To do this, we must compute the prior probability of the event prior to observing patient's data. If $A_i(a)$ represents the singleton assignment set $\{x_1 = a\}$ and $\Phi$ is the fully specified factor graph, this prior probability is:

$$P(x_i = a \mid \Phi) = \frac{1}{Z} \prod_{j=1}^{m} \sum_{S \subseteq A_i(a) X_j} \Phi_j(S), \tag{2}$$

where Z is the normalization constant introduced in Equation (1). Similarly, the probability of $x_i$ is in state a along with all of the observations for the patient is:

$$P(x_i = a, D \mid \Phi) = \frac{1}{Z} \prod_{j=1}^{m} \sum_{S \subset A_i(a) \cup D_{x_j}} \Phi_j(S). \quad (3)$$

We used the junction tree inference algorithm with HUGIN updates for the majority of pathways. For pathways that take longer than 3 seconds of inference per patient, we use Belief Propagation with sequential updates, a convergence tolerance of $10^{-9}$, and a maximum of 10,000 iterations. All inference was performed in the real domain, as opposed to the log domain, and was performed with libDAI (Mooij:2009 supra).

To learn the parameters of the observation factors we use the Expectation-Maximization (EM) algorithm (Dempster (1977) supra). Briefly, EM learns parameters in models with hidden variables by iterating between inferring the probabilities of hidden variables and changing parameters to maximize likelihood given the probabilities of hidden variables. We wrote and contributed code to libDAI to perform EM. For each pathway, we created a factor graph for each patient, applied the patient's data, and ran EM until the likelihood changed less than 0.1%. We averaged the parameters learned from each pathway, and then used these parameters to calculate final posterior beliefs for each variable.

After inference, we output an integrated pathway activity for each variable that has an "active" molecular type. We computed a log-likelihood ratio using quantities from equations 2 and 3 that reflects the degree to which a patient's data increases our belief that entity i's activity is up or down:

$$L(i, a) = \log\left(\frac{P(D_1 x_i = a \mid \Phi)}{P(D_1 x_i \neq a \mid \Phi)}\right) - \log\left(\frac{P(x_i = a \mid \Phi)}{P(x_i \neq a \mid \Phi)}\right) \quad (4)$$

$$= \log\left(\frac{P(D \mid x_i = a_1 \Phi)}{P(D \mid x_i \neq a_1 \Phi)}\right).$$

We then computed a single integrated pathway activity (IPA) for gene i based on the log-likelihood ratio as:

$$IPA(i) = \begin{cases} L(i, 1) & L(i, 1) > L(i, -1) \text{ and } L(i, 1) > L(i, 0) \\ -L(i, -1) & L(i, -1) > L(i, 1) \text{ and } L(i, -1) > L(i, 0) \\ 0 & \text{otherwise} \end{cases} \quad (5)$$

Intuitively, the IPA score reflects a signed analog of the log-likelihood ratio, L.

If the gene is more likely to be activated, the IPA is set to L. Alternatively, if the gene is more likely to be inactivated, the IPA is set to the negative of the log likelihood ratio. If the gene is most likely unchanged, the IPA is set to zero. Each pathway is analyzed independently of other pathways. Therefore, a gene can be associated with multiple inferences, one for each pathway in which it appears. Differing inferences for the same gene can be viewed as alternative interpretations of the data as a function of the gene's pathway context.

Example V: Significance Assessment

We assess the significance of IPA scores by two different permutations of the data. For the "within" permutation, a permuted data sample is created by choosing a new tuple of data (i.e. matched gene expression and gene copy number) first by choosing a random real sample, and then choosing a random gene from within the same pathway, until tuples have been chosen for each gene in the pathway. For the "any" permutation, the procedure is the same, but the random gene selection step could choose a gene from anywhere in the genome. For both permutation types, 1,000 permuted samples are created, and the perturbation scores for each permuted sample is calculated. The distribution of perturbation scores from permuted samples is used as a null distribution to estimate the significance of true samples.

Example VI: Signaling Pathway Impact Analysis (SPIA)

Signaling Pathway Impact Analysis (SPIA) from Tarca (2009, supra) was implemented in C to reduce runtime and to be compatible with our analysis environment. We also added the ability to offer more verbose output so that we could directly compare SPIA and PARADIGM outputs. Our version of SPIA can output the accumulated perturbation and the perturbation factor for each entity in the pathway. This code is available upon request.

Example VII: Decoy Pathways

A set of decoy pathways was created for each cancer dataset. Each NCI pathway was used to create a decoy pathway which consisted of the same structure but where every gene in the pathway was substituted for a random gene in RefGene. All complexes and abstract processes were kept the same and the significance analysis for both PARADIGM and SPIA was run on the set of pathways containing both real and decoy pathways. The pathways were ranked within each method and the fraction of real versus total pathways was computed and visualized.

Example VIII: Clustering and Kaplan-Meier Analysis

Uncentered correlation hierarchical clustering with centroid linkage was performed on the glioblastoma data using the methods from Eisen (1998 supra p1621). Only IPAs with a signal of at least 0.25 across 75 patient samples were used in the clustering. By visual inspection, four obvious clusters appeared and were used in the Kaplan-Meier analysis. The Kaplan-Meier curves were computed using R and p-values were obtained via the log-rank statistic.

Example IX: Validation of PARADIGM

Figure 4:
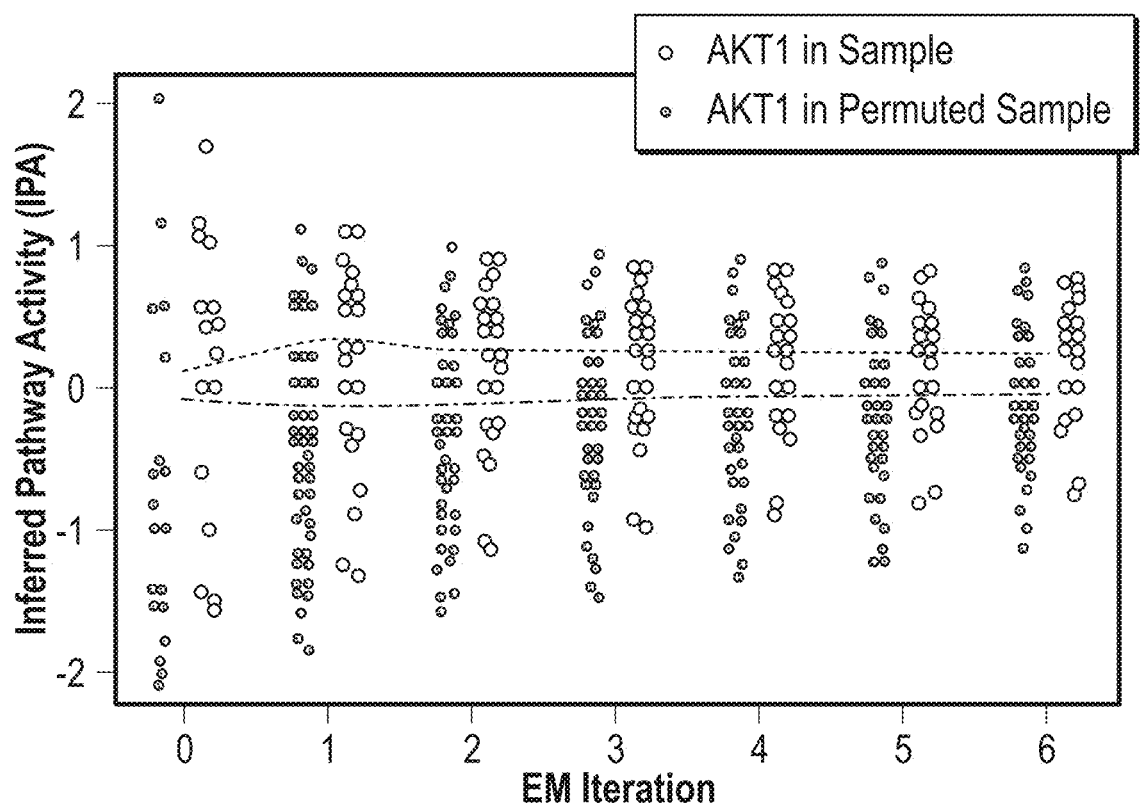
FIG. 4 illustrates exemplary learning parameters for the anti-apoptotic serine-threonine kinase 1 (AKTI). Integrated Pathway Activities (IPAs) are shown at each iteration of the Expectation-Maximization (EM) algorithm until convergence. Dots show IPAs from permuted samples and circles show IPAs fdrom real samples. The red line denotes the mean IPA in real samples and the green line denotes the man IPA of null samples.

To assess the quality of the EM training procedure, we compared the convergence of EM using the actual patient data relative to a null dataset in which tuples of gene expression and copy number (E,C) were permuted across the genes and patients. As expected, PARADIGM converged much more quickly on the true dataset relative to the null. As an example, we plotted the IPAs for the gene AKT I as a function of the EM iteration (FIG. 4). One can see that the activities quickly converge in the first couple of iterations. EM quickly converged to an activated level when trained with the actual patient data whereas it converged to an unchanged activity when given random data. The convergence suggests the pathway structures and inference are able to successfully identify patterns of activity in the integrated patient data.

We next ran PARADIGM on both breast cancer and GBM cohorts. We developed a statistical simulation procedure to determine which IPAs are significantly different than what would be expected from a negative distribution. We constructed the negative distribution by permuting across all of the patients and across the genes in the pathway. Empirically, we found that permuting only among genes in the pathway was necessary to help correct for the fact that each gene has a different topological context determined by the network. In the breast cancer dataset, 56,172 IPAs (7% of the total) were found to be significantly higher or lower than the matched negative controls. On average, NCI pathways had 497 significant entities per patient and 103 out of 127 pathways had at least one entity altered in 20% or more of the patients. In the GBM dataset, 141,682 IPAs (9% of the total) were found to be significantly higher or lower than the matched negative controls. On average, NCI pathways had 616 significant entities per patient and 110 out of 127 pathways had at least one entity altered in 20% or more of the patients.

As another control, we asked whether the integrated activities could be obtained from arbitrary genes connected in the same way as the genes in the NCI pathways. To do this, we estimated the false discovery rate and compared it to SPIA (Tarca: 2009 supra). Because many genetic networks have been found to be implicated in cancer, we chose to use simulated "decoy" pathways as a set of negative controls. For each NCI pathway, we constructed a decoy pathway by connecting random genes in the genome together using the same network structure as the NCI pathway.

Figure 5:
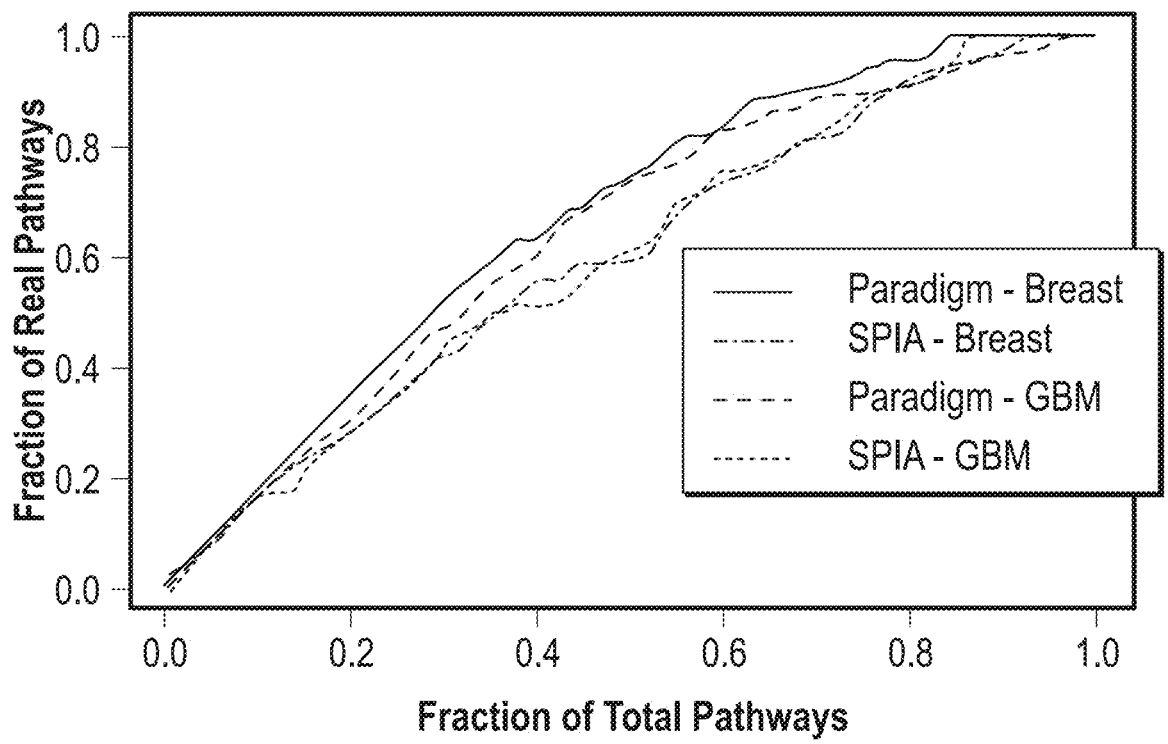
FIG. 5 illustrates distinguishing decoy from real pathways with PARADIGM and Signaling Pathway Impact Analysis (SPIA). Decoy pathways were created by assigning a new gene name to each gene in a pathway. PARADIGM and SPIA were then used to compute the perturbation of every pathway. Each line shows the receiver-operator characteristic for distinguishing real from decoy pathways using the perturbation ranking. In breast cancer, for example, the areas under the curve (AUCs) are 0.669 and 0.602 for PARADIGM and SPIA, respectively. In glioblastoma multiform (GBM), the AUCs are 0.642 and 0.604, respectively.

We then ran PARADIGM and SPIA to derive IPAs for both the NCI and decoy pathways. For PARADIGM, we ranked each pathway by the number of IPAs found to be significant across the patients after normalizing by the pathway size. For SPIA, pathways were ranked according to their computed impact factor. We found that PARADIGM excludes more decoy pathways from the top-most activated pathways compared to SP1A (FIG. 5). For example, in breast cancer, PARADIGM ranks 1 decoy in the top 10, 2 in the top 30, and 4 in the top 50. In comparison, SPIA ranks 3 decoys in the top 10, 12 in the top 30, and 22 in the top 50. The overall distribution of ranks for NCI IPAs are higher in PARADIGM than in SPIA, observed by plotting the cumulative distribution of the ranks (P 4 0.009, K-S test).

Example X: Top PARADIGM Pathways in Breast Cancer and GBM

We sorted the NCI pathways according to their average number of significant IPAs per entity detected by our permutation analysis and calculated the top 15 in breast cancer (Table 1) and GBM (Table 2)

Figure 6:
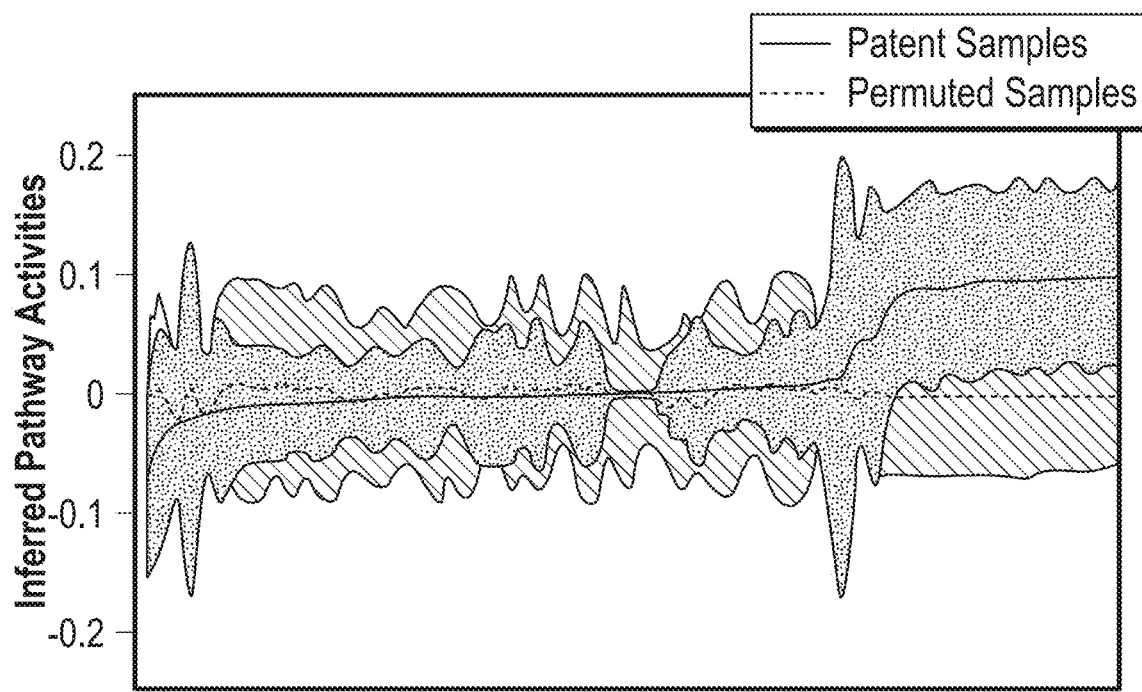
FIG. 6 illustrates exemplary patient sample IPAs compared with within permutations for Class I phosphatidylinositol-3-kinase (PI3K) signaling events mediated by Akt in breast cancer.

Several pathways among the top fifteen have been previously implicated in their respective cancers. In breast cancer, both SPIA and PARADIGM were able to detect the estrogen- and ErbB2-related pathways. In a recent major meta-analysis study (Wirapati P, Sotiriou C, Kunkel S, Farmer P, Pradervand S, Haibe-Kains B, Desmedt C, Ignatiadis M, Sengstag T, Schutz F, Goldstein D R, Piccart M, Delorenzi M. Meta-analysis of gene expression profiles in breast cancer: toward a unified understanding of breast cancer subtyping and prognosis signatures. Breast Cancer Res. 2008; 10(4):R65.), Wirapeti et al. found that estrogen receptor and ErbB2 status were two of only three key prognostic signatures in breast cancer. PARADIGM was also able to identify an AKT1-related PI3K signaling pathway as the top-most pathway with significant IPAs in several samples (see FIG. 6).

TABLE 1

Top PARADIGM pathways in breast cancer

| Rank | Name | Avg. | SPIA? |
|---|---|---|---|
| 1 | Class I P13K signaling events mediated by Akt | 20.7 | No |
| 2 | Nectin adhesion pathway | 14.1 | No |
| 3 | Insulin-mediated glucose transport | 13.8 | No |
| 4 | ErbB2IErbB3 signaling events | 12.1 | Yes |
| 5 | p75(NTR)-mediated signaling | 11.5 | No |
| 6 | HIF-1-alpha transcription factor network | 10.7 | No |
| 7 | Signaling events mediated by PTP1B | 10.7 | No |
| 8 | Plasma membrane estrogen inceptor signaling | 10.6 | Yes |
| 9 | TCR signaling in naive CD8+ T cells | 10.6 | No |
| 10 | Angiopoietin receptor Tie2-mediated signaling | 10.1 | No |
| 11 | Class 113 P13K non-lipid kinase events | 10.0 | No |
| 13 | Osteoponlin-mediated events • | 9.9 | Yes |
| 12 | IL4-mediated signaling events | 9.8 | No |
| 14 | Enclothel ins | 9.8 | No |
| 15 | Neurotrophic factor-mediated Trk signaling | 9.7 | No | aAverage number of samples in which significant activity was detected per entity.
$^b$Yes if the pathway was also ranked in SPINS top 15; No otherwise.

TABLE 2

Ibp PARADIGM pathways in GBM

| Rank | Name | Avg. | SPIA? |
|---|---|---|---|
| 1 | Signaling by Ret tyrosine kinase | 46.0 | No |
| 2 | Signaling events activated by Hepatocyte GFR | 43.7 | No |
| 3 | Endothelins | 42.5 | Yes |
| 4 | Arf6 downstream pathway | 42.3 | No |
| 5 | Signaling events mediated by HDAC Class III | 36.3 | No |
| 6 | FOXM1 transcription factor network | 35.9 | Yes |
| 7 | IL6-mediated signaling events | 33.2 | No |
| 8 | FoxO family signaling | 31.3 | No |
| 9 | IPA receptor mediated events | 30.7 | Yes |
| 10 | ErbB2JErbB3 signaling events | 30.1 | No |
| 11 | Signaling mediated by p38-alpha and p38-beta | 28.1 | No |
| 12 | HIF-1-alpha transcription factor network | 27.6 | Yes |
| 13 | Non-genotropic Androgen signaling | 27.3 | No |
| 14 | p38 MAPK signaling pathway | 27.2 | No |
| 15 | IL2 signnling events mediated by P13K | 26.9 | No |

Average number of samples in which significant activity was detected per entity.
Yes if the pathway was also ranked in SPIA's top 15; No otherwise.

The anti-apoptotic AKT1 serine-threonine kinase is known to be involved in breast cancer and interacts with the ERBB2 pathway (Ju X, Katiyar S, Wang C, Liu M, Jiao X, Li S. Zhou J, Turner J, Lisanti M P, Russell R G, Mueller S C, Ojeifo J, Chen W S, Hay N, Pestell R G. Aktl governs breast cancer progression in vivo. Proc. Natl. Acad. Sci. U.S.A. 2007 May; 104(18):7438-7443). In GBM, both FOXM1 and HIF-1-alpha transcription factor networks have been studied extensively and shown to be overexpressed in high-grade glioblastomas versus lower-grade gliomas (Liu M, Dai B, Kang S, Ban K, Huang F, Lang F F, Aldape K D, Xie T, Pelloski C E, Xie K, Sawaya R, Huang S. FOXM1B is overexpressed in human glioblastomas and critically regulates the tumorigenicity of glioma cells. Cancer Res. 2006 April; 66(7):3593-3602; Semenza G L. HIF-1 and human disease: one highly involved factor. Genes Dev. 2000 August; 14(16):1983-1991).

Example XI: Visualization of the Datasets

To visualize the results of PARADIGM inference, we developed a "CircleMap" visualization to display multiple datasets centered around each gene in a pathway (FIG. 7). In this display, each gene is associated with all of its data across the cohort by plotting concentric rings around the gene, where each ring corresponds to a single type of measurement or computational inference. Each tick in the ring corresponds to a single patient sample while the color corresponds to activated (red), deactivated (blue), or unchanged (white) levels of activity. We plotted CircleMaps for a subset of the ErbB2 pathway and included ER status, IPAs, expression, and copy number data from the breast cancer cohort.

Gene expression data has been used successfully to define molecular subtypes for various cancers. Cancer subtypes have been found that correlate with different clinical outcomes such as drug sensitivity and overall survival. We asked whether we could identify informative subtypes for GBM using PARADIGM IPAs rather than the raw expression data. The advantage of using IPAs is they provide a summarization of copy number, expression, and known interactions among the genes and may therefore provide more robust signatures for elucidating meaningful patient subgroups. We first determined all IPAs that were at least moderately recurrently activated across the GBM samples and found that 1,755 entities had IPAs of 0.25 in at least 75 of the 229 samples. We collected all of the IPAs for these entities in an activity matrix. The samples and entities were then clustered using hierarchical clustering with uncentered Pearson correlation and centroid linkage (FIG. 8).

Visual inspection revealed four obvious subtypes based on the IPAs with the fourth subtype clearly distinct from the first three. The fourth cluster exhibits clear downregulation of REF-I-alpha transcription factor network as well as overexpression of the E2F transcription factor network. HIF-1-alpha is a master transcription factor involved in regulation of the response to hypoxic conditions. In contrast, two of the first three clusters have elevated EGFR signatures and an inactive MAP kinase cascade involving the GATA interleukin transcriptional cascade. Interestingly, mutations and amplifications in EGFR have been associated with high grade gliomas as well as glioblastomas (Kuan C T, Wikstrand C J, Bigner D D. EGF mutant receptor vIII as a molecular target in cancer therapy. Endocr. Relat. Cancer 2001 June; 8(2):83-96). Amplifications and certain mutations can create a constitutively active EGFR either through self stimulation of the dimer or through ligand-independent activation. The constitutive activation of EGFR may promote oncogenesis and progression of solid tumors. Gefitinib, a molecule known to target EGFR, is currently being investigated for its efficacy in other EGFR-driven cancers. Thus, qualitatively, the clusters appeared to be honing in on biologically meaningful themes that can stratify patients.

To quantify these observations, we asked whether the different GBM subtypes identified by PARADIGM coincided with different survival profiles. We calculated Kaplan-Meier curves for each of the four clusters by plotting the proportion of patients surviving versus the number of months after initial diagnosis. We plotted Kaplan-Meier survival curves for each of the four clusters to see if any cluster associated with a distinct IPA signature was predictive of survival outcome (FIG. 9). The fourth cluster is significantly different from the other clusters ($P<2.11 \times 10$; Cox proportional hazards test). Half of the patients in the first three clusters survive past 18 months; the survival is significantly increased for cluster 4 patients where half survive past 30 months. In addition, over the range of 20 to 40 months, patients in cluster 4 are twice as likely to survive as patients in the other clusters.

Example XII: Kaplan-Meier Survival Plots for the Clusters

The survival analysis revealed that the patients in cluster 4 have a significantly better survival profile. Cluster 4 was found to have an up-regulation of E2F, which acts with the retinoblastoma tumor suppressor. Up-regulation of E2F is therefore consistent with an active suppression of cell cycle progression in the tumor samples from the patients in cluster 4. In addition, cluster 4 was associated with an inactivity of the HIF-1-alpha transcription factor. The inactivity in the fourth cluster may be a marker that the tumors are more oxygenated, suggesting that they may be smaller or newer tumors. Thus, PARADIGM IPAs provide a meaningful set of profiles for delineating subtypes with markedly different survival outcomes.

For comparison, we also attempted to cluster the patients using only expression data or CNA data to derive patient subtypes. No obvious groups were found from clustering using either of these data sources, consistent with the findings in the original TCGA analysis of this dataset (TCGA:2008) (see FIGS. 14A-14B). This suggests that the interactions among genes and resulting combinatorial outputs of individual gene expression may provide a better predictor of such a complex phenotype as patient outcome.

Example XIII: Integrated Genomic Analyses of Ovarian Carcinoma: Samples and Clinical Data This report covers analysis of 489 clinically annotated stage II-IV HGS-OvCa and corresponding normal DNA. Patients reflected the age at diagnosis, stage, tumor grade, and surgical outcome of individuals diagnosed with HGS-OvCa. Clinical data were current as of Aug. 25, 2010. HGS-OvCa specimens were surgically resected before systemic treatment but all patients received a platinum agent and 94% received a taxane. The median progression-free and overall survival of the cohort is similar to previously published trials11,12. Twenty five percent of the patients remained free of disease and 45% were alive at the time of last follow-up, while 31% progressed within 6 months after completing platinum-based therapy. Median follow up was 30 months (range 0 to 179). Samples for TCGA analysis were selected to have >70% tumor cell nuclei and <20% necrosis.

Coordinated molecular analyses using multiple molecular assays at independent sites were carried out as listed in Table 4 (Data are available at tcga.cancer.gov/dataportal) in two tiers. Tier one datasets are openly available, while tier two datasets include clinical or genomic information that could identify an individual hence require qualification as described at tcga.cancer.gov/dataportal/data/access/closed/.

Example XIV: Mutation Analysis

Exome Capture and Sequencing was Performed on DNA Isolated from 316 HGS-OvCa samples and matched normal samples for each individual. Capture reagents targeted –480, 000 exons from –48,500 genes totaling –33 megabases of non-redundant sequence. Massively parallel sequencing on the Illumina GAIIx platform (236 sample pairs) or ABI SOLiD 3 platform (80 sample pairs) yielded –14 gigabases per sample ($9 \times 10^9$ bases total). On average, 76% of coding bases were covered in sufficient depth in both the tumor and matched normal samples to allow confident mutation detection. 19,356 somatic mutations (–61 per tumor) were annotated and classified in Table 4. Mutations that may be important in HGS-OvCa pathophysiology were identified by (a) searching for non-synonymous or splice site mutations present at significantly increased frequencies relative to background, (b) comparing mutations in this study to those in COSMIC and OMIM and (c) predicting impact on protein function.

Two different algorithms identified 9 genes (Table 5) for which the number of non-synonymous or splice site mutations was significantly above that expected based on mutation distribution models. Consistent with published results13, TP53 was mutated in 303 of 316 samples (283 by automated methods and 20 after manual review), BRCA 0.1 and BRCA2 had germline mutations in 9% and 8% of cases, respectively, and both showed somatic mutations in an additional 3% of cases. Six other statistically recurrently mutated genes were identified; RB1, NF1. FAT3,CSMD3, GABRA6. and CDKI2. CDKI2 is involved in RNA splicing regulation14 and was previously implicated in lung and large intestine tumors. Five of the nine CDK12 mutations were either nonsense or indel, suggesting potential loss of function, while the four missense mutations (R882L, Y901C, K975E, and L996F) were clustered in its protein kinase domain. GABRA6 and FATS both appeared as significantly mutated but did not appear to be expressed in HGS-OvCa or fallopian tube tissue so it is less likely that mutation of these genes plays a significant role in HGS-OvCa.

Mutations from this study were compared to mutations in the COSMIC17 and OMIM18 databases to identify additional HGS-OvCa genes that are less commonly mutated. This yielded 477 and 211 matches respectively including mutations in BRAF (N581S), PIK3CA (E545K and H 1047R), KRAS (G12D), and NRAS (Q61R). These mutations have been shown to exhibit transforming activity so we believe that these mutations are rare but important drivers in HGS-OvCa.

We combined evolutionary information from sequence alignments of protein families and whole vertebrate genomes, predicted local protein structure and selected human SwissProt protein features to identify putative driver mutations using CHASM after training on mutations in known oncogenes and tumor suppressors. CHASM identified 122 mis-sense mutations predicted to be oncogenic. Mutation-driven changes in protein function were deduced from evolutionary information for all confirmed somatic missense mutations by comparing protein family sequence alignments and residue placement in known or homology-based three-dimensional protein structures using Mutation Assessor. Twenty-seven percent of missense mutations were predicted to impact protein function.

Example XV: Copy Number Analysis

Somatic copy number alterations (SCNAs) present in the 489 HGS-OvCa genomes were identified and compared with glioblastome multiforme data in FIG. 37A. SCNAs were divided into regional aberrations that affected extended chromosome regions and smaller focal aberrations. A statistical analysis of regional aberrations identified 8 recurrent gains and 22 losses, all of which have been reported previously (FIG. 37B). Five of the gains and 18 of the losses occurred in more than 50% of tumors.

GISTIC was used to identify recurrent focal SCNAs. This yielded 63 regions of focal amplification (FIG. 37C) including 26 that encoded 8 or fewer genes. The most common focal amplifications encoded CCNE1, MYC, and MECOM (FIG. 37C) each highly amplified in greater than 20% of tumors. New tightly-localized amplification peaks in HGS-OvCa encoded the receptor for activated C-kinase, ZMYND8; the p53 target gene, IRF2BP2; the DNA-binding protein inhibitor, ID4; the embryonic development gene, PAX8; and the telomerase catalytic subunit, TERT. Three data sources: www.ingenuity.com/, clinicaltrials.gov and www.drugbank.ca were used to identify possible therapeutic inhibitors of amplified, over-expressed genes. This search identified 22 genes that are therapeutic targets including MECOM, MAPK1, CCNE1 and KRAS amplified in at least 10% of the cases.

GISTIC also identified 50 focal deletions. The known tumor suppressor genes PTEN RB1, and NF1 were in regions of homozygous deletions in at least 2% of tumors. Importantly, RB1 and NF1 also were among the significantly mutated genes. One deletion contained only three genes, including the essential cell cycle control gene, CREBBP, which has 5 non-synonymous and 2 frameshift mutations.

Example XVI: mRNA and miRNA Expression and DNA Methylation Analysis

Expression measurements for 11,864 genes from three different platforms (Agilent, Affymetrix HuEx, Affymetrix U133A) were combined for subtype identification and outcome prediction. Individual platform measurements suffered from limited, but statistically significant batch effects, whereas the combined data set did not. Analysis of the combined dataset identified—1,500 intrinsically variable genes that were used for NMF consensus clustering. This analysis yielded four clusters (FIG. 38A). The same analysis approach applied to a publicly available dataset from Tothill et al., also yielded four clusters. Comparison of the Tothill and TCGA clusters showed a clear correlation. We therefore conclude that at least four robust expression subtypes exist in HGS-OvCa.

We termed the four HGS-OvCa subtypes Immunoreactive, Differentiated, Proliferative and Mesenchymal based on gene content in the clusters and on previous observations25. T-cell chemokine ligands, CXCL 1l and CXCLIO, and the receptor, CXCR3, characterized the Immunoreactive subtype. High expression of transcription factors such as HMGA2 and SOX/1, low expression of ovarian tumor markers (MUC1, WIC I 6) and high expression of proliferation markers such as MCM2 and PCNA defined the Proliferative subtype. The Differentiated subtype was associated with high expression of MUC I 6 and MUC1 and with expression of the secretory fallopian tube maker SLP1, suggesting a more mature stage of development. High expression of HOX genes and markers suggestive of increased stromal components such as for myofibroblasts (FAP) and microvascular pericytes (ANGPTL2, ANGPTL1) characterized the Mesenchymal subtype.

Elevated DNA methylation and reduced tumor expression implicated 168 genes as epigenetically silenced in HGS-OvCa compared to fallopian tube controls26. DNA methylation was correlated with reduced gene expression across all samples. AMT, CCL2I and SPARCLI were noteworthy because they showed promoter hypermethylation in the vast majority of the tumors. Curiously, RAB25, previously reported to be amplified and over-expressed in ovarian cancer, also appeared to be epigenetically silenced in a subset of tumors. The BRCA1 promoter was hypermethylated and silenced in 56 of 489 (11.5%) tumors as previously reported. Consensus clustering of variable DNA methylation across tumors identified four subtypes that were significantly associated with differences in age, BRCA inactivation events, and survival. However, the clusters demonstrated only modest stability.

Survival duration did not differ significantly for transcriptional subtypes in the TCGA dataset. The Proliferative group showed a decrease in the rate of MYC amplification and RB1 deletion, whereas the Immunoreactive subtype showed an increased frequency of 3q26.2 (MECOM) amplification. A moderate, but significant overlap between the DNA methylation clusters and gene expression subtypes was noted (p<2.2*10-16, Chi-square test, Adjusted Rand Index=0.07).

A 193 gene transcriptional signature predictive of overall survival was defined using the integrated expression data set from 215 samples. After univariate Cox regression analysis, 108 genes were correlated with poor survival, and 85 were correlated with good survival (p-value cutoff of 0.01). The predictive power was validated on an independent set of 255 TCGA samples as well as three independent expression data sets25,29,30. Each of the validation samples was assigned a prognostic gene score, reflecting the similarity between its expression profile and the prognostic gene signature31 (FIG. 38C). Kaplan-Meier survival analysis of this signature showed statistically significant association with survival in all validation data sets (FIG. 38D).

NMF consensus clustering of miRNA expression data identified three subtypes. Interestingly, miRNA subtype 1 overlapped the mRNA Proliferative subtype and miRNA subtype 2 overlapped the mRNAMesenchymal subtype (FIG. 38D). Survival duration differed significantly between iRNA subtypes with patients in miRNA subtype 1 tumors surviving significantly longer (FIG. 38e).

Example XVII: Pathways Influencing Disease

Several analyses integrated data from the 316 fully analyzed cases to identify biology that contributes to HGS-OvCa. Analysis of the frequency with which known cancer-associated pathways harbored one or more mutations, copy number changes, or changes in gene expression showed that the RB1 and PI3K/RAS pathways were deregulated in 67% and 45% of cases, respectively (FIG. 39A). A search for altered subnetworks in a large protein-protein interaction network32 using HotNet33 identified several known pathways, including the Notch signaling pathway, which was altered in 23% of HGS-OvCa samples (FIG. 39B).

Published studies have shown that cells with mutated or methylated BRCA1 or mutated BRCA2 have defective homologous recombination (FIR) and are highly responsive to PARP inhibitors 35-37. FIG. 39C shows that 20% of HGS-OvCa have germline or somatic mutations in BRCA1/2, that 11% have lost BRCA1 expression through DNA hypennethylation and that epigenetic silencing of BRCA1 is mutually exclusive of BRCA1/2 mutations (P=4.4×10-4, Fisher's exact test). Univariate survival analysis of BRCA status (FIG. 39C) showed better overall survival (OS) for BRCA mutated cases than BRCA wild-type cases. Interestingly, epigenetically silenced BRCA1 cases exhibited survival similar to BRCA1/2 WT HGS-OvCa (median OS 41.5 v. 41.9 months, P=0.69, log-rank test). This suggests that BRCA1 is inactivated by mutually exclusive genomic and epigenomic mechanisms and that patient survival depends on the mechanism of inactivation. Genomic alterations in other HR genes that might render cells sensitive to PARP inhibitors discovered in this study include amplification or mutation of EMSY (8%), focal deletion or mutation of PTEN (7%); hypermethylation of RAD51C (3%), mutation of ATM-ATR (2%), and mutation of Fanconi Anemia genes (5%). Overall, HR defects may be present in approximately half of HGS-OvCa, providing a rationale for clinical trials of PARP inhibitors targeting tumors these HR-related aberrations.

Comparison of the complete set of BRCA inactivation events to all recurrently altered copy number peaks revealed an unexpectedly low frequency of CCNE1 amplification in cases with BRCA inactivation (8% of BRCA altered cases had CCNE1 amplification v. 26% of BRCA wild type cases, FDR adjusted P=0.0048). As previously reported39, overall survival tended to be shorter for patients with CCNE1 amplification compared to all other cases (P=0.072, log-rank test). However, no survival disadvantage for CCNE1-amplified cases (P=0.24, log-rank test) was apparent when looking only at BRCA wild-type cases, suggesting that the previously reported CCNE1 survival difference can be explained by the better survival of BRCA-mutated cases.

Finally, a probabilistic graphical model (PARADIGM40) searched for altered pathways in the NCI Pathway Interaction Database identifying the FOXM1 transcription factor network (FIG. 39D) as significantly altered in 87% of cases. FOXM1 and its proliferation-related target genes; AURB, CCNE1, BIRC5, CDC25, and PLK1, were consistently over-expressed but not altered by DNA copy number changes, indicative of transcriptional regulation. TP53 represses FOXM1 following DNA damage42, suggesting that the high rate of TP53 mutation in HGS-OvCa contributes to FOXM1 overexpression. In other datasets, the FOXM1 pathway is significantly activated in tumors relative to adjacent epithelial tissue and is associated with HGS-OvCa.

Example XVIII: Frequently Altered Pathways in Ovarian Serous Carcinomas

To identify significantly altered pathways through an integrated analysis of both copy number and gene expression, we applied PARADIGM. The computational model incorporates copy number changes, gene expression data, and pathway structures to produce an integrated pathway activity (IPA) for every gene, complex, and genetic process present in the pathway database. We use the term "entity" to refer to any molecule in a pathway be it a gene, complex, or small molecule. The IPA of an entity refers only to the final activity. For a gene, the IPA only refers to the inferred activity of the active state of the protein, which is inferred from copy number, gene expression, and the signaling of other genes in the pathway. We applied PARADIGM to the ovarian samples and found alterations in many different genes and processes present in pathways contained in the National Cancer Institutes' Pathway Interaction Database (NCI-PID). We assessed the significance of the inferred alterations using 1000 random simulations in which pathways with the same structure were used but arbitrary genes were assigned at different points in the pathway. In other words, one random simulation for a given pathway kept the set of interactions fixed so that an arbitrary set of genes were connected together with the pathway's interactions. The significance of all samples' IPAs was assessed against the same null distribution to obtain a significance level for each entity in each sample. IPAs and the percentage of samples in which they are significant and IPAs with a standard deviation of at least 0.1 are displayed as a heatmap in FIG. 28.

Table 3 shows the pathways altered by at least three standard deviations with respect to permuted samples found by PARADIGM. The FOXM1 transcription factor network was altered in the largest number of samples among all pathways tested—67% of entities with altered activities when averaged across samples. In comparison, pathways with the next highest level of altered activities in the ovarian cohort included PLK1 signaling events (27%), Aurora B signaling (24%), and Thromboxane A2 receptor signaling (20%). Thus, among the pathways in NCI-PID, the FOXM1 network harbors significantly more altered activities than other pathways with respect to the ovarian samples.

The FOXM1 transcription factor network was found to be differentially altered in the tumor samples compared to the normal controls in the highest proportion of the patient samples (FIG. 29). FOXM1 is a multifunctional transcription factor with three known dominant splice forms, each regulating distinct subsets of genes with a variety of roles in cell proliferation and DNA repair. The FOXM1c isoform directly regulates several targets with known roles in cell proliferation including AUKB, PLK1, CDC25, and BIRC5. On the other hand, the FOXM1b isoform regulates a completely different subset of genes that include the DNA repair genes BRCA2 and XRCC I. CHEK2, which is under indirect control of ATM, directly regulates FOXM 1 s expression level.

We asked whether the IPAs of the FOXM1 transcription factor itself were more highly altered than the IPAs of other transcription factors. We compared the FOXM1 level of activity to all of the other 203 transcription factors in the NCI-PID. Even compared to other transcription factors in the NCI set, the FOXM1 transcription factor had significantly higher levels of activity (p<0.0001; K-S test) suggesting further that it may be an important signature (FIGS. 30A-30B).

Because FOXM1 is also expressed in many different normal tissues of epithelial origin, we asked whether the signature identified by PARADIGM was due to an epithelial signature that would be considered normal in other tissues. To answer this, we downloaded an independent dataset from GEO (GSE10971) in which fallopian tube epithelium and ovarian tumor tissue were microdissected and gene expression was assayed. We found that the levels of FOXM1 were significantly higher in the tumor samples compared to the normals, suggesting FOXM1 regulation is indeed elevated in cancerous tissue beyond what is seen in normal epithelial tissue (FIG. 31).

Because the entire cohort for the TCGA ovarian contained samples derived from high-grade serous tumors, we asked whether the FOXM1 signature was specific to high-grade serous. We obtained the log expression of FOXM1 and several of its targets from the dataset of Etemadmoghadam et al. (2009) in which both low- and high-grade serous tumors had been transcriptionally profiled. This independent data confirmed that FOXM 1 and several of its targets are significantly up-regulated in serous ovarian relative to low-grade ovarian cancers (FIG. 32). To determine if the 25 genes in the FOXM1 transcription factor network contained a significant proportion of genes with higher expression in high-grade disease, we performed a Student's t-test using the data from Etemadmoghadam. 723 genes in the genome (5.4%) were found to be significantly up-regulated in high- versus low-grade cancer at the 0.05 significance level (corrected for multiple testing using the Benjamini-Hochberg method). The FOXM1 network was found to have 13 of its genes (52%) differentially regulated, which is a significant proportion based on the hypergeometric test (P<$3.8*10^{-12}$). Thus, high expression of the FOXM1 network genes does appear to be specifically associated with high-grade disease when compared to the expression of typical genes in the genome.

FOXM1's role in many different cancers including breast and lung has been well documented but its role in ovarian cancer has not been investigated. FOXM1 is a multifunctional transcription factor with three known splice variants, each regulating distinct subsets of genes with a variety of roles in cell proliferation and DNA repair. An excerpt of FOXM1's interaction network relevant to this analysis is shown as FIG. 27. The FOXM1a isoform directly regulates several targets with known roles in cell proliferation including AUKB, PLK1, CDC25, and BIRC5. In contrast, the FOXM1b isoform regulates a completely different subset of genes that include the DNA repair genes BRCA2 and XRCC1. CHEK2, which is under indirect control of ATM, directly regulates FOXM1's expression level. In addition to increased expression of FOXM1 in most of the ovarian patients, a small subset also have increased copy number amplifications detected by CBS (19% with copy number increases in the top 5% quantile of all genes in the genome measured). Thus the alternative splicing regulation of FOXM1 may be involved in the control switch between DNA repair and cell proliferation. However, there is insufficient data at this point to support this claim since the exon structure distinguishing the isoforms and positions of the Exon array probes make it difficult to distinguish individual isoform activities. Future high-throughput sequencing of the mRNA of these samples may help determine the differential levels of the FOXM1 isoforms. The observation that PARADIGM detected the highest level of altered activity centered on this transcription factor suggests that FOXM1 resides at a critical regulatory point in the cell.

Example XIX: Data Sets and Pathway Interactions

Both copy number and expression data were incorporated into PARADIGM inference. Since a set of eight normal tissue controls was available for analysis in the expression data, each patient's gene-value was normalized by subtracting the gene's median level observed in the normal fallopian control. Copy number data was normalized to reflect the difference in copy number between a gene's level detected in tumor versus a blood normal. For input to PARADIGM, expression data was taken from the same integrated dataset used for subtype analysis and the copy number was taken from the segmented calls of MSKCC Agilent 1M copy number data.

A collection of pathways was obtained from NCI-PID containing 131 pathways, 11,563 interactions, and 7,204 entities. An entity is molecule, complex, small molecule, or abstract concept represented as "nodes" in PARADIGM's graphical model. The abstract concepts correspond to general cellular processes (such as "apoptosis" or "absorption of light,") and families of genes that share functional activity such as the RAS family of signal transducers. We collected interactions including protein-protein interactions, transcriptional regulatory interactions, protein modifications such as phosphorylation and ubiquitinylation interactions.

Example XX: Inference of Integrated Molecular Activities in Pathway Context

We used PARADIGM, which assigns an integrated pathway activity (IPA) reflecting the copy number, gene expression, and pathway context of each entity.

The significance of IPAs was assessed using permutations of gene- and patient-specific cross-sections of data. Data for 1000 "null" patients was created by randomly selecting a gene-expression and copy number pair of values for each gene in the genome. To assess the significance of the PARADIGM IPAs, we constructed a null distribution by assigning random genes to pathways while preserving the pathway structure.

Example XXI: Identification of FOXM1 Pathway

While all of the genes in the FOXM1 network were used to assess the statistical significance during the random simulations, in order to allow visualization of the FOXM1 pathway, entities directly connected to FOXM1 with significantly altered IPAs according to FIG. 29 were chosen for inclusion in FIG. 27. Among these, genes with roles in DNA repair and cell cycle control found to have literature support for interactions with FOXM1 were displayed. BRCC complex members, not found in the original NCI-PID pathway, were included in the plot along with BRCA2, which is a target of FOXM1 according to NCI-PID. Upstream DNA repair targets were identified by finding upstream regulators of CBEK2 in other NCI pathways (for example, an indirect link from ATM was found in the PLK3 signaling pathway).

Example XXII: Clustering

The use of inferred activities, which represent a change in probability of activity and not activity directly, it enables entities of various types to be clustered together into one heatmap. To globally visualize the results of PARADIGM inference, Eisen Cluster 3.0 was used to perform feature filtering and clustering. A standard deviation filtering of 0.1 resulted in 1598 out of 7204 pathway entities remaining, and average linkage, uncentered correlation hierarchical cluster was performed on both the entities and samples.

Example XXIII: Cell Lines Model Many Important Tumor Subtypes and Features

The utility of cell lines for identification of clinically relevant molecular predictors of response depends on the extent to which the diverse molecular mechanisms that determine response in tumors are operative in the cell lines. We reported previously on similarities between cell line models and primary tumors at both transcript and genome copy number levels' and we refine that comparison here using higher resolution platforms and analysis techniques. Specifically, we used hierarchical consensus clustering (HCC) of gene expression profiles to classify 50 breast cancer cell lines and 5 non-malignant breast cell lines into three transcriptional subtypes: luminal, basal and the newly described claudin-low (FIG. 14A). These subtypes are refined versions of those described earlier, where basal and caludin-low maps to the previously designated basal A and basal B subtypes, respectively, Table 7. A refined high-resolution SNP copy number analysis (FIG. 14B) confirms that the cell line panel models regions of recurrent amplification at 8q24 (MYC), 11q13 (CCND1), 17q12 (ERBB2), 20q13 (STK15/AURKA), and homozygous deletion at 9p21 (CDKN2A) found in primary tumors. Given the clinical relevance of the ERBB2 tumor subtype as determined by trastuzumab and lapatinib therapy, we examined cell lines with DNA amplification of ERBB2 as a special subtype designated ERBB2$^{AMP}$. Overall, our identification of luminal, basal, claudin-low and ERBB2$^{"P}$ cell lines is consistent with the clinical biology.

Example XIX: The Cell Lines Exhibit Differential Sensitivities to Most Therapeutic Compounds We examined the sensitivity of our cell line panel to 77 therapeutic compounds. We used a cell growth assay with a quantitative endpoint measured after three days of continuous exposure to each agent at nine concentrations. The anti-cancer compounds tested included a mix of conventional cytotoxic agents (for example, taxanes, platinols, anthracylines) and targeted agents (for example, SERMs and kinase inhibitors). In many cases, several agents targeted the same protein or molecular mechanism of action. We determined a quantitative measure of response for each compound as the concentration required to inhibit growth by 50% (designated the $GI_{50}$), In cases where the underlying growth data are of high quality, but 50% inhibition was not achieved, we set $GI_{50}$ to the highest concentration tested. $GI_{50}$ values are provided in Table 8 for all compounds. We excluded three compounds (PS1145, cetuximab and baicalein) from further analysis because the variability in cell line response was minimal.

A representative waterfall plot illustrating the variation in response to the Sigma AKT1-2 inhibitor along with associated transcriptional subtypes is shown in FIG. 10A. Sensitivity to this compound is highest in luminal and ERBB2$^{AmP}$ and lower in basal and claudin-low breast cancer cell lines. Waterfall plots showing the distribution of $GI_{50}$ values among the cell lines for all compounds are in the Supplementary Appendix. We established the reproducibility of the overall data set by computing the median absolute deviation of $GI_{50}$ values for 229 compound/cell line combinations with 3 or 4 replicates. The median average deviation was 0.15 across these replicates (FIGS. 15A-15B). We assessed concordance of response to 8 compounds by computing the pairwise Pearson's correlation between sets of 0150 values (FIG. 15B. Sensitivities for pairs of drugs with similar mechanisms of action were highly correlated, suggesting similar modes of action.

Example XX: Many Compounds were Preferentially Effective in Subsets of the Cell Lines A central premise of this study is that associations between responses and molecular subtypes observed in preclinical cell line analyses will be recapitulated in the clinic in instances where the predictive molecular features in the cell lines are mirrored in human tumors. We established response-subtype associations by using non-parametric ANOVAs to compare $GI_{50}$ values across transcriptional and genomics subtypes.

Overall, 33 of 74 compounds tested showed transcription subtype-specific responses (FDR p<0.2, Table 7 and Table 9). FIG. 10C shows a hierarchical clustering of the 34 agents with significant associations with one or more of the luminal, basal, claudin-low and ERBB2$^{AmP}$ subtypes. The 11 agents most strongly associated with subtype were inhibitors of receptor tyrosine kinase signaling and histone deacetylase and had the highest efficacy in luminal and/or ERBB2' cell lines. The three next most subtype-specific agents—etoposide, cisplatin, and docetaxel—show preferential activity in basal and/or claudin-low cell lines as observed clinically. Agents targeting the mitotic apparatus, including ixabepilone, GSK461364 (polo kinase inhibitor) and GSK1070916 (aurora kinase inhibitor) also were more active against basal and claudin-low cell lines. AG1478, BIBW2992 and gefitinib, all of which target EGFR and/or ERBB2 were positively associated with ERBB2 amplification. Geldanamycin, an inhibitor of HSP90 also was positively associated with ERBB2 amplification. Interestingly, VX-680 (aurora kinase inhibitor) and CGC-11I44 (polyamine analogue) both were negatively associated with ERBB2 amplification indicating that these are relatively poor therapies for ERBB2$^{ANW}$ tumors.

We identified 7 associations (6 unique compounds) between response and recurrent focal high-level copy number aberrations (CNAs; sample t-tests, FDR p<0.2, Table 10). FIG. 10D shows that (a) Homozygous deletion at 9p21 (CDKN2A and CDKN2B) was associated with response to vinorelbine, ixabepilone and fascalypsin. Fascalypsin inhibited CDK4 and this specificity is consistent with the role of the, $_{6INK4A}$ product of CDKN2A in inhibiting CDK4$^{20}$. (b) Amplification at 20q13 (which encodes AURKA), was associated with resistance, rather than sensitivity, to GSK1070916 and VX-680 which target A URKB and AURKC$^{23}$. This suggests that amplification of AURKA provides a bypass mechanism for A URKB and AURKC inhibitors. (c) Amplification at 11q13 (CCND1) was associated with sensitivity to carboplatin and the AURKB/C inhibitor GSK1070916.

Example XXI: Subtype Specificity Dominates Growth Rate Effects

In general, we found that luminal subtype cell lines grew more slowly than basal or claudin-low cells (Kruskal-Wallis test p=0.006, FIG. 16A and Table 7) and the range of doubling times was broad (18 to 300 hours). This raised the possibility that the most sensitive cell lines were those that grew most rapidly. If so, then the observed associations to subtype could represent an association to a covariate. We tested this hypothesis by assessing the effects of subtype and doubling time simultaneously using Analysis of Covariance (ANCOVA) and found that 22 of the 33 subtype-specific compounds had better associations with subtype than with doubling time (mean log ratio of p-values=0.92, standard deviation 1.11). This supports the idea that subtype membership is a better predictor of response than growth rate. Moreover, 15 of 33 subtype-specific compounds were more effective in the more slowly growing luminal cell lines (Table 7). One agent, 5-florouracil, was not significant in the subtype test alone but showed strong significance in the ANCOVA model for both class and doubling time. The response to 5-florouracil decreased as doubling time increased in both luminal and basal cell lines (FIG. 16B). We conclude that in most cases, the 3-day growth inhibition assay is detecting molecular signature-specific responses that are not strongly influenced by growth rate.

Example XXII: Integration of Copy Number and Transcription Measurements Identifies Pathways of Subtype Specific Responses We used the network analysis tool PARADIGM$^{24}$ to identify differences in pathway activity among the subtypes in the cell line panel. The analysis is complicated by the fact that the curated pathways are partially overlapping. For example EGFR, PI3 kinase and MEK are often curated as separate pathways when in fact they are components of a single larger pathway. To address this issue, PARADIGM merges approximately 1400 curated signal transduction, transcriptional and metabolic pathways into a single superimposed pathway (SuperPathway) to eliminate such redundancies. Using both the copy number and gene expression data for a particular cell line, PARADIGM uses the pathway interactions to infer integrated pathway levels (IPLs) for every gene, complex, and cellular process.

We compared cell lines to primary breast tumors by their pathway activations using the PARADIGM IPLs. Data for the cell line-tumor comparison was carried out using data generated by The Cancer Genome Atlas (TCGA) project (cancergenome.nih.gov). FIG. 11 shows pathway activities for each tumor and cell line after hierarchical clustering. The top five pathway features for each subtype are listed in Table 11. Overall, the tumors and cell line subtypes showed similar pathway activities and the deregulated pathways were better associated with transcriptional subtype than origin (FIGS. 13A-13B). However, pathways associated with the claudin low cell line subtype are not well represented in the tumor—possibly because the claudin-low subtype is over-represented in the cell line collection and the luminal. A subtype is missing (FIGS. 12A-12D).

Example XXIII: Identification of Subtype-Specific Pathway Markers

We asked whether intrinsic pathway activities underlie the differences between the subtypes. To this end, we identified subnetworks of the SuperPathway containing gene activities differentially up- or down-regulated in cell lines of one subtype compared to the rest. Comparison of pathway activities between basal cell lines and all others in the collection identified a network comprised of 965 nodes connected by 941 edges, where nodes represent proteins, protein complexes, or cellular processes and edges represent interactions, such as protein phosphorylation, between these elements (see FIGS. 18-22). FIG. 35A shows upregulation of the MYC/MAX subnetwork associated with proliferation, angiogenesis, and oncogenesis; and upregulation of the ERK1/2 subnetwork controlling cell cycle, adhesion, invasion, and macrophage activation. The FOXM1 and DNA damage subnetworks also were markedly upregulated in the basal cell lines. Comparison of the claudin-low subtype with all others showed upregulation of many of the same subnetworks as in basal cell lines with some exceptions, including upregulation of the beta-catenin (CTNNB I) network in claudin low cell lines as compared to the basal cells (FIG. 35B). Beta-catennin has been implicated in tumorigenesis, and is associated with poor prognosis. Comparison of the luminal cell lines with all others showed down-regulation of an ATF2 network, which inhibits tumorigenicity in melanoma, and up-regulation of FOXA1/FOXA2 networks that control transcription of ER-regulated genes and are implicated in good prognosis luminal breast cancers (FIG. 35C). Comparison of ERBB2$^{AmP}$ cell lines with all others showed many network features common to luminal cells—not surprising because most ERBB2$^{AmP}$ cells also are classified as luminal cells. However, FIG. 35D shows down regulation centered on RPS6KBP1 in ERBB2$^{Asc}$ cell lines.

Comparative analysis of differential drug response among the cell lines using the IPLs revealed pathway activities that provide information about mechanisms of response. For example, the basal cell lines are preferentially sensitive to cisplatin, a DNA damaging agent, and also showed upregulation of a DNA-damage response subnetwork that includes ATM, CHEK1 and BRCA1, key players associated with response to cisplatin (FIG. 36A). Likewise, ERBB2$^{AmP}$ cell lines are sensitive to geldanamycin, an inhibitor of HSP90, and also showed up-regulation in the ERBB2-HSP90 subnetwork (FIG. 36B). This observation is consistent with the mechanism of action for geldanamycin: it binds ERBB2 leading to its degredation. We found that the ERBB2$^{AmP}$ cell lines were resistant to the aurora kinase inhibitor VX-680, and further that sensitivity to this compound was not associated with amplification at 20q13 (AURKA). This raises the possibility that this resistance may be mediated through CCNB I, which is co-regulated with AURKB by FOXM1. Of the four subtypes, ERBB2$^{AmP}$ is the only one that shows substantial down-regulation of CCNB1 (FIGS. 22A-22C). This proposed mechanism is supported by the observation that in primary tumors, CCNB1 gene expression is significantly correlated with AURKB gene expression.

Example XXIV: Cell Growth Inhibition Assay and Growth Rate

We assessed the efficacy of 77 compounds in our panel of 55 breast cancer cell lines. This assay was performed as previously described (Kuo, W. L. et al. A systems analysis of the chemosensitivity of breast cancer cells to the polyamine analogue PG-11047. *BMC Med* 7, 77, doi:1741-7015-7-77 [pii] 10.1186/1741-7015-7-77 (2009)). Briefly, cells were treated for 72 hours with a set of 9 doses of each compound in 1:5 serial dillution. Cell viability was determined using the Cell Titer Glo assay. Doubling time (DT) was estimated from the ratio of 72 h to Oh for untreated wells.

We used nonlinear least squares to fit the data with a Gompertz curve with the following parameters: upper and lower asymptotes, slope and inflection point. The fitted curve was transformed into a GI curve using the method described by the NC1/NIH DTP Human Tumor Cell Line Screen Process and previously described (Screening Services—NCI-60 DTP Human Tumor Cell Line Screen. dtp.n-cl.nih.gov/branchsibtbflvisp.html. Monks, A. et al. Feasibility of a high-flux anticancer drug screen using a diverse panel of cultured human tumor cell lines. *J Natl Cancer Inst* 83, 757-766 (1991)).

We assessed a variety of response measures including the compound concentration required to inhibit growth by 50% ($GI_{50}$), the concentration necessary to completely inhibit growth (Total Growth Inihibition, TGI) and the concentration necessary to reduce the population by 50% (Lethal Concentration 50%, $LC_{50}$). In cases where the underlying growth data are of high quality, but the end point response ($GI_{50}$, TG1, $LC_{50}$) was not reached, the values were set to the highest concentration tested. $GI_{50}$ represents the first threshold reached, and therefore contains the most accurate set of measurements.

The drug response data was filtered to meet the following criteria: 1) median standard deviation across the 9 triplicate datapoints <0.20; 2) DT+1-2SD of the median DT for a particular cell line; 3) slope of the fitted curve >0.25; 4) growth inhibition at the maximum concentration <50% for datasets with no clear response. Approximately 80% of the drug plates pass all filtering requirements. We used the median absolute deviation (MAD), a robust version of standard deviation, to assess the reliability of our replicate measures of $GI_{50}$. Curve fitting and filtering were performed with custom-written R packages.

Example XXV: Drug Screening

Each drug included in the statistical analysis satisfied the following screening criteria for data quality: 1) Missing values: No more than 40% of $GI_{50}$ values can be missing across the entire set of cell lines; 2) Variability: For at least 3 cell lines, either $GI_{50}$>1.5. m$GI_{50}$ or $GI_{50}$<0.5. m$GI_{50}$, where m$GI_{50}$ is the median GIso for a given drug. Compounds failing these criteria were excluded from analysis.

Example XXVI: SNP Array and DNA Copy Number Analysis

Affymetrix Genome-Wide Human SNP Array 6.0 was used to measure DNA copy number data. The array quality and data processing was performed using the R statistical framework (www.r-projectorg.) based aroma.affymetrix. The breast cancer cell line SNP arrays were normalized using 20 normal sample arrays as described (Bcngtsson, H., Irizarry, R., Carvalho, B. & Speed, T. P. Estimation and assessment of raw copy numbers at the single locus level. *Bioinformatics (Oxford, England)* 24, 759-767 (2008)). Data were segmented using circular binary segmentation (CBS) from the bioconductor package DNAcopy (Olshen, A. B., Venkatraman, E. S., Lucito, R. & Wigler, M. Circular binary segmentation for the analysis of array-based DNA copy number data. *Biostatistics (Oxford, England)* 5, 557-572 (2004)). Significant DNA copy number changes were analyzed using MATLAB based Genomic Identification of Significant Targets in Cancer (GISTIC) (Beroukhim, R. et al. Assessing the significance of chromosomal aberrations in cancer: methodology and application to glioma. *Proc Natl Acrd Sci USA* 104, 20007-20012 (2007)). Raw data are available in The European Genotype Archive (EGA) with accession number, EGAS00000000059.

In order to ensure the greatest chance at detecting significant changes in copy number, we omitted the non-malignant cell lines from the GISTIC analysis. GISTIC scores for one member of each isogenic cell line pair was used to infer genomic changes in the other: AU565 was inferred from SKBR3; HCC1500 was inferred from HCC1806; LY2 was inferred from MCF7; ZR75B was inferred from ZR751.

Example XXVII: Exon Array Analysis

Gene expression data for the cell lines were derived from Affymetrix GeneChip Human Gene 1.0 ST exon arrays. Gene-level summaries of expression were computed using the aroma.affymetrix R package, with quantile normalization and a log-additive probe-level model (PLM) based on the "HuEx-_0-st-v2,core" chip type. Transcript identifiers were converted to HGNC gene symbols by querying the Ensembl database using the BioMart R package. The resulting expression profiles were subsequently filtered to capture only those genes expressing a standard deviation greater than 1.0 on the $\log_e$-scale across all cell lines. The raw data are available in ArrayExpress (E-MTAB-181).

Example XXVIII: Consensus Clustering

Cell line subtypes were identified using hierarchical consensus clustering (Monti, S., Tamayo, P., Mesirov, J. P. & Golub, T. A. Consensus Clustering: A Resampling-Based Method for Class Discovery and Visualization of Gene Expression Microarray Data. *Machine Learning* 52, 91-118 (2003). Consensus was computed using 500 samplings of the cell lines, 80% of the cell lines per sample, agglomerative hierarchical clustering, Euclidean distance metric and average linkage.

Example XXIX: Associations of Clinically Relevant Subtypes and Response to Therapeutic Agents We used three schemes to compare $GI_{50}$s: 1) luminal vs. basal vs. claudin-low; 2) luminal vs. basal+claudin-low; and 3) ERBB2-AMP vs. non-ERBB2-AMP. Differences between GI50s of the groups were compared with a nonparametric ANOVA or t-test, as appropriate, on the ranks. We combined the p-values for the three sets of tests and used false discovery rate (FDR) to correct for multiple testing. For the three-sample test, we performed a post-hoc analysis on the compounds with a significant class effect by comparing each group to all others to determine which group was most sensitive. The p-values for the post-hoc test were FDR-corrected together. In all cases, FDR p<0.20 was deemed significant. If it was the case that the basal+claudin-low group was found to be significant in scheme 2, but only one of these groups was significant in scheme 1, we gave precedence to the 3 sample case when assigning class specificity. Analyses were performed in R.

Example XXX: Association of Genomic Changes and Response to Therapeutic Agents

We used a t-test to assess the association between recurrent copy number changes (at 8q24 (MYC), 11q13 (CCND1), 20q13 (STK15/AURKA)) and drug sensitivity. We combined into a single group cell lines with low or no amplification and compared them to cell lines with high amplification. The comparable analysis was performed for regions of deletion. Cell lines for which the $GI_{50}$ was equal to the maximum concentration tested were omitted from analysis. We omitted compounds where any group had fewer than five samples.

Example XXXI: Association of Growth Rate and Response to Therapeutic Agents

To assess the effects of cell line class and growth rate on drug sensitivity, we performed a set of 2-way Analysis of Covariance (ANCOVA) tests, one for each of the three cell line classification schemes described above. This yielded six sets of p-values (2 main effects×3 classification schemes); we used a single FDR correction to assess significance, and declared FDR p-values<0.20 to be of interest. We performed these analyses in R with the functions lm and ANOVA, which is available as part of the car package.

Example XXXII: Integrated Pathway Analysis

Integration of copy number, gene expression, and pathway interaction data was performed using the PARADIGM software. Briefly, this procedure infers integrated pathway levels (IPLs) for genes, complexes, and processes using pathway interactions and genomic and functional genomic data from a single cell line or patient sample. See Example XL for details.

Example XXXIII: TCGA and Cell Line Clustering

We asked whether the activities inferred for the cell lines clustered with their respective subtypes in the TCGA tumor samples. To avoid biases caused by highly connected hub genes and highly correlated activities, cell lines and tumor samples were clustered using a set of 2351 non-redundant activities determined by a correlation analysis (see Supplemental Methods). The degree to which cell lines clustered with tumor samples of the same subtype was calculated using a Kolmogorov-Smirnov test to compare a distribution of t-statistics calculated from correlations between pairs of cell lines and tumor samples of the same subtype to a distribution calculated from cell line pairs of different subtypes (see Supplemental Methods). See Example XLI for details.

Example XXXIV: Identification of Subtype Pathway Markers

We searched for interconnected genes that collectively show differential activity with respect to a particular subtype. Each subtype was treated as a dichotomization of the cell lines into two groups: one group contained the cell lines belong to the subtype and the second group contained the remaining cell lines. We used the R implementation of the two-class Significance Analysis of Microarrays (SAM) algorithm (Tusher, V. G., Tibshirani, R. & Chu, G. Significance analysis of microarrays applied to the ionizing radiation response. *Proc Natl Acad Sci USA* 98, 5116-5121, doi: 10.1073/pnas.091062498 [pii] (2001)) to compute a differential activity (DA) score for each concept in the SuperPathway. For subtypes, positive DA corresponds to higher activity in the subtype compared to the other cell lines.

The coordinated up- and down-regulation of closely connected genes in the SuperPathway reinforces the activities inferred by PARADIGM. If the activities of neighboring genes are also correlated to a particular phenotype, we expect to find entire subnetworks with high DA scores. We identified regions in the SuperPathway in which concepts of high absolute DA were interconnected by retaining only those links that connected two concepts in which both concepts had DA scores higher than the average absolute DA.

Example XXXV: Integrated Pathway Analysis

Integration of copy number, gene expression, and pathway interaction data was performed using the PARADIGM software[24]. Briefly, this procedure infers integrated pathway levels (IPLs) for genes, complexes, and processes using pathway interactions and genomic and functional genomic data from a single cell line or patient sample. TCGA BRCA data was obtained from the TCGA DCC on Nov. 7, 2010. TCGA and cell line gene expression data were median probe centered within each data set separately. All of the values in an entire dataset (either the cell lines or TCGA tumor samples), were rank transformed and converted to −log 10 rank ratios before supplying to PARADIGM. Pathways were obtained in BioPax Level 2 format from pid.nci.nih.gov/ and included NCI-PID, Reactome, and BioCarta databases. Interactions were combined into a merged Superimposed Pathway (SuperPathway). Genes, complexes, and abstract processes (for example, "cell cycle") were retained as pathway concepts. Before merging gene concepts, all gene identifiers were translated into HUGO nomenclature. All interactions were included and no attempt was made to resolve conflicting influences. A breadth-first undirected traversal starting from P53 (the most connected component) was performed to build one single component. The resulting merged pathway structure contained a total of 8768 concepts representing 3491 proteins, 4757 complexes, and 520 processes. Expectation-Maximization parameters for PARADIGM were trained on the cell line data and then applied to the TCGA samples. Data from the cell lines and tumor samples were then combined into a single data matrix. Any entry without at least 1 value above 0.5 IPL in either the data from cell lines or tumor samples was removed from further analysis.

Example XXXVI: TCGA and Cell Line Clustering

Using PARADIGM IPLs, cell lines were clustered together with TCGA tumor samples to determine if cell lines were similar to tumor samples of the same subtype. Well-studied areas of the SuperPathway contain genes with many interactions (hubs) and large signaling chains of many intermediate complexes and abstract processes for which no direct data is available. To avoid bias toward hubs, pathway concepts with highly correlated vectors (Pearson correlation coefficient >0.9) across both the cell line and tumor samples were unified into a single vector prior to clustering. This unification resulted in 2351 non-redundant vectors from the original 8939 pathway concepts.

Samples were clustered using the resulting set of non-redundant concepts. The matrix of inferred pathway activities for both the 47 cell lines and 183 TCGA tumor samples was clustered using complete linkage hierarchical agglomerative clustering implemented in the Eisen Cluster software package version 3.0 Uncentered Pearson correlation was used as the metric for the pathway concepts and Euclidean distance was used for sample metric.

To quantify the degree to which cell lines clustered with tumor samples of the same subtype, we compared two distributions oft-statistics derived from Pearson correlations. Let $C_s$ be the set of cell lines of subtypes. Similarly, let T, be the set of TCGA tumor samples of subtype s. For example, $C_{basai}$ and $T_{basai}$ are the set of all basal cell lines and basal tumor samples respectively. The first distribution was made up of t-statistics derived from the Pearson correlations between every possible pair containing a cell line and tumor sample of the same subtype; i.e. for all subtypes s, every pairwise correlation t-statistics was computed between a pair (a, h) such that a F C, and b F T. The second distribution was made of correlation t-statistics between cell lines of different subtypes; that is, computed over pairs (a, b) such that a E C., and b E c* and s s'. We performed a Kolmogorov-Smirnov test to compare the distributions.

Example XXXVII: Integrated Pathway Analysis

Integration of copy number, gene expression, and pathway interaction data was performed using the PARADIGM software. Briefly, this procedure infers integrated pathway levels (IPLs) for genes, complexes, and processes using pathway interactions and genomic and functional genomic data from a single cell line or patient sample. TCGA BRCA data was obtained from the TCGA DCC on Nov. 7, 2010. TCGA and cell line gene expression data were median probe centered within each data set separately. All of the values in an entire dataset (either the cell lines or TCGA tumor samples), were rank transformed and converted to −log 10 rank ratios before supplying to PARADIGM. Pathways were obtained in BioPax Level 2 format on Oct. 13, 2010 from pid.nci.nih.gov/ and included NCI-PID, Reactome, and Bio-Carta databases. Interactions were combined into a merged Superimposed Pathway (SuperPathway). Genes, complexes, and abstract processes (for example, "cell cycle") were retained as pathway concepts. Before merging gene concepts, all gene identifiers were translated into HUGO nomenclature. All interactions were included and no attempt was made to resolve conflicting influences. A breadth-first undirected traversal starting from P53 (the most connected component) was performed to build one single component. The resulting merged pathway structure contained a total of 8768 concepts representing 3491 proteins, 4757 complexes, and 520 processes. Expectation-Maximization parameters for PARADIGM were trained on the cell line data and then applied to the TCGA samples. Data from the cell lines and tumor samples were then combined into a single data matrix. Any entry without at least 1 value above 0.5 IPL in either the data from cell lines or tumor samples was removed from further analysis.

Example XXXVIII: TCGA and Cell Line Clustering

Using PARADIGM IPLs, cell lines were clustered together with TCGA tumor samples to determine if cell lines were similar to tumor samples of the same subtype. Well-studied areas of the SuperPathway contain genes with many interactions (hubs) and large signaling chains of many intermediate complexes and abstract processes for which no direct data is available. To avoid bias toward hubs, pathway concepts with highly correlated vectors (Pearson correlation coefficient >0.9) across both the cell line and tumor samples were unified into a single vector prior to clustering. This unification resulted in 2351 non-redundant vectors from the original 8939 pathway concepts. Samples were clustered using the resulting set of non-redundant concepts. The matrix of inferred pathway activities for both the 47 cell lines and 183 TCGA tumor samples was clustered using complete linkage hierarchical agglomerative clustering implemented in the Eisen Cluster software package version $3.0^{45}$ Uncentered Pearson correlation was used as the metric for the pathway concepts and Euclidean distance was used for sample metric.

To quantify the degree to which cell lines clustered with tumor samples of the same subtype, we compared two distributions of t-statistics derived from Pearson correlations. Let C, be the set of cell lines of subtype s. Similarly, let T, be the set of TCGA tumor samples of subtype s. For example, $C_{ba\_}$, and 7' $b_{ay,\ a}$l are the set of all basal cell lines and basal tumor samples respectively. The first distribution was made up of t-statistics derived from the Pearson correlations between every possible pair containing a cell line and tumor sample of the same subtype; i.e. for all subtypes s, every pairwise correlation t-statistics was computed between a pair (a, b) such that a E $C_s$ and b E T. The second distribution was made of correlation t-statistics between cell lines of different subtypes; i.e. computed over pairs (a, b) such that a e $C_c$ and b E $C_s$. and s s'. We performed a Kohnogorov-Sminiov test to compare the distributions.

Example XXXIX: Molecular Subtypes of Tumors at Various Genetic Molecular Levels The pioneering studies of whole genome gene expression analysis performed on breast tumors have identified different subclasses most notably belonging to the estrogen receptor (ER) negative basal-like and the ER positive luminal subgroups (Perou, C. M. et al., (2000), Molecular portraits of human breast tumours, 406: 747-752) with differences in clinical outcome (Sorlie, T. et al., (2001), Gene expression patterns of breast carcinomas distinguish tumor subclasses with clinical implications, 98: 10869-10874). The existence of several molecular subtypes has also been observed by DNA copy number analysis (2Russnes et al. (2007) supra), DNA methylation (Ronneberg et al. (2011) supra) and miRNA expression analyses (Enerly et al. (2011) supra). However, the questions are to what extent these new profiles, acquired by molecular analyses at various new molecular levels, recapitulate the initially discovered subclasses by mRNA expression, and what is the potential of these new classifications to identify novel patient subgroups of clinical importance? To address these questions we first clustered the breast cancer patients of the MicMa dataset according to each molecular level studied (FIG. 23) using an unbiased, unsupervised method. The histograms of the clustering of patients by each molecular level separately and the survival KM plot for each patient subgroup are shown in FIG. 23. Interestingly, this clustering procedure lead to the identification of 7 clusters of mRNA expression that correlated highly with the clusters derived from Pam50 classification. It was consistent with the Pam50, but split the Luminal A cluster between exp 1-4 mRNA clusters, and the basal and the ERBB2 among the last three (exp5-7) clusters. At the miRNA level three different clusters were obtained as previously described in (Enerly et al. (2011) supra); at methylation level three main clusters were seen as described and one much smaller, fourth cluster that was also observed but not further discussed in Ronneberg et al. (2011, supra). At CNA level six different clusters appeared. Clearly, at every level the distinct patient clusters were associated with a particular pattern of survival (FIG. 23). Whether the same patients formed the corresponding clusters at different molecular levels was then evaluated. Indeed, there was to a great extent a good concordance between the clustering at different levels, most notably between DNA methylation and mRNA expression and DNA copy number (Table 12). However, while some samples always cluster together at any level, others cluster in different groups according to each particular molecular endpoint in study.

TABLE 12

|  | mrna | meth | mir | paradigm |
|---|---|---|---|---|
| cna | 1.38E−04 | 6.99E−03 | 9.09E−02 | 1.20E−05 |
| mrna |  | 6.30E−05 | 4.12E−03 | 1.36E−09 |
| meth |  |  | 1.83E−01 | 1.26E−05 |
| mir |  |  |  | 2.57E−02 |

The consistent splitting of one subclass derived from one molecular level, by the clustering according to another may reveal important biological implications. For instance, as discussed in (3), while good correlation between methylation and mRNA expression based classification was observed (p=2.29.10-6), still Luminal-A class (by mRNA expression) was split between two different methylation clusters. The same applied to the basal-like tumors suggesting that despite the strong concordance to the mRNA expression clusters additional information was provided by the clustering according to DNA methylation. Luminal A samples with different DNA methylation profiles differ in survival (3 Ronneberg, J. A. et al., (2011), Methylation profiling with a panel of cancer related genes: association with estrogen receptor, TP53 mutation status and expression subtypes in sporadic breast cancer, 5: 61-76). The increasing number of new datasets from both us and others will in the future reveal whether these clusters will converge to several most and many less frequent combinations.

Although reclassification at different molecular levels is worth of further studies as it may point to new interesting biological pathways affected on different levels, the information content in this horizontal reshuffling of samples from class to class may be limited. Looking at differentially expressed/altered genes within these clusters per pathway is dependent on the a priori knowledge and choices of known interactions and is unable to identify novel pathways. Further, these approaches treat genes and measurements in different datasets as independent variables and do not take into consideration the position of a gene in a pathway, or the number of its interactive partners (i.e. the pathway's topology) and may be vulnerable to large fluctuations in the expression of one or few genes in a gene set. It is commonly observed that a particular pathway may be deregulated in many tumors in cancer, but that the particular gene and method of deregulation varies in different tumors (Cancer Genome Atlas Research Network. Comprehensive genomic characterization defines human glioblastoma genes and core pathways. Nature 2008 October; 455(7216):1061-1068). We therefore next applied a pathway based modeling methodology that models the interactions between the different data type measurements on a single gene as well as known interactions between genes, in order to characterize each gene's activity level in a tumor in the context of a pathway and associated clinical data. We used each gene's Integrated Pathway Levels (IPL) to directly identify and classify the patients according to these deregulated pathways (across molecular data types) and then investigate the relationship of the new clusters with the previously described classes at various molecular levels.

Example XL: PARADIGM for Classification of Invasive Cancers with Prognostic Significance In order to understand how genomic changes disturb distinct biological functions that can explain tumor phenotypes and make tumors vulnerable to targeted treatment, we need an understanding of perturbations at a pathway level. PARADIGM identifies consistent active pathways in subsets of patients that are indistinguishable if genes are studied at a single level. The method uses techniques from probabilistic graphical models (PGM) to integrated functional genomics data onto a known pathway structure. It has previously been applied to analysis of copy number and mRNA expression data from the TCGA glioblastoma and ovarian datasets. PARADIGM analysis can also be used to connect genomic alterations at multiple levels such as DNA methylation or copy number, mRNA and miRNA expression and can thus integrate any number of omics layers of data in each individual sample. Although DNA methylation and miRNA expression contribute to the observed here deregulated pathways and seem to have distinct contribution to the prognosis and molecular profiles of breast cancer each in its own right in the MicMa cohort (FIG. 23) we did not find improvement of the prognostic value of the PARADIGM clusters by adding these two molecular profile types. One explanation for this is that the prognostic value of miRNA and DNA methylation analyses is recapitulated by mRNA expression due to their high correlation. However, such conclusion requires further analysis regarding, for example, whether the choice of analysis platforms (limited Illumina 1505 CpG cancer panel for methylation) and our limited knowledge of true miRNA targets may be the factors limiting our ability to comprehensively measure and effectively model miRNA and DNA methylation information.

PARADIGM analyses based on mRNA expression and copy number alterations of the MicMa cohort identified the existence of 5 different clusters (FIG. 24) and showed that combining mRNA expression and DNA copy number leads to better discrimination of patients with respect to prognosis than any of the molecular levels studied separately (FIG. 24 and FIG. 23). The pathways whose perturbations most strongly contributed to this classification were those of Angiopoicntin receptor Tie2-mediated signaling and most notably the immune response (TCR) and interleukin signaling, where nearly every gene or complex in the pathway deviated from the normal (FIG. 25). Most prominently seen were IL4, IL6, IL12 and IL23 signaling. Other prominent pathways are Endothelins, FOXM1 transcription, deregulated also in the ovarian and glioblastome TCGA datasets and ERBB4, also previously found deregulated in breast and ovarian cancers. Based on this analysis we have identified the following patients groups with significantly different prognosis, which can be roughly characterized as follows:

pdgm. I=high FOXM1, high immune signaling,
pdgm.2=high FOXM1, Low immune signaling, macrophage dominated,
pdgm.3=low FOXM1, low immune signaling,
pdgm.4=high ERBB4, low Angiopoietin signaling,
pdgm.5=high FOXM1, low macrophage signature.

The identification of the Paradigm clusters was validated in two previously published datasets, one by Chin et al 2007 (Chin, S. F. et al., (2007), Using array-comparative genomic hybridization to define molecular portraits of primary breast cancers, 26: 1959-1970), which compared to the MicMa dataset was with higher frequency of ER- and high grade tumors and even more interestingly in another set enriched for non malignant DCIS (Ductal carcinoma in situ) (12 Muggerud, A. A. et al., (2010), Molecular diversity in ductal carcinoma in situ (DCIS) and early invasive breast cancer, 4: 357-368) (FIG. 25). The heatmap for the pure DCIS tumors is shown in FIG. 25.

In the cluster with worst prognosis in MicMa, pdgm.2, IL4 signaling is strongly down-regulated in conjunction with STAT6, which has been shown in human breast cancer cells to prevent growth inhibition (16 Gooch, J. L., Christy B., and Yee, D., (2002), STAT6 mediates interleukin-4 growth inhibition in human breast cancer cells, 4: 324-331). Down-regulation of IL4 signaling has also promoted mast cell activation which can support greater tumor growth (17 de Visser, K. E., Eichten, A., and Coussens, L. M., (2006), Paradoxical roles of the immune system during cancer development, 6: 24-37). Conversely, in pdgm.5, macrophage activation is decreased and natural killer cell activity is increased due to IL23 signaling. A cancer dependent polarization of the immune response towards Th-2 and B cells recruitment on one side and Th-1 proliferation on the other, has been discussed (1 Ursini-Siegel, J. et al., (2010), Receptor tyrosine kinase signaling favors a protumorigenic state in breast cancer cells by inhibiting the adaptive immune response, 70: 7776-7787). It has been hypothesized that under certain conditions Th1/CTL immune response may prevent the transition of hyperplasia to adenoma in mice, while Th2 response may by conferring a chronic inflammatory state to promote the transition to carcinoma. I L4 is a Th-2 derived cytokine that stimulates B cells differentiation and chronic inflammation in cancer cells. Further Th-2 cells secrete IL10 that mediates immunosuppression in these cancers. This immunosuppression was shown to occur predominantly in basal and ERBB2 cancers. In support to this, it has been shown recently that "antitumor acquired immune programs can be usurped in pro-tumor microenvironments and instead promote malignancy by engaging cellular components of the innate immune system functionally involved in regulating epithelial cell behavior" (DeNardo, D. G. et al., (2009), CD4(+) T cells regulate pulmonary metastasis of mammary carcinomas by enhancing protumor properties of macrophages, 16: 91-102).

There was a considerable concordance between this immunoclassification, proposed here and the well established classification by mRNA expression (luminal A,B, basal, ERBB2, normal like) (FIG. 24. Samples belonging to the basal and ERBB2 clusters were of predominantly prgm1 (worse prognosis), Luminal A—prgm 3 (best prognosis). The Paradigm clustering offers however a rather significant distinction between luminal A (prgm3) and luminal B (prgm4) clusters, as well as the identification of a subset of basal tumors with very bad prognosis (prgm2).

Example XLI: Identified Pathways Whose Perturbation Specifically Influences the PARADIGM Clustering FOXM1 Transcription.

FOXM1 is a key regulator of cell cycle progression and its endogenous FOXM1 expression oscillates according to the phases of the cell cycle. FOXM1 confirmed as a human proto-oncogene is found upregulated in the majority of solid human cancers including liver, breast, lung, prostate, cervix of uterus, colon, pancreas, brain as well as basal cell carcinoma, the most common human cancer. FOXM1 is thought to promote oncogenesis through its multiple roles in cell cycle and chromosomal/genomic maintenance (Wonsey, D. R. and Follettie, M. T., (2005), Loss of the forkhead transcription factor FOXM1 causes centrosome amplification and mitotic catastrophe, 65: 5181-5189). Aberrant upregulation of FOXM1 in primary human skin keratinocytes can directly induce genomic instability in the form of loss of heterozygosity (LOH) and copy number aberrations (Teh M, Gemenetzidis E, Chaplin T, Young B D, Philpott M P. Upregulation of FOXM1 induces genomic instability in human epidermal keratinocytes. Mol. Cancer 2010; 9:45). A recent report showed that aberrant upregulation of FOXM1 in adult human epithelial stem cells induces a pre-cancer phenotype in a 3D-organotypic tissue regeneration system—a condition similar to human hyperplasia (Gemenetzidis, E. et al., (2010), Induction of human epithelial stem/progenitor expansion by FOXM1, 70: 9515-952). The authors showed that excessive expression of FOXM1 exploits the inherent self-renewal proliferation potential of stem cells by interfering with the differentiation pathway, thereby expanding the progenitor cell compartment. It was therefore hypothesized that FOXM1 induces cancer initiation through stem/progenitor cell expansion. We see clearly two groups of breast cancer patients with high and low activity of this pathway, broken mainly according to interleukin signaling activity. FIG. 26 illustrates the opposite activation modus of this pathway (red as activated vs blue inactivated) for cluster pdgm 3 (best survival) as opposed to the rest of the clusters with worse survival and the molecular levels that contribute to it (mRNA, CNA, miRNA or DNA methylation according to the shape of the figures). One can notice that down regulation of MMP2 in pdgm3 is due to DNA methylation, while in the rest of the tumors—due to DNA deletion. Of the miRNAs, has-let?-b was upregulated in pgm3 and downregulated in the rest, complementary to its target, the AURKB. Both DNA amplification and mRNA expression were seen as causes of deregulation of expression.

Angiopoietin Receptor Tie2-Mediated Signaling.

The Ang family plays an important role in angiogenesis during the development and growth of human cancers. Ang2's role in angiogenesis generally is considered as an antagonist for Ang I, inhibiting Ang 1-promoted Tie2 signaling, which is critical for blood vessel maturation and stabilization (23). Ang2 modulates angiogenesis in a cooperative manner with another important angiogenic factor, vascular endothelial growth factor A (VEGFA) (Hashizume, H. et al., (2010), Complementary actions of inhibitors of angiopoietin-2 and VEGF on tumor angiogenesis and growth, 70: 2213-2223). New data suggests more complicated roles for Ang2 in angiogenesis in invasive phenotypes of cancer cells during progression of human cancers. Certain angiopoietin (Ang) family members can activate Tie1, for example, Ang I induces Tie1 phosphorylation in endothelial cells (2 Yuan, H. T. et al., (2007), Activation of the orphan endothelial receptor Tie1 modifies Tie2-mediated intracellular signaling and cell survival, 21: 3171-3183). Tie1 phosphorylation is, however, Tie2 dependent because Ang1 fails to induce Tie1 phosphorylation when Tie2 is down-regulated in endothelial cells and Tie1 phosphorylation is induced in the absence of Ang 1 by either a constitutively active form of Tie2 or a Tie2 agonistic antibody (25 Yuan et al. (2007) supra). Ang 1-mediated AKT and 42/44MAPK phosphorylation is predominantly Tie2 mediated, and Tie1 down-regulates this pathway. Thus the main role for Tie1 is to modulate blood vessel morphogenesis due to its ability to down-regulate Tie2-driven signaling and endothelial survival. Both Tie2 mediated signaling as well as VEGFR1 and 2 mediated signaling and specific signals were observed in this dataset.

ERBB4

ERBB4 contributes to proliferation and cell movements in mammary morphogenesis and the directional cell movements of Erbb4-expressing mammary primordial epithelia while promoting mammary cell fate. Candidate effectors of Nrg3/Erbb4 signaling have been identified and shown here to interacts with other signalling pathways relevant to early mammary gland development and cancer. One of the primary functions of ErbB4 in vivo is in the maturation of mammary glands during pregnancy and lactation induction. Pregnancy and extended lactation durations have been correlated with reduced risk of breast cancer, and the role of ErbB4 in tumor suppression may therefore be linked with its role in lactation. Most reports are consistent with a role for ErbB4 in reversing growth stimuli triggered by other ErbB family members during puberty, however significant association of survival to ERBB4 expression has not been confirmed (2 Sundvall, M. et al., (2008), Role of ErbB4 in breast cancer, 13: 259-268).

Example XLII: PARADIGM for Classification in Ductal Carcinoma In Situ (DCIS)

Given the involvement of immune response in premalignant hyperplastic glands in mouse models (18 Ursini-Siegel, J. et al., (2010), Receptor tyrosine kinase signaling favors a protumorigenic state in breast cancer cells by inhibiting the adaptive immune response, 70: 7776-7787), we analyzed a previously published dataset comprising of DCIS cases to find whether the observed strong immune response and interleukin signaling in invasive tumors is present in premalignant stages as well. Ductal carcinoma in situ (DCIS) is a non-invasive form of breast cancer where some lesions are believed to rapidly transit to invasive ductal carcinomas (IDCs), while others remain unchanged. We have previously studied gene expression patterns of 31 pure DCIS, 36 pure invasive cancers and 42 cases of mixed diagnosis (invasive cancer with an in situ component) (1Muggerud et al. (2010) supra) and observed heterogeneity in the transcriptomes among DCIS of high histological grade, identifying a distinct subgroup of DCIS with gene expression characteristics more similar to advanced tumors. The heatmap, of the PARADIGM results for this entire cohort (including IDC and ILC) in FIG. 25 and for the pure DCIS samples, in FIG. 25. None of the pure DCIS tumors were of prgm2 type, characterized by signaling typical for high macrophage activity (FIG. 25). In agreement, experimental studies have demonstrated that macrophages in primary mammary adenocarcinomas regulate late-stage carcinogenesis thanks to their proangiogenic properties (Lin, E. Y. and Pollard, J. W., (2007), Tumor-associated macrophages press the angiogenic switch in breast cancer, 67: 5064-5066; Lin, E. Y. et al., (2007), Vascular endothelial growth factor restores delayed tumor progression in tumors depleted of macrophages, 1: 288-302), as well as foster pulmonary metastasis by providing epidermal growth factor (EGF) to malignant mammary epithelial cells. Again among the top deregulated pathways identified by the PARDIGM analysis in DCIS were those involving IL2, 4, 6, 12, 23, and 23 signaling.

In both datasets (DCIS, MicMa) TCR signaling in naive CD8+ T cells was on top of the list alongside with a large number of chemokines that are known to recruit CD8+ T cells. One is IL-12, produced by the antigen presenting cells that was shown to stimulate IFN-gamma production from NK and T cells. IFN-gamma pathway was one of the deregulated pathways, higher up on the list in DCIS. IFN-gamma is produced from the Th1 cells and the NK cells and was shown to initiate an antitumor immune response. Phase I clinical trials have shown that the clinical effect of trastuzumab (herceptin) is potentiated by the co-administration of IL-12 to patients with HER2-overexpressing tumors, and this effect is mediated by the stimulation of IFNgamma production in the NK cells (29). In DCIS, other most strong contributor (Table 8) was 84 NOX4. NOX4, an oxygen-sensing NAPHD oxidase, and a phagocyte-type A oxidase, is similar to that responsible for the production of large amounts of reactive oxygen species (ROS) in neutrophil granulocytes, primary immune response. Also FN1 (fibronectin) and PDGFRB, the platelet-derived growth factor receptor, appeared repeatedly together specifically in the DCIS together with COL1A2, IL12/1L12R/TYK2/JAK2/SPHK2, ESR1 and ICRT14.

These genes/pathways seem to be all contributing to functions in the extracellular matrix, the cell-cell interaction, and fibrosis and keratinization. For instance, FN1 Fibronectin-1 belongs to a family of high molecular weight glycoproteins that are present on cell surfaces, in extracellular fluids, connective tissues, and basement membranes. Fibronectins interact with other extracellular matrix proteins and cellular ligands, such as collagen, fibrin, and integrins. Fibronectins are involved in adhesive and migratory processes of cells. PDGFR, the platelet-derived growth factor receptor, together with the Epidermal growth factor (EGF) signals through EGF and PDGF receptors, which are important receptor tyrosine kinases (RTKs). Importantly, PDGFR found here to be overexpressed in certain DCIS is a target of Sunitinib (30 Fratto, M. E. et al., (2010), New perspectives: role of sunitinib in breast cancer, 161: 475-482) and a secondary target of Imatinib mesylate (Gleevec) (Weigel, M. T. et al., (2010), In vitro effects of imatinib mesylate on radiosensitivity and chemosensitivity of breast cancer cells, 10: 412). Contrary to the immunostimulatory role of trastuzumab (herceptin) described above to mediated by increased INFgamma production, imatinib was shown to inhibit interferon-gamma production by TCR-activated CD4 (+) T cells. These observations are of interest for our argument to the degree that they illuminate the interaction between growth factor receptors presented on the surface of DCIS and malignant cells and immune constitution. It was shown that stimulatory autoantibodies to PDGFR appeared to trigger an intracellular loop that involves Ras, ERK1/ERK2, and reactive oxygen species (ROS) that leads to increased type I collagen expression. This is in line with COL1A2 expression also observed as deregulated in DCIS in our study.

Example XLIII: Materials and Methods

The analysis was applied to data collected from ca 110 breast carcinomas with mRNA expression analyzed by Agilent whole human genome 4×44K one color oligo array. The copy number alterations (CNA) was analyzed using the Illumina Human-1 109K BeadChip. This SNP array is gene centric and contains markers covering the entire genome with an average physical distance of 30 kb and represents 15,969 unique genes (May 2004 assembly, hg17, NCBI Build 35). Each sample was subjected to whole genome amplification. Genotype reports and logR values were extracted with reference to dbSNP's (build 125) forward allele orientation using BeadStudio (v. 2.0, Illumina), and logR values were adjusted for CNAs.

miRNA profiling from total RNA was performed using Agilent Technologies "Human miRNA Microarray Kit (V2)" according to manufacturer's protocol. Scanning on Agilent Scanner G2565A and Feature Extraction (FE) v9.5 was used to extract signals. Experiments were performed using duplicate hybridizations (99 samples) on different arrays and time points. Two samples were profiled only once. miRNA signal intensities for replicate probes were averaged across the platform, log 2 transformed and normalized to the 75 percentile. miRNA expression status was scored as present or absent for each gene in each sample by default settings in FE v9.5.

DNA methylation, One microgram of DNA was bisulphite treated using the EpiTect 96 Bisulfite Kit (Qiagen GmbH, Germany). 500 ng of bisulphite treated DNA was analyzed using the GoldenGate Methylation Cancer Panel I (Illumina Inc, CA, USA) that simultaneously analyses 1505 CpG sites in 807 cancer related genes. At least 2 CpG sites were analyzed per gene were one CpG site is in the promoter region and one CpG site is in the 1st exon Bead studio software was used for the initial processing of the methylation data according to the manufacturer's protocol. The detection p-value for each CpG site was used to validate sample performance and the dataset was filtered based on the detection p-value were CpG sites with a detection p-value>0.05 was omitted from further analysis.

Data pre-processing and Paradigm parameters. Copy number was segmented using CBS, then mapped to gene-level measurements by taking the median of all segments that span a RefSeq gene's coordinates in hg18. For mRNA expression, measurements were first probe-normalized by subtracting the median expression value for each probe. The manufacturer's genomic location for each probe was converted from hg17 to hg18 using UCSCs liftOver tool. Per-gene measurements were then obtained by taking the median value of all probes overlapping a RefSeq gene. Methylation probes were matched to genes using manufacturers description. Paradigm was run as previously (10), by quantile transforming each data set separately, but data was discretized into bins of equal size, rather than at the 5% and 95% quantiles. Pathway files were from the PID (36) as previously parsed. FIG. 26 shows summaries of discretized input data, and not rin, values, by counting the fraction of observations in either an up or down bin in each datatype, and then labeling each node with the bin with the highest fraction of observations in any datatype.

HOPACH Unsupervised Clustering. Clusters were derived using the HOPACH R implementation version 2.10 (37) running on R version 2.12. The correlation distance metric was used with all data types, except for Paradigm IPLs, which used cosangle duc to the non-normal distribution and prevalence of zero values. For any cluster of samples that contained fewer than 5 samples, each sample was mapped to the same cluster as the most similar sample in a larger cluster. Paradigm clusters in the MicMa dataset were mapped to other datatypes by determining each cluster's mediod (using the median function) in the MicMa dataset, then assigning each sample in another dataset to whichever cluster mediod was closest by cosangle distance.

Kaplain-Meier, Cluster enrichments. Kaplan-Meier statistics, plots, and cluster enrichments were determined using R version 2.12. Cox p-values were determined using the Wald test from the coxph( ) proportional hazards model, and log-rank p-values from a chi-square test from the survdiff( ) function. Overall enrichment of a gene's or pathway member's values for a clustering were determined by ANOVA, and enrichment of a gene for a particular cluster label were determined by a T-test of a gene's values in a particular cluster vs. the gene's values in all other clusters. FDR was determined using the Benjamini &Hochberg method of p.adjust.

Example XLIV: Data Sets and Pathway Interactions

Both copy number and expression data were incorporated into PARADIGM inference. Since a set of eight normal tissue controls was available for analysis in the expression data, each patient's gene-value was normalized by subtracting the gene's median level observed in the normal fallopian control. Copy number data was normalized to reflect the difference in copy number between a gene's level detected in tumor versus a blood normal. For input to PARADIGM, expression data was taken from the same integrated dataset used for subtype analysis and the copy number was taken from the segmented calls of MSKCC Agilent 1M copy number data.

A collection of pathways was obtained from NCI-PID containing 131 pathways, 11,563 interactions, and 7,204 entities. An entity is molecule, complex, small molecule, or abstract concept represented as "nodes" in PARADIGM's graphical model. The abstract concepts correspond to general cellular processes (such as "apoptosis" or "absorption of light,") and families of genes that share functional activity such as the RAS family of signal transducers. We collected interactions including protein-protein interactions, transcriptional regulatory interactions, protein modifications such as phosphorylation and ubiquitinylation interactions.

Example XLV: Inference of Integrated Molecular Activities in Pathway Context

We used PARADIGM, which assigns an integrated pathway activity (IPA) reflecting the copy number, gene expression, and pathway context of each entity.

The significance of IPAs was assessed using permutations of gene- and patient-specific cross-sections of data. Data for 1000 "null" patients was created by randomly selecting a gene-expression and copy number pair of values for each gene in the genome. To assess the significance of the PARADIGM IPAs, we constructed a null distribution by assigning random genes to pathways while preserving the pathway structure.

Example XLVI: Identification of FOXM1 Pathway

While all of the genes in the FOXM1 network were used to assess the statistical significance during the random simulations, in order to allow visualization of the FOXM1 pathway, entities directly connected to FOXM1 with significantly altered IPAs according to FIG. 29 were chosen for inclusion in FIG. 27. Among these, genes with roles in DNA repair and cell cycle control found to have literature support for interactions with FOXM1 were displayed. BRCC complex members, not found in the original NCI-PID pathway, were included in the plot along with BRCA2, which is a target of FOXM1 according to NCI-PID. Upstream DNA repair targets were identified by finding upstream regulators of CHEK2 in other NCI pathways (for example, an indirect link from ATM was found in the PLK3 signaling pathway).

Example XLVII: Clustering

The use of inferred activities, which represent a change in probability of activity and not activity directly, it enables entities of various types to be clustered together into one heatmap. To globally visualize the results of PARADIGM inference, Eisen Cluster 3.0 was used to perform feature filtering and clustering. A standard deviation filtering of 0.1 resulted in 1598 out of 7204 pathway entities remaining, and average linkage, uncentered correlation hierarchical cluster was performed on both the entities and samples.

Example XLVIII Isolation of Genomic DNA

Blood samples (2-3 ml) are collected from patients and stored in EDTA-containing tubes at −80° C. until use. Genomic DNA is extracted from the blood samples using a DNA isolation kit according to the manufacturer's instruction (PUREGENE, Gentra Systems, Minneapolis Minn.). DNA purity is measured as the ratio of the absorbance at 260 and 280 nm (1 cm lightpath; $A_{260}/A_{280}$) measured with a Beckman spectrophotometer.

Example XLIX: Identification of SNPs

A region of a gene from a patient's DNA sample is amplified by PCR using the primers specifically designed for the region. The PCR products are sequenced using methods well known to those of skill in the art, as disclosed above. SNPs identified in the sequence traces are verified using Phred/Phrap/Consed software and compared with known SNPs deposited in the NCBI SNP databank.

Example L: Statistical Analysis

Values are expressed as mean±SD. $x^2$ analysis (Web Chi Square Calculator, Georgetown Linguistics, Georgetown University, Washington D.C.) is used to assess differences between genotype frequencies in normal subjects and patients with a disorder. One-way ANOVA with post-hoc analysis is performed as indicated to compare hemodynamics between different patient groups.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A pathway analysis computing system comprising:
a computer readable, non-transitory memory storing software instructions and a probabilistic graphical model (PGM) of a gene expression pathway network, the PGM including:
directed graphs that include pathway interactions and that include hidden cell states and observed cell states of biological cellular entities for a set of genes, wherein the biological cellular entities include gene copy number, mRNA expression, protein level, and protein activity for each of the set of genes, and wherein measurements are available for the observed cell states and not available for the hidden cell states;
wherein the directed graphs form a data structure including nodes representing the biological cellular entities and edges representing the pathway interactions among the nodes of the biological cellular entities associated with the pathway interactions; and
wherein variables of the directed graphs represent differential states of the hidden cell states and the observed cell states relative to corresponding normal levels of the biological cellular entities, and where factors of edges of the directed graphs are assigned to the edges representing the pathway interactions between the biological cellular entities, and wherein the pathway interactions are biochemical interactions; and
a processor coupled with the memory and configured, upon execution of the software instructions, to output integrated pathway activities for pathways associated with a patient by:
initializing the PGM by assigning, in the memory, values measured from a tissue sample of the patient to the observed cell states of observed nodes in the directed graphs;
simulating the gene expression pathway network, using the initialized PGM, to estimate the hidden cell states of hidden nodes of the directed graphs for the tissue sample based on the assigned observed cell states in the directed graphs and according to the factors of edges of the directed graphs that connect the hidden nodes and the observed nodes, wherein the simulating includes:
determining a probability of a given hidden cell state for each hidden node of the hidden nodes based on (1) probabilities of cell states of parent nodes of the hidden node and (2) the factors of edges from the parent nodes, and
iteratively updating the hidden cell states based on the probabilities of the cell states and the factors of edges; and
outputting, from the memory, the estimated hidden cell states of the biological cellular entities for the tissue sample as integrated pathway activities of the tissue sample, wherein the estimated hidden cell states include a protein activity.

2. The system of claim 1, wherein the probabilistic graphical model comprises at least two directed graphs.

3. The system of claim 1, wherein the directed graphs comprise a factor graphs.

4. The system of claim 1, wherein the directed graphs comprise a Bayesian network.

5. The system of claim 1, wherein the pathways are formatted according to BioPAX formatting rules.

6. The system of claim 5, wherein the pathways are formatted according to BioPAX level 2.

7. The system of claim 1, wherein the biological cellular entities include at least four different biological cellular entities.

8. The system of claim 1, wherein the integrated pathway activities include at least three states for the biological cellular entities.

9. The system of claim 8, wherein the at least three states include: an active state, an inactive state, and a nominal state.

10. The system of claim 1, wherein the estimated hidden cell states are estimated by belief propagation.

11. The system of claim 1, wherein the estimated hidden cell states are estimated by iterating between inferring probabilities of the hidden cell states and updating the hidden cell states to maximize likelihood given probabilities of the hidden cell states.

12. The system of claim 11, wherein the estimated hidden cell states are estimated via an implementation of an expectation-maximization algorithm.

13. The system of claim 1, wherein the factors between the biological cellular entities include non-negative functions.

14. The system of claim 13, wherein the non-negative functions constrain values of the cell states.

15. The system of claim 1, wherein the factors define probabilities associated with states of the biological cellular entities.

16. The system of claim 1, wherein the gene expression pathway network includes at least one of: a regulatory pathway network and a signaling pathway network.

17. The system of claim 1, wherein the values obtained from the tissue sample of the patient and assigned to the observed cell states include at least one of the following: mutation, a differential genetic sequence object, a gene copy number, a transcription level, a translation level, a protein activity, and a protein interaction.

18. The system of claim 1, wherein the tissue sample is at least one of the following: a diseased tissue, a normal tissue, an aging tissue, a recovering tissue, an animal tissue, an experimentally treated tissue, a cancer tissue, and a patient fluid.

19. The system of claim 1, wherein the PGM is generated using observed cell states of a cohort of patients that have a same condition as the patient.

20. A method comprising:
measuring values from a tissue sample of a patient, wherein the measured values correspond to observed cell states and not to hidden cell states;
storing, by a computer in a database, a probabilistic graphical model (PGM) of a gene expression pathway network, the PGM including:
directed graphs that include pathway interactions and that include hidden cell states and observed cell states of biological cellular entities for a set of genes, wherein the biological cellular entities include gene copy number, mRNA expression, protein level, and protein activity for each of the set of genes, and wherein measurements are available for the observed cell states and not available for the hidden cell states;
wherein the directed graphs form a data structure including nodes representing the biological cellular entities and edges representing the pathway interactions among the nodes of the biological cellular entities associated with the pathway interactions; and
wherein variables of the directed graphs represent differential states of the hidden cell states and the observed cell states relative to corresponding normal levels of the biological cellular entities, and where factors of edges of the directed graphs are assigned to the edges representing the pathway interactions between the biological cellular entities, and wherein the pathway interactions are biochemical interactions;
initializing, by the computer, the PGM by assigning values measured from the tissue sample of the patient to the observed cell states of observed nodes in the directed graphs;
simulating, by the computer, the gene expression pathway network, using the initialized PGM, to estimate the hidden cell states of hidden nodes of the directed graphs for the tissue sample based on the assigned observed cell states in the directed graphs and according to the factors of edges of the directed graphs that connect the hidden nodes and the observed nodes, wherein the simulating includes:
determining a probability of a given hidden cell state for each hidden node of the hidden nodes based on (1) probabilities of cell states of parent nodes of the hidden node and (2) the factors of edges from the parent nodes, and
iteratively updating the hidden cell states based on the probabilities of the cell states and the factors of edges; and
outputting, by the computer, the estimated hidden cell states of the biological cellular entities for the tissue sample as integrated pathway activities of the tissue sample, wherein the estimated hidden cell states include a protein activity.

21. The method of claim 20, further comprising:
determining integrated pathway activities by comparing the probabilities of the estimated hidden cell states determined using the observed cell states and the factors to prior probabilities of hidden states iteratively determined without the observed cell states,
wherein outputting the estimated hidden cell states is accomplished by outputting the integrated pathway activities.

22. The system of claim 1, wherein the processor is further configured, upon execution of the software instructions, to perform:
determining integrated pathway activities by comparing the probabilities of the estimated hidden cell states determined using the observed cell states and the factors to prior probabilities of hidden states iteratively determined without the observed cell states,
wherein outputting the estimated hidden cell states is accomplished by outputting the integrated pathway activities.

23. The system of claim 1, wherein the probabilistic graphical model includes at least 55 nodes.

* * * * *